United States Patent
Zon et al.

(10) Patent No.: US 12,146,165 B2
(45) Date of Patent: Nov. 19, 2024

(54) ENDOTHELIAL CELL FACTORS AND METHODS THEREOF

(71) Applicant: THE CHILDREN'S MEDICAL CENTER CORPORATION, Boston, MA (US)

(72) Inventors: Leonard I. Zon, Brookline, MA (US); Elliott J. Hagedorn, Jamaica Plain, MA (US)

(73) Assignee: THE CHILDREN'S MEDICAL CENTER CORPORATION

( * ) Notice: Subject to any disclaimer, the term of this patent is extended or adjusted under 35 U.S.C. 154(b) by 771 days.

(21) Appl. No.: 17/040,421

(22) PCT Filed: Mar. 22, 2019

(86) PCT No.: PCT/US2019/023637
§ 371 (c)(1),
(2) Date: Sep. 22, 2020

(87) PCT Pub. No.: WO2019/183508
PCT Pub. Date: Sep. 26, 2019

(65) Prior Publication Data
US 2021/0079343 A1    Mar. 18, 2021

Related U.S. Application Data

(60) Provisional application No. 62/647,433, filed on Mar. 23, 2018.

(51) Int. Cl.
C12N 5/071 (2010.01)
A61K 35/44 (2015.01)
C12N 15/90 (2006.01)

(52) U.S. Cl.
CPC .............. *C12N 5/069* (2013.01); *A61K 35/44* (2013.01); *C12N 15/907* (2013.01); *C12N 2501/60* (2013.01); *C12N 2510/00* (2013.01)

(58) Field of Classification Search
None
See application file for complete search history.

(56) References Cited

U.S. PATENT DOCUMENTS

2014/0017784 A1    1/2014    Zhang et al.

FOREIGN PATENT DOCUMENTS

| WO | 2009042910 A2 | 4/2009 | |
| WO | WO-2014006228 A1 * | 1/2014 | ............ C12N 5/069 |
| WO | 2014113415 A1 | 7/2014 | |
| WO | 2016201133 A2 | 12/2016 | |
| WO | 2017015245 A1 | 1/2017 | |
| WO | WO-2017015246 A1 * | 1/2017 | ............ A61K 35/28 |

OTHER PUBLICATIONS

Tyagi S, Gupta P, Saini AS, Kaushal C, Sharma S. The peroxisome proliferator-activated receptor: A family of nuclear receptors role in various diseases. J Adv Pharm Technol Res. Oct. 2011;2(4):236-40. doi: 10.4103/2231-4040.90879. PMID: 22247890; PMCID: PMC3255347. (Year: 2011).*

Wolf, A., Aggio, J., Campbell, C et al. Zebrafish Caudal Haematopoietic Embryonic Stromal Tissue (CHEST) Cells Support Haematopoiesis. Sci Rep 2017; 7: 44644. https://doi.org/10.1038/srep44644. (Year: 2017).*

Hagedorn EJ, et al. Transcription factor induction of vascular blood stem cell niches in vivo. Dev Cell. Jun. 19, 2023;58(12):1037-1051. e4. doi: 10.1016/j.devcel.2023.04.007. Epub Apr. 28, 2023. PMID: 37119815; PMCID: PMC10330626. (Year: 2023).*

Lee SJ, Park C, Lee JY, Kim S, Kwon PJ, Kim W, Jeon YH, Lee E, Yoon YS. Generation of pure lymphatic endothelial cells from human pluripotent stem cells and their therapeutic effects on wound repair. Sci Rep. Jun. 12, 2015;5:11019. doi: 10.1038/srep11019. PMID: 26066093; PMCID: PMC4464258. (Year: 2015).*

Fujimoto N, He Y, D'Addio M, Tacconi C, Detmar M, Dieterich LC. Single-cell mapping reveals new markers and functions of lymphatic endothelial cells in lymph nodes. PLoS Biol. Apr. 6, 2020;18(4): e3000704. doi: 10.1371/journal.pbio.3000704. PMID: 32251437; PMCID: PMC7162550. (Year: 2020).*

Aranguren et al. Transcription factor COUP-TFII is indispensable for venous and lymphatic development in zebrafish and Xenopus laevis. Biochemical and biophysical research communications 410, 121-126, 2011.

Chen et al. Mobilization as a preparative regimen for hematopoietic stem cell transplantation. Blood 107, 3764-3771, 2006.

Jung et al. Development of the larval lymphatic system in zebrafish. Development 144, 2070-2081, 2017.

Junker et al. Genome-wide RNA Tomography in the zebrafish embryo. Cell 159, 662-675, 2014.

Letarte et al., Reduced endothelial secretion and plasma levels of transforming growth factor-beta1 in patients with hereditary hemorrhagic telangiectasia type 1, Cardiovascular Research 68, 155-164, 2005.

Quillien et al. Robust Identification of Developmentally Active Endothelial Enhancers in Zebrafish Using FANS-Assisted ATAC-Seq. Cell reports 20, 709-720, 2017.

Sun et al., E-Selectin Medicated Adhesion and Migration of Endothelial Colony Forming Cells Is Enhanced by SDF-1alpha/CXCR4, PLoS One 8(4), e60890, 2013.

(Continued)

*Primary Examiner* — Allison M Fox
*Assistant Examiner* — Alyssa G Weston
(74) *Attorney, Agent, or Firm* — NIXON PEABODY LLP; David S. Resnick; Ravinderjit S. Braich

(57) ABSTRACT

The technology described herein relates to compositions and methods of generating endothelial niche cells. Embodiments of the technology described herein comprise compositions, kits, vectors, and methods related to generating or engineering endothelial niche cells. One aspect comprises a method to generate/engineer endothelial niche cells, comprising expressing one or more transcription factors in an endothelial cell, wherein the one or more transcription factors are from the Ets family, the Sox family, and/or the Nuclear Hormone (NHR) family.

12 Claims, 51 Drawing Sheets

Specification includes a Sequence Listing.

(56) References Cited

OTHER PUBLICATIONS

Swift et al. SoxF factors and Notch regulate nr2f2 gene expression during venous differentiation in zebrafish. Developmental biology 390, 116-125, 2014.

Tamplin et al. Hematopoietic stem cell arrival triggers dynamic remodeling of the perivascular niche, Cell, 160(1-2), 241-52, 2015.

Tang et al. Dissecting hematopoietic and renal cell heterogeneity in adult zebrafish at single-cell resolution using RNA sequencing. The Journal of experimental medicine 214(10), 2875-2887, 2017.

Theodore et al. Distinct Roles for Matrix Metalloproteinases 2 and 9 in Embryonic Hematopoietic Stem Cell Emergence, Migration, and Niche Colonization. Stem cell reports 8, 1226-1241, 2017.

You et al, "Suppression of Notch signalling by the COUP-TFII transcription factor regulates vein identity." Nature 435.7038: 98-104 (2005).

Butler et al. "Endothelial cells are essential for the self-renewal and repopulation of Notch-dependent hematopoietic stem cells." Cell stem cell 6(3): 251-264 (2010).

Hagedorn et al. "Defining the Transcriptional Code That Specifies Sinusoidal Endothelial Cells in the HSPC Niche." Blood 130: 136-137 (2017).

Meadows et al. "Regulation of endothelial cell development by ETS transcription factors." Seminars in cell & developmental biology 22(9): 976-84 (2011).

Park et al. "Transcriptional regulation of endothelial cell and vascular development." Circulation research 112(10): 1380-1400 (2013).

Zhang Kaizi, et al., "Clinical Heart Failure", Hunan Science and Technology Press, pp. 781-785 (2014).

\* cited by examiner

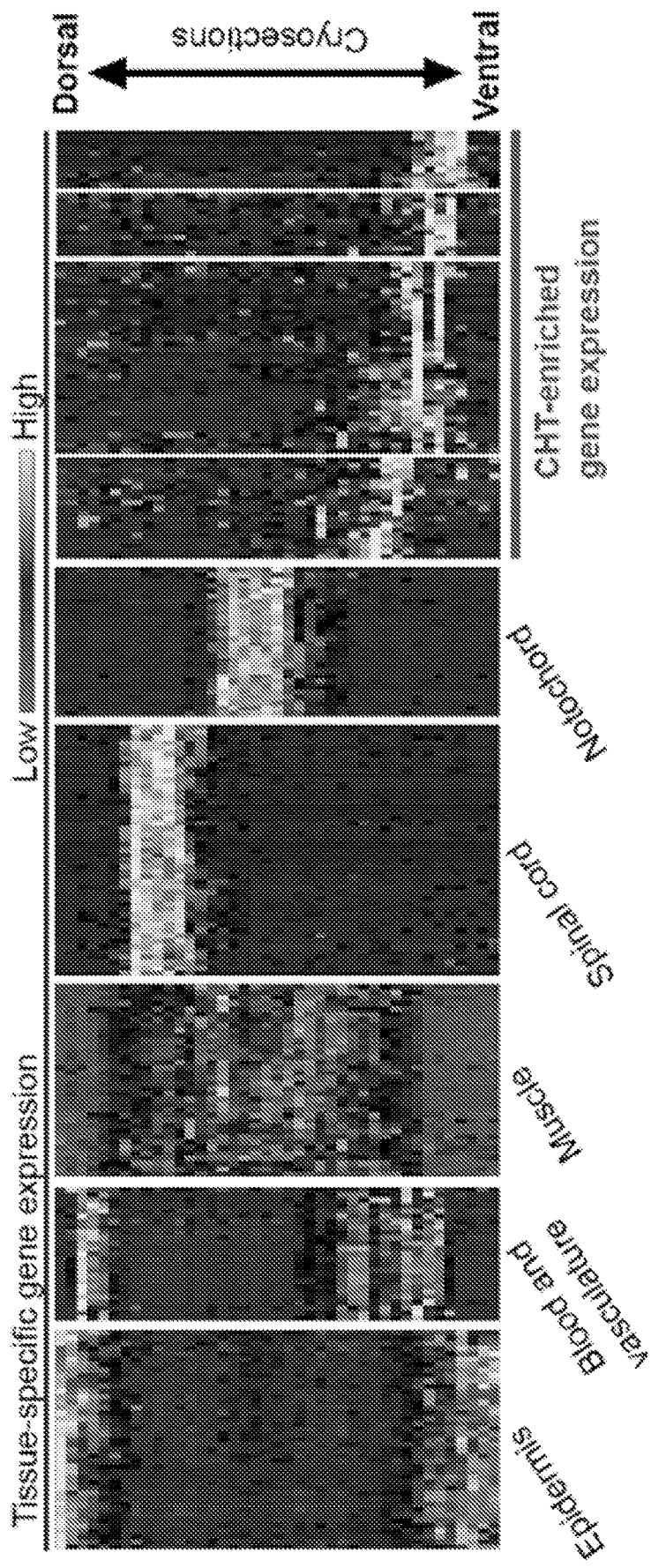
Fig. 1B, cont.

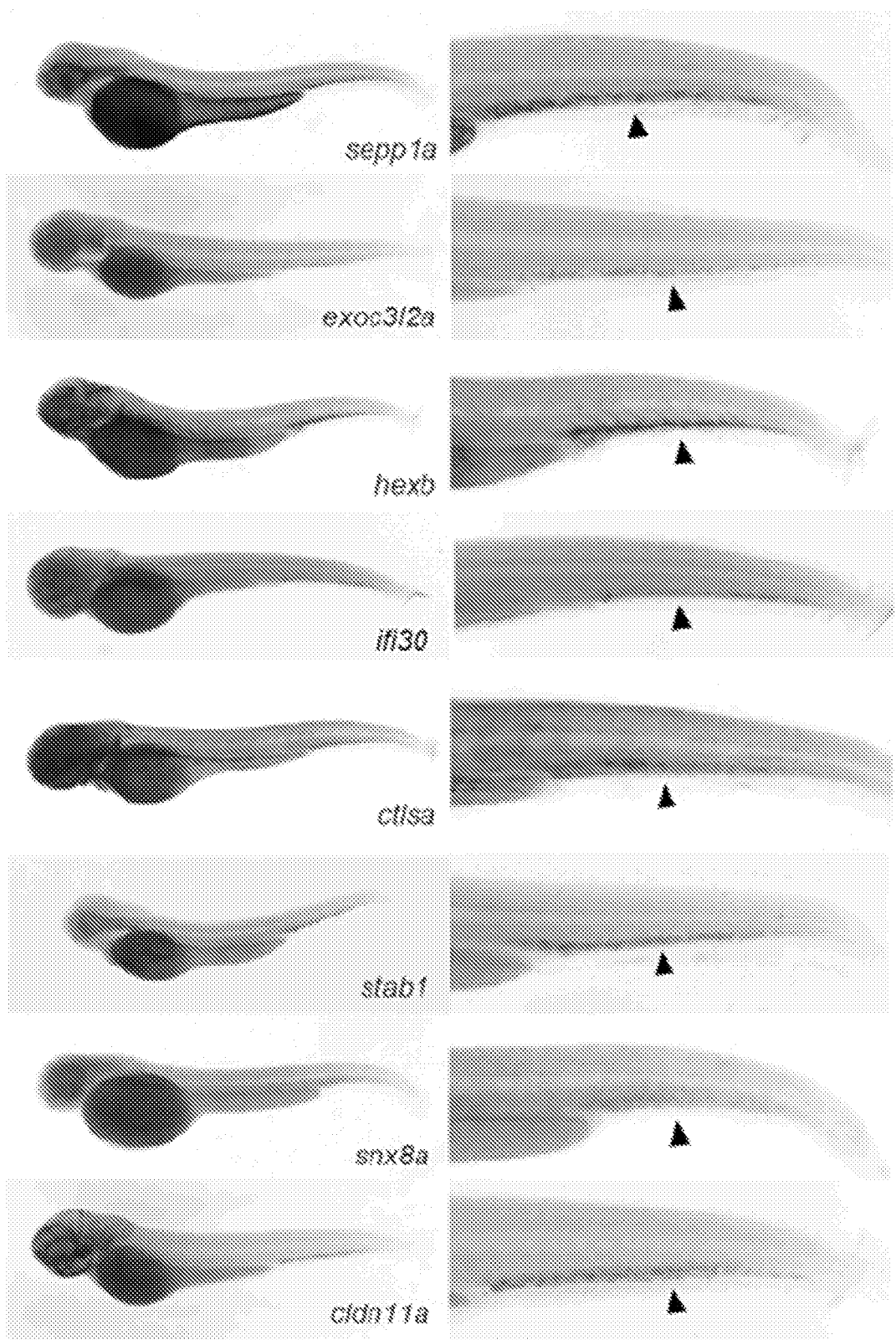
Fig. 7B, cont.

Motifs over-represented in CHT endothelial elements

| Rank | Motif | p-value | % of Targets | TF Family | Best Match/Details |
|---|---|---|---|---|---|
| 1 | ACTTCCTGT | 1e-1487 | 58.15% | Ets | ERG(ETS)/VCaP-ERG-ChIP-Seq(GSE14097)/Homer(0.948) |
| 2 | CCATTGTC | 1e-206 | 16.95% | Sox | MA0078.1 Sox17/Jaspar(0.950) |
| 3 | AGGTCA | 1e-153 | 23.79% | NHR | MF0004.1 Nuclear Receptor class/Jaspar(0.943) |

Motifs over-represented in pan-endothelial elements

| Rank | Motif | p-value | % of Targets | TF Family | Best Match/Details |
|---|---|---|---|---|---|
| 1 | CACTTCCTGT | 1e-886 | 53.67% | Ets | MA0474.1 Erg/Jaspar(0.951) |
| 2 | CTCTCTCT | 1e-89 | 32.09% | Zinc Finger | PRDM1(ZF)/Hela-PRDM1-ChIP-Seq(GSE31477)/Homer(0.678) |
| 3 | TGACTCA | 1e-81 | 19.22% | Leucine Zipper | Atf7(bZIP)/3T3L1-Atf7-ChIP-Seq(GSE56872)/Homer(0.940) |

Fig. 9C

| TF Family | Gene | CHT endothelial cells (GFP+ mCherry+) FPKM |
|---|---|---|
| Ets | etv2 | 192.3 |
| | fli1a | 480.4 |
| | ets1 | 183.0 |
| Sox | sox18 | 206.4 |
| | sox7 | 125.1 |
| Nuclear Hormone | rxraa | 45.9 |
| | nr2f2 | 84.6 |

Are a combination of these transcription factors sufficient to induce an ectopic niche?

SEQUENCE LISTING

<160> NUMBER OF SEQ ID NOS: 246

<210> SEQ ID NO 1
<211> LENGTH: 342
<212> TYPE: PRT
<213> ORGANISM: Homo sapiens

<400> SEQUENCE: 1

Met Asp Leu Trp Asn Trp Asp Glu Ala Ser Pro Gln Glu Val Pro Pro
1               5                   10                  15

Gly Asn Lys Leu Ala Gly Leu Glu Gly Ala Lys Leu Gly Phe Cys Phe
            20                  25                  30

-continued

```
Pro Asp Leu Ala Leu Gln Gly Asp Thr Pro Thr Ala Thr Ala Glu Thr
            35                  40                  45

Cys Trp Lys Gly Thr Ser Ser Leu Ala Ser Phe Pro Gln Leu Asp
 50                  55                  60

Trp Gly Ser Ala Leu Leu His Pro Glu Val Pro Trp Gly Ala Glu Pro
 65                  70                  75                  80

Asp Ser Gln Ala Leu Pro Trp Ser Gly Asp Trp Thr Asp Met Ala Cys
                 85                  90                  95

Thr Ala Trp Asp Ser Trp Ser Gly Ala Ser Gln Thr Leu Gly Pro Ala
                100                 105                 110

Pro Leu Gly Pro Gly Pro Ile Pro Ala Ala Gly Ser Glu Gly Ala Ala
                115                 120                 125

Gly Gln Asn Cys Val Pro Val Ala Gly Glu Ala Thr Ser Trp Ser Arg
130                 135                 140

Ala Gln Ala Ala Gly Ser Asn Thr Ser Trp Asp Cys Ser Val Gly Pro
145                 150                 155                 160

Asp Gly Asp Thr Tyr Trp Gly Ser Gly Leu Gly Glu Pro Arg Thr
                165                 170                 175

Asp Cys Thr Ile Ser Trp Gly Gly Pro Ala Gly Pro Asp Cys Thr Thr
                180                 185                 190

Ser Trp Asn Pro Gly Leu His Ala Gly Gly Thr Thr Ser Leu Lys Arg
                195                 200                 205

Tyr Gln Ser Ser Ala Leu Thr Val Cys Ser Glu Pro Ser Pro Gln Ser
                210                 215                 220

Asp Arg Ala Ser Leu Ala Arg Cys Pro Lys Thr Asn His Arg Gly Pro
225                 230                 235                 240

Ile Gln Leu Trp Gln Phe Leu Leu Glu Leu Leu His Asp Gly Ala Arg
                245                 250                 255

Ser Ser Cys Ile Arg Trp Thr Gly Asn Ser Arg Glu Phe Gln Leu Cys
                260                 265                 270

Asp Pro Lys Glu Val Ala Arg Leu Trp Gly Arg Lys Arg Lys Pro
                275                 280                 285

Gly Met Asn Tyr Glu Lys Leu Ser Arg Gly Leu Arg Tyr Tyr Tyr Arg
290                 295                 300

Arg Asp Ile Val Arg Lys Ser Gly Arg Lys Tyr Thr Tyr Arg Phe
305                 310                 315                 320

Gly Gly Arg Val Pro Ser Leu Ala Tyr Pro Asp Cys Ala Gly Gly Gly
                325                 330                 335

Arg Gly Ala Glu Thr Gln
                340

<210> SEQ ID NO 2
<211> LENGTH: 452
<212> TYPE: PRT
<213> ORGANISM: Homo sapiens

<400> SEQUENCE: 2

Met Asp Gly Thr Ile Lys Glu Ala Leu Ser Val Val Ser Asp Asp Gln
 1               5                  10                  15

Ser Leu Phe Asp Ser Ala Tyr Gly Ala Ala Ala His Leu Pro Lys Ala
                20                  25                  30

Asp Met Thr Ala Ser Gly Ser Pro Asp Tyr Gly Gln Pro His Lys Ile
            35                  40                  45

Asn Pro Leu Pro Pro Gln Gln Glu Trp Ile Asn Gln Pro Val Arg Val
 50                  55                  60
```

Asn Val Lys Arg Glu Tyr Asp His Met Asn Gly Ser Arg Glu Ser Pro
 65                  70                  75                  80

Val Asp Cys Ser Val Ser Lys Cys Ser Lys Leu Val Gly Gly Gly Glu
                 85                  90                  95

Ser Asn Pro Met Asn Tyr Asn Ser Tyr Met Asp Glu Lys Asn Gly Pro
            100                 105                 110

Pro Pro Pro Asn Met Thr Thr Asn Glu Arg Arg Val Ile Val Pro Ala
        115                 120                 125

Asp Pro Thr Leu Trp Thr Gln Glu His Val Arg Gln Trp Leu Glu Trp
    130                 135                 140

Ala Ile Lys Glu Tyr Ser Leu Met Glu Ile Asp Thr Ser Phe Phe Gln
145                 150                 155                 160

Asn Met Asp Gly Lys Glu Leu Cys Lys Met Asn Lys Glu Asp Phe Leu
                165                 170                 175

Arg Ala Thr Thr Leu Tyr Asn Thr Glu Val Leu Leu Ser His Leu Ser
            180                 185                 190

Tyr Leu Arg Glu Ser Ser Leu Leu Ala Tyr Asn Thr Thr Ser His Thr
        195                 200                 205

Asp Gln Ser Ser Arg Leu Ser Val Lys Glu Asp Pro Ser Tyr Asp Ser
    210                 215                 220

Val Arg Arg Gly Ala Trp Gly Asn Asn Met Asn Ser Gly Leu Asn Lys
225                 230                 235                 240

Ser Pro Pro Leu Gly Gly Ala Gln Thr Ile Ser Lys Asn Thr Glu Gln
                245                 250                 255

Arg Pro Gln Pro Asp Pro Tyr Gln Ile Leu Gly Pro Thr Ser Ser Arg
            260                 265                 270

Leu Ala Asn Pro Gly Ser Gly Gln Ile Gln Leu Trp Gln Phe Leu Leu
        275                 280                 285

Glu Leu Leu Ser Asp Ser Ala Asn Ala Ser Cys Ile Thr Trp Glu Gly
    290                 295                 300

Thr Asn Gly Glu Phe Lys Met Thr Asp Pro Asp Glu Val Ala Arg Arg
305                 310                 315                 320

Trp Gly Glu Arg Lys Ser Lys Pro Asn Met Asn Tyr Asp Lys Leu Ser
                325                 330                 335

Arg Ala Leu Arg Tyr Tyr Tyr Asp Lys Asn Ile Met Thr Lys Val His
            340                 345                 350

Gly Lys Arg Tyr Ala Tyr Lys Phe Asp Phe His Gly Ile Ala Gln Ala
        355                 360                 365

Leu Gln Pro His Pro Thr Glu Ser Ser Met Tyr Lys Tyr Pro Ser Asp
    370                 375                 380

Ile Ser Tyr Met Pro Ser Tyr His Ala His Gln Gln Lys Val Asn Phe
385                 390                 395                 400

Val Pro Pro His Pro Ser Ser Met Pro Val Thr Ser Ser Ser Phe Phe
                405                 410                 415

Gly Ala Ala Ser Gln Tyr Trp Thr Ser Pro Thr Gly Gly Ile Tyr Pro
            420                 425                 430

Asn Pro Asn Val Pro Arg His Pro Asn Thr His Val Pro Ser His Leu
        435                 440                 445

Gly Ser Tyr Tyr
    450

<210> SEQ ID NO 3
<211> LENGTH: 441

<212> TYPE: PRT
<213> ORGANISM: Homo sapiens

<400> SEQUENCE: 3

Met Lys Ala Ala Val Asp Leu Lys Pro Thr Leu Thr Ile Ile Lys Thr
1               5                   10                  15

Glu Lys Val Asp Leu Glu Leu Phe Pro Ser Pro Asp Met Glu Cys Ala
            20                  25                  30

Asp Val Pro Leu Leu Thr Pro Ser Ser Lys Glu Met Met Ser Gln Ala
        35                  40                  45

Leu Lys Ala Thr Phe Ser Gly Phe Thr Lys Glu Gln Gln Arg Leu Gly
    50                  55                  60

Ile Pro Lys Asp Pro Arg Gln Trp Thr Glu Thr His Val Arg Asp Trp
65                  70                  75                  80

Val Met Trp Ala Val Asn Glu Phe Ser Leu Lys Gly Val Asp Phe Gln
            85                  90                  95

Lys Phe Cys Met Asn Gly Ala Ala Leu Cys Ala Leu Gly Lys Asp Cys
            100                 105                 110

Phe Leu Glu Leu Ala Pro Asp Phe Val Gly Asp Ile Leu Trp Glu His
        115                 120                 125

Leu Glu Ile Leu Gln Lys Glu Asp Val Lys Pro Tyr Gln Val Asn Gly
    130                 135                 140

Val Asn Pro Ala Tyr Pro Glu Ser Arg Tyr Thr Ser Asp Tyr Phe Ile
145                 150                 155                 160

Ser Tyr Gly Ile Glu His Ala Gln Cys Val Pro Pro Ser Glu Phe Ser
            165                 170                 175

Glu Pro Ser Phe Ile Thr Glu Ser Tyr Gln Thr Leu His Pro Ile Ser
            180                 185                 190

Ser Glu Glu Leu Leu Ser Leu Lys Tyr Glu Asn Asp Tyr Pro Ser Val
        195                 200                 205

Ile Leu Arg Asp Pro Leu Gln Thr Asp Thr Leu Gln Asn Asp Tyr Phe
    210                 215                 220

Ala Ile Lys Gln Glu Val Val Thr Pro Asp Asn Met Cys Met Gly Arg
225                 230                 235                 240

Thr Ser Arg Gly Lys Leu Gly Gly Gln Asp Ser Phe Glu Ser Ile Glu
            245                 250                 255

Ser Tyr Asp Ser Cys Asp Arg Leu Thr Gln Ser Trp Ser Ser Gln Ser
            260                 265                 270

Ser Phe Asn Ser Leu Gln Arg Val Pro Ser Tyr Asp Ser Phe Asp Ser
        275                 280                 285

Glu Asp Tyr Pro Ala Ala Leu Pro Asn His Lys Pro Lys Gly Thr Phe
    290                 295                 300

Lys Asp Tyr Val Arg Asp Arg Ala Asp Leu Asn Lys Asp Lys Pro Val
305                 310                 315                 320

Ile Pro Ala Ala Ala Leu Ala Gly Tyr Thr Gly Ser Gly Pro Ile Gln
            325                 330                 335

Leu Arg Gln Phe Leu Leu Glu Leu Leu Thr Asp Lys Ser Cys Gln Ser
            340                 345                 350

Phe Ile Ser Trp Thr Gly Asp Gly Trp Glu Phe Lys Leu Ser Asp Pro
        355                 360                 365

Asp Glu Val Ala Arg Arg Trp Gly Lys Arg Lys Asn Lys Pro Lys Met
    370                 375                 380

Asn Tyr Glu Lys Leu Ser Arg Gly Leu Arg Tyr Tyr Tyr Asp Lys Asn
385                 390                 395                 400

```
Ile Ile His Lys Thr Ala Gly Lys Arg Tyr Val Tyr Arg Phe Val Cys
            405                 410                 415

Asp Leu Gln Ser Leu Leu Gly Tyr Thr Pro Glu Glu Leu His Ala Met
            420                 425                 430

Leu Asp Val Lys Pro Asp Ala Asp Glu
            435                 440

<210> SEQ ID NO 4
<211> LENGTH: 384
<212> TYPE: PRT
<213> ORGANISM: Homo sapiens

<400> SEQUENCE: 4

Met Gln Arg Ser Pro Gly Tyr Gly Ala Gln Asp Pro Pro Ala
1               5                   10                  15

Arg Arg Asp Cys Ala Trp Ala Pro Gly His Gly Ala Ala Asp Thr
                20                  25                  30

Arg Gly Leu Ala Ala Gly Pro Ala Ala Leu Ala Ala Pro Ala Ala Pro
            35                  40                  45

Ala Ser Pro Pro Ser Pro Gln Arg Ser Pro Pro Arg Ser Pro Glu Pro
        50                  55                  60

Gly Arg Tyr Gly Leu Ser Pro Ala Gly Arg Gly Glu Arg Gln Ala Ala
65                  70                  75                  80

Asp Glu Ser Arg Ile Arg Arg Pro Met Asn Ala Phe Met Val Trp Ala
                85                  90                  95

Lys Asp Glu Arg Lys Arg Leu Ala Gln Gln Asn Pro Asp Leu His Asn
                100                 105                 110

Ala Val Leu Ser Lys Met Leu Gly Lys Ala Trp Lys Glu Leu Asn Ala
            115                 120                 125

Ala Glu Lys Arg Pro Phe Val Glu Glu Ala Glu Arg Leu Arg Val Gln
        130                 135                 140

His Leu Arg Asp His Pro Asn Tyr Lys Tyr Arg Pro Arg Arg Lys Lys
145                 150                 155                 160

Gln Ala Arg Lys Ala Arg Arg Leu Glu Pro Gly Leu Leu Pro Gly
                165                 170                 175

Leu Ala Pro Pro Gln Pro Pro Glu Pro Phe Pro Ala Ala Ser Gly
            180                 185                 190

Ser Ala Arg Ala Phe Arg Glu Leu Pro Pro Leu Gly Ala Glu Phe Asp
        195                 200                 205

Gly Leu Gly Leu Pro Thr Pro Glu Arg Ser Pro Leu Asp Gly Leu Glu
    210                 215                 220

Pro Gly Glu Ala Ala Phe Phe Pro Pro Ala Ala Pro Glu Asp Cys
225                 230                 235                 240

Ala Leu Arg Pro Phe Arg Ala Pro Tyr Ala Pro Thr Glu Leu Ser Arg
                245                 250                 255

Asp Pro Gly Gly Cys Tyr Gly Ala Pro Leu Ala Glu Ala Leu Arg Thr
            260                 265                 270

Ala Pro Pro Ala Ala Pro Leu Ala Gly Leu Tyr Tyr Gly Thr Leu Gly
        275                 280                 285

Thr Pro Gly Pro Tyr Pro Gly Pro Leu Ser Pro Pro Glu Ala Pro
    290                 295                 300

Pro Leu Glu Ser Ala Glu Pro Leu Gly Pro Ala Ala Asp Leu Trp Ala
305                 310                 315                 320

Asp Val Asp Leu Thr Glu Phe Asp Gln Tyr Leu Asn Cys Ser Arg Thr
```

```
            325                 330                 335
Arg Pro Asp Ala Pro Gly Leu Pro Tyr His Val Ala Leu Ala Lys Leu
            340                 345                 350

Gly Pro Arg Ala Met Ser Cys Pro Glu Glu Ser Ser Leu Ile Ser Ala
            355                 360                 365

Leu Ser Asp Ala Ser Ser Ala Val Tyr Tyr Ser Ala Cys Ile Ser Gly
            370                 375                 380

<210> SEQ ID NO 5
<211> LENGTH: 388
<212> TYPE: PRT
<213> ORGANISM: Homo sapiens

<400> SEQUENCE: 5

Met Ala Ser Leu Leu Gly Ala Tyr Pro Trp Pro Glu Gly Leu Glu Cys
1               5                   10                  15

Pro Ala Leu Asp Ala Glu Leu Ser Asp Gly Gln Ser Pro Pro Ala Val
            20                  25                  30

Pro Arg Pro Pro Gly Asp Lys Gly Ser Glu Ser Arg Ile Arg Arg Pro
        35                  40                  45

Met Asn Ala Phe Met Val Trp Ala Lys Asp Glu Arg Lys Arg Leu Ala
    50                  55                  60

Val Gln Asn Pro Asp Leu His Asn Ala Glu Leu Ser Lys Met Leu Gly
65                  70                  75                  80

Lys Ser Trp Lys Ala Leu Thr Leu Ser Gln Lys Arg Pro Tyr Val Asp
                85                  90                  95

Glu Ala Glu Arg Leu Arg Leu Gln His Met Gln Asp Tyr Pro Asn Tyr
            100                 105                 110

Lys Tyr Arg Pro Arg Arg Lys Lys Gln Ala Lys Arg Leu Cys Lys Arg
        115                 120                 125

Val Asp Pro Gly Phe Leu Leu Ser Ser Leu Ser Arg Asp Gln Asn Ala
130                 135                 140

Leu Pro Glu Lys Arg Ser Gly Ser Arg Gly Ala Leu Gly Glu Lys Glu
145                 150                 155                 160

Asp Arg Gly Glu Tyr Ser Pro Gly Thr Ala Leu Pro Ser Leu Arg Gly
                165                 170                 175

Cys Tyr His Glu Gly Pro Ala Gly Gly Gly Gly Gly Thr Pro Ser
            180                 185                 190

Ser Val Asp Thr Tyr Pro Tyr Gly Leu Pro Thr Pro Glu Met Ser
        195                 200                 205

Pro Leu Asp Val Leu Glu Pro Glu Gln Thr Phe Phe Ser Ser Pro Cys
    210                 215                 220

Gln Glu Glu His Gly His Pro Arg Arg Ile Pro His Leu Pro Gly His
225                 230                 235                 240

Pro Tyr Ser Pro Glu Tyr Ala Pro Ser Pro Leu His Cys Ser His Pro
                245                 250                 255

Leu Gly Ser Leu Ala Leu Gly Gln Ser Pro Gly Val Ser Met Met Ser
            260                 265                 270

Pro Val Pro Gly Cys Pro Pro Ser Pro Ala Tyr Tyr Ser Pro Ala Thr
        275                 280                 285

Tyr His Pro Leu His Ser Asn Leu Gln Ala His Leu Gly Gln Leu Ser
    290                 295                 300

Pro Pro Pro Glu His Pro Gly Phe Asp Ala Leu Asp Gln Leu Ser Gln
305                 310                 315                 320
```

```
Val Glu Leu Leu Gly Asp Met Asp Arg Asn Glu Phe Asp Gln Tyr Leu
                325                 330                 335

Asn Thr Pro Gly His Pro Asp Ser Ala Thr Gly Ala Met Ala Leu Ser
            340                 345                 350

Gly His Val Pro Val Ser Gln Val Thr Pro Thr Gly Pro Thr Glu Thr
            355                 360                 365

Ser Leu Ile Ser Val Leu Ala Asp Ala Thr Thr Tyr Tyr Asn Ser
    370                 375                 380

Tyr Ser Val Ser
385

<210> SEQ ID NO 6
<211> LENGTH: 462
<212> TYPE: PRT
<213> ORGANISM: Homo sapiens

<400> SEQUENCE: 6

Met Asp Thr Lys His Phe Leu Pro Leu Asp Phe Ser Thr Gln Val Asn
1               5                   10                  15

Ser Ser Leu Thr Ser Pro Thr Gly Arg Gly Ser Met Ala Ala Pro Ser
                20                  25                  30

Leu His Pro Ser Leu Gly Pro Gly Ile Gly Ser Pro Gly Gln Leu His
            35                  40                  45

Ser Pro Ile Ser Thr Leu Ser Ser Pro Ile Asn Gly Met Gly Pro Pro
    50                  55                  60

Phe Ser Val Ile Ser Ser Pro Met Gly Pro His Ser Met Ser Val Pro
65                  70                  75                  80

Thr Thr Pro Thr Leu Gly Phe Ser Thr Gly Ser Pro Gln Leu Ser Ser
                85                  90                  95

Pro Met Asn Pro Val Ser Ser Glu Asp Ile Lys Pro Pro Leu Gly
            100                 105                 110

Leu Asn Gly Val Leu Lys Val Pro Ala His Pro Ser Gly Asn Met Ala
            115                 120                 125

Ser Phe Thr Lys His Ile Cys Ala Ile Cys Gly Asp Arg Ser Ser Gly
    130                 135                 140

Lys His Tyr Gly Val Tyr Ser Cys Glu Gly Cys Lys Gly Phe Phe Lys
145                 150                 155                 160

Arg Thr Val Arg Lys Asp Leu Thr Tyr Thr Cys Arg Asp Asn Lys Asp
                165                 170                 175

Cys Leu Ile Asp Lys Arg Gln Arg Asn Arg Cys Gln Tyr Cys Arg Tyr
            180                 185                 190

Gln Lys Cys Leu Ala Met Gly Met Lys Arg Glu Ala Val Gln Glu Glu
    195                 200                 205

Arg Gln Arg Gly Lys Asp Arg Asn Glu Asn Glu Val Glu Ser Thr Ser
210                 215                 220

Ser Ala Asn Glu Asp Met Pro Val Glu Arg Ile Leu Glu Ala Glu Leu
225                 230                 235                 240

Ala Val Glu Pro Lys Thr Glu Thr Tyr Val Glu Ala Asn Met Gly Leu
                245                 250                 255

Asn Pro Ser Ser Pro Asn Asp Pro Val Thr Asn Ile Cys Gln Ala Ala
            260                 265                 270

Asp Lys Gln Leu Phe Thr Leu Val Glu Trp Ala Lys Arg Ile Pro His
    275                 280                 285

Phe Ser Glu Leu Pro Leu Asp Asp Gln Val Ile Leu Leu Arg Ala Gly
    290                 295                 300
```

Trp Asn Glu Leu Leu Ile Ala Ser Phe Ser His Arg Ser Ile Ala Val
305                 310                 315                 320

Lys Asp Gly Ile Leu Leu Ala Thr Gly Leu His Val His Arg Asn Ser
            325                 330                 335

Ala His Ser Ala Gly Val Gly Ala Ile Phe Asp Arg Val Leu Thr Glu
        340                 345                 350

Leu Val Ser Lys Met Arg Asp Met Gln Met Asp Lys Thr Glu Leu Gly
    355                 360                 365

Cys Leu Arg Ala Ile Val Leu Phe Asn Pro Asp Ser Lys Gly Leu Ser
370                 375                 380

Asn Pro Ala Glu Val Glu Ala Leu Arg Glu Lys Val Tyr Ala Ser Leu
385                 390                 395                 400

Glu Ala Tyr Cys Lys His Lys Tyr Pro Glu Gln Pro Gly Arg Phe Ala
            405                 410                 415

Lys Leu Leu Leu Arg Leu Pro Ala Leu Arg Ser Ile Gly Leu Lys Cys
            420                 425                 430

Leu Glu His Leu Phe Phe Phe Lys Leu Ile Gly Asp Thr Pro Ile Asp
        435                 440                 445

Thr Phe Leu Met Glu Met Leu Glu Ala Pro His Gln Met Thr
    450                 455                 460

<210> SEQ ID NO 7
<211> LENGTH: 414
<212> TYPE: PRT
<213> ORGANISM: Homo sapiens

<400> SEQUENCE: 7

Met Ala Met Val Val Ser Thr Trp Arg Asp Pro Gln Asp Glu Val Pro
1               5                   10                  15

Gly Ser Gln Gly Ser Gln Ala Ser Gln Ala Pro Pro Val Pro Gly Pro
            20                  25                  30

Pro Pro Gly Ala Pro His Thr Pro Gln Thr Pro Gly Gln Gly Gly Pro
        35                  40                  45

Ala Ser Thr Pro Ala Gln Thr Ala Ala Gly Gly Gln Gly Gly Pro Gly
    50                  55                  60

Gly Pro Gly Ser Asp Lys Gln Gln Gln Gln His Ile Glu Cys Val
65                  70                  75                  80

Val Cys Gly Asp Lys Ser Ser Gly Lys His Tyr Gly Gln Phe Thr Cys
                85                  90                  95

Glu Gly Cys Lys Ser Phe Phe Lys Arg Ser Val Arg Arg Asn Leu Ser
            100                 105                 110

Tyr Thr Cys Arg Ala Asn Arg Asn Cys Pro Ile Asp Gln His His Arg
        115                 120                 125

Asn Gln Cys Gln Tyr Cys Arg Leu Lys Lys Cys Leu Lys Val Gly Met
    130                 135                 140

Arg Arg Glu Ala Val Gln Arg Gly Arg Met Pro Pro Thr Gln Pro Thr
145                 150                 155                 160

His Gly Gln Phe Ala Leu Thr Asn Gly Asp Pro Leu Asn Cys His Ser
                165                 170                 175

Tyr Leu Ser Gly Tyr Ile Ser Leu Leu Leu Arg Ala Glu Pro Tyr Pro
            180                 185                 190

Thr Ser Arg Phe Gly Ser Gln Cys Met Gln Pro Asn Asn Ile Met Gly
        195                 200                 205

Ile Glu Asn Ile Cys Glu Leu Ala Ala Arg Met Leu Phe Ser Ala Val

```
            210                 215                 220
Glu Trp Ala Arg Asn Ile Pro Phe Phe Pro Asp Leu Gln Ile Thr Asp
225                 230                 235                 240

Gln Val Ala Leu Leu Arg Leu Thr Trp Ser Glu Leu Phe Val Leu Asn
                245                 250                 255

Ala Ala Gln Cys Ser Met Pro Leu His Val Ala Pro Leu Leu Ala Ala
            260                 265                 270

Ala Gly Leu His Ala Ser Pro Met Ser Ala Asp Arg Val Val Ala Phe
                275                 280                 285

Met Asp His Ile Arg Ile Phe Gln Glu Gln Val Glu Lys Leu Lys Ala
290                 295                 300

Leu His Val Asp Ser Ala Glu Tyr Ser Cys Leu Lys Ala Ile Val Leu
305                 310                 315                 320

Phe Thr Ser Asp Ala Cys Gly Leu Ser Asp Val Ala His Val Glu Ser
                325                 330                 335

Leu Gln Glu Lys Ser Gln Cys Ala Leu Glu Glu Tyr Val Arg Ser Gln
                340                 345                 350

Tyr Pro Asn Gln Pro Thr Arg Phe Gly Lys Leu Leu Leu Arg Leu Pro
                355                 360                 365

Ser Leu Arg Thr Val Ser Ser Val Ile Glu Gln Leu Phe Phe Val
370                 375                 380

Arg Leu Val Gly Lys Thr Pro Ile Glu Thr Leu Ile Arg Asp Met Leu
385                 390                 395                 400

Leu Ser Gly Ser Ser Phe Asn Trp Pro Tyr Met Ala Ile Gln
                405                 410

<210> SEQ ID NO 8
<211> LENGTH: 362
<212> TYPE: PRT
<213> ORGANISM: Xenopus tropicalis

<400> SEQUENCE: 8

Met His Arg Pro Glu Pro Ser Tyr Cys Arg Glu Pro Thr Pro Cys
1               5                   10                  15

Gln Gly Val Asn Ser Thr Trp Val Pro Ala Asp Thr Val Pro Glu
                20                  25                  30

Thr Ser Pro Thr Pro Ser Ser Pro Ala Pro Asp Ser Pro Thr Pro
            35                  40                  45

Ser Pro Gln Pro Gly Tyr Gly Tyr Ser Pro Cys Glu Glu Lys Pro Gly
            50                  55                  60

Asp Pro Arg Ile Arg Arg Pro Met Asn Ala Phe Met Val Trp Ala Lys
65                  70                  75                  80

Asp Glu Arg Lys Arg Leu Ala Gln Gln Asn Pro Asp Leu His Asn Ala
                85                  90                  95

Val Leu Ser Lys Met Leu Gly Gln Ser Trp Lys Asn Leu Ser Ser Ala
            100                 105                 110

Glu Lys Arg Pro Phe Val Glu Glu Ala Glu Arg Leu Arg Val Gln His
            115                 120                 125

Leu Gln Asp His Pro Asn Tyr Lys Tyr Arg Pro Arg Arg Lys Lys Gln
130                 135                 140

Ala Lys Lys Leu Lys Arg Val Asp Pro Ser Pro Leu Leu Arg Asn Glu
145                 150                 155                 160

Gly Tyr Arg Gly Gln Ala Met Ala Asn Leu Ser His Phe Arg Asp Leu
                165                 170                 175
```

His Pro Leu Gly Gly Ser Gly Asp Leu Glu Ser Tyr Gly Leu Pro Thr
                180                 185                 190

Pro Glu Met Ser Pro Leu Asp Val Val Glu Pro Ser Glu Pro Ala Phe
            195                 200                 205

Phe Pro Pro His Met Arg Glu Glu Ala Asp Pro Gly Pro Phe Arg Thr
    210                 215                 220

Tyr Gln His Gly Val Asp Phe Gly Gln Glu Lys Thr Leu Arg Glu Ile
225                 230                 235                 240

Ser Leu Pro Tyr Ser Ser Ser Pro Ser His Met Gly Gly Phe Leu Arg
                245                 250                 255

Thr Pro Thr Ala Ser Ala Phe Tyr Tyr Asn Pro His Gly Gly Ser Pro
            260                 265                 270

Ala Cys Thr Pro Leu Gly Gln Leu Ser Pro Pro Glu Ala Pro Ala
        275                 280                 285

Leu Glu Ala Met Asp His Leu Gly Pro Ala Glu Leu Trp Gly Asp Phe
        290                 295                 300

Asp Arg Asn Glu Phe Asp Gln Tyr Leu Asn Met Ser Arg Thr Gln Gly
305                 310                 315                 320

Pro Gly Tyr Pro Phe Pro Met Ser Lys Leu Gly Ala Pro Arg Thr Ile
                325                 330                 335

Pro Cys Glu Glu Ser Ser Leu Ile Ser Ala Leu Ser Asp Ala Ser Thr
            340                 345                 350

Ala Met Tyr Tyr Thr Pro Cys Ile Thr Gly
            355                 360

<210> SEQ ID NO 9
<211> LENGTH: 428
<212> TYPE: PRT
<213> ORGANISM: Danio rerio

<400> SEQUENCE: 9

Met Ala Met Val Val Trp Arg Gly Ser Gln Asp Asp Val Ala Glu Thr
1               5                   10                  15

His Gly Thr Leu Ser Ser Gln Thr Gln Gly Gly Leu Ser Leu Pro Thr
                20                  25                  30

Pro Gln Pro Gly Gln Leu Gly Leu Thr Ala Ser Gln Val Ala Pro Pro
            35                  40                  45

Thr Pro Gln Thr Pro Val Gln Gly Pro Pro Asn Asn Asn Asn Asn Thr
        50                  55                  60

Gln Ser Thr Pro Thr Asn Gln Thr Thr Gln Ser Gln Ser Glu Lys Gln
65                  70                  75                  80

Gln Pro Gln His Ile Glu Cys Val Val Cys Gly Asp Lys Ser Ser Gly
                85                  90                  95

Lys His Tyr Gly Gln Phe Thr Cys Glu Gly Cys Lys Ser Phe Phe Lys
            100                 105                 110

Arg Ser Val Arg Arg Asn Leu Thr Tyr Thr Cys Arg Ala Asn Arg Asn
        115                 120                 125

Cys Pro Ile Asp Gln His His Arg Asn Gln Cys Gln Tyr Cys Arg Leu
    130                 135                 140

Lys Lys Cys Leu Lys Val Gly Met Arg Arg Glu Val Ser Leu Phe Thr
145                 150                 155                 160

Ala Ala Val Gln Arg Gly Arg Met Pro Pro Thr Gln Pro His Gly
                165                 170                 175

Gln Phe Ala Leu Thr Asn Gly Asp Pro Leu His Cys His Ser Tyr Leu
            180                 185                 190

```
Ser Gly Tyr Ile Ser Leu Leu Leu Arg Ala Glu Pro Tyr Pro Thr Ser
        195                 200                 205

Arg Tyr Gly Ser Gln Cys Met Gln Pro Asn Asn Ile Met Gly Ile Glu
210                 215                 220

Asn Ile Cys Glu Leu Ala Ala Arg Met Leu Phe Ser Ala Val Glu Trp
225                 230                 235                 240

Ala Arg Asn Ile Pro Phe Phe Pro Asp Leu Gln Ile Thr Asp Gln Val
                245                 250                 255

Ala Leu Leu Arg Leu Thr Trp Ser Glu Leu Phe Val Leu Asn Ala Ala
            260                 265                 270

Gln Cys Ser Met Pro Leu His Val Ala Pro Leu Leu Ala Ala Ala Gly
        275                 280                 285

Leu His Ala Ser Pro Met Ser Ala Asp Arg Val Val Ala Phe Met Asp
    290                 295                 300

His Ile Arg Ile Phe Gln Glu Gln Val Glu Lys Leu Lys Ala Leu His
305                 310                 315                 320

Val Asp Ser Ala Glu Tyr Ser Cys Leu Lys Ala Ile Val Leu Phe Thr
                325                 330                 335

Ser Asp Ala Cys Gly Leu Ser Asp Val Ala His Val Glu Ser Leu Gln
            340                 345                 350

Glu Lys Ser Gln Cys Ala Leu Glu Glu Tyr Val Arg Ser Gln Tyr Pro
        355                 360                 365

Asn Gln Pro Thr Arg Phe Gly Lys Leu Leu Leu Arg Leu Pro Ser Leu
    370                 375                 380

Arg Thr Val Ser Ser Ser Val Ile Glu Gln Leu Phe Phe Val Arg Leu
385                 390                 395                 400

Val Gly Lys Thr Pro Ile Glu Thr Leu Ile Arg Asp Met Leu Leu Ser
                405                 410                 415

Gly Ser Ser Phe Asn Trp Pro Tyr Met Ser Ile Gln
            420                 425

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cattaaccct cataaaggga a                                            21

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
taatacgact cactataggg                                              20

<210> SEQ ID NO 12
<211> LENGTH: 125
<212> TYPE: DNA
<213> ORGANISM: Danio rerio

<400> SEQUENCE: 12
```

```
tgaagcttgt acctttcatt tccttttgc tgagctttat tttctctaga attgccattg      60
tgtttccatt ctagcaaatc agcattttt tttcagctga aagaaaaata ccaggaactg     120
agagc                                                                 125
```

<210> SEQ ID NO 13
<211> LENGTH: 158
<212> TYPE: DNA
<213> ORGANISM: Danio rerio

<400> SEQUENCE: 13

```
ccatgaaact gggaagatga aagcattagt tgaattgtta ctggcaacat cttctctgta      60
atgccccctg tgacccatat tgtctcgctc tttcctttat aaacagagct gtagatatcc    120
acaggaaatg ggggtgtttt tgccattatt tcttcctg                             158
```

<210> SEQ ID NO 14
<211> LENGTH: 820
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 14

```
ttgtgggtgc tatttctgta atgaggaagc tggtacaaca ctgagcaaac acactaaaca      60
gagtggcatc ctagaaggtt caaggtctca cgaaatttca taatgagaaa ttcctggaga    120
gcttaacaat aatggctttt aaacaaagca aatataatac caccctattt ttaaattcaa    180
ttaaatggta ttggacatat attattgtca aatacgtctt ctgatctaac gcttgttatt    240
ttggtatgag aaaattttag tttatggttt atttttattaa cattttatgg gagtcatatg    300
cttatggcat gtttacatga tgttctcttt ccatgaaact gggaagatga aagcattagt    360
tgaattgtta ctggcaacat cttctctgta atgccccctg tgacccatat tgtctcgctc    420
tttcctttat aaacagagct gtagatatcc acaggaaatg ggggtgtttt tgccattatt    480
tcttcctgct aaagttaatc aggtggtcca aaaattggta taattcattc cttcatttgc    540
ttttcggctt agtccatcag ttaatcaggg gtcgccacag tggaatgaac ctatatccaa    600
tgtatgtttt acgcagcgga tgcccttcca gctgcaaccc aacactggga aacattttag    660
cttactcaat tcacctatac cacgtctttg ggcttgtggg ggaaaccaga gcacccggag    720
gaaacccatg caaacacggg gagaacatga aaactccaaa cagaaacgct aactgaccca    780
gccagggctc gaaccagcaa gcttcctgct gtgaggcgat                           820
```

<210> SEQ ID NO 15
<211> LENGTH: 405
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 15

```
ctgtttcctg gcagctctgg cccgtgtctc aaaatctctg atgttacatt gcacaagata      60
aaaatatatc atcatgaaca ataaaactgt ctgcttacat aaacagtaat acaaggggtg    120
ttatgagcca tattcattta tgaagcttgt acctttcatt tccttttgc tgagctttat    180 tttctctaga attgccattg tgtttccatt ctagcaaatc agcattttt tttcagctga    240
```
aagaaaaata ccaggaactg agagcgcggc tcctggcagc tctggcccgt gtctcaaaat    300
ctctgatgtt acattgcaca agataaaaat atatcatcat gaacaataaa actgtctgct    360
tacataaaca gtaatacaag gggtgttatg agccatattc aacgg                    405

<210> SEQ ID NO 16
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cattaaccct cataaaggga agctccatag tatcgtctga acc                       43

<210> SEQ ID NO 17
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cattaaccct cataaaggga agggagttct tcgggtgact g                         41

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cattaaccct cataaaggga atgtgtgatc tcaactgcgc t                         41

<210> SEQ ID NO 19
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cattaaccct cataaaggga accagcaaac cccatggatc t                         41

<210> SEQ ID NO 20
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cattaaccct cataaaggga acgactggag aaccaaggga c                         41

<210> SEQ ID NO 21
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 21
cattaaccct cataaaggga accatgcaac agaggaaggg t                          41

<210> SEQ ID NO 22
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cattaaccct cataaaggga aaagttccgc aggatggact g                          41

<210> SEQ ID NO 23
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cattaaccct cataaaggga aagttatgcc agctcagtgg g                          41

<210> SEQ ID NO 24
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cattaaccct cataaaggga acttcccaca gcagcacaaa c                          41

<210> SEQ ID NO 25
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cattaaccct cataaaggga agaatttgct cgcatgaggg g                          41

<210> SEQ ID NO 26
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cattaaccct cataaaggga aatggaggtc taccacaggc t                          41

<210> SEQ ID NO 27
<211> LENGTH: 41
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 27
cattaaccct cataaaggga attcggcttt aacctgtgcg t                        41

<210> SEQ ID NO 28
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cattaaccct cataaaggga aagttagaat gggcgccacc                          40

<210> SEQ ID NO 29
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cattaaccct cataaaggga aaacttgagc caccgaggat tt                       42

<210> SEQ ID NO 30
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cattaaccct cataaaggga agctacagtc tgcgtagcat                          40

<210> SEQ ID NO 31
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cattaaccct cataaaggga atacccaatg gttcgagtgg c                        41

<210> SEQ ID NO 32
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cattaaccct cataaaggga agtgtcccct catcaatgcc a                        41

<210> SEQ ID NO 33
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
```
cattaaccct cataaaggga atgcccagcc cttgataatc t          41

<210> SEQ ID NO 34
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cattaaccct cataaaggga aaggcagcac tggactttag c          41

<210> SEQ ID NO 35
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cattaaccct cataaaggga aacaaagaga tctgcattcc aagc       44

<210> SEQ ID NO 36
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cattaaccct cataaaggga aaaggcgtac tatgtcctca ggc        43

<210> SEQ ID NO 37
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cattaaccct cataaaggga attgtggatt acggggttcg g          41

<210> SEQ ID NO 38
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cattaaccct cataaaggga agagctttac tctgctggcg a          41

<210> SEQ ID NO 39
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cattaaccct cataaaggga actgttttcc cccaccagtg a                41

<210> SEQ ID NO 40
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cattaaccct cataaaggga atgggattta tttgtaacta cacgga          46

<210> SEQ ID NO 41
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cattaaccct cataaaggga accaggaagc gcaaagaaca g               41

<210> SEQ ID NO 42
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cattaaccct cataaaggga agcagcaaac gactgctaca a               41

<210> SEQ ID NO 43
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cattaaccct cataaaggga atcatccaca cctgagacgc a               41

<210> SEQ ID NO 44
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cattaaccct cataaaggga aatccgactg ctggaatgga c               41

<210> SEQ ID NO 45
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
cattaaccct cataaaggga agtgctggtc aacatgtacg c               41

<210> SEQ ID NO 46
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cattaaccct cataaaggga atccactggg aaaagctgga at                     42

<210> SEQ ID NO 47
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cattaaccct cataaaggga aatggggctg acggatacc                         39

<210> SEQ ID NO 48
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cattaaccct cataaaggga attgtccaga ctaccaaggc g                      41

<210> SEQ ID NO 49
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cattaaccct cataaaggga aatccaaact gaggccggaa g                      41

<210> SEQ ID NO 50
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cattaaccct cataaaggga aggcccaagc atggcagaaa c                      41

<210> SEQ ID NO 51
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cattaaccct cataaaggga aacatgggac atggagcgaa g                      41

```
<210> SEQ ID NO 52
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cattaaccct cataaaggga agactctctg cggatgtcag g                          41

<210> SEQ ID NO 53
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
cattaaccct cataaaggga acatgtccac ccctgaagct g                          41

<210> SEQ ID NO 54
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
cattaaccct cataaaggga aggcgtctct ttttctgctg c                          41

<210> SEQ ID NO 55
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cattaaccct cataaaggga accctagtgt ccgaggtctc a                          41

<210> SEQ ID NO 56
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
cattaaccct cataaaggga agataccgtg ctgggcgatt a                          41

<210> SEQ ID NO 57
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cattaaccct cataaaggga atcccggtgc aaaatctgag g                          41
```

<210> SEQ ID NO 58
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
cattaaccct cataaaggga agtttattgc tggcgcctac g                         41

<210> SEQ ID NO 59
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cattaaccct cataaaggga agctgccgaa caacgaaaca t                         41

<210> SEQ ID NO 60
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
cattaaccct cataaaggga aagtacactc cggacccaag a                         41

<210> SEQ ID NO 61
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
cattaaccct cataaaggga atccagagcg attcagcatc a                         41

<210> SEQ ID NO 62
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cattaaccct cataaaggga aagtctccta cttcgagtgg ct                        42

<210> SEQ ID NO 63
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
cattaaccct cataaaggga aaactgttct ttctcccggt ccc                       43

<210> SEQ ID NO 64

```
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cattaaccct cataaaggga aactggtcaa ccacctcctc t                           41

<210> SEQ ID NO 65
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
cattaaccct cataaaggga atgcctttca aagtggaccg t                           41

<210> SEQ ID NO 66
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
cattaaccct cataaaggga aagcctgttc ctggaccatt g                           41

<210> SEQ ID NO 67
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
cattaaccct cataaaggga aggttcgcca gaaggacaag a                           41

<210> SEQ ID NO 68
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
cattaaccct cataaaggga aaagctgtca tcaaagccgg a                           41

<210> SEQ ID NO 69
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
cattaaccct cataaaggga atgaaagccc tgaacgagac c                           41

<210> SEQ ID NO 70
<211> LENGTH: 41
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
cattaaccct cataaaggga aaggagtttg gcttcgacca g                    41

<210> SEQ ID NO 71
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cattaaccct cataaaggga atcgctctga tgctcagctt g                    41

<210> SEQ ID NO 72
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cattaaccct cataaaggga atacacattt tctgccccac tga                  43

<210> SEQ ID NO 73
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
cattaaccct cataaaggga actcaccctc ggtccagaac t                    41

<210> SEQ ID NO 74
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
cattaaccct cataaaggga aacagccatc agttcctctg c                    41

<210> SEQ ID NO 75
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
cattaaccct cataaaggga aggaagccac tcctgatacg g                    41

<210> SEQ ID NO 76
<211> LENGTH: 41
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 76
cattaaccct cataaaggga aggtcacgca ccaaatgaac c                        41

<210> SEQ ID NO 77
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
cattaaccct cataaaggga atctgcatct cgcaagctga t                        41

<210> SEQ ID NO 78
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
cattaaccct cataaaggga aagaactacg acagcgactg c                        41

<210> SEQ ID NO 79
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
cattaaccct cataaaggga aacagactct gtacgtttga atgcgt                   46

<210> SEQ ID NO 80
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
cattaaccct cataaaggga atatgactgc agtggtgaag acc                      43

<210> SEQ ID NO 81
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
cattaaccct cataaaggga acagacccgt ctctgtggtc                          40

<210> SEQ ID NO 82
<211> LENGTH: 41
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 82
cattaaccct cataaaggga aaccccgaa caacaataac a                              41

<210> SEQ ID NO 83
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
cattaaccct cataaaggga atatagccct tcgttccccc a                            41

<210> SEQ ID NO 84
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
cattaaccct cataaaggga atccttggac gctgtggacc aac                          43

<210> SEQ ID NO 85
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
taatacgact cactataggg aaaccattgc cattttgcca                              40

<210> SEQ ID NO 86
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
taatacgact cactataggg gcttgcaaca aaaagcgcag                              40

<210> SEQ ID NO 87
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
taatacgact cactataggg ggtgcaatct agtctgatcg gt                           42

<210> SEQ ID NO 88
<211> LENGTH: 40
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 88
taatacgact cactataggg aaccgagtac aggacacacg                            40

<210> SEQ ID NO 89
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
taatacgact cactataggg tggaggctaa tcgagtgtgc                            40

<210> SEQ ID NO 90
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
taatacgact cactataggg tactgggcgg gtctccttta                            40

<210> SEQ ID NO 91
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
taatacgact cactataggg tcgcttgtgt gatcaagtat gac                        43

<210> SEQ ID NO 92
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
taatacgact cactataggg ggcctcccca agaaaccatt                            40

<210> SEQ ID NO 93
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
taatacgact cactataggg gaaagttgtt gttgaagtga acg                        43

<210> SEQ ID NO 94
<211> LENGTH: 40
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 94
taatacgact cactataggg cggcagtggc caacaaatag                              40

<210> SEQ ID NO 95
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
taatacgact cactataggg agtgcaggta tgtgtccgtg                              40

<210> SEQ ID NO 96
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
taatacgact cactataggg cctgacgcga gtagtgttgt                              40

<210> SEQ ID NO 97
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
taatacgact cactataggg ggcaagacca ctggcatttg                              40

<210> SEQ ID NO 98
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
taatacgact cactataggg ccctaactcc agcacacact                              40

<210> SEQ ID NO 99
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
taatacgact cactataggg tggaagcagc tctaagtgac ag                           42

<210> SEQ ID NO 100
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
taatacgact cactataggg gcttaggtga tcaattttgg gaca                    44

<210> SEQ ID NO 101
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
taatacgact cactataggg acggcattcc acaaaccaga                         40

<210> SEQ ID NO 102
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
taatacgact cactataggg acccaaactg actttatatg tgc                     43

<210> SEQ ID NO 103
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
taatacgact cactataggg aggtacaaat gcaagtacaa cactg                   45

<210> SEQ ID NO 104
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
taatacgact cactataggg agcctgtcag ctcactttat t                       41

<210> SEQ ID NO 105
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
taatacgact cactataggg cgccgttcta taatgcaccg                         40

<210> SEQ ID NO 106
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 106
taatacgact cactataggg aaagagagct gcaccgact                    39

<210> SEQ ID NO 107
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
taatacgact cactataggg acaaatgatg tctgtctccg ct                42

<210> SEQ ID NO 108
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
taatacgact cactataggg caaaggattg gcagggacca                   40

<210> SEQ ID NO 109
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
taatacgact cactataggg ttttaagcac atttctgaag caca              44

<210> SEQ ID NO 110
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
taatacgact cactataggg acattaggcg ggcaaaacaa a                 41

<210> SEQ ID NO 111
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
taatacgact cactataggg cccacttcgc tgctctttac                   40

<210> SEQ ID NO 112
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
```
taatacgact cactataggg acaccttaaa accgcagcc                              39

<210> SEQ ID NO 113
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
taatacgact cactataggg gctttgagga gcttaagagg c                           41

<210> SEQ ID NO 114
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
taatacgact cactataggg cgtcactttt caccccaga                              40

<210> SEQ ID NO 115
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
taatacgact cactataggg tttcagatgc agcacaggca                             40

<210> SEQ ID NO 116
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
taatacgact cactataggg gcacaggaaa cgcacatgat                             40

<210> SEQ ID NO 117
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
taatacgact cactataggg ttacttcact gccagtcggc                             40

<210> SEQ ID NO 118
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
taatacgact cactataggg agaaaataca gtgcatacat gtcaa                45

<210> SEQ ID NO 119
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
taatacgact cactataggg cctacaagcc tcattcagac agt                  43

<210> SEQ ID NO 120
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
taatacgact cactataggg acactagaaa accgatcgtg tca                  43

<210> SEQ ID NO 121
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
taatacgact cactataggg ggtcatgccc ttttggcttg                      40

<210> SEQ ID NO 122
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
taatacgact cactataggg gggttctgtt gtggagtgct                      40

<210> SEQ ID NO 123
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
taatacgact cactataggg tgacgcttaa acagagcggt                      40

<210> SEQ ID NO 124
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
taatacgact cactataggg tttcccctgt gtggatgagc                      40

<210> SEQ ID NO 125
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
taatacgact cactataggg ccaccactca ctcattcaga ca                          42

<210> SEQ ID NO 126
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
taatacgact cactataggg agtcatgcac aaaatctgcg g                           41

<210> SEQ ID NO 127
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
taatacgact cactataggg ttcttggggt agttgcagcc                             40

<210> SEQ ID NO 128
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
taatacgact cactataggg taggacgcgt cattgtgctt                             40

<210> SEQ ID NO 129
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
taatacgact cactataggg caccagaaag aatgtcaccg t                           41

<210> SEQ ID NO 130
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
taatacgact cactataggg cagtccctca gtattccccg                             40

```
<210> SEQ ID NO 131
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
taatacgact cactataggg acgcctgaga ttcatcctgc                          40

<210> SEQ ID NO 132
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
taatacgact cactataggg cctctggctg aacaggaagg                          40

<210> SEQ ID NO 133
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
taatacgact cactataggg acacaatcag gcaaggtctc                          40

<210> SEQ ID NO 134
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
taatacgact cactataggg accagtcaca ccagccattc                          40

<210> SEQ ID NO 135
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
taatacgact cactataggg agctacaacc attgagggct                          40

<210> SEQ ID NO 136
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
taatacgact cactataggg agcatccaaa agtactcggt gt                       42
```

```
<210> SEQ ID NO 137
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
taatacgact cactataggg ttctcgacct gtcagctgtt                              40

<210> SEQ ID NO 138
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
taatacgact cactataggg cgtcagcatc caaacgcaat                              40

<210> SEQ ID NO 139
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
taatacgact cactataggg gtgacgctgg aatatcccgt                              40

<210> SEQ ID NO 140
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
taatacgact cactataggg cactcggcga cagtattccc                              40

<210> SEQ ID NO 141
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
taatacgact cactataggg aatggggcaa gagtccatct                              40

<210> SEQ ID NO 142
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
taatacgact cactataggg acagacacac ttgccagtca                              40

<210> SEQ ID NO 143
```

```
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
taatacgact cactataggg agctttgcat ccccatcact                              40

<210> SEQ ID NO 144
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
taatacgact cactataggg gtacaacatt tacttgctgt cca                         43

<210> SEQ ID NO 145
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
taatacgact cactataggg aacagttctg attggatttt gctca                       45

<210> SEQ ID NO 146
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
taatacgact cactataggg catgtgtagt gcagacagaa ca                          42

<210> SEQ ID NO 147
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
taatacgact cactataggg ggttttggat aagagctgtg tca                         43

<210> SEQ ID NO 148
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
taatacgact cactataggg gtccagactt tactcgtccg tgtc                        44

<210> SEQ ID NO 149
<211> LENGTH: 40
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
taatacgact cactataggg ctttcccgcc gttttgtgaa                          40

<210> SEQ ID NO 150
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
taatacgact cactataggg ccagtatggg gttgtgggac                          40

<210> SEQ ID NO 151
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
taatacgact cactataggg agagggcaag cgcagtaata                          40

<210> SEQ ID NO 152
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
taatacgact cactataggg accgaaaccg gctaaactga                          40

<210> SEQ ID NO 153
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
taatacgact cactataggg tcaaagcgct gctttcctcg c                        41

<210> SEQ ID NO 154
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
cttttggcca ttactgccg                                                 19

<210> SEQ ID NO 155
<211> LENGTH: 24
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 155
gctctcagtt cctggtattt ttct                                         24

<210> SEQ ID NO 156
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
tcgttactgc acttgaaagc gt                                           22

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
ccatgaaact gggaagatga a                                            21

<210> SEQ ID NO 158
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
gaagctctcc agcagctca                                               19

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
gctgtcagca cattcttttc c                                            21

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
actgctcctc accaatcgtc                                              20

<210> SEQ ID NO 161
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
tttatataat cggaaggaac cttttt                                          26

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
ggcaaaatgc ttagatgcag a                                               21

<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
tagccttgtg caatgcttgt                                                 20

<210> SEQ ID NO 164
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
cacttctggt accaaatgat caac                                            24

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
gcggcaaact ttttgagtgt                                                 20

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
cgcgtgatga ggatctgatt                                                 20

<210> SEQ ID NO 167
<211> LENGTH: 21
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 167
aaaattaaga gcgggcagac t                                          21

<210> SEQ ID NO 168
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
aaagcacttg attgagaatt gc                                         22

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
cagtttccca agcttcaagg                                            20

<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
aatggttgca gcattgtgtt                                            20

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
gttacctggc aaccaccaac                                            20

<210> SEQ ID NO 172
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
acgttaacaa aggcgatgtt tt                                         22

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 173
tgacaggact catcagcacg                                               20

<210> SEQ ID NO 174
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
tgggaaaaat accaggaagc gt                                            22

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
agatcaatga gagcgaggcg                                               20

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
cggacagtaa tgtctggatg g                                             21

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
tcatcatggc caacagaatg                                               20

<210> SEQ ID NO 178
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
tgactcaacc aatcaatcag cct                                           23

<210> SEQ ID NO 179
<211> LENGTH: 23
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 179 ttctgtctt taatcagcaa tcc                                              23

<210> SEQ ID NO 180
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
tgaagcttgt acctttcatt tcc                                             23

<210> SEQ ID NO 181
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
tatcagtgat gttctgcagt ggtc                                            24

<210> SEQ ID NO 182
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
caggaagaaa taatggcaaa aa                                              22

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
catttccacc agctgtctga t                                               21

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
ccctgctgat cacacatgac                                                 20

<210> SEQ ID NO 185
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 185
tgcactaaat ctgtgccaag tc                                            22

<210> SEQ ID NO 186
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
tcctgtcagc tgttttcatc c                                             21

<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
tgcgaggagg acataaacaa                                               20

<210> SEQ ID NO 188
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
tgctgaattc aaaagccact t                                             21

<210> SEQ ID NO 189
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
gagggttaaa cgtggcctta                                               20

<210> SEQ ID NO 190
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
gccagcctca aagtttgttc t                                             21

<210> SEQ ID NO 191
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
```
ggtgttgaaa ggtgatgctg                                               20

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
tggaaacaac aacagcctga                                               20

<210> SEQ ID NO 193
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
tgtttggttc agttacacgt ttt                                           23

<210> SEQ ID NO 194
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
tgtgattaca cattcccaca cat                                           23

<210> SEQ ID NO 195
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
gcttttgttt ggtgatgtgc                                               20

<210> SEQ ID NO 196
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
tggtcagaat aagcacgttt ca                                            22

<210> SEQ ID NO 197
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
tctaaacaat ttttaaggta aaccaaa                                27

<210> SEQ ID NO 198
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
aatagtctct ggtctgctgt taaa                                   24

<210> SEQ ID NO 199
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
aagcagcgag ctctcataat aaa                                    23

<210> SEQ ID NO 200
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
ggagcagatg aggttaagtc ct                                     22

<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
ccacaactcc atactgggaa a                                      21

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
gtgcaggaaa tgagcacaga                                        20

<210> SEQ ID NO 203
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
tagcaaagct ctcaggccc                                         19

<210> SEQ ID NO 204
<211> LENGTH: 158
<212> TYPE: DNA
<213> ORGANISM: Danio rerio

<400> SEQUENCE: 204

```
ccatgaaact gggaagatga aagcattagt tgaattgtta ctggcaacat cttctctgta    60
atgccccctg tgacccatat tgtctcgctc tttcctttat aaacagagct gtagatatcc   120
acaggaaatg ggggtgtttt tgccattatt tcttcctg                           158
```

<210> SEQ ID NO 205
<211> LENGTH: 125
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 205

```
tgaagcttgt acctttcatt taaattttgc tgagctttat tttctctaga attgccattg    60
tgtttccatt ctagcaaatc agcattttt tttcagctga agaaaaata ccatttactg    120 agagc                                                               125
```

<210> SEQ ID NO 206
<211> LENGTH: 124
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 206

```
tgaagcttgt acctttcatt tccttttgc tgagcgggcg gggatctaga attgcacggt    60
ggtttccatt ctagcaaatc agccggggg tttcagctaa agaaaaatac caggaactga   120
gagc                                                               124
```

<210> SEQ ID NO 207
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 207

```
attagcagat ttaatttcat ttcctttttg cattaattta ttttctctag aattgccatt    60
gtgtttccat tctagcaaat cagcattttt ttttcagctg aaagaaaaat accaggaact   120
gagagc                                                              126
```

<210> SEQ ID NO 208
<211> LENGTH: 125
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 208

```
tgaagcttgt acctttcatt tccttttgc tgagctttat tttctctaga attgccattg    60
```

```
tgtttccatt ccggcaaatc agcattttt tttcagctga ccgaaaaata ccaggaactg    120
agagc                                                              125
```

<210> SEQ ID NO 209
<211> LENGTH: 158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 209

```
ccatgaaact gggaagatga aagcattagt tgaattgtta ctggcaacat cttctctgta    60
atgccccctg tgacccatat tgtctcgctc tttaaattat aaacagagct gtagatatcc   120
acatttaatg ggggtgtttt tgccattatt tctaaatg                           158
```

<210> SEQ ID NO 210
<211> LENGTH: 158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 210

```
ccatgaaact gggaagatga aagcattagt tgaaggtgga ctggcaacat cttctctgta    60
atgccccctg tgacccatag gtgatcgctc tttcctttat aaacagagct gtagatatcc   120
acaggaaatg ggggtgtttt tgccattatt tcttcctg                           158
```

<210> SEQ ID NO 211
<211> LENGTH: 158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 211

```
ccatgaaact gggaagatga aagcattagt tgaattgtta ctggcaacat cttctctgta    60
atgccccctg attaacatat tgtctcgctc tttcctttat aaacagagct gtagatatcc   120
acaggaaatg ggggtgtttt tgccattatt tcttcctg                           158
```

<210> SEQ ID NO 212
<211> LENGTH: 158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 212

```
ccatgaaact gggaatctga aagcattagt tgaattgtta ctggcaacat cttctctgta    60
atgccccctg tgacccatat tgtctcgctc tttcctttat aaacagagag gtagatatcc   120
acaggaaatg ggggactttt tgccattatt tcttcctg                           158
```

<210> SEQ ID NO 213
<211> LENGTH: 74
<212> TYPE: DNA
<213> ORGANISM: Artificial Sequence
<220> FEATURE:
<223> OTHER INFORMATION: Description of Artificial Sequence: Synthetic primer

<400> SEQUENCE: 213
tgaagcttgt acctttcatt tccttttgc tgagctttat tttctctaga attgccattg    60
tgtttccatt ctag    74

<210> SEQ ID NO 214
<211> LENGTH: 74
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
tgaagcttgt acctttcatt taaattttgc tgagctttat tttctctaga attgccattg    60
tgtttccatt ctag    74

<210> SEQ ID NO 215
<211> LENGTH: 74
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
tgaagcttgt acctttcatt tccttttgc tgagcgggcg gggatctaga attgcacggt    60
ggtttccatt ctag    74

<210> SEQ ID NO 216
<211> LENGTH: 74
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
attagcagat ttaatttcat ttccttttg cattaattta ttttctctag aattgccatt    60
gtgtttccat tcta    74

<210> SEQ ID NO 217
<211> LENGTH: 74
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
tgaagcttgt acctttcatt tccttttgc tgagctttat tttctctaga attgccattg    60
tgtttccatt ctag    74

<210> SEQ ID NO 218
<211> LENGTH: 91
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
ccatgaaact gggaagatga aagcattagt tgaattgtta ctggcaacat cttctctgta    60
atgccccctg tgacccatat tgtctcgctc t                                  91

<210> SEQ ID NO 219
<211> LENGTH: 91
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
ccatgaaact gggaagatga aagcattagt tgaattgtta ctggcaacat cttctctgta    60
atgccccctg tgacccatat tgtctcgctc t                                  91

<210> SEQ ID NO 220
<211> LENGTH: 91
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
ccatgaaact gggaagatga aagcattagt tgaaggtgga ctggcaacat cttctctgta    60
atgccccctg tgacccatag gtgatcgctc t                                  91

<210> SEQ ID NO 221
<211> LENGTH: 91
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
ccatgaaact gggaagatga aagcattagt tgaattgtta ctggcaacat cttctctgta    60
atgccccctg attaacatat tgtctcgctc t                                  91

<210> SEQ ID NO 222
<211> LENGTH: 91
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
ccatgaaact gggaatctga aagcattagt tgaattgtta ctggcaacat cttctctgta    60
atgccccctg tgacccatat tgtctcgctc t                                  91

<210> SEQ ID NO 223
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
gctctcagtt cctggtattt ttctttcagc tgaaaaaaaa atgctgattt gctagaatgg    60
aaacacaatg gcaat                                                    75

<210> SEQ ID NO 224
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
gctctcagta aatggtattt ttctttcagc tgaaaaaaaa atgctgattt gctagaatgg     60
aaacacaatg gcaat                                                     75

<210> SEQ ID NO 225
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
gctctcagtt cctggtattt ttctttcagc tgaaaccccc cggctgattt gctagaatgg     60
aaaccaccgt gcaat                                                     75

<210> SEQ ID NO 226
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
gctctcagtt cctggtattt ttctttcagc tgaaaaaaaa atgctgattt gctagaatgg     60
aaacacaatg gcaat                                                     75

<210> SEQ ID NO 227
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
gctctcagtt cctggtattt ttcggtcagc tgaaaaaaaa atgctgattt gccggaatgg     60
aaacacaatg gcaat                                                     75

<210> SEQ ID NO 228
<211> LENGTH: 91
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
caggaagaaa taatggcaaa aacacccccca tttcctgtgg atatctacag ctctgtttat    60
aaaggaaaga gcgagacaat atgggtcaca g                                   91

<210> SEQ ID NO 229
<211> LENGTH: 91
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 229
catttagaaa taatggcaaa aacacccca ttaaatgtgg atatctacag ctctgtttat      60
aatttaaaga gcgagacaat atgggtcaca g                                    91

<210> SEQ ID NO 230
<211> LENGTH: 91
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
caggaagttt attaggcaaa aacacccca tttcctgtgg atatctacag ctctgtttat      60
aaaggaaaga gcgatcacct atgggtcaca g                                    91

<210> SEQ ID NO 231
<211> LENGTH: 91
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
caggaagaaa taatggcaaa aacacccca tttcctgtgg atatctacag ctctgtttat      60
aaaggaaaga gcgagacaat atgttaatca g                                    91

<210> SEQ ID NO 232
<211> LENGTH: 91
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
caggaagaaa taatggcaaa aagtcccca tttcctgtgg atatctacct ctctgtttat      60
aaaggaaaga gcgagacaat atgggtcaca g                                    91

<210> SEQ ID NO 233
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
cgggatccat ggcaatggta gtcagcacg                                       29

<210> SEQ ID NO 234
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
```
tttatgaagc ttgtaccttt catttccttt ttg                                  33

<210> SEQ ID NO 235
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
tttaattagc agatttaatt tcatttcctt tttg                                 34

<210> SEQ ID NO 236
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
ttcatttcct ttttgctgag ctttattttc                                      30

<210> SEQ ID NO 237
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
ttcatttcct ttttgcatta atttattttc                                      30

<210> SEQ ID NO 238
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
gtaatgcccc ctgtgaccca tattgtctcg ctctttcctt tata                      44

<210> SEQ ID NO 239
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
gtaatgcccc ctgattaaca tattgtctcg ctctttcctt tata                      44

<210> SEQ ID NO 240
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240

```
ccggaattcc ggttgaattg ccatatatgg c                                    31

<210> SEQ ID NO 241
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
caaaaaggaa atgaaaggta caagcttcat aaa                                  33

<210> SEQ ID NO 242
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
caaaaaggaa atgaaattaa atctgctaat taaa                                 34

<210> SEQ ID NO 243
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
gaaaataaag ctcagcaaaa aggaaatgaa                                      30

<210> SEQ ID NO 244
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
gaaaataaat taatgcaaaa aggaaatgaa                                      30

<210> SEQ ID NO 245
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
tataaaggaa agagcgagac aatatgggtc acaggggggca ttac                     44

<210> SEQ ID NO 246
<211> LENGTH: 44
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
tataaaggaa agagcgagac aatatgttaa tcagggggca ttac                    44
```

ENDOTHELIAL CELL FACTORS AND METHODS THEREOF

CROSS-REFERENCE TO RELATED APPLICATIONS

This application is a 35 U.S.C. § 371 National Phase Entry Application of International Patent Application No. PCT/US2019/023637 filed on Mar. 22, 2019 which claims benefit under 35 U.S.C. § 119 (e) of U.S. Provisional Application No. 62/647,433 filed Mar. 23, 2018, the contents of which are incorporated herein by reference in their entireties.

GOVERNMENT SUPPORT

This invention was made with government support under grant number DK111790 and HL048801 awarded by the National Institutes of Health. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Apr. 15, 2019, is named 701039-091810-seq_ST25.txt and is 90,597 bytes in size.

TECHNICAL FIELD

The technology described herein relates to compositions and methods of generating endothelial niche cells.

BACKGROUND

Haematopoietic stem and progenitor cells (HSPCs) are a rare cell population capable of reconstituting the entire blood system after transplantation. As the functional unit of a bone marrow transplant, these cells offer a curative treatment for many blood and immune diseases. Unfortunately, transplantation is not a viable treatment option for many individuals, particularly those lacking an immune-matched donor. A long-term goal of haematological research has been to culture and expand HSPCs in vitro, for use in transplantation and/or genetic modification. While umbilical cord blood-derived HSPCs are somewhat amenable to in vitro expansion, maintaining and inducing self-renewal of adult-derived HSPCs, in the absence of niche signals, has proven challenging.

Strategies aimed at in vitro expansion have co-cultured HSPCs with supportive cells in an effort to recapitulate aspects of the microenvironment or 'niche' that supports HSPCs in vivo. In the adult bone marrow, multiple cell types are thought to collectively comprise the HSPC niche, with primary contributors being endothelial cells (ECs) and perivascular mesenchymal stromal cells. Different endothelial cell subtypes in the bone marrow can differentially regulate HSPC homeostasis. Arterial ECs (AECs) are less permeable and are believed to promote HSPC quiescence, while sinusoidal ECs (SECs) are leaky and support the differentiation and mobilization of HSPCs. In addition, during haematopoietic recovery after myelosuppression, ECs play a critical role in niche reconstruction and reconstitution of multi-lineage haematopoiesis. HSPCs can also be supported outside the bone marrow, during embryonic development and under stress conditions that induce extramedullary haematopoiesis in tissues such as the liver, spleen and skull. As in the bone marrow, ECs are thought to function as critical, core components of the HSPC niches in these tissues.

Researchers have focused on the development of in vitro cultures where HSPCs can be grown in the lab with other cells types that support the maintenance or expansion of the HSPCs for subsequent use in transplantation. To date, however, these in vitro cultures have been only modestly successful.

SUMMARY

In studies of the vascular HSPC niche in the zebrafish embryo a combination of transcription factors (from the Ets, Sox and Nuclear Hormone families) that are normally expressed in the endogenous niche endothelial cells were studied. When human orthologs of these same transcription factors were ectopically expressed, ectopic vascular niches in the zebrafish embryo were generated, to which HSPCs are recruited and maintained.

As a step towards translating these findings into a clinical application, transcriptions factors (which initially were identified in the zebrafish studies) can be expressed in human endothelial cells to reprogram these cells into an HSPC niche-like identity. These niche endothelial cells can be used in co-cultures with HSPCs in order to expand HSPC numbers or extend culture times, for subsequent use in transplantation.

For example, the transcription factors known to bind Ets, Sox and Nuclear hormone motifs can be expressed in niche endothelial cells. In the Ets family these factors include etv2, fli1a and ets1; where the corresponding human factors are ETV2, FLI1 and ETS1. In the Sox family these transcription factors include sox18 and sox7; where the corresponding human factors are SOX7 and SOX18. In the Nuclear hormone family these transcription factors include rxraa and nr2f2; where the corresponding human factors are RXRA and NR2R2.

The present invention provides a method for making synthetic niche endothelial cells, to stimulate blood stem cells. Transcription factors include Ets family, etv2, fli1a, ets1; SOX family: sox 18, sox7, and Nuclear hormone family: rxraa, nr2f2) and the corresponding human factors: ETV2, FLI1, ETS1, SOX7, SOX18, RXRA, and NR2F2.

The method comprises expressing transcription factors in endothelial cells (e.g., human) to reprogram these cells into an HSPC niche-like identity.

In another embodiment, the niche endothelial cells are used in co-cultures with HSPCs in order to expand HSPC numbers or extend culture times, for subsequent use in transplantation.

One aspect provides a method to generate/engineer endothelial niche cells, comprising expressing one or more transcription factors in an endothelial cell, wherein the one or more transcription factors are from the Ets family, the Sox family, and/or the Nuclear Hormone Receptor family.

Another aspect provides an engineered endothelial niche cell comprising one or more exogenous nucleic acid sequences encoding one or more transcription factors, wherein the one or more transcription factors are from the Ets family, the Sox family and/or the Nuclear Hormone Family.

Another aspect provides a composition comprising the engineered endothelial niche described herein.

Another aspect provides a method for culturing HSPCs, the method comprising culturing HSPCs in the presence of a population of engineered endothelial niche cells.

Another aspect provides a method of treating a subject, the method comprising, transplanting a composition comprising HSPCs and a population of engineered endothelial niche-cells into the subject.

Another aspect provides a method for enhancing engraftment of HSPCs, the method comprising administering a composition comprising HSPCs and a population of engineered endothelial niche cells to a subject in need thereof.

Another aspect provides a co-culture comprising engineered endothelial niche cells and HSPCs.

Another aspect provides a kit for culturing HSPCs, the kit comprising: a population of engineered endothelial niche cells, reagents and instructions for use thereof.

Another aspect provides a kit for generating engineered endothelial niche cells comprising: a vector(s) comprising one or more exogenous nucleic acid sequences encoding one or more transcription factors of the Ets family, the Sox family or the nuclear hormone family and instructions for use thereof.

Another aspect provides a method for generating an ectopic vascular niche, the method comprising: administering an engineered endothelial niche cell to a target site in a subject in need thereof.

Another aspect provides a method for extra medullary hematopoiesis, the method comprising transplanting engineered-niche endothelial cells into a subject at a location outside of the bone marrow (e.g., the forearm), thereby creating a synthetic niche.

Another aspect provides a vector comprising one or more exogenous nucleic acid sequences encoding one or more transcription factors of the Ets family, the Sox family or the nuclear hormone family operably linked to a promoter.

BRIEF DESCRIPTION OF THE DRAWINGS

(FIG. 1A) Schematic diagram illustrates the haematopoietic tissues of the zebrafish embryo (top) and the sectioning strategy used to perform RNA tomography (tomo-seq) on the CHT (bottom; double transgenic embryo carrying the HSPC markers cd41:GFP and runx1:mCherry is shown). (FIG. 1B) Schematic cross-section and (FIG. 1B, cont.) hierarchical clustering heat map reveal clusters of gene expression that correspond to distinct tissues along the dorsal-ventral axis of the zebrafish tail. (FIG. 1C) Schematic depicts strategy using kdrl:GFP transgenic embryos and FACS to isolate ECs from whole embryos for analysis by RNA-seq. (FIG. 1D) Individual tomo-seq expression traces are shown for pan-endothelial expressed genes (left) and CHT EC-enriched genes (right). (FIG. 1E) Images show whole mount in situ hybridization (WISH) for the pan-endothelial gene kdrl (top) and CHT EC-enriched genes identified by tomo-seq and tissue-specific RNA-seq. Arrows point to expression in dorsal vasculature and arrowheads point to expression in the CHT. Scale bars represent 250 µm unless noted otherwise.

(FIG. 2A) Image and schematic depict the four cell populations that were isolated from mrc1a:GFP, kdrl:mCherry double positive embryos for analysis by ATAC-seq. (FIG. 2B) Gene tracks show regions of chromatin that were uniquely open in the mCherry$^+$; GFP$^+$ CHT EC fraction (boxes and arrows). (FIG. 2C) Images show embryos injected with CHT EC enhancer-GFP reporter constructs corresponding to the boxed regions in FIG. 2B. Arrowheads point to GFP expression in CHT ECs. Scale bars represent 250 µm unless noted otherwise.

(FIG. 3A) Gene tracks show a region of chromatin (box and lower arrow) upstream of mrc1a that is uniquely open in the double positive CHT EC fraction but not the other three cell populations. Bars denote the position of the 125 bp enhancer sequence and the 1.3 kb sequence used to generate the mrc1a:GFP reporter transgene. (FIG. 3B) Images show transient GFP expression in an F0 embryo injected with the 125 bp enhancer sequence coupled to a minimal promoter and GFP. (FIG. 3C) Images show an F0 embryo simultaneously injected with kdrl:mCherry and mrc1a 125 bp:GFP plasmids. (FIG. 3D) Images show an embryo expressing the stably integrated mrc1a 125 bp:GFP transgene. (FIG. 3E) Wild-type sequence of the 125 bp mrc1a enhancer is shown (see e.g., SEQ ID NO: 12), annotated highlighting the Ets, Sox and NHR binding motifs. Schematic depicts enhancer-reporter constructs in which each class of motif or control regions was targeted by mutation. X's denote the location of targeted sites. mp-GFP:mouse Beta-globin minimal promoter fused to GFP. (FIG. 3F) Graphs report the frequency of embryos with GFP expression in CHT ECs after injection with wild-type sequences or mutated variants of the mrc1a 125 bp (top) or sele 158 bp (bottom) enhancers. Data is normalized to the respective wild-type control for each experiment (44% (155/356) for the mrc1a 125 bp enhancer and 23% (176/775) for the sele 158 bp enhancer). Mean+/−standard error of the mean (s.e.m.), One-way ANOVA; P<0.01, *P<0.001. Scale bars represent 250 µm unless noted otherwise.

(FIG. 4A) Schematic depicts the strategy used in transcription factor overexpression experiments. (FIG. 4B) Images show embryos that were injected with control DNA (left) or a pool of seven transcription factors (right) from the Ets, Sox and NHR families (FLI1, ETV2, ETS1, SOX7, Sox18, Nr2f2 and RXRA) and then stained by WISH for mrc1a (top) or sele (bottom). Arrows denote regions of ectopic expression and arrowheads point to normal domains of expression in all panels of FIG. 4A-FIG. 4E. (FIG. 4C) Images show mrc1a:GFP; kdrl:mCherry double transgenic embryos that were injected with the control DNA or the 7-factor pool. (FIG. 4D) Injection of a 3-factor pool containing ETV2, SOX7 and Nr2f2 results in ectopic expression of mrc1a:GFP (arrows). (FIG. 4E) Images show WISH for mrc1a in a control embryo (top) or after injection of a 3-factor pool containing ETV2, SOX7 and Nr2f2 (middle) or ETS1, SOX7 and Nr2f2 (bottom). (FIG. 4F) Graph reports quantification of the percentage of injected embryos that displayed ectopic mrc1a expression after transcription factor overexpression. Chi Square Test; P<0.01, *P<0.001. Scale bars represent 250 µm in FIG. 4B and FIG. 4E, and 100 µm in FIG. 4C and FIG. 4D.

(FIG. 5A) Images show runx1:mCherry$^+$ HSPCs localized outside the CHT within a dorsal ectopic region of mrc1a:GFP expression in an embryo injected with a pool of ETV2, SOX7 and Nr2f2 (top) or a pool of ETS1, SOX7 and Nr2f2 (bottom). Inset magnifications with gray scale images for each channel are shown at right. Arrows point to ectopic expression or localization while arrowheads point to normal expression or localization in all panels in FIG. 5A-FIG. 5E. (FIG. 5B) WISH for runx1 shows HSPC localization in a control (top) and 3-factor injected embryo (bottom). (FIG. 5C) ECs ectopically expressing mrc1a:GFP are associated with cxcl12a:DsRed2' stromal cells, similar to ECs in the CHT. Asterisk denotes notochord expression of cxcl12a:DsRed. (FIG. 5D) Time-lapse series shows a runx1:mCherry+ HSPC initially arriving in the CHT and subsequently dividing. Time is shown as hh:mm. (FIG. 5E) Time-lapse series from a different embryo than in FIG. 5D shows runx1:mCherry+ HSPCs dividing and migrating away into circulation. Scale bars represent 100 µm in FIG. 5A-FIG. 5C and 30 µm in FIG. 5D-FIG. 5E.

(FIG. 6A) Heat map shows the expression of the 29 CHT EC genes in the different cell populations that comprise the adult zebrafish kidney marrow. Spectral scale shows normalized expression between 0 (low) and 1 (high). (FIG. 6B) Heat map shows the expression of orthologs of the CHT EC genes in ECs from different organs of the mouse at different stages of development and postnatal transition to adulthood. Arrows denote haematopoietic tissues at the respective stage of development. Black bracket denotes genes enriched in fetal liver ECs at the E14-17 stages and then later in the adult bone marrow. Spectral scale reports z-scores. BM: Bone Marrow.

(FIG. 7A) Graphs show tomo-seq expression traces for individual tissue-specific genes. Images showing whole mount in situ hybridization (WISH) for 35 CHT-enriched genes are available on the world wide web on zfin.org. (FIG. 7B) WISH validates the CHT-enriched expression (arrowheads) of CHT EC genes identified using a combination of tomo-seq and tissue-specific RNA-seq. Scale bars represent 250 µm unless noted otherwise.

(FIG. 8A) Images show a double transgenic embryo carrying the pan-endothelial marker kdrl:mCherry and the mrc1a:GFP transgene, which is selectively expressed in CHT ECs. Magnification of boxed area is shown on the right. (FIG. 8B) Images show runx1:mCherry+ HSPCs directly interacting with mrc1a:GFP+ ECs within the CHT niche (arrows). Middle panel shows magnification of boxed area. Additional magnification (bottom) shows an HSPC in a pocket of mrc1a:GFP+ ECs. (FIG. 8C) cxcl12a:DsRed2+ stromal cells are closely associated with mrc1a:GFP+ ECs in the CHT. (FIG. 8D) Images show a double transgenic embryo carrying the pan-endothelial marker kdrl:mCherry and the sele:GFP transgene, which is selectively expressed in CHT ECs. Magnification of boxed area is shown on the right. (FIG. 8E) Images show runx1:mCherry+ HSPCs directly interacting with sele:GFP+ ECs within the CHT niche (arrows). Magnification of boxed area is shown on the right. Scale bars represent 250 µm in FIG. 8A and FIG. 8D, and 100 µm in FIG. 8B, FIG. 8C, and FIG. 8E.

FIG. 9A-FIG. 9C is a series of images and graphs showing a pan-endothelial regulatory elements and genome-wide motif enrichment analysis. (FIG. 9A) Gene tracks show regions of chromatin that were open in both the mCherry+GFP+ (CHT EC) and mCherry+GFP+ (non-CHT EC) populations (boxes and straight arrows). (FIG. 9B) Images show embryos injected with pan-endothelial enhancer-GFP reporter constructs corresponding to the boxed regions in FIG. 9A. Arrows point to GFP expression in non-CHT ECs and arrowheads point to expression in CHT ECs. (FIG. 9C) Images show the transcription factor binding motifs most enriched in CHT EC regions (top) or pan-endothelial regions (bottom). Scale bars represent 250 µm unless noted otherwise.

(FIG. 10A) Graph reports the anatomical location of endothelial expression in F0 embryos that were injected with mrc1a 125 bp:GFP and kdrl:mCherry plasmids. (FIG. 10B) Gene tracks show a region of chromatin upstream of sele that was uniquely open in the double positive CHT EC fraction but not the other three cell populations (box and lower arrow). Bars denote the position of the 158 bp enhancer sequence and the 5.3 kb sequence used to generate the sele:GFP reporter transgene. (FIG. 10C) Images show transient F0 (top) and stable F2 expression (bottom) of the sele 158 bp:GFP construct. (FIG. 10D) Wild-type sequence of the 158 bp sele enhancer is shown (see e.g., SEQ ID NO: 13), annotated highlighting the Ets, Sox and NHR binding motifs (top). Schematic depicts sequence variants in which each class of motif or control regions were targeted by mutation. X's denote the location of targeted sites. mp-GFP:mouse Beta-globin minimal promoter fused to GFP. (FIG. 10E) Images show electrophoretic mobility shift assays with recombinant Nr2f2-GST that was incubated with DNA sequences spanning the NHR motifs present in the 125 bp mrc1a (left two gels) or 158 bp sele (right gel) enhancer sequences. Arrows point to DNA:protein binding while arrowheads point to super-shifted DNA:protein complexes. Labeled DNA:protein complexes were outcompeted by unlabeled wild-type probe (lane 4) but not by probe in which the NHR motif was disrupted by mutation (arrows with asterisks). Scale bars represent 250 µm unless noted otherwise.

(FIG. 11A) Images show WISH for mrc1a over the yolk ball in a control (left) and 7-factor injected embryo (right). Arrows point to ectopic expression and arrowheads point to normal domains of expression in all panels of FIG. 11A-FIG. 11C. (FIG. 11B) Images show ectopic expression of the mrc1a:GFP and kdrl:mCherry transgenes over the yolk extension in a 7-factor injected embryo. Magnification of the boxed area is shown at the bottom. (FIG. 11C) Images show WISH for sele, gpr182 and lgmn in control embryos (left) and embryos injected with a combination of ETV2, SOX7 and Nr2f2 (right). Scale bars in FIG. 11A-FIG. 11C represent 100 µm.

(FIG. 12A-FIG. 12B) Injection of ETV2 alone induces ectopic expression of the endogenous mrc1a gene (FIG. 12A) and the mrc1a:GFP transgene (FIG. 12B). Arrows point to ectopic expression and black arrowhead point to the normal domain of expression in all panels in FIG. 12A-FIG. 12D. (FIG. 12C) Injection of human ETV2 alone induces ectopic expression of zebrafish transcription factors, including sox7, sox18, fli1a and etv2. (FIG. 12D) Injection of a 3-factor pool containing ETS1, SOX7 and Nr2f2 results in ectopic expression of mrc1a:GFP. Scale bar represents 250 µm in FIG. 12A and FIG. 12C and 50 µm in FIG. 12B and FIG. 12D.

(FIG. 13A) Images show a segment of vasculature (white arrows) dissected from the kidney of a kdrl: mCherry, mrc1a:GFP double transgenic adult zebrafish. (FIG. 13B) Images show sequential sections through an adult kidney isolated from a sele:GFP transgenic fish. Sections were stained with H & E (left) and with an antibody against GFP (right). Black arrows point to GFP+ vascular endothelial cells. Scale bar represents 50 μm in FIG. 13A and 100 μm in FIG. 13B.

FIG. 15A shows visualization of the dorsal aorta and caudal hematopoietic tissue. FIG. 15B shows an HSPC surrounded by 5 endothelial cells and attached to stromal cell.

DETAILED DESCRIPTION

Figure 1A:
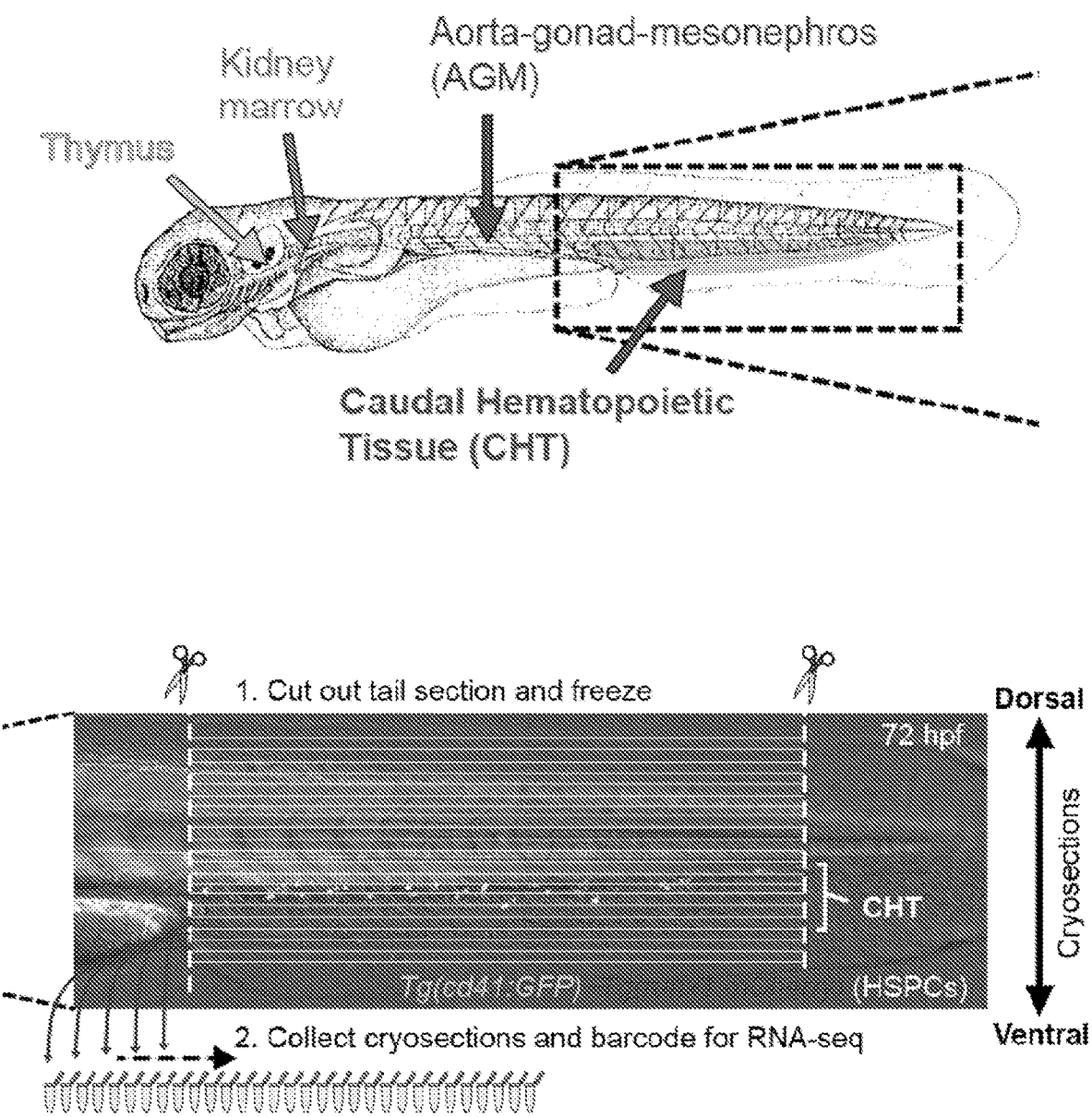
FIG. 1A-FIG. 1E is a series of images and graphs showing an endothelial expression signature in the fetal HSPC niche.

Embodiments of the technology described herein comprise compositions, kits, vectors, and methods related to generating or engineering endothelial niche cells. One aspect comprises a method to generate/engineer endothelial niche cells, comprising expressing one or more transcription factors in an endothelial cell, wherein the one or more transcription factors are from the Ets family, the Sox family, and/or the Nuclear Hormone Receptor (NHR) family.

In some embodiments, at least one transcription factor is selected from the Ets family. In some embodiments, at least one transcription factor is selected from the Sox family. In some embodiments, at least one transcription factor is selected from the NHR family.

In some embodiments, at least one transcription factor is selected from the Ets family, and at least one transcription factor is selected from the Sox family. In some embodiments, at least one transcription factor is selected from the Ets family, and at least one transcription factor is selected from the NHR family. In some embodiments, at least one transcription factor is selected from the Sox family, and at least one transcription factor is selected from the NHR family.

In some embodiments, at least one transcription factor is selected from the Ets family, at least one transcription factor is selected from the Sox family, and at least one transcription factor is selected from the NHR family. In some embodiments, at least one transcription factor is selected from the Ets family, at least one transcription factor is selected from the Sox family, or at least one transcription factor is selected from the NHR family.

Ets Family

In some embodiments of any of the aspects, endothelial niche cells express transcription factors from the ETS family. The ETS (E26 transformation-specific or E-twenty-six) family is one of the largest families of transcription factors and is unique to animals. The ETS family is divided into 12 subfamilies: 1) ELF (e.g., ELF1, ELF2/NERF, ELF4/MEF); 2) ELG (e.g., GABPα, ELG); 3) ERG (e.g., ERG, FL1, FEV); 4) ERF (e.g., ERF/PE2, ETV3/PE1); 5) ESE (e.g., ELF3/ESE1/ESX, ELF5/ESE2, ESE3/EHF); 6) ETS (e.g., ETS1, ETS, POINTED); 7) PDEF (e.g., SPDEF/PDEF/PSE); 8) PEA3 (e.g., ETV4/PEA3/E1AF, ETV5/ERM, ETV1/ER81); 9) ERF71 (e.g., ETV2/ER71); 10) SPI (e.g., SPI1/PU.1, SPIB, SPIC); 11) TCF (e.g., ELK1, ELK4/SAP1, ELK3/NET/SAP2, LIN); 12) TEL (e.g., ETV6/TEL, ETV7/TEL2, YAN).

All ETS family members are identified through a highly conserved DNA binding domain, the ETS domain, which is a winged helix-turn-helix structure that binds to DNA sites with a central GGA (A/T) DNA sequence. DNA motifs for the Ets family can also comprise a central TTCCT sequence (e.g., on DNA strand complementary to the first motif). As well as DNA-binding functions, evidence suggests that the ETS domain is also involved in protein-protein interactions.

The ETS family is present throughout the body and is involved in a wide variety of functions including the regulation of cellular differentiation, cell cycle control, cell migration, cell proliferation, apoptosis (programmed cell death) and angiogenesis.

Non-limiting examples of members of the human Ets family that are relevant to endothelial niche cells comprise ETV2, FLI1, and ETS1. The corresponding factors in zebrafish comprise etv2, fli1, and ets1.

ETV2 can also be referred to herein as ETS Variant 2, ETS Translocation Variant 2, Ets-Related Protein 71, Ets Variant Gene 2, ETSRP71, or ER71.

Friend leukemia integration 1 transcription factor (FLI1), also known as transcription factor ERGB, is a protein that in humans is encoded by the FLI1 gene. FLI1 can also be referred to herein as Fli-1 Proto-Oncogene, ETS Transcription Factor, Friend Leukemia Integration 1 Transcription Factor, Friend Leukemia Virus Integration 1, Transcription Factor ERGB, Ewing Sarcoma Breakpoint Region, Proto-Oncogene Fli-1, BDPLT21, EWSR2, or SIC-1.

ETS1 or protein C-ets-1 is a protein that in humans is encoded by the ETS1 gene. The protein encoded by this gene belongs to the ETS family of transcription factors. ETS1 can also be referred to herein as ETS Proto-Oncogene 1 Transcription Factor, Avian Erythroblastosis Virus E26 (V-Ets) Oncogene Homolog-1, V-Ets Avian Erythroblastosis Virus E26 Oncogene Homolog 1, Protein C-Ets-1, EWSR2, P54, V-Ets Avian Erythroblastosis Virus E2 Oncogene Homolog 1, Ets Protein, C-Ets-1, or ETS-1.

In some embodiments of any of the aspects, cells are generated which or engineered to express an Ets family member selected from the group consisting of ETV2, FLI1, and ETS1.

In some embodiments, the Ets gene or protein can be ETV2 or the corresponding zebrafish etv2. In some embodiments, the Ets gene or protein can be FLI1 or the corresponding zebrafish fli1. In some embodiments, the Ets gene or protein can be ETS1 or the corresponding zebrafish ets1.

In some embodiments, the Ets gene or protein can be ETV2 and FLI1 or the corresponding zebrafish factors. In some embodiments, the Ets gene or protein can be ETV2 and ETS1 or the corresponding zebrafish factors. In some embodiments, the Ets gene or protein can be ETS1 and FLI1 or the corresponding zebrafish factors. In some embodiments, the Ets gene or protein can be ETV2, FLI1, and ETS1 or the corresponding zebrafish factors. In some embodiments, the Ets gene or protein can be ETV2, FLI1, or ETS1 or the corresponding zebrafish factors.

The amino acid sequences of the polypeptides described herein have been assigned NCBI accession numbers for different species such as human, mouse, rat, and zebrafish. In particular, the NCBI accession numbers for non-limiting examples of the amino acid sequences of human ETV2 (e.g. SEQ ID NO: 1), human FLI1 (e.g., SEQ ID NO: 2), and human ETS1 (e.g., SEQ ID NO: 3) are included herein.

(Homo sapiens ETV2, NCBI accession number
AAI40747, 342 amino acids (aa)):
SEQ ID NO: 1
MDLWNWDEASPQEVPPGNKLAGLEGAKLGFCFPDLALQGDTPTATAETCW

KGTSSSLASFPQLDWGSALLHPEVPWGAEPDSQALPWSGDWTDMACTAWD

SWSGASQTLGPAPLGPGPIPAAGSEGAAGQNCVPVAGEATSWSRAQAAGS

NTSWDCSVGPDGDTYWGSGLGGEPRTDCTISWGGPAGPDCTTSWNPGLHA

GGTTSLKRYQSSALTVCSEPSPQSDRASLARCPKTNHRGPIQLWQFLLEL

LHDGARSSCIRWTGNSREFQLCDPKEVARLWGERKRKPGMNYEKLSRGLR

YYYRRDIVRKSGGRKYTYRFGGRVPSLAYPDCAGGGRGAETQ (Homo sapiens FLI1, NCBI accession number
AAH10115.1, 452 aa):
SEQ ID NO: 2
MDGTIKEALSVVSDDQSLFDSAYGAAAHLPKADMTASGSPDYGQPHKINP

LPPQQEWINQPVRVNVKREYDHMNGSRESPVDCSVSKCSKLVGGGESNPM

NYNSYMDEKNGPPPPNMTTNERRVIVPADPTLWTQEHVRQWLEWAIKEYS

LMEIDTSFFQNMDGKELCKMNKEDFLRATTLYNTEVLLSHLSYLRESSLL

AYNTTSHTDQSSRLSVKEDPSYDSVRRGAWGNNMNSGLNKSPPLGGAQTI

SKNTEQRPQPDPYQILGPTSSRLANPGSGQIQLWQFLLELLSDSANASCI

TWEGTNGEFKMTDPDEVARRWGERKSKPNMNYDKLSRALRYYYDKNIMTK

VHGKRYAYKFDFHGIAQALQPHPTESSMYKYPSDISYMPSYHAQQKVNFV

PPHPSSMPVTSSSFFGAASQYWTSPTGGIYPNPNVPRHPNTHVPSHLGSY

Y (Homo sapiens ETS1, NCBI accession number
CAG47050.1, 441 aa):
SEQ ID NO: 3
MKAAVDLKPTLTIIKTEKVDLELFPSPDMECADVPLLTPSSKEMMSQALK

ATFSGFTKEQQRLGIPKDPRQWTETHVRDWVMWAVNEFSLKGVDFQKFCM

NGAALCALGKDCFLELAPDFVGDILWEHLEILQKEDVKPYQVNGVNPAYP

ESRYTSDYFISYGIEHAQCVPPSEFSEPSFITESYQTLHPISSEELLSLK

YENDYPSVILRDPLQTDTLQNDYFAIKQEVVTPDNMCMGRTSRGKLGGQD

SFESIESYDSCDRLTQSWSSQSSFNSLQRVPSYDSFDSEDYPAALPNHKP

KGTFKDYVRDRADLNKDKPVIPAAALAGYTGSGPIQLRQFLLELLTDKSC

QSFISWTGDGWEFKLSDPDEVARRWGKRKNKPKMNYEKLSRGLRYYYDKN

IIHKTAGKRYVYRFVCDLQSLLGYTPEELHAMLDVKPDADE

In some embodiments, an ETV2 amino acid or DNA sequence can be at least 90%, at least 91%, at least 92%, at least 93%, at least 94%, at least 95%, at least 96%, at least 97%, at least 98%, at least 99%, or more, identical to a native or reference sequence. In some embodiments, a FLI1 amino acid or DNA sequence can be at least 90%, at least 91%, at least 92%, at least 93%, at least 94%, at least 95%, at least 96%, at least 97%, at least 98%, at least 99%, or more, identical to a native or reference sequence. In some embodiments, an ETS amino acid or DNA sequence can be at least 90%, at least 91%, at least 92%, at least 93%, at least 94%, at least 95%, at least 96%, at least 97%, at least 98%, at least 99%, or more, identical to a native or reference sequence.

SOX Family

SOX genes encode a family of transcription factors that bind to the minor groove in DNA, and belong to a superfamily of genes characterized by a homologous sequence called the HMG-box (for high mobility group). This HMG box is a DNA binding domain that is highly conserved throughout eukaryotic species. Homologues have been identified in insects, nematodes, amphibians, reptiles, birds and a range of mammals.

Sox genes are defined as containing the HMG box of a gene involved in sex determination called SRY, which resides on the Y-chromosome (Sox stands for Sry-related HMG box). There are 20 SOX genes present in humans and mice. The family is divided into subgroups according to homology within the HMG domain and other structural motifs, as well as according to functional assays. In humans the members of the SOX groups comprise: 1) SoxA (e.g., SRY); 2) SoxB1 (e.g., SOX1, SOX2, SOX3); 3) SoxB2 (e.g., SOX14, SOX21); 4) SoxC (e.g., SOX4, SOX11, SOX12); 5) SoxD (e.g., SOX5, SOX6, SOX13); 6) SoxE (e.g., SOX8, SOX9, SOX10); 7) SoxF (e.g., SOX7, SOX17, SOX18); 8) SoxG (e.g., SOX15); 9) SoxH (e.g., SOX30).

The developmentally important Sox family has no singular function, and many members possess the ability to regulate several different aspects of development. While many Sox genes are involved in sex determination, some are also important in processes such as neuronal development. Sox proteins bind to the sequence WWCAAW and similar sequences (W-A or T). DNA motifs for the Sox family can also comprise a central ATTGT sequence (e.g., on DNA strand complementary to the first motif).

Non-limiting examples of members of the human Sox family that are relevant to endothelial niche cells comprise SOX18 and SOX7. The corresponding factors in zebrafish or *Xenopus* comprise sox 18 and sox7.

SOX18 can also be referred to herein as SRY-Box 18, SRY (Sex Determining Region Y)-Box 18, Transcription Factor SOX-18, SRY Box 18, HLTRS, or HLTS.

SOX7 can also be referred to herein as SRY-Box 7, SRY (Sex Determining Region Y)-Box 7, Transcription Factor SOX-7, or SRY Box 7.

In some embodiments of any of the aspects, cells are generated which or engineered to express a Sox family member selected from the group consisting of SOX18 and SOX7. In some embodiments, the Sox gene or protein can be SOX18 or the corresponding zebrafish sox 18 or *Xenopus* SOX18. In some embodiments, the Ets gene or protein can be SOX7 or the corresponding zebrafish sox7. In some embodiments, the Sox gene or protein can be SOX18 and SOX7 or the corresponding zebrafish or *Xenopus* factors. In some embodiments, the Sox gene or protein can be SOX18 or SOX7 or the corresponding zebrafish or *Xenopus* factors.

The amino acid sequences of the polypeptides described herein have been assigned NCBI accession numbers for different species such as human, mouse, rat, and zebrafish. In particular, the NCBI accession numbers for non-limiting examples of the amino acid sequences of human SOX18 (e.g. SEQ ID NO: 4), human SOX7 (e.g., SEQ ID NO: 5), and *Xenopus* SOX18 (e.g., SEQ ID NO: 8) are included herein.

(Homo sapiens SOX18, NCBI accession number
BAA94874.1, 384 aa):
SEQ ID NO: 4
MQRSPPGYGAQDDPPARRDCAWAPGGAAADTRGLAAGPAALAAPAAPASP

PSPQRSPPRSPEPGRYGLSPAGRGERQAADESRIRRPMNAFMVWAKDERK

RLAQQNPDLHNAVLSKMLGKAWKELNAAEKRPFVEEAERLRVQHLRDHPN

YKYRPRRKKQARKARRLEPGLLLPGLAPPQPPPEPFPAASGSARAFRELP

PLGAEFDGLGLPTPERSPLDGLEPGEAAFFPPPAAPEDCALRPFRAPYAP

TELSRDPGGCYGAPLAEALRTAPPAAPLAGLYYGTLGTPGPYPGPLSPPP

EAPPLESAEPLGPAADLWADVDLTEFDQYLNCSRTRPDAPGLPYHVALAK

LGPRAMSCPEESSLISALSDASSAVYYSACISG (Homo sapiens SOX7, NCBI accession number,
CAC84226.1, 388 aa):
SEQ ID NO: 5
MASLLGAYPWPEGLECPALDAELSDGQSPPAVPRPPGDKGSESRIRRPMN

AFMVWAKDERKRLAVQNPDLHNAELSKMLGKSWKALTLSQKRPYVDEAER

LRLQHMQDYPNYKYRPRRKKQAKRLCKRVDPGFLLSSLSRDQNALPEKRS

GSRGALGEKEDRGEYSPGTALPSLRGCYHEGPAGGGGGGTPSSVDTYPYG

LPTPPEMSPLDVLEPEQTFFSSPCQEEHGHPRRIPHLPGHPYSPEYAPSP

LHCSHPLGSLALGQSPGVSMMSPVPGCPPSPAYYSPATYHPLHSNLQAHL

GQLSPPPEHPGFDADLQLSQVELLGDMDRNEFDQYLNTPGHPDSATGAMA

LSGHVPVSQVTPTGPTETSLISVLADATATYYNSYSVS (Xenopus tropicalis SOX18, NCI accession number:
AAI67402.1, 362 aa):
SEQ ID NO: 8
MHRPEPSYCREEPTPCQGVNSTWVPPADTVPETSPTPSSPPAPDSPTPSP

QPGYGYSPCEEKPGDPRIRRPMNAFMVWAKDERKRLAQQNPDLHNAVLSK

MLGQSWKNLSSAEKRPFVEEAERLRVQHLQDHPNYKYRPRRKKQAKKLKR

VDPSPLLRNEGYRGQAMANLSHFRDLHPLGGSGDLESYGLPTPEMSPLDV

VEPSEPAFFPPHMREEADPGPFRTYQHGVDFGQEKTLREISLPYSSSPSH

MGGFLRTPTASAFYYNPHGGSPACTPLGQLSPPPEAPALEAMDHLGPAEL

WGDFDRNEFDQYLNMSRTQGPGYPFPMSKLGAPRTIPCEESSLISALSDA

STAMYYTPCITG

In some embodiments, a SOX7 amino acid or DNA sequence can be at least 90%, at least 91%, at least 92%, at least 93%, at least 94%, at least 95%, at least 96%, at least 97%, at least 98%, at least 99%, or more, identical to a native or reference sequence. In some embodiments, a SOX18 amino acid or DNA sequence can be at least 90%, at least 91%, at least 92%, at least 93%, at least 94%, at least 95%, at least 96%, at least 97%, at least 98%, at least 99%, or more, identical to a native or reference sequence.

NHR Family

The Nuclear Hormone Receptor (NHR) family, also referred to as nuclear receptors, are a class of proteins found within cells that are responsible for sensing steroid and thyroid hormones and certain other molecules. In response, these receptors work with other proteins to regulate the expression of specific genes, thereby controlling the development, homeostasis, and metabolism of the organism. A unique property of nuclear receptors that differentiates them from other classes of receptors is their ability to directly interact with and control the expression of genomic DNA. As a consequence, nuclear receptors play key roles in both embryonic development and adult homeostasis. A non-limiting example of a DNA motifs for NHR family members comprises RRGGTCA, where R denotes a purine (e.g., A or G).

At least 48 nuclear receptors have been identified in humans, classified into the following subfamilies: 1) Thyroid-Hormone Receptor-like (e.g., Thyroid hormone receptor, Retinoic acid receptor, Peroxisome proliferator-activated receptor, Rev-ErbA, RAR-related orphan receptor, Liver X receptor-like, Vitamin D receptor-like, NRs with two DNA binding domains, RORA); 2) Retinoid X Receptor-like (e.g., Hepatocyte nuclear factor-4, Retinoid X receptor, Testicular receptor, TLX, PNR, COUP, EAR, RXRA, NR2F2); 3) Estrogen Receptor-like (e.g., Estrogen receptor, Estrogen related receptor, 3-Ketosteroid receptors); 4) Nerve Growth Factor IB-like (e.g., NGFIB, NURR1, NOR1); 5) Steroidogenic Factor-like (e.g., SF1, LRH1); 6) Germ Cell Nuclear Factor-like (e.g., GCNF); 7) miscellaneous nuclear receptors (e.g., DX, SHP1).

Non-limiting examples of members of the human NHR family that are relevant to endothelial niche cells comprise RXRA and NR2F2. The corresponding factors in zebrafish comprise rxraa and nr2f2.

RXRA is a nuclear receptor that belongs to the RXR transcription factor group. RXRA can also be referred to herein as Retinoid X Receptor Alpha, Nuclear Receptor Subfamily 2 Group B Member 1, Retinoic Acid Receptor RXR-Alpha, NR2B1, Retinoid X Nuclear Receptor Alpha, or Retinoid X Receptor Alpha.

The retinoid X receptor (RXR) is a type of nuclear receptor that is activated by 9-cis retinoic acid and 9-cis-13,14-dihydro-retinoic acid, which is likely to be the major endogenous mammalian RXR-selective agonist. There are three retinoic X receptors (RXR): RXR-alpha, RXR-beta, and RXR-gamma, encoded by the RXRA, RXRB, RXRG genes, respectively. RXR heterodimerizes with subfamily 1 nuclear receptors including CAR, FXR, LXR, PPAR, PXR, RAR, TR, and VDR. As with other type II nuclear receptors, the RXR heterodimer in the absence of ligand is bound to hormone response elements complexed with corepressor protein. Binding of agonist ligands to RXR results in dissociation of corepressor and recruitment of coactivator protein, which, in turn, promotes transcription of the downstream target gene into mRNA and eventually protein.

NR2F2 is a nuclear receptor that belongs to the COUP transcription factor group. NR2F2 can also be referred to herein as Nuclear Receptor Subfamily 2 Group F Member 2, Apolipoprotein A-I Regulatory Protein 1, COUP Transcription Factor II, COUP Transcription Factor 2, TFCOUP2, ARP-1, ARP1, Chicken Ovalbumin Upstream Promoter Transcription Factor 2, Chicken Ovalbumin Upstream Promoter-Transcription Factor I, Nuclear Receptor Subfamily 2 Group F Member 2, ADP-Ribosylation Factor Related Protein 1, Apolipoprotein AI Regulatory Protein 1, COUP-TF II, COUPTFII, COUP-TF2, COUPTF2, COUPTFB, CHTD4, NF-E3, or SVP40.

The chicken ovalbumin upstream promoter transcription factor (COUP-TFs) proteins are members of the nuclear receptor family of intracellular transcription factors. There are two variants of the COUP-TFs, labeled as COUP-TFI and COUP-TFII encoded by the NR2F1 and NR2F2 genes respectively. COUP-TFs play critical roles in the development of organisms.

In some embodiments of any of the aspects, cells are generated which or engineered to express an NHR family member selected from the group consisting of RXRA and NR2F2. In some embodiments, the NHR gene or protein can be RXRA or the corresponding zebrafish rxraa. In some embodiments, the NHR gene or protein can be NR2F2 or the corresponding zebrafish nr2/2. In some embodiments, the NHR gene or protein can be RXRA and NR2F2 or the corresponding zebrafish factors. In some embodiments, the NHR gene or protein can be RXRA or NR2F2 or the corresponding zebrafish factors.

The amino acid sequences of the polypeptides described herein have been assigned NCBI accession numbers for different species such as human, mouse, rat, and zebrafish. In particular, the NCBI accession numbers for non-limiting examples of the amino acid sequences of human RXRA (e.g. SEQ ID NO: 6), human NR2F2 (e.g., SEQ ID NO: 7), and zebrafish Nr2l2 (e.g., SEQ ID NO: 9) are included herein.

(Homo sapiens RXRA isoform A, NCBI accession number NP_002948.1, 462 aa):
SEQ ID NO: 6
MDTKHFLPLDFSTQVNSSLTSPTGRGSMAAPSLHPSLGPGIGSPGQLHSP

ISTLSSPINGMGPPFSVISSPMGPHSMSVPTTPTLGFSTGSPQLSSPMNP

VSSSEDIKPPLGLNGVLVKPAHPSGNMASFTKHICAICGDRSSGKHYGVY

SCEGCKGFFKRTVRKDLTYTCRDNKDCLIDKRQRNRCQYCRYQKCLAMGM

KREAVQEERQRGKDRNENEVESTSSANEDMPVERILEAELAVEPKTETYV

EANMGLNPSSPNDPVTNICQAADKQLFTLVEWAKRIPHFSELPLDDQVIL

LRAGWNELLIASFSHRSIAVKDGILLATGLHVHRNSAHSAGVGAIFDRVL

TELVSKMRDMQMDKTELGCLRAIVLFNPDSKGLSNPAEVEALREKVYASL

EAYCKHKYPEQPGRFAKLLLRLPALRSIGLKCLEHLFFFKLIGDTPIDTF

LMEMLEAPHQMT (Homo sapiens NR2F2 isoform A, NCBI accession number NP_066285.1, 414 aa):
SEQ ID NO: 7
MAMVVSTWRDPQDEVPGSQGSQASQAPPVPGPPPGAPHTPQTPGQGGPAS

TPAQTAAGGQGGPGGPGSDKQQQQQHIECVVCGDKSSGKHYGQFTCEGCK

SFFKRSVRRNLSYTCRANRNCPIDQHHRNQCQYCRLKKCLKVGMRREAVQ

RGRMPPTQPTHGQFALTNGDPLNCHSYLSGYISLLLRAEPYPTSRFGSQC

MQPNNIMGIENICELAARMLFSAVEWARNIPFFPDLQITDQVALLRLTWS

ELFVLNAAQCSMPLHVAPLLAAAGLHASPMSADRVVAFMDHIRIFQEQVE

KLKALHVDSAEYSCLKAIVLFTSDACGLSDVAHVESLQEKSQCALEEYVR

SQYPNQPTRFGKLLLRLPSLRTVSSSVIEQLFFVRLVKTPIETLIRDMLL

SGSSFNWPYMAIQ (Danio rerio Nr2f2; NCBI accession number: AAI62484.1; 428 aa):
SEQ ID NO: 9
MAMVVWRGSQDDVAETHGTLSSQTQGGLSLPTPQPGQLGLTASQVAPPTP

QTPVQGPPNNNNNTQSTPTNQTTQSQSEKQQPQHIECVVCGDKSSGKHYG

QFTCEGCKSFFKRSVRRNLTYTCRANRNCPIDQHHRNQCQYCRLKKCLKV

GMRREVSLFTAAVQRGRMPPTQPHHGQFALTNGDPLHCHSYLSGYISLLL

RAEPYPTSRYGSQCMQPNNIMGIENICELAARMLFSAVEWARNIPFFPDL

QITDQVALLRLTWSELFVLNAAQCSMPLHVAPLLAAAGLHASPMSADRVV

AFMDHIRIFQEQVEKLKALHVDSAEYSCLKAIVLFTSDACGLSDVAHVES

LQEKSQCALEEYVRSQYPNQPTRFGKLLLRLPSLRTVSSSVIEQLFFVRL

VGKTPIETLIRDMLLSGSSFNWPYMSIQ

In some embodiments, a RXRA amino acid or DNA sequence can be at least 90%, at least 91%, at least 92%, at least 93%, at least 94%, at least 95%, at least 96%, at least 97%, at least 98%, at least 99%, or more, identical to a native or reference sequence. In some embodiments, a NR2F2 amino acid or DNA sequence can be at least 90%, at least 91%, at least 92%, at least 93%, at least 94%, at least 95%, at least 96%, at least 97%, at least 98%, at least 99%, or more, identical to a native or reference sequence.

In some embodiments, the transcription factors can be selected from the group consisting of ETV2, FLI1, ETS1, SOX18, SOX7, RXRA, and NR2F2 or the corresponding zebrafish or *Xenopus* factors. In some embodiments, the transcription factors can be ETV2, FLI1, ETS1, SOX18, SOX7, RXRA, or NR2F2 or the corresponding zebrafish or *Xenopus* factors. In some embodiments, the transcription factors can be ETV2, FLI1, ETS1, SOX18, SOX7, RXRA, and NR2F2 or the corresponding zebrafish or *Xenopus* factors.

In some embodiments, the transcription factors can be ETV2, SOX7, and NR2F2 or the corresponding zebrafish or *Xenopus* factors. In some embodiments, the transcription factors can be ETS1, SOX7, and NR2F2 or the corresponding zebrafish or *Xenopus* factors. In some embodiments, the transcription factors can be ETV2 alone or the corresponding zebrafish or *Xenopus* factor.

In some embodiments, the transcription factors can be at least 1 factor, at least 2 factors, at least 3 factors, at least 4 factors, at least 5 factors, at least 6 factors, or at least 7 factors selected from the group consisting of ETV2, FLI1, ETS1, SOX18, SOX7, RXRA, and NR2F2 or the corresponding zebrafish or *Xenopus* factors.

In some embodiments, transcription factors can be at ETV2 and at least 1 factor selected from the group consisting of FLI1, ETS1, SOX18, SOX7, RXRA, and NR2F2 or the corresponding zebrafish or *Xenopus* factors. In some embodiments, transcription factors can be at ETS1 and at least 1 factor selected from the group consisting of ETV2, FLI1, SOX18, SOX7, RXRA, and NR2F2 or the corresponding zebrafish or *Xenopus* factors.

Hematopoietic System Development

The development of the haematopoietic system, including the cell populations and molecular pathways, is highly conserved between fish and mammals. HSPCs are born in the aorta-gonad-mesonephric (AGM) region and then migrate to a transient fetal niche, the fetal liver in mammals or a vascular plexus in the tail of the fish called the caudal haematopoietic tissue (CHT). HSPCs reside and expand in these developmental sites for several days before migrating to the adult niche—the bone marrow in mammals or the kidney marrow in fish.

The CHT is comprised primarily of low-flow sinusoids surrounded by mesenchymal stromal cells. HSPCs initially colonize the CHT niche by lodging within the vascular plexus and interacting directly with cxcl12a' stromal cells. In a characteristic vascular remodeling step, endothelial cells (ECs) reorganize to form a supportive pocket around the HSPCs, which together with stromal cells and possibly other cell types, forms a niche for the stem cells (the endothelial cells surrounding the HSPCs can be referred to herein as endothelial niche cells). In mammals and zebrafish, specific signaling molecules, adhesion proteins and transcription factors have been implicated in mediating communication and physical interaction between stem cells and ECs in the niche. Collectively, these studies suggest that ECs within the vascular niches of haematopoietic organs express niche-specific gene programs. To date, however, a comprehensive investigation of the transcriptional circuitry that specifies the niche identity of ECs in the HSPC niche has not been undertaken. Understanding this regulation guides new strategies to improve the efficacy and availability of bone marrow transplantation therapies.

Endothelial Niche Cells

As described herein, endothelial niche cells are endothelial cells that provide an instructive niche for the differentiation of HSPCs. Endothelial niche cells are typically found in the bone marrow. However, as described herein, exogenous expression of specific transcription factors (e.g., ETV2, FLI1, ETS1, SOX18, SOX7, RXRA, NR2F2) can cause endothelial niche cells to be found in non-bone marrow tissues, thus providing for extramedullary hematopoiesis.

In some embodiments of any of the aspects, endothelial niche cells comprise cells that express one are more genes selected from the group consisting of sele, exoc3l2a, snx8a, cltca, aqp7, ap1b1, lgmn, prcp, cldn11a, lyve1b, adra1d, hya12a, hya12b, tll1, il13ra2, glu1a, hexb, slc16a9a, and sepp1a. In some embodiments, the endothelial cells are human.

In some embodiments of any of the aspects, the endothelial niche cells are generated or engineered to express transcription factors, comprising at least one of the human transcription factors ETV2, FLI1, ETS1, SOX18, SOX7, RXRA, or NR2F2. In some embodiments, the transcription factor comprises at least one transcription factor from the Ets family, at least one transcription factor from the Sox family, and at least one transcription factor from the Nuclear Hormone Receptor family. In some embodiments, the transcription factors comprise ETV2, FLI1, ETS1, SOX18, SOX7, RXRA, and NR2F2.

In some embodiments of any of the aspects, the transcription factors are expressed from at least one vector. In some embodiments, the vector comprises an exogenous nucleic acid sequence or sequences encoding the one or more transcription factors. In some embodiments, the exogenous nucleic acid sequences are incorporated into the genome of the endothelial cell. As a non-limiting example, the exogenous nucleic acid sequences can be incorporated into the genome using viral vectors (e.g., AAV, lentivirus) or CRISPR technologies.

One aspect provides for a composition comprising an engineered endothelial niche cell comprising one or more exogenous nucleic acid sequences encoding one or more transcription factors, wherein the one or more transcription factors are from the Ets family, the Sox family and/or the Nuclear Hormone Family. In some embodiments of any of the aspects, the composition can comprise engineered endothelial niche cells. In some embodiments, the composition is a therapeutic agent or the composition further comprises a pharmaceutically acceptable carrier. In some embodiments, the composition further comprises a culture dish, 3D cell system, or suspension system. In some embodiments, the composition comprises a scaffold.

Another aspect provides a method for culturing HSPCs, the method comprising culturing HSPCs in the presence of a population of engineered endothelial niche cells. In some embodiments of any of the aspects, the method is performed in vitro. In some embodiments, the engineered endothelial niche cells secrete a factor (e.g., growth factors) that affects the growth and/or expansion of the HSPC cells.

In some embodiments, the HSPCs cultured in the presence of the engineered endothelial niche cells can be cultured for at least 3 days longer than HSPCs that are cultured in the absence of such engineered endothelial niche cells. In, some embodiments, the HSPCs cultured in the presence of the engineered endothelial niche cells can be cultured for at 1 day longer, at least 2 days longer, at least 3 days longer, at least 4 days longer, at least 5 days longer, at least 6 days longer, at least 7 days longer, at least 8 days longer, at least 9 days longer, at least 10 days longer, at least 11 days longer, at least 12 days longer, at least 13 days longer, or at least 14 days longer than HSPCs that are cultured in the absence of such engineered endothelial niche cells.

In some embodiments, the cells are cultured on a biologically compatible scaffold. Non-limiting examples of a biologically compatible scaffold comprise: a hydrogel, biopolymers, or another biomaterial with the ability to grow cells in vitro in preparation for transplantation. In some embodiments, the HSPCs cultured in the presence of the engineered endothelial niche cells have increased engraftment when administered to a subject compared to the engraftment of substantially similar HSPCs that were not cultured with engineered endothelial niche cells. As used herein, "engraftment" refers to the process wherein transplanted HSPCs begin to grow and produce healthy blood cells. Engraftment is a critical milestone in recovery from an HSPC transplant.

Another aspect provides a method of treating a subject, the method comprising, transplanting a composition comprising a population of engineered endothelial niche-cells into the subject. As a non-limiting example, the method can be used to treat myelofibrosis or other hematopoietic diseases where the endogenous bone marrow niche is compromised, non-limiting examples of which are disclosed herein. In some embodiments, the method can comprise transplanting a composition comprising a population of HSPCs into the subject. In some embodiments, the method can comprise transplanting a composition comprising a population of HSPCs and engineered endothelial niche-cells into the subject.

Another aspect provides a method for enhancing engraftment of HSPCs, the method comprising administering a composition comprising HSPCs and a population of engineered endothelial niche cells to a subject in need thereof. In some embodiments of any of the aspects, engraftment of the HSPCs is increased by at least 10% compared to the engraftment of substantially similar HSPCs in the absence of engineered endothelial niche cells. In some embodiments of any of the aspects, engraftment of the HSPCs is increased by at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% compared to the engraftment of substantially similar HSPCs in the absence of engineered endothelial niche cells.

Another aspect provides a co-culture comprising engineered endothelial niche cells and HSPCs. In some embodiments of any of the aspects, the endothelial cells are made by a method described herein.

Another aspect provides a method for generating an ectopic vascular niche, the method comprising: administering an engineered endothelial niche cell to a target site in a subject in need thereof. As used herein "ectopic vascular niche" refers to an atypical site for endothelial niche cells. For example, the vascular niche can be found outside of the bone marrow. The ectopic vascular niche comprising generated or engineered endothelial niche cells can be anywhere in the body. The ectopic vascular niche can be found in a location where HSPCs, generated or engineered endothelial niche cells, and/or their associated transcription factors (e.g., ETV2, FLI1, ETS1, SOX18, SOX7, RXRA, or NR2F2) have been injected.

Another aspect provides a method for extra medullary hematopoiesis, the method comprising transplanting engineered-niche endothelial cells into a subject at a location outside of the bone marrow (e.g., the forearm), thereby creating a synthetic niche. As used herein, "extra medullary hematopoiesis" refers to hematopoiesis occurring in organs outside of the bone marrow. In some embodiments of any of the aspects, the endothelial cells are made by a method described herein.

Myelofibrosis

In some embodiments of any of the aspects, generated or engineered endothelial niche cells or their associated transcription factors (e.g., ETV2, FLI1, ETS1, SOX18, SOX7, RXRA, or NR2F2) can be used to treat myelofibrosis.

Myelofibrosis is an uncommon type of chronic leukemia. Myelofibrosis belongs to a group of diseases called myeloproliferative disorders, often of a chronic form. Chronic myeloproliferative disorders are a group of slow-growing blood cancers in which the bone marrow makes too many abnormal red blood cells, white blood cells, or platelets, which accumulate in the blood. Non-limiting examples of chronic myeloproliferative neoplasms comprise: Chronic myelogenous leukemia, Polycythemia vera, Primary myelofibrosis (also called chronic idiopathic myelofibrosis), Essential thrombocythemia, Chronic neutrophilic leukemia, and Chronic eosinophilic leukemia.

Myelofibrosis is a serious bone marrow disorder that disrupts the body's normal production of blood cells. The result is extensive scarring in bone marrow, leading to severe anemia, weakness, fatigue and often an enlarged spleen. Many subjects or patients with myelofibrosis get progressively worse, and some subjects or patients may eventually develop a more serious form of leukemia. Myelofibrosis can occur when blood stem cells (e.g., HSPCs) develop a genetic mutation. Several specific gene mutations have been identified in people with myelofibrosis. The most common is the Janus kinase 2 (JAK2) gene.

Although the cause of myelofibrosis often isn't known, certain factors are known to increase risk. Increased age can be associated with the development of myelofibrosis. Myelofibrosis can affect anyone, but it's most often diagnosed in people older than 50. Patients with another blood cell disorder are at higher risk for developing myelofibrosis. A small portion of people with myelofibrosis develop the condition as a complication of essential thrombocythemia or polycythemia vera. Exposure to certain chemicals can increase the risk for myelofibrosis. Myelofibrosis has been linked to exposure to industrial chemicals such as toluene and benzene. Exposure to radiation can increase the risk for myelofibrosis. People exposed to high levels of radiation, such as survivors of atomic bomb attacks, have an increased risk of myelofibrosis. Some people who received a radioactive contrast material called Thorotrast, used until the 1950s, have developed myelofibrosis.

Multiple complications can result from myelofibrosis. A complication of myelofibrosis can include increased pressure on blood flowing into a patient's liver. Normally, blood flow from the spleen enters the liver through a large blood vessel called the portal vein. Increased blood flow from an enlarged spleen can lead to high blood pressure in the portal vein (e.g., portal hypertension). This in turn can force excess blood into smaller veins in the stomach and esophagus, potentially causing these veins to rupture and bleed. Pain can be another complication of myelofibrosis. A severely enlarged spleen can cause abdominal pain and back pain. Myelofibrosis can lead to growths in other areas of the body. Myelofibrosis can be associated with bleeding complications. As the disease progresses, platelet count tends to drop below normal (thrombocytopenia) and platelet function becomes impaired. An insufficient number of platelets can lead to easy bleeding. Myelofibrosis can also be associated with painful bones and joints. Myelofibrosis can lead to hardening of bone marrow and inflammation of the connective tissue that is found around the bones. This may cause bone and joint pain. Myelofibrosis can also be associated with development of acute leukemia. Some patients with myelofibrosis develop acute myelogenous leukemia, a type of blood and bone marrow cancer that progresses rapidly.

Bone marrow transplantation is currently the only approved treatment for myelofibrosis. Additional treatments can only ameliorate the symptoms of myelofibrosis (e.g., anemia, enlarged spleen). Ruxolitinib, a JAK inhibitor which targets the gene mutation found in most cases of myelofibrosis, can be used to reduce symptoms of an enlarged spleen.

Treatment Methods

As described herein, levels of functional hematopoiesis can be decreased in myelofibrosis and/or in subjects with myelofibrosis. As used herein, "functional hematopoiesis" refers to hematopoiesis that produces normal levels and proportions of blood cells (e.g., red blood cells, white blood cells, platelets). In some embodiments of any of the aspects, the level of hematopoiesis can be decreased in myelofibrosis or a myeloproliferative disorder and/or in subjects with myelofibrosis or a myeloproliferative disorder. Accordingly, in one aspect of any of the embodiments, described herein is a method of treating myelofibrosis or a myeloproliferative disorder in a subject in need thereof, the method comprising administering HSPCs, engineered endothelial cells, and/or transcription factors (e.g., ETV2, FLI1, ETS1, SOX18, SOX7, RXRA, or NR2F2) to a subject determined to have a level of functional hematopoiesis that is decreased relative to a reference. In one aspect of any of the embodiments, described herein is a method of treating myelofibrosis or a myeloproliferative disorder in a subject in need thereof, the method comprising: a) determining the level of functional hematopoiesis in a sample obtained from a subject; and b) administering HSPCs, engineered endothelial cells, and/or transcription factors (e.g., ETV2, FLI1, ETS1, SOX18, SOX7, RXRA, or NR2F2) to the subject if the level of functional hematopoiesis is decreased relative to a reference.

In some embodiments of any of the aspects, the method comprises administering HSPCs, engineered endothelial cells, and/or transcription factors (e.g., ETV2, FLI1, ETS1, SOX18, SOX7, RXRA, or NR2F2) to a subject previously determined to have a level of functional hematopoiesis that is decreased relative to a reference. In some embodiments of any of the aspects, described herein is a method of treating myelofibrosis or a myeloproliferative disorder in a subject in need thereof, the method comprising: a) first determining the level of functional hematopoiesis in a sample obtained from a subject; and b) then administering HSPCs, engineered endothelial cells, and/or transcription factors (e.g., ETV2, FLI1, ETS1, SOX18, SOX7, RXRA, or NR2F2) to the subject if the level of functional hematopoiesis is decreased relative to a reference.

In one aspect of any of the embodiments, described herein is a method of treating myelofibrosis or a myeloproliferative disorder in a subject in need thereof, the method comprising: a) determining if the subject has a decreased level of hematopoiesis; and b) administering HSPCs, engineered endothelial cells, and/or transcription factors (e.g., ETV2, FLI1, ETS1, SOX18, SOX7, RXRA, or NR2F2) to the subject if the level of functional hematopoiesis is decreased relative to a reference. In some embodiments of any of the aspects, the step of determining if the subject has a decreased level of functional hematopoiesis can comprise i) obtaining or having obtained a sample from the subject and ii) performing or having performed an assay on the sample obtained from the subject to determine/measure the level of hematopoiesis in the subject. In some embodiments of any of the aspects, the step of determining if the subject has a decreased level of functional hematopoiesis can comprise performing or having performed an assay on a sample obtained from the subject to determine/measure the level of hematopoiesis in the subject. In some embodiments of any of the aspects, the step of determining if the subject has a decreased level of functional hematopoiesis can comprise ordering or requesting an assay on a sample obtained from the subject to determine/measure the level of hematopoiesis in the subject. In some embodiments of any of the aspects, the step of determining if the subject has a decreased level of functional hematopoiesis can comprise receiving the results of an assay on a sample obtained from the subject to determine/measure the level of functional hematopoiesis in the subject. In some embodiments of any of the aspects, the step of determining if the subject has a decreased level of functional hematopoiesis can comprise receiving a report, results, or other means of identifying the subject as a subject with a decreased level of functional hematopoiesis.

In one aspect of any of the embodiments, described herein is a method of treating myelofibrosis or a myeloproliferative disorder in a subject in need thereof, the method comprising: a) determining if the subject has a decreased level of functional hematopoiesis; and b) instructing or directing that the subject be administered HSPCs, engineered endothelial niche cells, and/or transcription factors (e.g., ETV2, FLI1, ETS1, SOX18, SOX7, RXRA, or NR2F2) if the level of functional hematopoiesis is decreased relative to a reference. In some embodiments of any of the aspects, the step of determining if the subject has a decreased level of functional hematopoiesis can comprise i) obtaining or having obtained a sample from the subject and ii) performing or having performed an assay on the sample obtained from the subject to determine/measure the level of functional hematopoiesis in the subject. In some embodiments of any of the aspects, the step of determining if the subject has a decreased level of functional hematopoiesis can comprise performing or having performed an assay on a sample obtained from the subject to determine/measure the level of functional hematopoiesis in the subject. In some embodiments of any of the aspects, the step of determining if the subject has a functional level of functional hematopoiesis can comprise ordering or requesting an assay on a sample obtained from the subject to determine/measure the level of functional hematopoiesis in the subject. In some embodiments of any of the aspects, the step of instructing or directing that the subject be administered a particular treatment can comprise providing a report of the assay results. In some embodiments of any of the aspects, the step of instructing or directing that the subject be administered a particular treatment can comprise providing a report of the assay results and/or treatment recommendations in view of the assay results.

Administration

In some embodiments, the methods described herein relate to treating a subject having or diagnosed as having myelofibrosis or a myeloproliferative disorder. Subjects having myelofibrosis or a myeloproliferative disorder can be identified by a physician using current methods of diagnosing myelofibrosis or a myeloproliferative disorder. Symptoms and/or complications of myelofibrosis or a myeloproliferative disorder which characterize these conditions and aid in diagnosis are well known in the art and include but are not limited to anemia, splenomegaly (i.e. an enlarged and painful spleen), fatigue, weak or short of breath, pain or fullness below the ribs on the left side, easy bruising, easy bleeding, excessive sweating during sleep (night sweats), fever, and/or bone pain. Tests that may aid in a diagnosis of myelofibrosis or a myeloproliferative disorder include but are not limited to a blood test (e.g., a complete blood count)

or a bone marrow biopsy. Myelofibrosis or a myeloproliferative disorder can also be detected with a physical exam, imaging tests, or genetic tests. A family history of myelofibrosis or a myeloproliferative disorder, or exposure to risk factors for myelofibrosis or a myeloproliferative disorder (e.g. industrial chemicals, radiation) can also aid in determining if a subject is likely to have myelofibrosis or a myeloproliferative disorder or in making a diagnosis of myelofibrosis or a myeloproliferative disorder.

The compositions and methods described herein can be administered to a subject having or diagnosed as having myelofibrosis or a myeloproliferative disorder. In some embodiments, the methods described herein comprise administering an effective amount of compositions described herein, e.g. HSPCs, engineered endothelial niche cells, and/or transcription factors (e.g., ETV2, FLI1, ETS1, SOX18, SOX7, RXRA, or NR2F2) to a subject in order to alleviate a symptom of myelofibrosis or a myeloproliferative disorder. As used herein, "alleviating a symptom of myelofibrosis or a myeloproliferative disorder" is ameliorating any condition or symptom associated with the myelofibrosis or a myeloproliferative disorder. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic.

The term "effective amount" as used herein refers to the amount of HSPCs, engineered endothelial niche cells, and/or transcription factors (e.g., ETV2, FLI1, ETS1, SOX18, SOX7, RXRA, or NR2F2) needed to alleviate at least one or more symptom of the disease or disorder, and relates to a sufficient amount of pharmacological composition to provide the desired effect. The term "therapeutically effective amount" therefore refers to an amount of HSPCs, engineered endothelial niche cells, and/or transcription factors (e.g., ETV2, FLI1, ETS1, SOX18, SOX7, RXRA, or NR2F2) that is sufficient to provide a particular anti-myelofibrosis or anti-myeloproliferative disorder effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of HSPCs, engineered endothelial niche cells, and/or transcription factors (e.g., ETV2, FLI1, ETS1, SOX18, SOX7, RXRA, or NR2F2) which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

In some embodiments, the technology described herein relates to a pharmaceutical composition comprising HSPCs, engineered endothelial niche cells, and/or transcription factors (e.g., ETV2, FLI1, ETS1, SOX18, SOX7, RXRA, or NR2F2) as described herein, and optionally a pharmaceutically acceptable carrier. In some embodiments, the active ingredients of the pharmaceutical composition comprise HSPCs, engineered endothelial niche cells, and/or transcription factors (e.g., ETV2, FLI1, ETS1, SOX18, SOX7, RXRA, or NR2F2) as described herein. In some embodiments, the active ingredients of the pharmaceutical composition consist essentially of HSPCs, engineered endothelial niche cells, and/or transcription factors (e.g., ETV2, FLI1, ETS1, SOX18, SOX7, RXRA, or NR2F2) as described herein. In some embodiments, the active ingredients of the pharmaceutical composition consist of HSPCs, engineered endothelial niche cells, and/or transcription factors (e.g., ETV2, FLI1, ETS1, SOX18, SOX7, RXRA, or NR2F2) as described herein.

Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. HSPCs, engineered endothelial niche cells, and/or transcription factors (e.g., ETV2, FLI1, ETS1, SOX18, SOX7, RXRA, or NR2F2) as described herein.

In some embodiments, the pharmaceutical composition comprising HSPCs, engineered endothelial niche cells, and/ or transcription factors (e.g., ETV2, FLI1, ETS1, SOX18, SOX7, RXRA, or NR2F2) as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of HSPCs, engineered endothelial niche cells, and/or transcription factors (e.g., ETV2, FLI1, ETS1, SOX18, SOX7, RXRA, or NR2F2) as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

In some embodiments of any of the aspects, the HSPCs, engineered endothelial niche cells, and/or transcription factors (e.g., ETV2, FLI1, ETS1, SOX18, SOX7, RXRA, or NR2F2) described herein is administered as a monotherapy, e.g., another treatment for the myelofibrosis or a myeloproliferative disorder is not administered to the subject.

In some embodiments of any of the aspects, the methods described herein can further comprise administering a second agent and/or treatment to the subject, e.g. as part of a combinatorial therapy. Non-limiting examples of a second agent and/or treatment can include radiation therapy, surgery, gemcitabine, cisplastin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredepa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew, Chem. Intl. Ed. Engl., 33:183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE.® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb.®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

In addition, the methods of treatment can further include the use of radiation or radiation therapy. Further, the methods of treatment can further include the use of surgical treatments.

The methods described herein can further comprise administering a second agent and/or treatment to the subject, e.g. as part of a combinatorial therapy. By way of non-limiting example, if a subject is to be treated for pain or inflammation according to the methods described herein, the subject can also be administered a second agent and/or treatment known to be beneficial for subjects suffering from pain or inflammation. In some embodiments, the second agent is an anti-inflammation agent. Examples of such agents and/or treatments include, but are not limited to, non-steroidal anti-inflammatory drugs (NSAIDs-such as aspirin, ibuprofen, or naproxen); corticosteroids, including glucocorticoids (e.g. cortisol, prednisone, prednisolone, methylprednisolone, dexamethasone, betamethasone, triamcinolone, and beclometasone); methotrexate; sulfasalazine; leflunomide; anti-TNF medications; cyclophosphamide; pro-resolving drugs; mycophenolate; or opiates (e.g. endorphins, enkephalins, and dynorphin), steroids, analgesics, barbiturates, oxycodone, morphine, lidocaine, and the like.

In certain embodiments, an effective dose of a composition comprising HSPCs, engineered endothelial niche cells, and/or transcription factors (e.g., ETV2, FLI1, ETS1, SOX18, SOX7, RXRA, or NR2F2) as described herein can be administered to a patient once. In certain embodiments, an effective dose of a composition comprising HSPCs, engineered endothelial niche cells, and/or transcription factors (e.g., ETV2, FLI1, ETS1, SOX18, SOX7, RXRA, or NR2F2) can be administered to a patient repeatedly. For systemic administration, subjects can be administered a therapeutic amount of a composition comprising HSPCs, engineered endothelial niche cells, and/or transcription factors (e.g., ETV2, FLI1, ETS1, SOX18, SOX7, RXRA, or NR2F2), such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. HSPCs, engineered endothelial niche cells, and/or transcription factors (e.g., ETV2, FLI1, ETS1, SOX18, SOX7, RXRA, or NR2F2) by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to HSPCs, engineered endothelial niche cells, and/or transcription factors (e.g., ETV2, FLI1, ETS1, SOX18, SOX7, RXRA, or NR2F2). The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising HSPCs, engineered endothelial niche cells, and/or transcription factors (e.g., ETV2, FLI1, ETS1, SOX18, SOX7, RXRA, or NR2F2) can be administered over a period of time, such as over a 5 minute, 10 minute, 15 minute, 20 minute, or 25 minute period.

The dosage ranges for the administration of HSPCs, engineered endothelial niche cells, and/or transcription factors (e.g., ETV2, FLI1, ETS1, SOX18, SOX7, RXRA, or NR2F2), according to the methods described herein depend upon, for example, its form, its potency, and the extent to which symptoms, markers, or indicators of a condition described herein are desired to be reduced, for example the extent to which, for example, myelofibrosis or a myeloproliferative disorder is desired to be reduced functional hematopoiesis is desired to be induced. The dosage should not be so large as to cause adverse side effects, such as excessive hematopoiesis or excessive extramedullary hematopoiesis. Generally, the dosage will vary with the age, condition, and sex of the patient and can be determined by one of skill in the art. The dosage can also be adjusted by the individual physician in the event of any complication.

The efficacy of HSPCs, engineered endothelial niche cells, and/or transcription factors (e.g., ETV2, FLI1, ETS1, SOX18, SOX7, RXRA, or NR2F2) in, e.g. the treatment of a condition described herein, or to induce a response as described herein (e.g. functional hematopoiesis) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. blood cell counts. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of myelofibrosis or a myeloproliferative disorder. When using an experimental animal model, efficacy of treatment is evidenced when a statistically significant change in a marker is observed.

Kits

One aspect described herein provides a kit for culturing HSPCs, the kit comprising: a population of engineered endothelial niche cells, reagents and instructions for use thereof. Another aspect provides for a kit for generating engineered endothelial niche cells comprising: a vector(s) comprising one or more exogenous nucleic acid sequences encoding one or more transcription factors of the Ets family, the Sox family or the nuclear hormone family and instructions for use thereof. Described herein are kit components that can be included in one or more of the kits described herein.

In some embodiments, the kit comprises an effective amount of reagents for culturing HSPCs and/or endothelial niche cells. As will be appreciated by one of skill in the art, reagents can be supplied in a lyophilized form or a concentrated form that can diluted prior to use with cultured cells. Preferred formulations include those that are non-toxic to the cells and/or does not affect growth rate or viability etc. reagents can be supplied in aliquots or in unit doses.

In some embodiments the kit further comprises a vector comprising a nucleic acid encoding a gene to one or more transcription factors of the Ets family, the Sox family or the nuclear hormone family under the control of a promoter.

In some embodiments, the components described herein can be provided singularly or in any combination as a kit. The kit includes the components described herein, e.g., a composition comprising HSPCs, engineered endothelial niche cells, and/or transcription factors (e.g., ETV2, FLI1, ETS1, SOX18, SOX7, RXRA, or NR2F2), a composition(s) that includes a vector comprising e.g., a gene to one or more transcription factors of the Ets family, the Sox family or the nuclear hormone family under the control of a promoter as described throughout the specification. In addition, the kit optionally comprises informational material. The kit can also contain culture dishes and/or a substrate for coating culture dishes, such as laminin, fibronectin, Poly-L-Lysine, or methylcellulose.

In some embodiments, the compositions in the kit can be provided in a watertight or gas tight container which in some embodiments is substantially free of other components of the kit. For example, a HSPCs, engineered endothelial niche cells, and/or transcription factors (e.g., ETV2, FLI1, ETS1, SOX18, SOX7, RXRA, or NR2F2) composition can be supplied in more than one container, e.g., it can be supplied in a container having sufficient reagent for a predetermined number of experiments, e.g., 1, 2, 3 or greater. One or more components as described herein can be provided in any form, e.g., liquid, dried or lyophilized form. It is preferred that the components described herein are substantially pure and/or sterile. When the components described herein are provided in a liquid solution, the liquid solution preferably is an aqueous solution, with a sterile aqueous solution being preferred.

The informational material can be descriptive, instructional, marketing or other material that relates to the methods described herein. The informational material of the kits is not limited in its form. In one embodiment, the informational material can include information about production of endothelial niche cells and/or HSPCs, concentration, date of expiration, batch or production site information, and so forth. In one embodiment, the informational material relates to methods for using or administering the components of the kit.

The kit can include a component for the detection of a marker for HSPC differentiation and/or endothelial niche cell differentiation. In addition, the kit can include one or more antibodies that bind a cell marker, or primers for an RT-PCR or PCR reaction, e.g., a semi-quantitative or quantitative RT-PCR or PCR reaction. Such components can be used to assess the activation of maturation markers or the loss of immature cell markers of endothelial niche cells and/or HSPCs. If the detection reagent is an antibody, it can be supplied in dry preparation, e.g., lyophilized, or in a solution. The antibody or other detection reagent can be linked to a label, e.g., a radiological, fluorescent (e.g., GFP) or colorimetric label for use in detection. If the detection reagent is a primer, it can be supplied in dry preparation, e.g., lyophilized, or in a solution.

The kit will typically be provided with its various elements included in one package, e.g., a fiber-based, e.g., a cardboard, or polymeric, e.g., a Styrofoam box. The enclosure can be configured so as to maintain a temperature differential between the interior and the exterior, e.g., it can provide insulating properties to keep the reagents at a preselected temperature for a preselected time.

Vectors

In some embodiments, one or more of the factors described herein is expressed in a recombinant expression vector or plasmid. As used herein, the term "vector" refers to a polynucleotide sequence suitable for transferring transgenes into a host cell. The term "vector" includes plasmids, mini-chromosomes, phage, naked DNA and the like. See, for example, U.S. Pat. Nos. 4,980,285; 5,631,150; 5,707,828; 5,759,828; 5,888,783 and, 5,919,670, and, Sambrook et al, *Molecular Cloning: A Laboratory Manual*, 2nd Ed., Cold Spring Harbor Press (1989). One type of vector is a "plasmid," which refers to a circular double stranded DNA loop into which additional DNA segments are ligated. Another type of vector is a viral vector, wherein additional DNA segments are ligated into the viral genome. Certain vectors are capable of autonomous replication in a host cell into which they are introduced (e.g., bacterial vectors having a bacterial origin of replication and episomal mammalian vectors). Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" is used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

A cloning vector is one which is able to replicate autonomously or integrated in the genome in a host cell, and which is further characterized by one or more endonuclease restriction sites at which the vector may be cut in a determinable fashion and into which a desired DNA sequence can be ligated such that the new recombinant vector retains its ability to replicate in the host cell. In the case of plasmids, replication of the desired sequence can occur many times as the plasmid increases in copy number within the host cell such as a host bacterium or just a single time per host before the host reproduces by mitosis. In the case of phage, replication can occur actively during a lytic phase or passively during a lysogenic phase.

An expression vector is one into which a desired DNA sequence can be inserted by restriction and ligation such that it is operably joined to regulatory sequences and can be expressed as an RNA transcript. Vectors can further contain one or more marker sequences suitable for use in the identification of cells which have or have not been transformed or transformed or transfected with the vector. Markers include, for example, genes encoding proteins which increase or decrease either resistance or sensitivity to antibiotics or other compounds, genes which encode enzymes whose activities are detectable by standard assays known in the art (e.g., ß-galactosidase, luciferase or alkaline phosphatase), and genes which visibly affect the phenotype of transformed or transfected cells, hosts, colonies or plaques (e.g., green fluorescent protein). In certain embodiments, the vectors used herein are capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When the nucleic acid molecule that encodes any of the factors/polypeptides described herein is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression can vary between species or cell types, but in general can include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences can also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA). That heterologous DNA (RNA) is placed under operable control of transcriptional elements to permit the expression of the heterologous DNA in the host cell.

In some embodiments, the vector is pME Gateway vector (Invitrogen™). In some embodiments, the vector is p5E Gateway™ vector. In some other embodiments, the vector is pGEX2TK™ vector. In some other embodiments, the vector is TOPO-TA™ vector.

Without limitations, the genes described herein can be included in one vector or separate vectors. For example, at least one gene from the Ets family (e.g., ETV2, FLI1, ETS1) and at least one gene from the SOX family (e.g., SOX18, SOX7) and at least one gene from the NHR family (e.g., RXRA, NR2F2) can be included in the same vector.

In some embodiments, at least one gene from the Ets family (e.g., ETV2, FLI1, ETS1) and at least one gene from the SOX family (e.g., SOX18, SOX7) can be included in a first vector, and at least one gene from the NHR family (e.g., RXRA, NR2F2) can be included in a second vector.

In some embodiments, at least one gene from the NHR family (e.g., RXRA, NR2F2) and at least one gene from the SOX family (e.g., SOX18, SOX7) can be included in a first vector, and at least one gene from the Ets family (e.g., ETV2, FLI1, ETS1) can be included in a second vector.

In some embodiments, at least one gene from the Ets family (e.g., ETV2, FLI1, ETS1) and at least one gene from the NHR family (e.g., RXRA, NR2F2) can be included in a first vector, and at least one gene from the SOX family (e.g., SOX18, SOX7) can be included in a second vector.

In some embodiments, at least one gene from the Ets family (e.g., ETV2, FLI1, ETS1) can be included in a first vector, at least one gene from the SOX family (e.g., SOX18, SOX7) can be included in a second vector, and at least one gene from the NHR family (e.g., RXRA, NR2F2) can be included in a third vector.

In some embodiments, the promoter operably linked to the gene(s) can be zebrafish ubi promoter.

In some embodiments, one or more of the recombinantly expressed gene can be integrated into the genome of the cell.

A nucleic acid molecule that encodes the enzyme of the claimed invention can be introduced into a cell or cells using methods and techniques that are standard in the art. For example, nucleic acid molecules can be introduced by standard protocols such as transformation including chemical transformation and electroporation, transduction, particle bombardment, etc. Expressing the nucleic acid molecule encoding the enzymes of the claimed invention also may be accomplished by integrating the nucleic acid molecule into the genome.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of myelofibrosis or a myeloproliferative disorder. A subject can be male or female.

A subject can be one who has been previously diagnosed with or identified as suffering from or having a condition in need of treatment (e.g. myelofibrosis or a myeloproliferative disorder) or one or more complications related to such a condition, and optionally, have already undergone treatment for myelofibrosis or a myeloproliferative disorder or the one or more complications related to myelofibrosis or a myeloproliferative disorder. Alternatively, a subject can also be one who has not been previously diagnosed as having myelofibrosis or a myeloproliferative disorder or one or more complications related to myelofibrosis or a myeloproliferative disorder. For example, a subject can be one who exhibits one or more risk factors for myelofibrosis or a myeloproliferative disorder or one or more complications related to myelofibrosis or a myeloproliferative disorder or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. transcription factor activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser(S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

In some embodiments, the polypeptide described herein can be a variant of a sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

The term "expression" refers to the cellular processes involved in producing RNA and proteins and as appropriate, secreting proteins, including where applicable, but not limited to, for example, transcription, transcript processing, translation and protein folding, modification and processing. Expression can refer to the transcription and stable accumulation of sense (mRNA) or antisense RNA derived from a nucleic acid fragment or fragments of the invention and/or to the translation of mRNA into a polypeptide.

In some embodiments, the expression of a biomarker(s), target(s), or gene/polypeptide described herein is/are tissue-specific. In some embodiments, the expression of a biomarker(s), target(s), or gene/polypeptide described herein is/are global. In some embodiments, the expression of a biomarker(s), target(s), or gene/polypeptide described herein is systemic.

"Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

"Marker" in the context of the present invention refers to an expression product, e.g., nucleic acid or polypeptide which is differentially present in a sample taken from subjects having myelofibrosis or a myeloproliferative disorder, as compared to a comparable sample taken from control subjects (e.g., a healthy subject). The term "biomarker" is used interchangeably with the term "marker."

In some embodiments, the methods described herein relate to measuring, detecting, or determining the level of at least one marker. As used herein, the term "detecting" or "measuring" refers to observing a signal from, e.g. a probe, label, or target molecule to indicate the presence of an analyte in a sample. Any method known in the art for detecting a particular label moiety can be used for detection. Exemplary detection methods include, but are not limited to, spectroscopic, fluorescent, photochemical, biochemical, immunochemical, electrical, optical or chemical methods. In some embodiments of any of the aspects, measuring can be a quantitative observation.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

In some embodiments of any of the aspects, the HSPCs, engineered endothelial niche cells, and/or transcription factors (e.g., ETV2, FLI1, ETS1, SOX18, SOX7, RXRA, or NR2F2) described herein is exogenous. In some embodiments of any of the aspects, the HSPCs, engineered endothelial niche cells, and/or transcription factors (e.g., ETV2, FLI1, ETS1, SOX18, SOX7, RXRA, or NR2F2) described herein is ectopic. In some embodiments of any of the aspects, the HSPCs, engineered endothelial niche cells, and/or transcription factors (e.g., ETV2, FLI1, ETS1, SOX18, SOX7, RXRA, or NR2F2) described herein is not endogenous.

The term "exogenous" refers to a substance present in a cell other than its native source. The term "exogenous" when used herein can refer to a nucleic acid (e.g. a nucleic acid encoding a polypeptide) or a polypeptide that has been introduced by a process involving the hand of man into a biological system such as a cell or organism in which it is not normally found and one wishes to introduce the nucleic acid or polypeptide into such a cell or organism. Alternatively, "exogenous" can refer to a nucleic acid or a polypeptide that has been introduced by a process involving the hand of man into a biological system such as a cell or organism in which it is found in relatively low amounts and one wishes to increase the amount of the nucleic acid or polypeptide in the cell or organism, e.g., to create ectopic expression or levels. In contrast, the term "endogenous" refers to a substance that is native to the biological system or cell. As used herein, "ectopic" refers to a substance that is found in an unusual location and/or amount. An ectopic substance can be one that is normally found in a given cell, but at a much lower amount and/or at a different time. Ectopic also includes substance, such as a polypeptide or nucleic acid that is not naturally found or expressed in a given cell in its natural environment.

In some embodiments, a nucleic acid encoding a polypeptide as described herein (e.g. a ETV2, FLI1, ETS1, SOX18, SOX7, RXRA, or NR2F2 polypeptide) is comprised by a vector. In some of the aspects described herein, a nucleic acid sequence encoding a given polypeptide as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

In some embodiments of any of the aspects, the vector is recombinant, e.g., it comprises sequences originating from at least two different sources. In some embodiments of any of the aspects, the vector comprises sequences originating from at least two different species. In some embodiments of any of the aspects, the vector comprises sequences originating from at least two different genes, e.g., it comprises a fusion protein or a nucleic acid encoding an expression product which is operably linked to at least one non-native (e.g., heterologous) genetic control element (e.g., a promoter, suppressor, activator, enhancer, response element, or the like).

In some embodiments of any of the aspects, the vector or nucleic acid described herein is codon-optimized, e.g., the native or wild-type sequence of the nucleic acid sequence has been altered or engineered to include alternative codons such that altered or engineered nucleic acid encodes the same polypeptide expression product as the native/wild-type sequence, but will be transcribed and/or translated at an improved efficiency in a desired expression system. In some embodiments of any of the aspects, the expression system is an organism other than the source of the native/wild-type sequence (or a cell obtained from such organism). In some embodiments of any of the aspects, the vector and/or nucleic acid sequence described herein is codon-optimized for expression in a mammal or mammalian cell, e.g., a mouse, a murine cell, or a human cell. In some embodiments of any of the aspects, the vector and/or nucleic acid sequence described herein is codon-optimized for expression in a human cell. In some embodiments of any of the aspects, the vector and/or nucleic acid sequence described herein is codon-optimized for expression in a yeast or yeast cell. In some embodiments of any of the aspects, the vector and/or nucleic acid sequence described herein is codon-optimized for expression in a bacterial cell. In some embodiments of any of the aspects, the vector and/or nucleic acid sequence described herein is codon-optimized for expression in an *E. coli* cell.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification.

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art.

It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. myelofibrosis or a myeloproliferative disorder. The term "treating" includes reducing or alleviating at least one adverse effect or symptom of a condition, disease or disorder associated with myelofibrosis or a myeloproliferative disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject. In some embodiments, administration comprises physical human activity, e.g., an injection, act of ingestion, an act of application, and/or manipulation of a delivery device or machine. Such activity can be performed, e.g., by a medical professional and/or the subject being treated.

As used herein, "contacting" refers to any suitable means for delivering, or exposing, an agent to at least one cell. Exemplary delivery methods include, but are not limited to, direct delivery to cell culture medium, perfusion, injection, or other delivery method well known to one skilled in the art. In some embodiments, contacting comprises physical human activity, e.g., an injection; an act of dispensing, mixing, and/or decanting; and/or manipulation of a delivery device or machine.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean ±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, the term "corresponding to" refers to an amino acid or nucleotide at the enumerated position in a first polypeptide or nucleic acid, or an amino acid or nucleotide that is equivalent to an enumerated amino acid or nucleotide in a second polypeptide or nucleic acid. Equivalent enumerated amino acids or nucleotides can be determined by alignment of candidate sequences using degree of homology programs known in the art, e.g., BLAST.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeck, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method to generate/engineer endothelial niche cells, comprising expressing one or more transcription factors in an endothelial cell, wherein the one or more transcription factors are from the Ets family, the Sox family, and/or the Nuclear Hormone Receptor family.
2. The method of any one of the above paragraphs, wherein the endothelial niche cells express one are more genes comprising; sele, exoc312a, snx8a, cltca, aqp7, ap1b1, lgmn, prcp, cldn11a, lyve1b, adra1d, hya12a, hya12b, tll1, i113ra2, glu1a, hexb, slc16a9a, or sepp1a.
3. The method of any one of the above paragraphs, wherein the endothelial cells are human.
4. The method of any one of the above paragraphs, wherein the transcription factors comprises at least one of the human transcription factors ETV2, FLI1, ETS1, SOX18, SOX7, RXRA, or NR2F2.
5. The method of any one of the above paragraphs, wherein the transcription factor includes at least one transcription factor from the Ets family, at least one transcription factor from the Sox family, and at least one transcription factor from the Nuclear Hormone Receptor family.
6. The method of any one of the above paragraphs, wherein the transcription factors include ETV2, FLI1, ETS1, SOX18, SOX7, RXRA, and NR2F2.
7. The method of any one of the above paragraphs, wherein the transcription factors are expressed from at least one vector.
8. The method of any one of the above paragraphs, wherein the vector comprises an exogenous nucleic acid sequence(s) encoding the one or more transcription factors.
9. The method of any one of the above paragraphs, wherein the exogenous nucleic acid sequences are incorporated into the genome of the endothelial cell.
10. An engineered endothelial niche cell comprising one or more exogenous nucleic acid sequences encoding one or more transcription factors, wherein the one or more transcription factors are from the Ets family, the Sox family and/or the Nuclear Hormone Family.
11. A composition comprising the engineered endothelial niche cells of paragraph 10.
12. The composition of any one of the above paragraphs, wherein the composition is a therapeutic agent or the composition further comprises a pharmaceutically acceptable carrier.
13. The composition of any one of the above paragraphs, wherein the composition further comprises a culture dish, 3D cell system, or suspension system.
14. The composition of any one of the above paragraphs, wherein the composition comprises a scaffold.
15. A method for culturing HSPCs, the method comprising culturing HSPCs in the presence of a population of engineered endothelial niche cells.

16. The method of any one of the above paragraphs, wherein the method is performed in vitro.
17. The method of any one of the above paragraphs, wherein the engineered endothelial niche cells secrete a factor that affects the growth and/or expansion of the HSPC cells.
18. The method of any one of the above paragraphs, wherein the HSPCs cultured in the presence of the engineered endothelial niche cells can be cultured for at least 3 (e.g., at least 4, at least 5, at least 6, at least 7) days longer than HSPCs that are cultured in the absence of such engineered endothelial niche cells.
19. The method of any one of the above paragraphs, wherein the cells are cultured on a biologically compatible scaffold.
20. The method of any one of the above paragraphs, wherein the HSPCs cultured in the presence of the engineered endothelial niche cells have increased engraftment when administered to a subject compared to the engraftment of substantially similar HSPCs that were not cultured with engineered endothelial niche cells.
21. A method of treating a subject, the method comprising, transplanting a composition comprising HSPCs and a population of engineered endothelial niche-cells into the subject.
22. A method for enhancing engraftment of HSPCs, the method comprising administering a composition comprising HSPCs and a population of engineered endothelial niche cells to a subject in need thereof.
23. The method of any one of the above paragraphs, wherein engraftment of the HSPCs is increased by at least 10% compared to the engraftment of substantially similar HSPCs in the absence of engineered endothelial niche cells.
24. A co-culture comprising engineered endothelial niche cells and HSPCs.
25. The co-culture of paragraph 24 wherein the endothelial cells are made by the method of any one of the above paragraphs.
26. A kit for culturing HSPCs, the kit comprising: a population of engineered endothelial niche cells, reagents and instructions for use thereof.
27. A kit for generating engineered endothelial niche cells comprising: a vector(s) comprising one or more exogenous nucleic acid sequences encoding one or more transcription factors of the Ets family, the Sox family or the nuclear hormone family and instructions for use thereof.
28. A method for generating an ectopic vascular niche, the method comprising: administering an engineered endothelial niche cell to a target site in a subject in need thereof.
29. A method for extra medullary hematopoiesis, the method comprising transplanting engineered-niche endothelial cells into a subject at a location outside of the bone marrow (e.g., the forearm), thereby creating a synthetic niche.
30. The method of any one of the above paragraphs, wherein the endothelial cells are made by any of the methods in the above paragraphs.
31. A vector comprising one or more exogenous nucleic acid sequences encoding one or more transcription factors of the Ets family, the Sox family or the nuclear hormone family operably linked to a promoter.

EXAMPLES

Example 1

Transcription Factor Induction of Vascular Blood Stem Cell Niches In Vivo.

The haematopoietic niche is a supportive in vivo microenvironment comprised of distinct cell types, including specialized vascular endothelial cells that directly interact with haematopoietic stem and progenitor cells (HSPCs) to facilitate stem cell function. The molecular factors that specify niche endothelial cells and their pro-haematopoietic activity remain largely unknown. Using multi-dimensional gene expression analyses and a chromatin accessibility assay, defined herein is a conserved gene expression signature and cis-regulatory landscape unique to sinusoidal endothelial cells in the HSPC niche. Using enhancer mutagenesis and transcription factor overexpression, a transcriptional code was elucidated involving members of the Ets, Sox and Nuclear Hormone Receptor families that is sufficient to induce ectopic niche endothelial cells that recruit HSPCs and support their homeostasis in vivo. Together, these studies have important implications for generating more efficient synthetic vascular niches for blood stem cells or for modulating the niche in a therapeutic context.

Results

An Endothelial Gene Expression Signature Unique to the Fetal HSPC Niche.

Figure 1B:
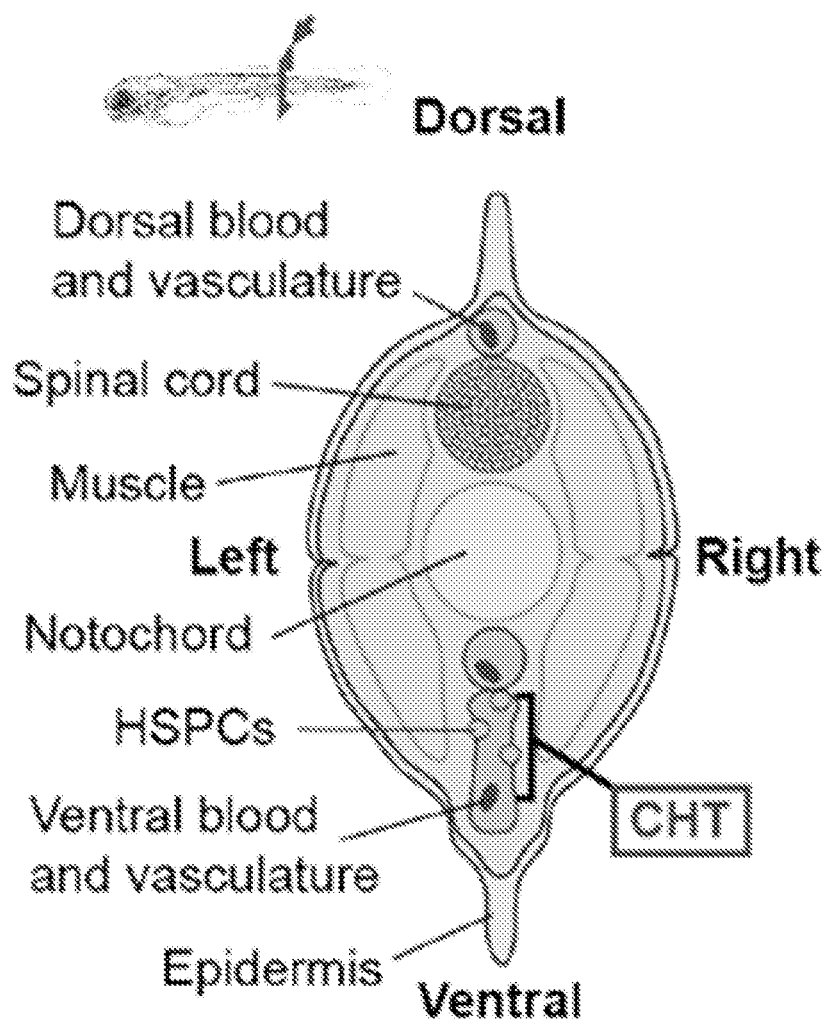
Figure 1C:
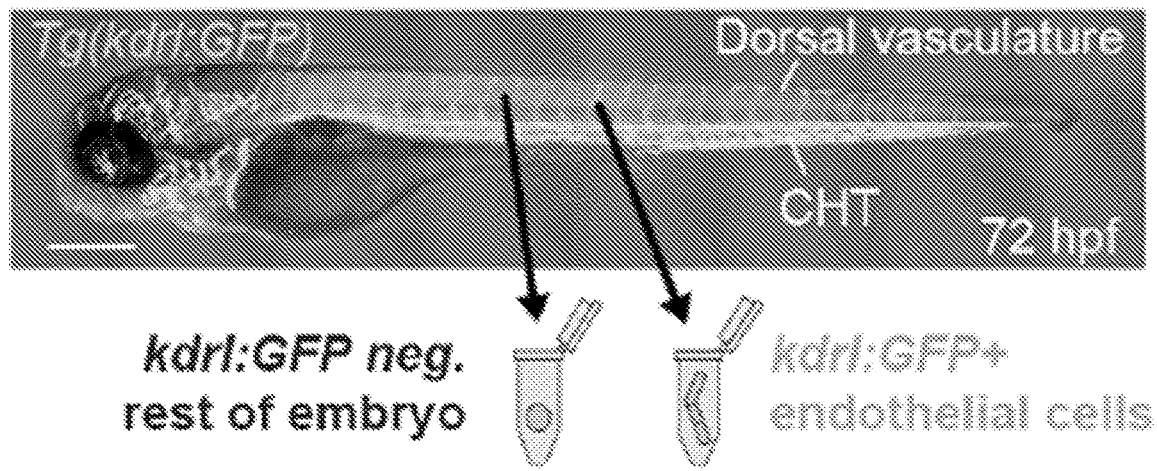
Figure 1D:
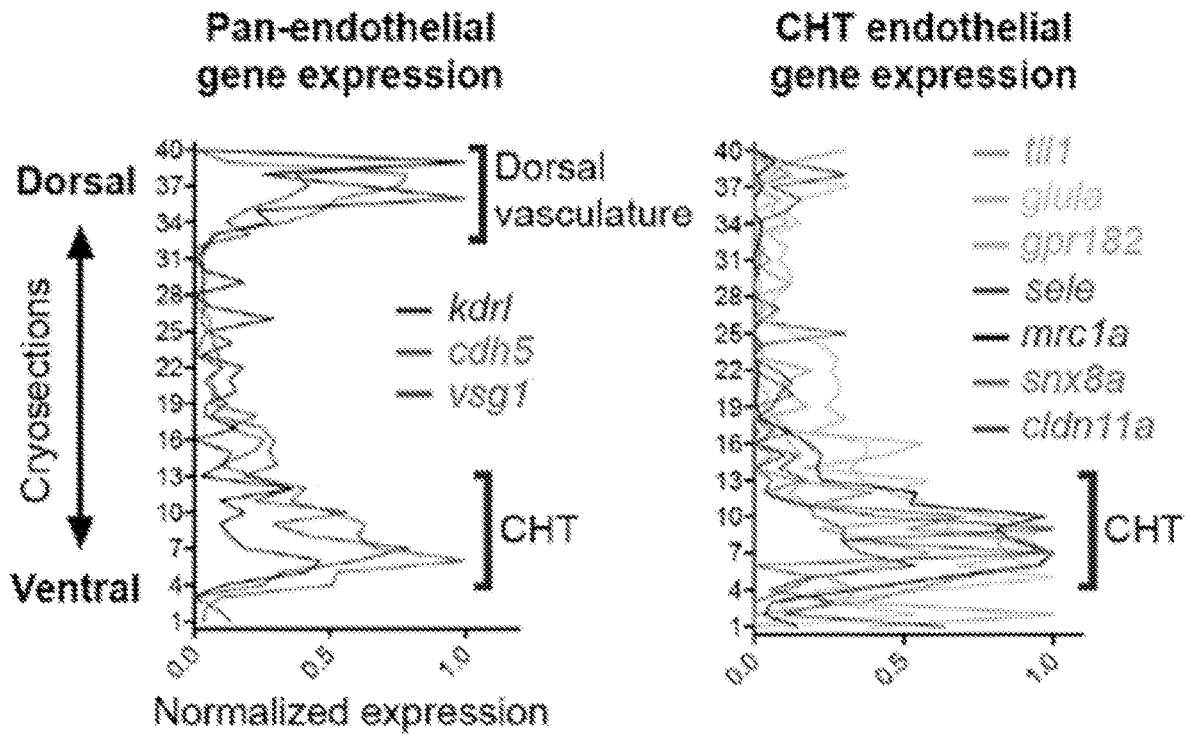
Figure 1E:
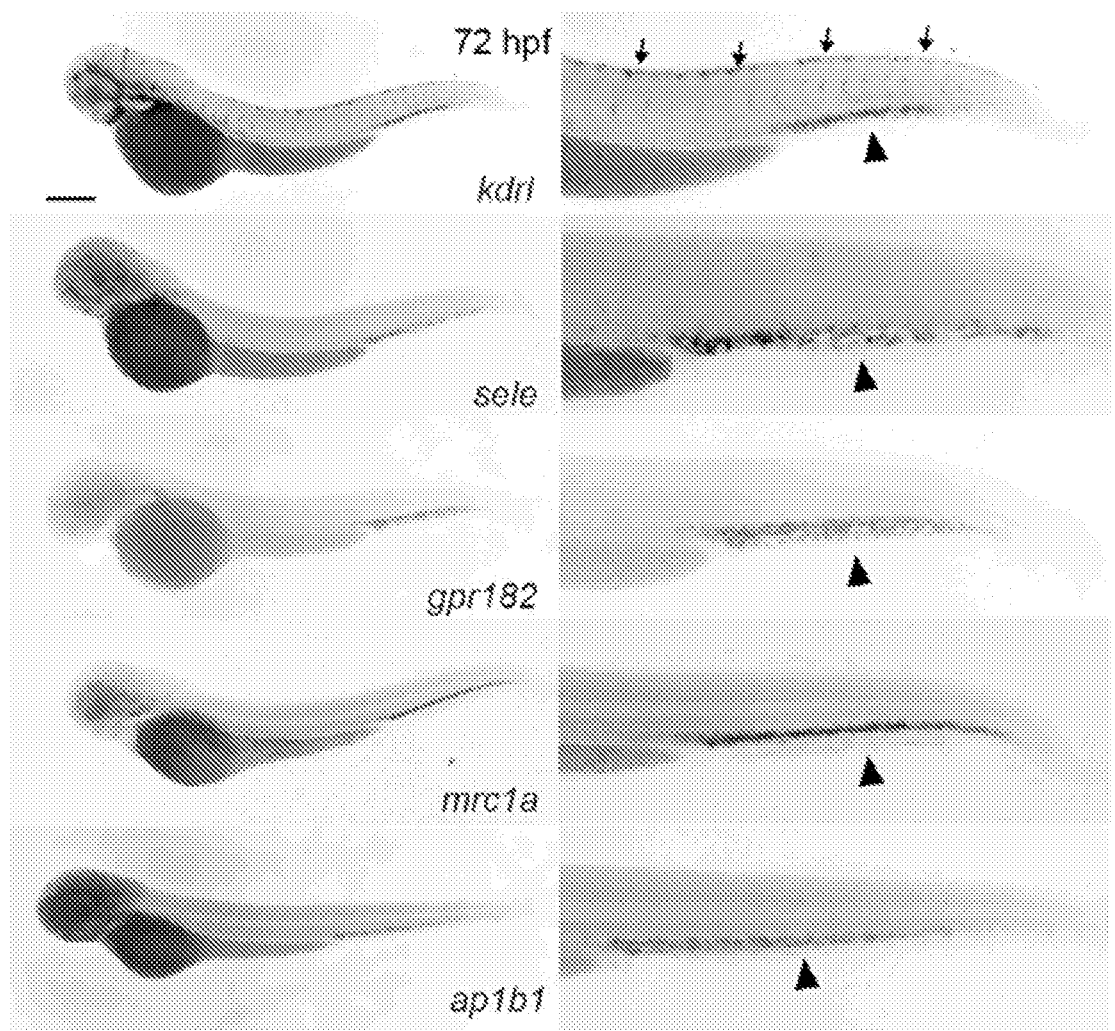
Figure 7A:
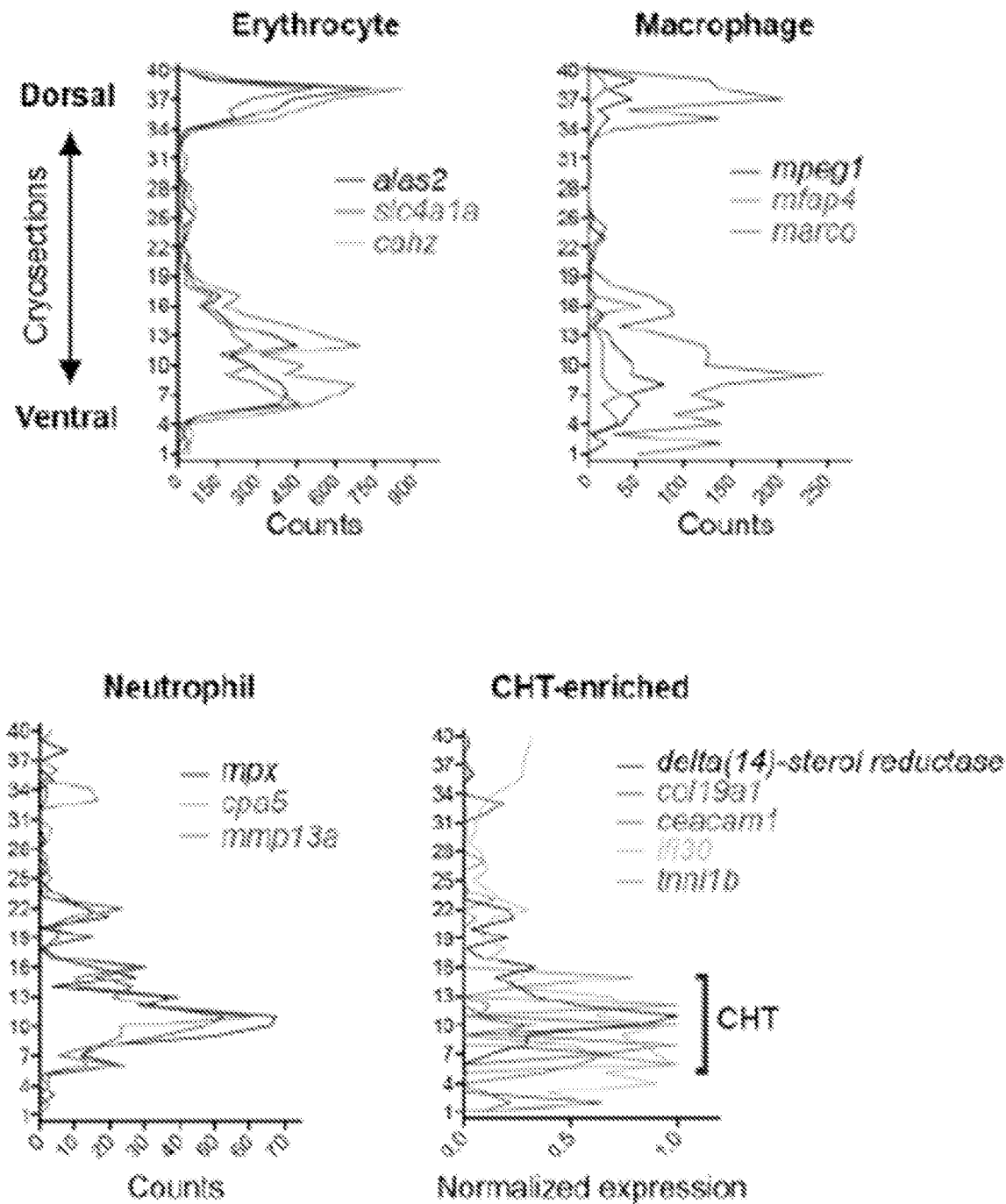
FIG. 7A-FIG. 7B is a series of images and graphs showing RNA tomography and niche-specific endothelial gene expression.
Figure 7B:
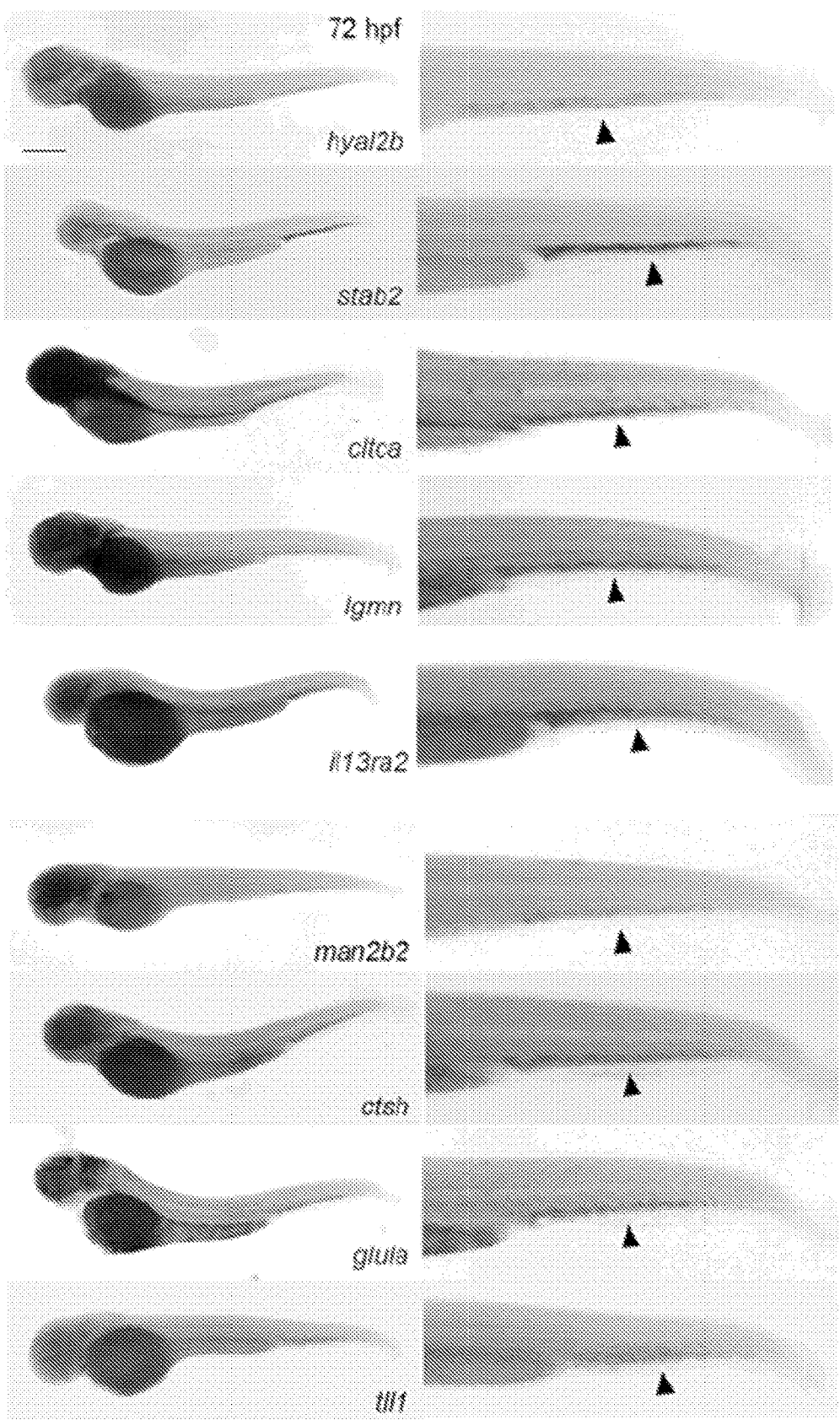
Figure 8A:
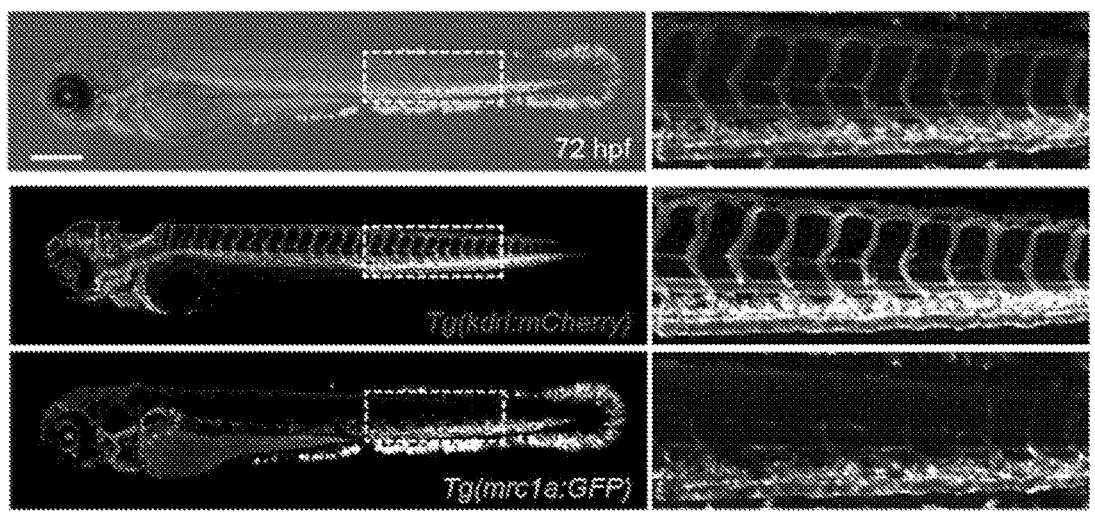
FIG. 8A-FIG. 8E is a series of images and graphs showing that GFP reporter transgenes selectively label ECs in the HSPC niche.
Figure 8B:
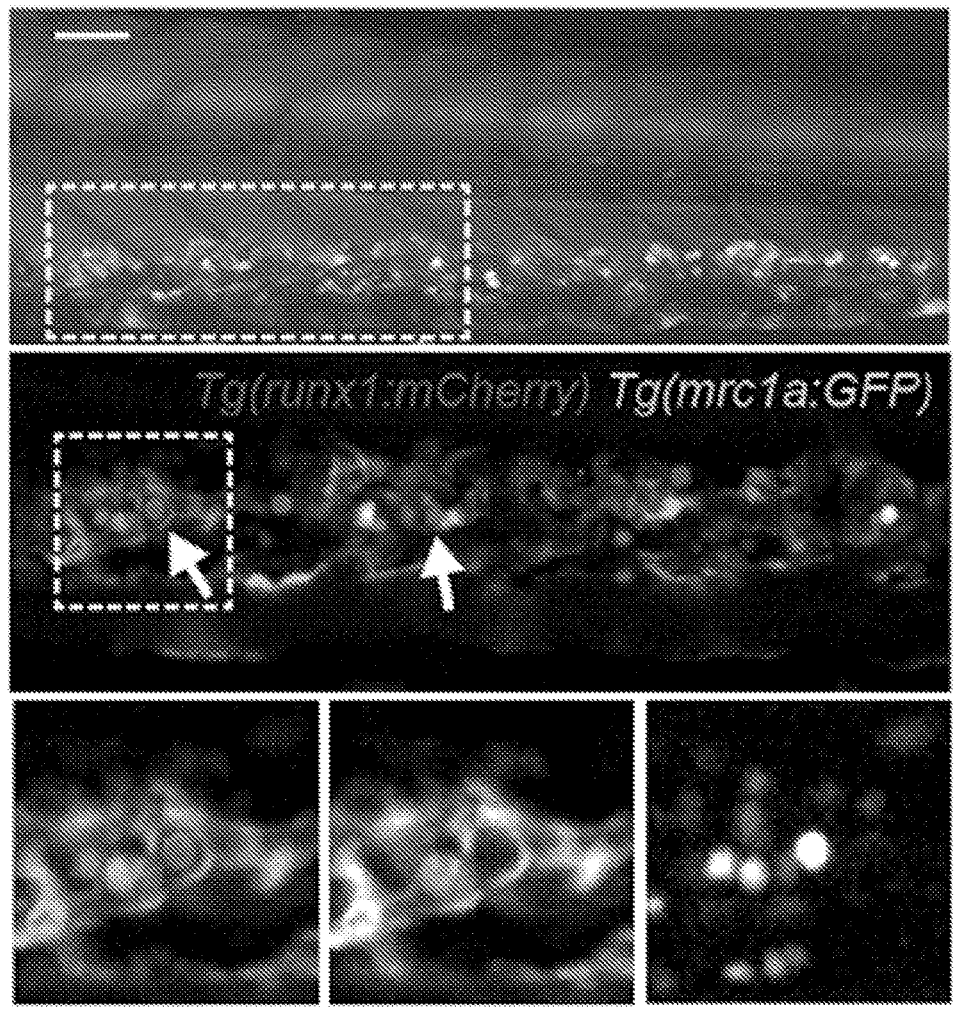
Figure 8C:
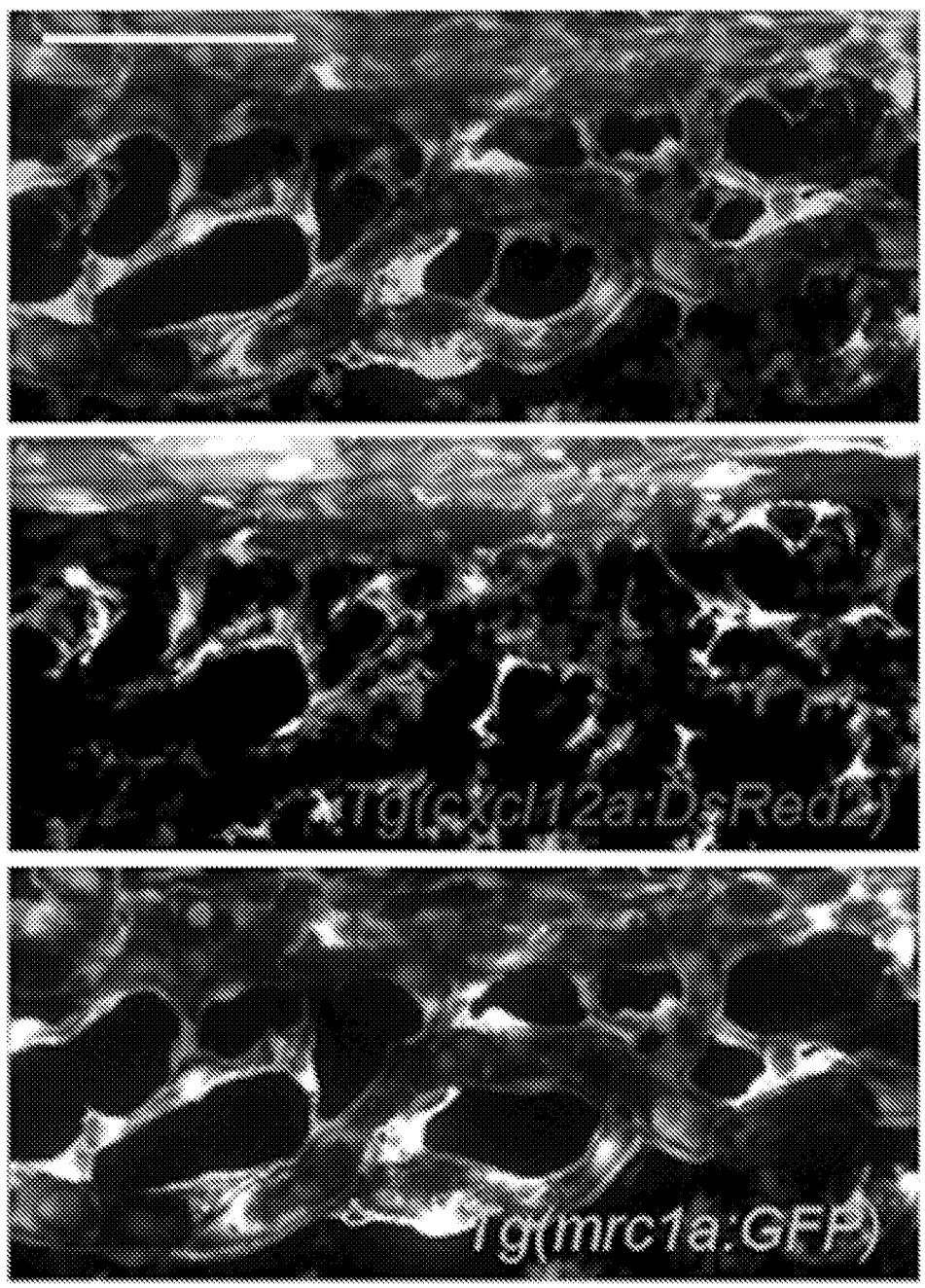
Figure 8D:
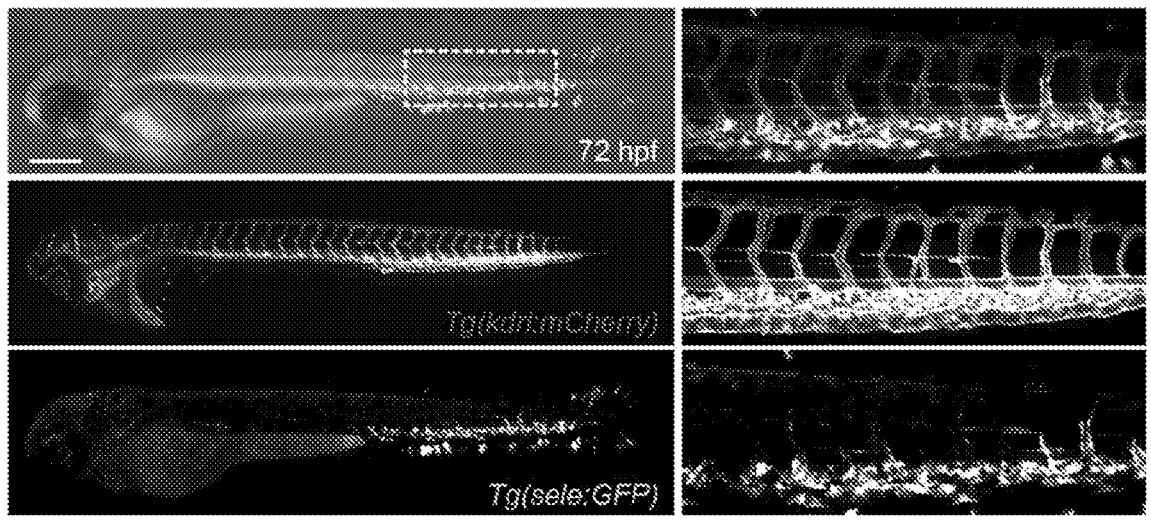
Figure 8E:
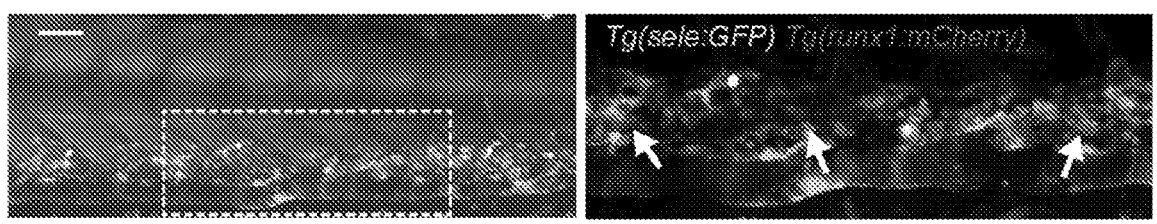

ECs from different organs express distinct genes, but whether this is regulated by organ-specific transcriptional programs remains poorly understood. To investigate the regulation of gene expression in the CHT niche, RNA tomography (tomo-seq) was performed on the zebrafish tail at 72 hours post fertilization (hpf; see e.g., FIG. 1A). This tomo-seq analysis revealed clusters of gene expression corresponding to specific tissues along the dorsal-ventral axis of the tail, including spinal cord, notochord, muscle and epidermis, as well as specific blood and immune cell populations (see e.g., FIG. 1B, FIG. 7A, FIG. 7B). In total, 144 genes displayed enriched expression within the few cryosections spanning the CHT (see e.g., Table 3). Using whole mount in situ hybridization (WISH), CHT expression of 35 of these genes was confirmed (see e.g., Table 3; images available on the world wide web at zfin.org). To determine whether any of the 144 genes were expressed by ECs, the pan-endothelial transgene kdrl:GFP and fluorescence activated cell sorting (FACS) was used to isolate ECs for bulk and single cell RNA-seq (see e.g., FIG. 1C). In addition, these genes were cross-referenced with macrophage and neutrophil RNA-seq datasets (see e.g., Theodore et al. Distinct Roles for Matrix Metalloproteinases 2 and 9 in Embryonic Hematopoietic Stem Cell Emergence, Migration, and Niche Colonization. Stem cell reports 8, 1226-1241, 2017). Twenty-nine genes were identified that were selectively enriched in CHT ECs (see e.g., Table 1). In contrast to pan-endothelial genes, the tomo-seq expression traces for these CHT endothelial genes lacked the strong peak corresponding to expression in dorsal vasculature (see e.g., FIG. 1D). For 25 out of 29 genes the CHT EC-enriched expression was confirmed by WISH (see e.g., FIG. 1E, FIG. 7A, FIG. 7B, and Table 1).

To selectively isolate CHT ECs, transgenic lines were designed to label these cells. 1.3 or 5.3 kb upstream regulatory sequences were cloned for two CHT endothelial genes, mrc1a and sele to generate GFP reporter transgenes that were then crossed to the pan-endothelial marker kdrl:mCherry. For both the mrc1a:GFP and sele:GFP transgenes, the highest levels of expression were observed in the venous sinusoids of the CHT, while low levels of GFP expression were detected in the posterior cardinal vein above the yolk extension and in a small number of vessels in the head (see e.g., FIG. 8A-FIG. 8E). Although GFP expression was also observed in mesenchymal cells in the outer tail fin, these cells are a frequent site of ectopic transgene expression and do not represent the endogenous expression of these genes. Notably, robust GFP expression was observed in sinusoidal ECs that directly interacted with HSPCs, confirming that the mrc1a:GFP and sele:GFP transgenes labeled ECs in the HSPC niche (see e.g., FIG. 8A-FIG. 8E). These GFP$^+$ ECs closely associated with cxcl12a:DsRed2$^+$ stromal cells and were observed to form pockets around HSPCs—a cellular behavior characteristic of ECs in the CHT niche (see e.g., FIG. 8A-FIG. 8E).

Endothelial Niche-Specific Cis-Regulatory Elements.

Figure 2A:
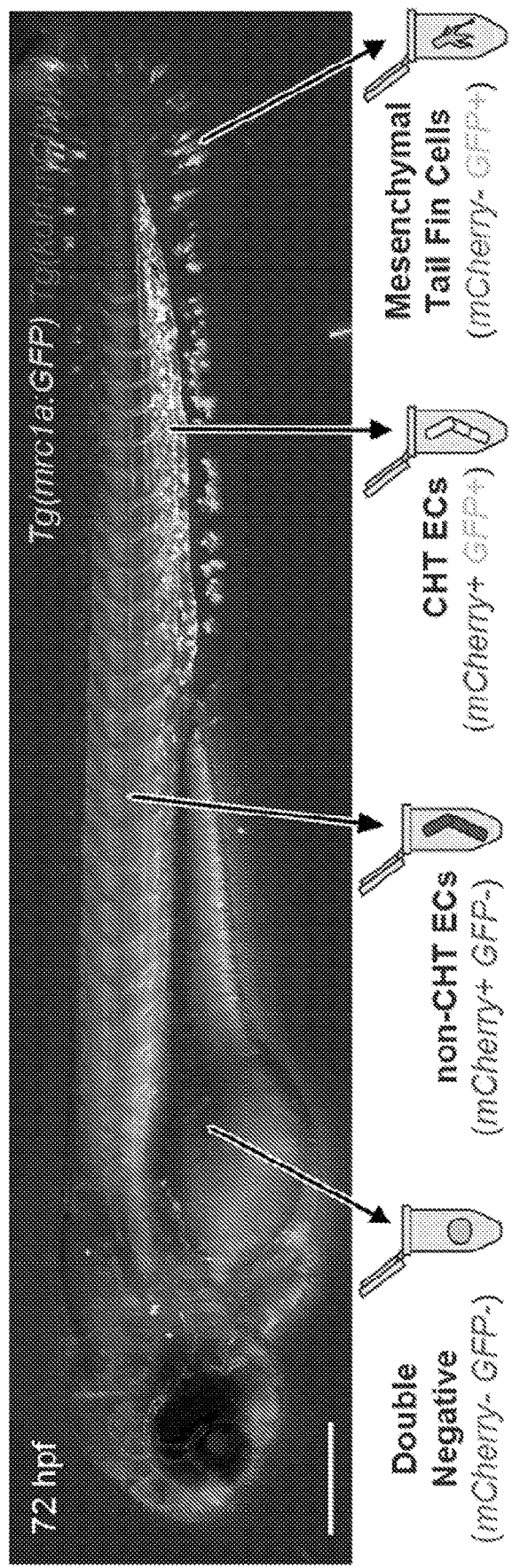
FIG. 2A-FIG. 2C is a series of images and graphs showing endothelial niche-specific cis-regulatory elements.
Figure 2B:
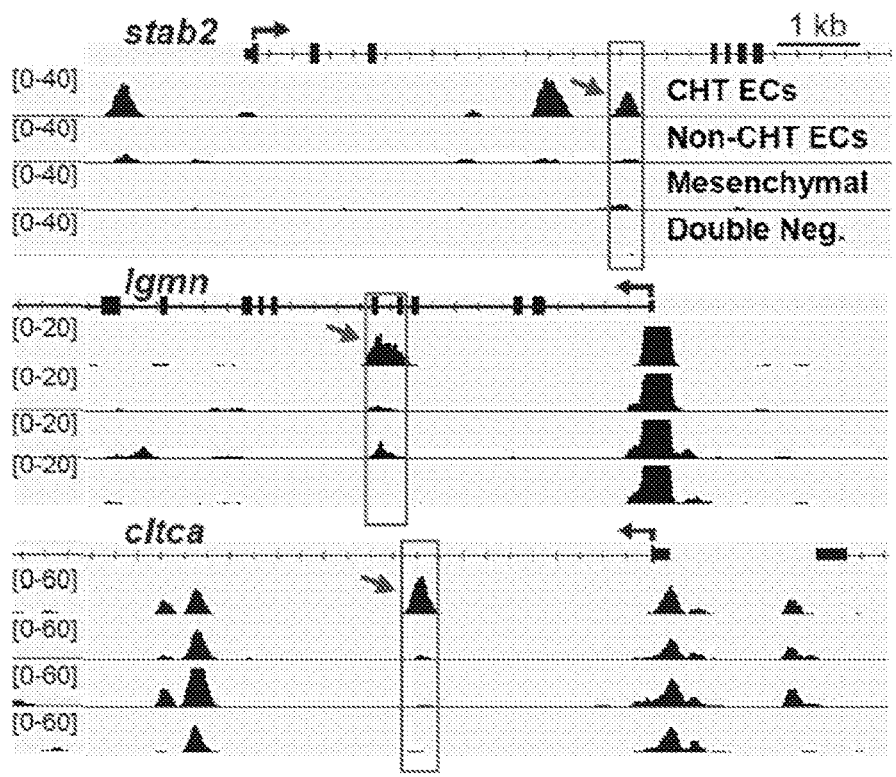
Figure 2C:
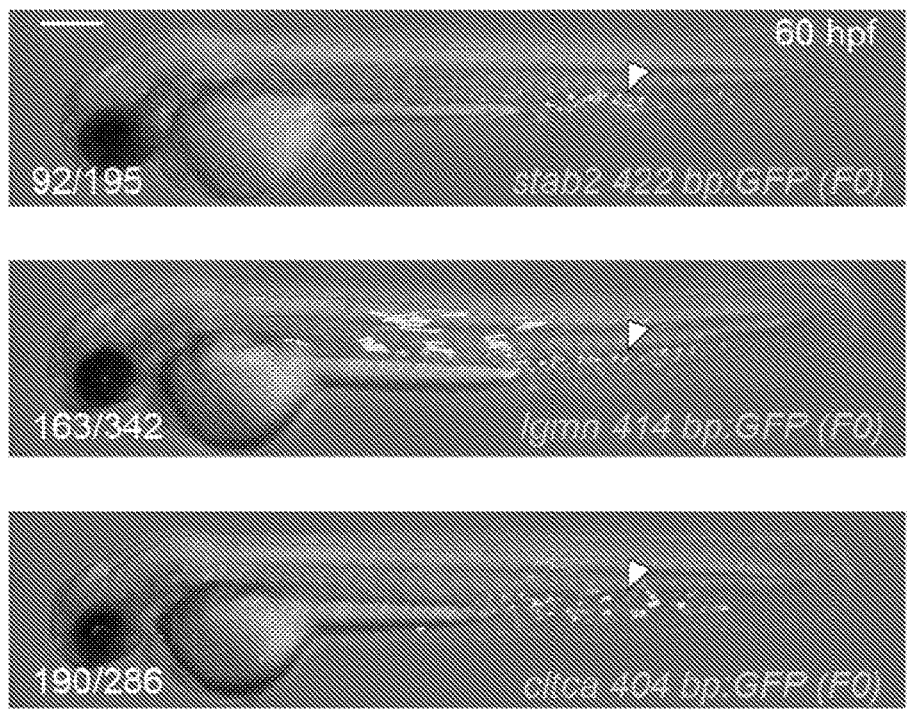
Figure 9A:
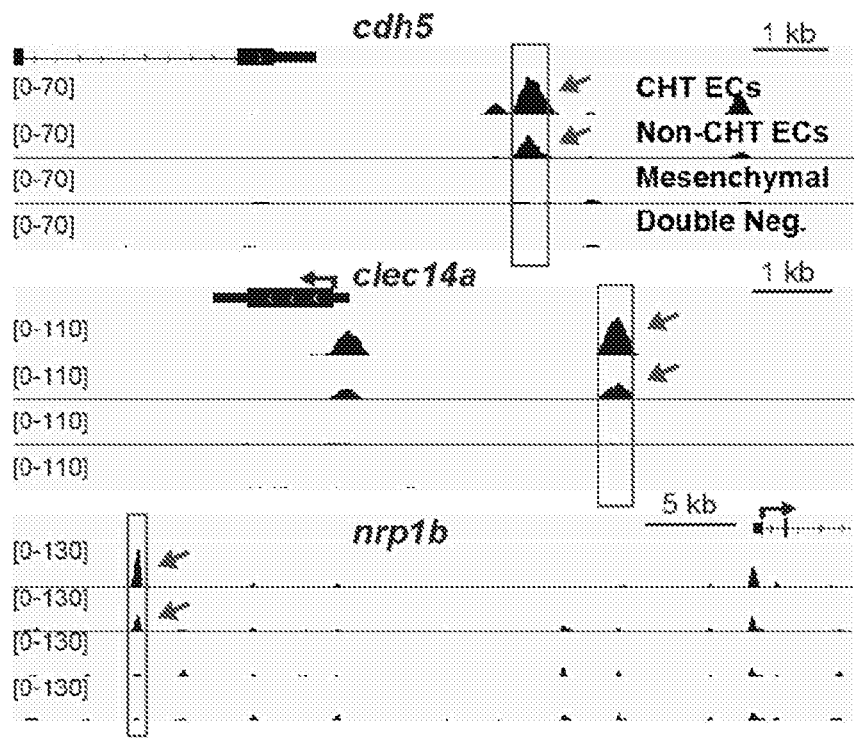
Figure 9B:
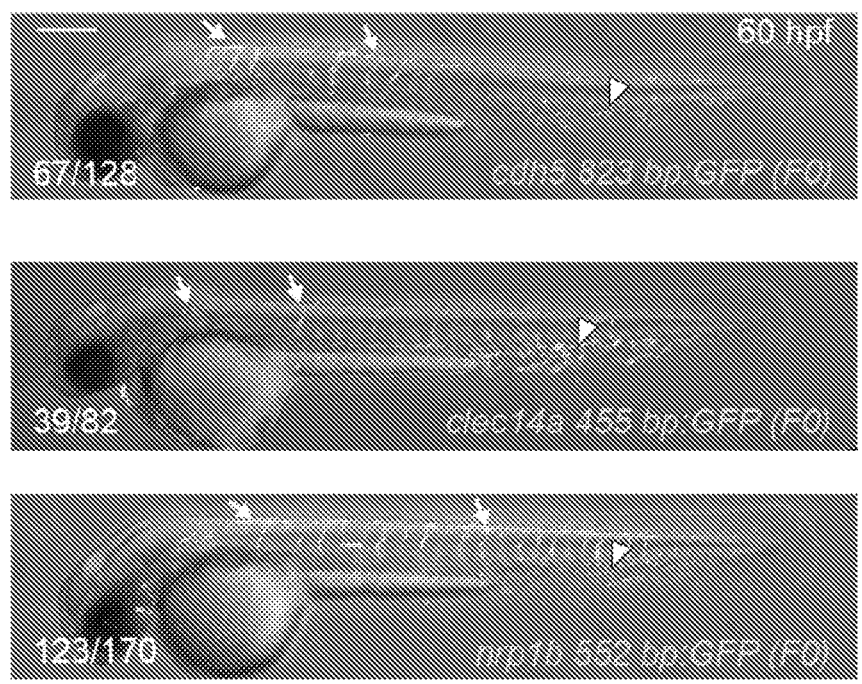
Figure 10A:
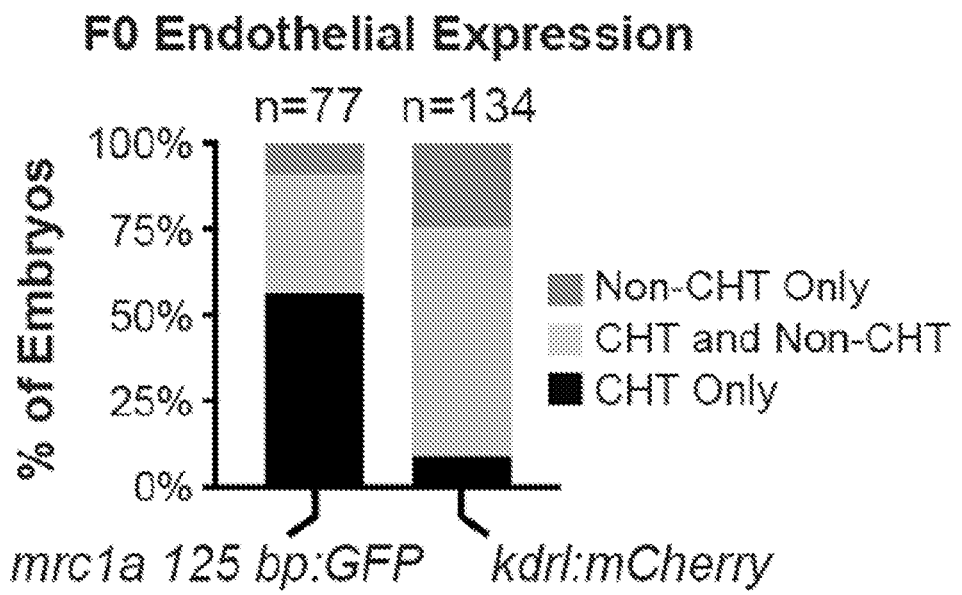
FIG. 10A-FIG. 10E is a series of images and graphs showing CHT endothelial cis-regulatory elements.
Figure 10B:
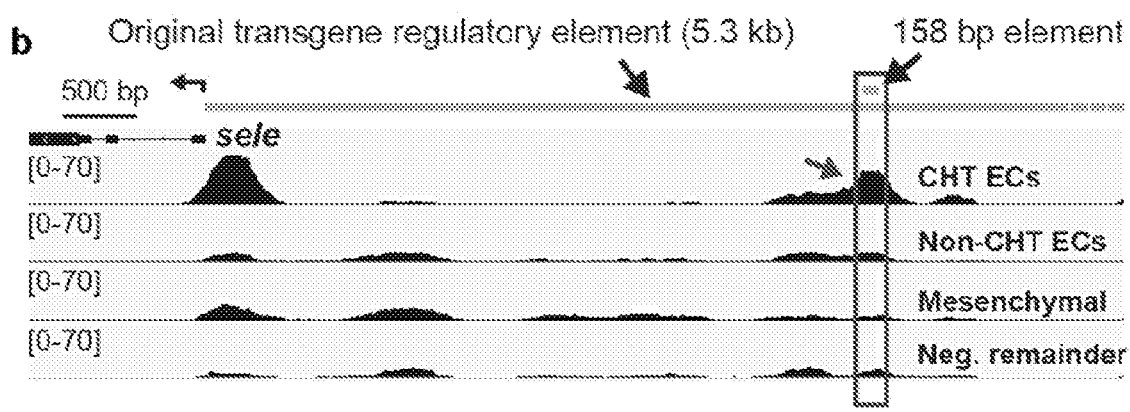
Figure 10C:
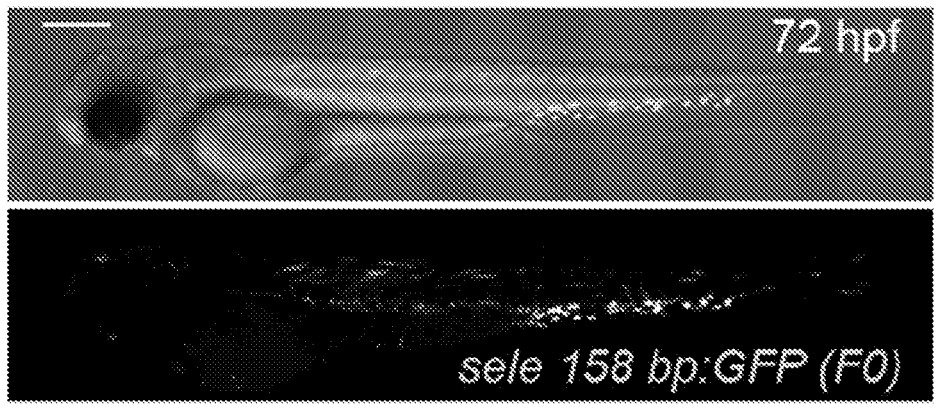
Figure 10C:
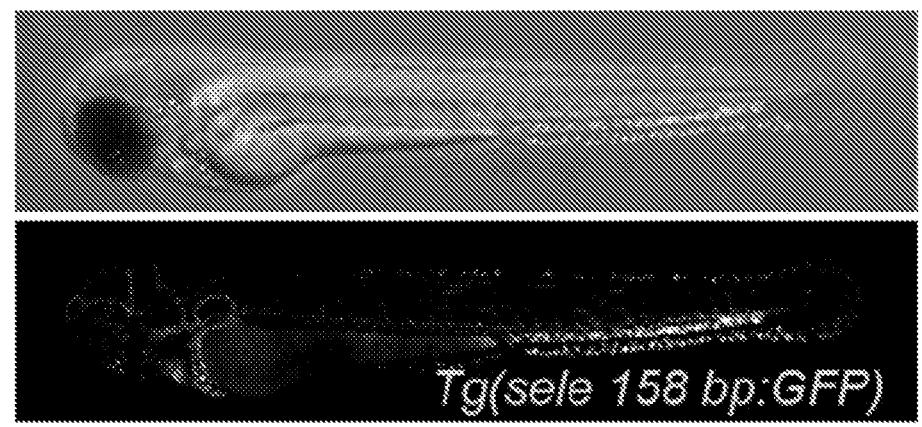
Figure 10D:
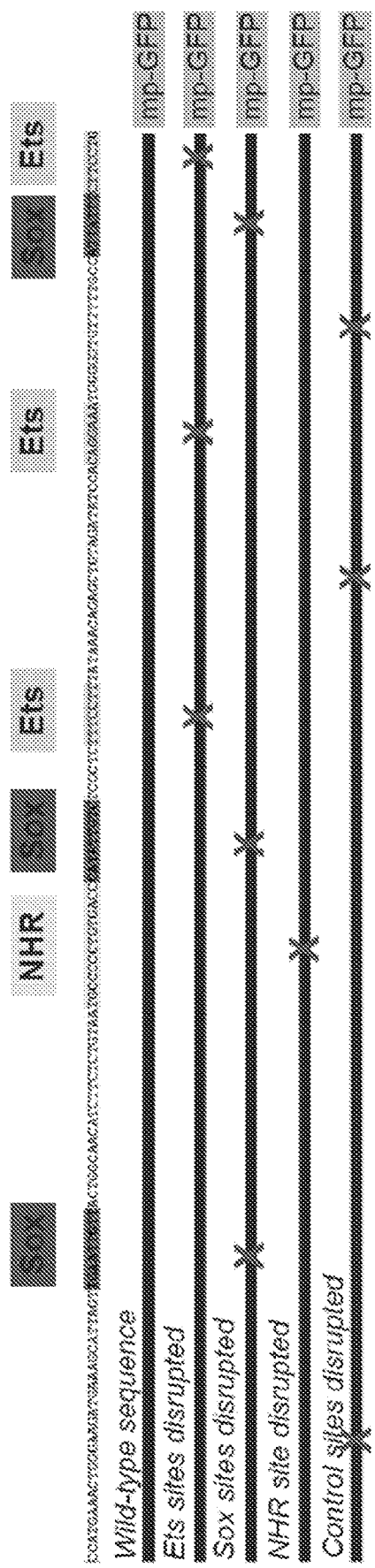
Figure 10E:
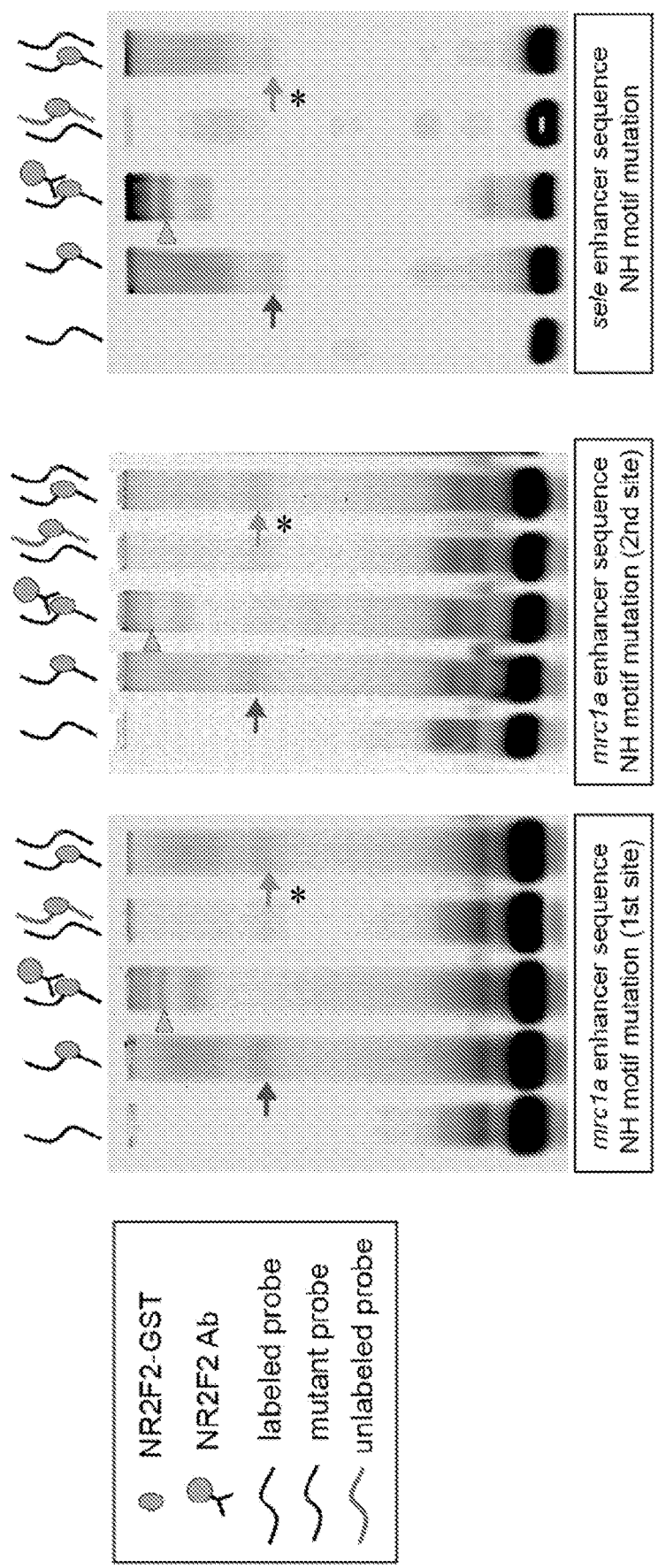
Figure 11A:
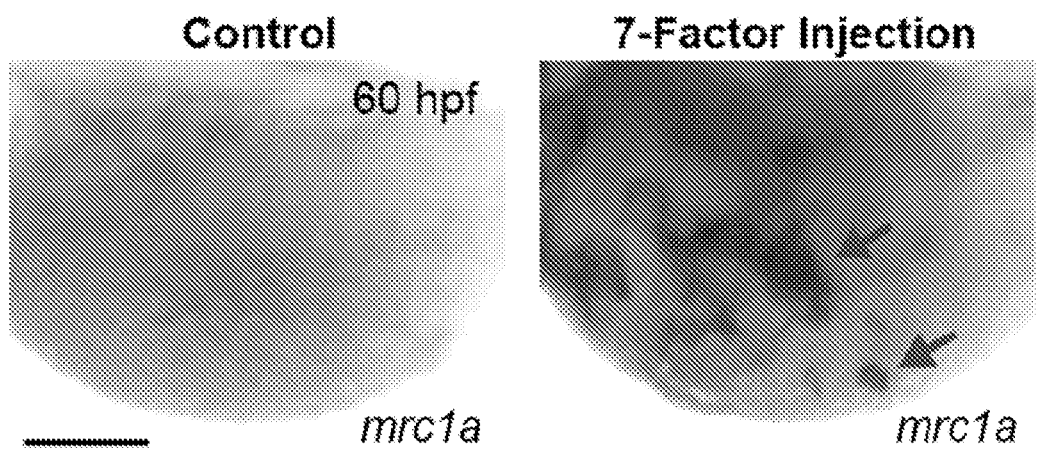
FIG. 11A-FIG. 11C is a series of images and graphs showing that transcription factor overexpression induces ectopic CHT endothelial program.
Figure 11B:
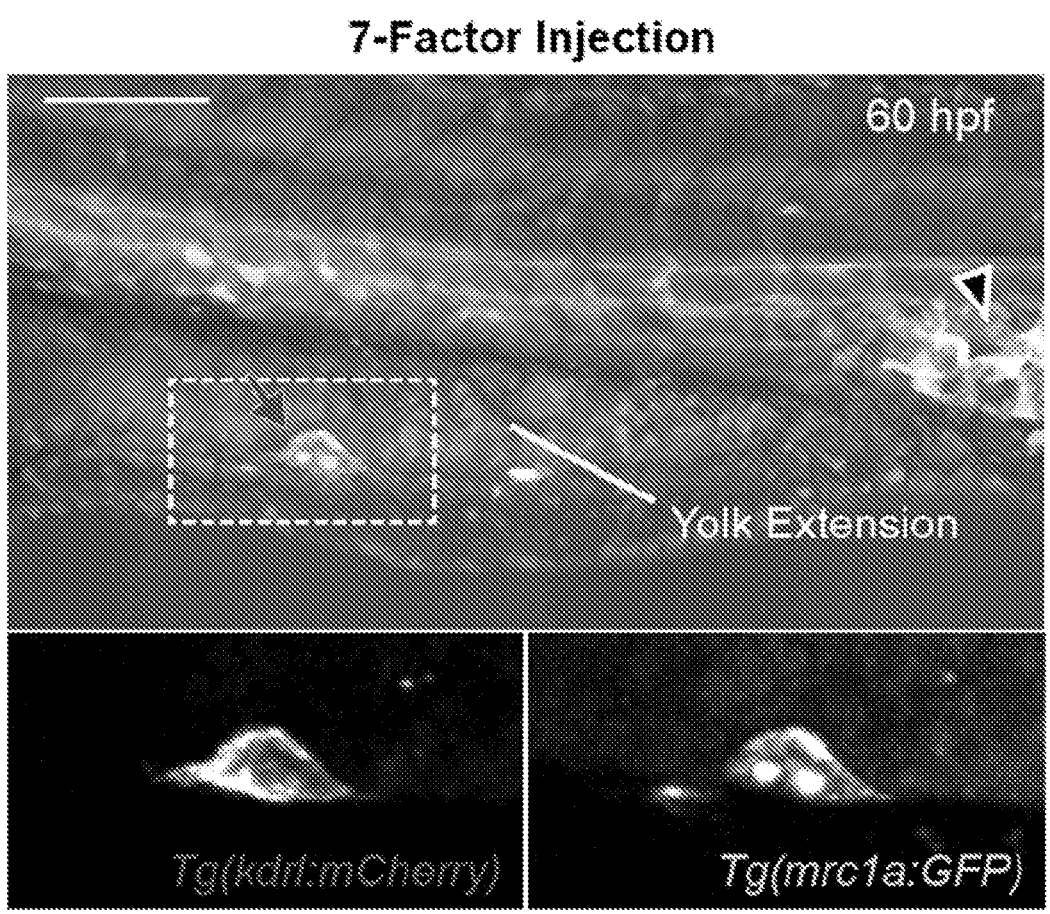
Figure 11C:
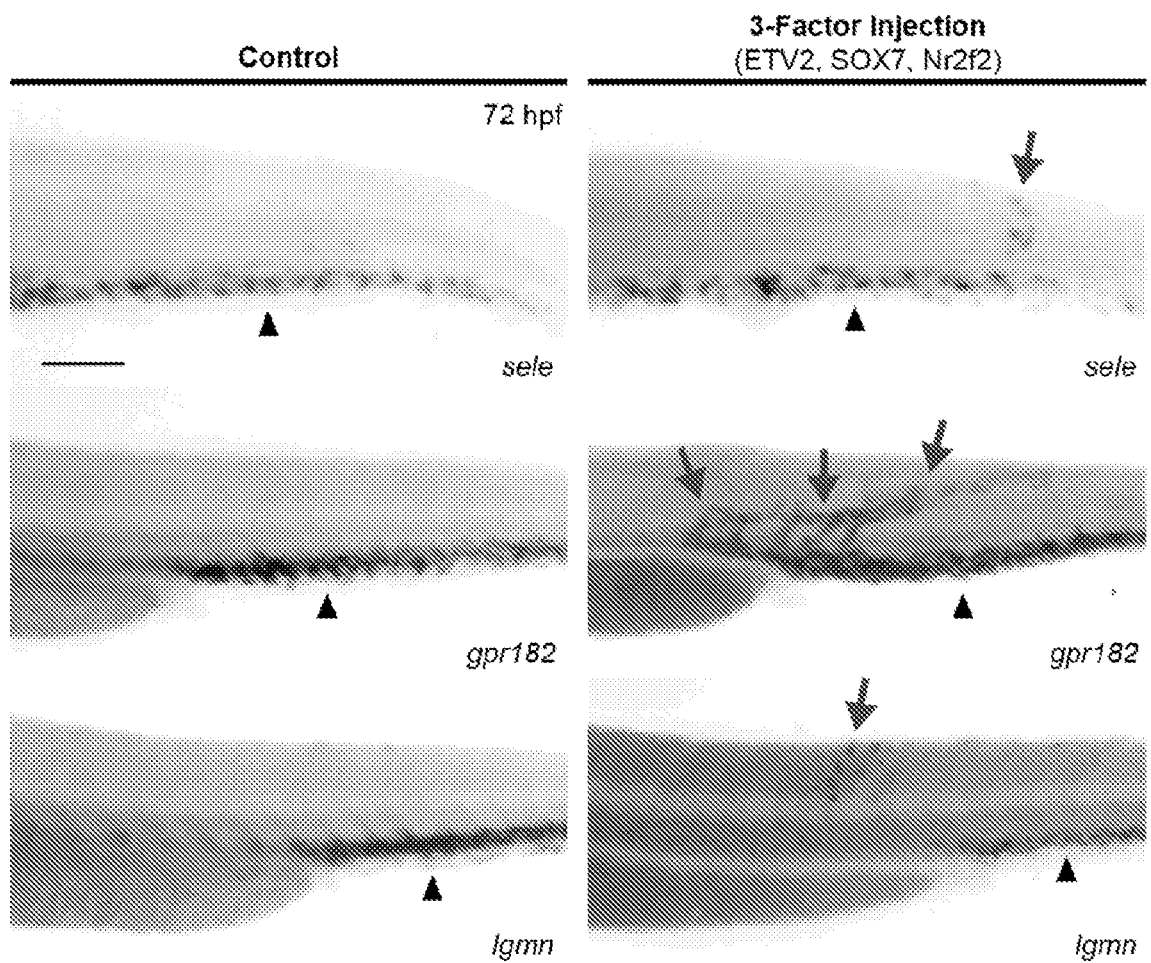

To investigate the transcriptional control of niche-specific gene expression within CHT ECs, double positive mrc1a: GFP/kdrl:mCherry embryos were dissociated and FACS was used to isolate four different populations for RNA-seq and ATAC-seq analyses: GFP$^+$/mCherry$^+$ (CHT ECs), GFP$^-$/mCherry$^+$ (ECs outside the CHT), GFP$^+$/mCherry$^-$ (mesenchymal cells in the tail fin), and GFP$^-$/mCherry$^+$ (negative remainder of the embryo; see e.g., FIG. 2A). By comparing regions of chromatin accessibility across the four populations, 6,848 regions uniquely open were identified in CHT ECs. Of the 29 CHT EC genes, 26 out of 29 had an ATAC-seq element within 100 kb of the transcriptional start site that was found only in CHT ECs (see e.g., FIG. 2B, Table 1). To test whether these regions might be tissue-specific enhancers, the sequences were cloned for 15 of the elements, which were then fused to a minimal promoter and GFP, and then injected into zebrafish embryos. 12 out of 15 constructs showed GFP expression enriched in CHT ECs at 60-72 hpf (see e.g., FIG. 2C, Table 2). As a control, regions of chromatin were cloned, which were predicted to contain pan-endothelial regulatory elements based on proximity to previously annotated vascular-specific genes and their accessibility in both the CHT and non-CHT EC fractions (see e.g., FIG. 9A-FIG. 9C, Table 2). A number of these regions were previously shown to contain endothelial enhancers (see e.g., Quillien et al. Robust Identification of Developmentally Active Endothelial Enhancers in Zebrafish Using FANS-Assisted ATAC-Seq. Cell reports 20, 709-720, 2017). For 6 out of 6 pan-endothelial regions, mosaic GFP expression in ECs were observed throughout the embryo that was not restricted to the CHT (see e.g., FIG. 9A-FIG. 9C). Thus, the zebrafish system was able to rapidly validate, in vivo, niche-specific endothelial enhancers predicted by ATAC-seq analysis.

Transcription Factor Binding Sites for Niche Endothelial Expression.

To identify transcription factors that might bind the CHT EC enhancers, a motif enrichment analysis was performed on the 6,848 regions of chromatin that were uniquely accessible in CHT ECs. This analysis revealed that Ets, Sox (SoxF factors, specifically) and Nuclear Hormone Receptor (NR2F2/RORA/RXRA factors, specifically, abbreviated hereafter as NHR) binding motifs were most enriched in the 6,848 regions (see e.g., FIG. 9A-FIG. 9C). In contrast, there were 4,522 pan-endothelial elements (i.e., regions of chromatin accessible in both CHT and non-CHT ECs) across the genome enriched for Ets sites, but not SoxF or NHR binding motifs (see e.g., FIG. 9A-FIG. 9C). Of note, the 12 CHT-EC elements that drove GFP expression in the in vivo reporter assay all harbored Ets, SoxF and NHR sites, whereas one of the three CHT-EC elements that failed to drive GFP expression and three of the six pan-endothelial regions lacked a NHR binding site (see e.g., Table 2).

To determine a minimal sequence sufficient to drive CHT EC expression, a 125 base pair (bp) sequence upstream of mrc1a and a 158 bp sequence upstream of sele were cloned; these sequences had been included the our original transgenes and corresponded to the strongest ATAC-seq signal in these regions (see e.g., FIG. 3A, FIG. 10A-FIG. 10E). When coupled to a minimal promoter, these elements drove GFP expression in CHT ECs in 44% (125 bp mrc1a sequence; 155 out of 356) and 23% (158 bp sele sequence; 176 out of 775) of injected embryos (see e.g., FIG. 3B, FIG. 10A-FIG. 10E). Compared to injection of a kdrl:mCherry construct, in which mosaic expression was observed in ECs throughout the embryo, expression of the mrc1a and sele enhancer-GFP constructs was restricted to CHT ECs (see e.g., FIG. 3C, FIG. 10A-FIG. 10E). Moreover, when stable transgenic lines were established using these short constructs, GFP was specifically expressed in CHT ECs (see e.g., FIG. 3D, FIG. 10A-FIG. 10E). Mammalian Mrc1 is prominently expressed by macrophages and venous sinusoidal ECs. Zebrafish have two homologous genes, mrc1a and mrc1b. A recent study of mrc1a reported expression in both macrophages and FCs when the promoter was coupled to an intronic enhancer that showed conservation with mrc1b (see e.g., Jung et al. Development of the larval lymphatic system in zebrafish. Development 144, 2070-2081, 2017). The 125 bp enhancer element, in contrast, drove expression specifically in CHT ECs, illustrating the specificity in the enhancers.

Figure 3A:
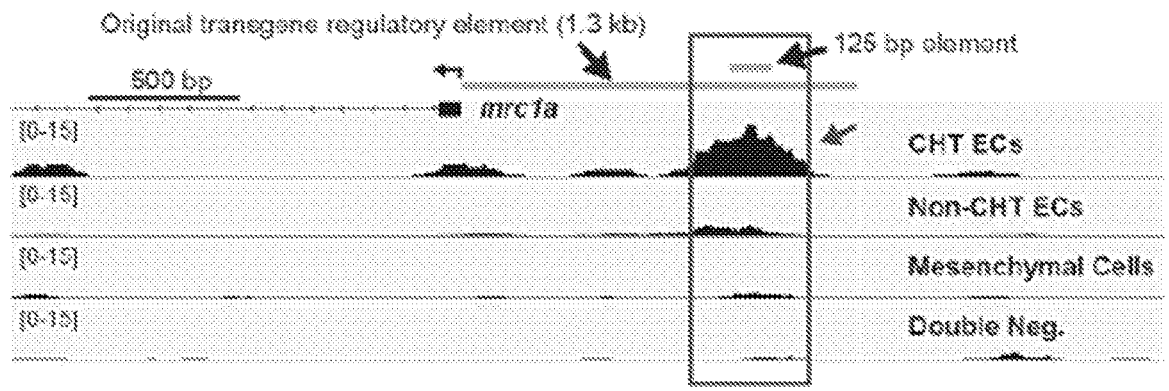
FIG. 3A-FIG. 3F is a series of images and graphs showing that Ets, Sox and NHR binding sites are required for selective expression in niche ECs.
Figure 3B:
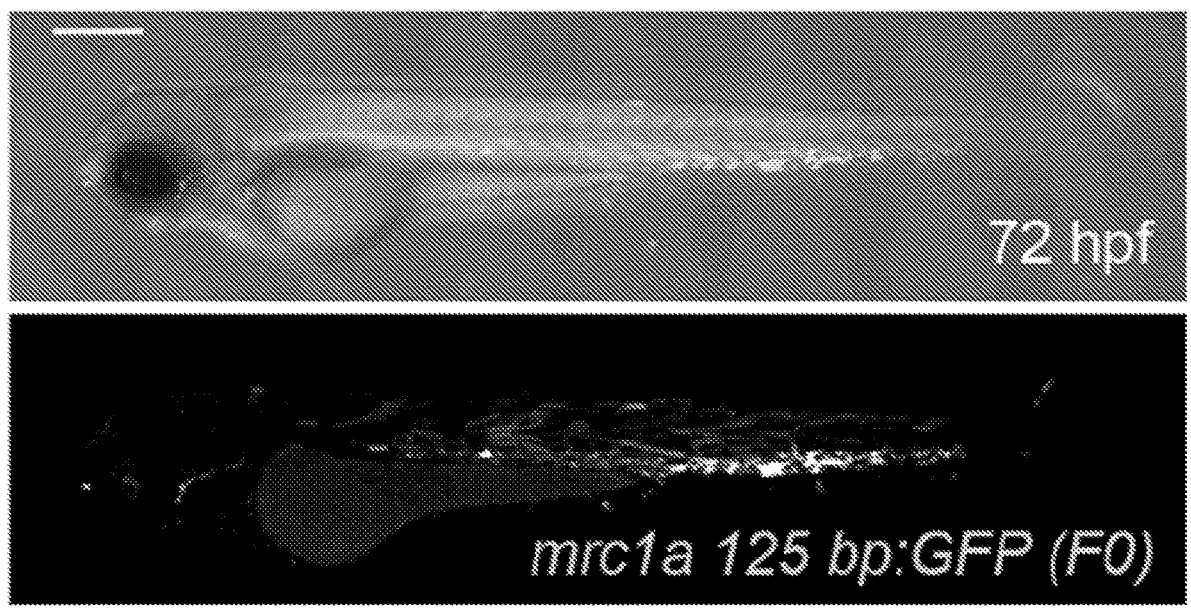
Figure 3C:
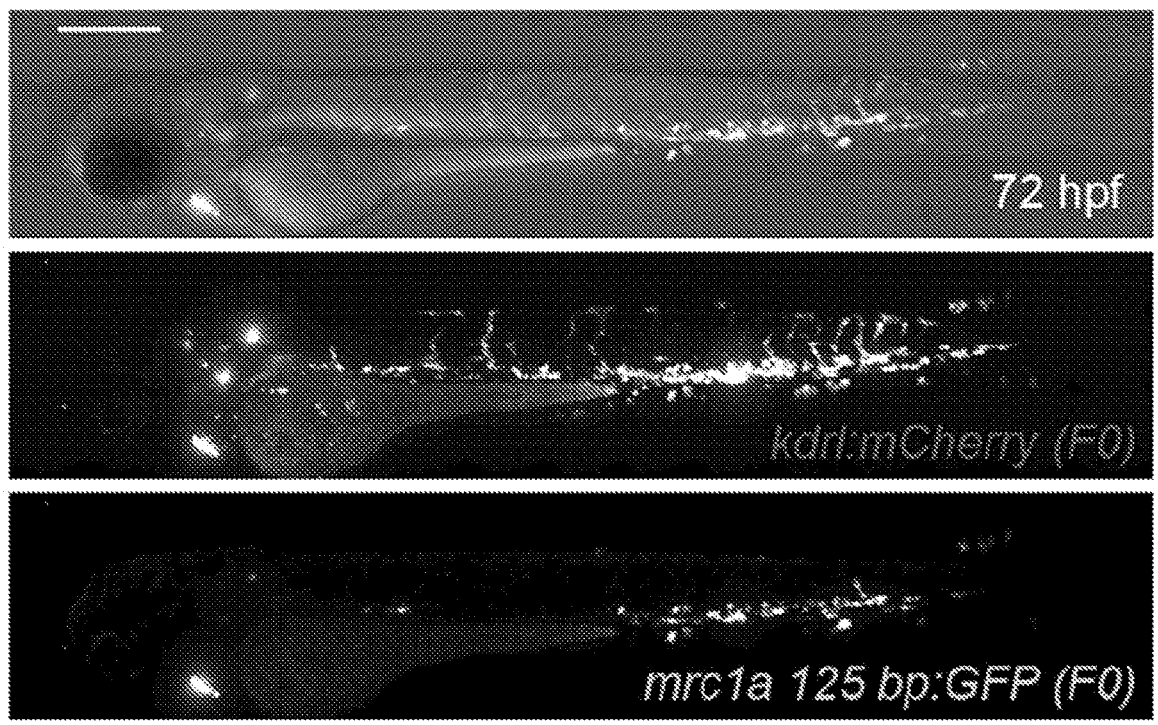
Figure 3D:
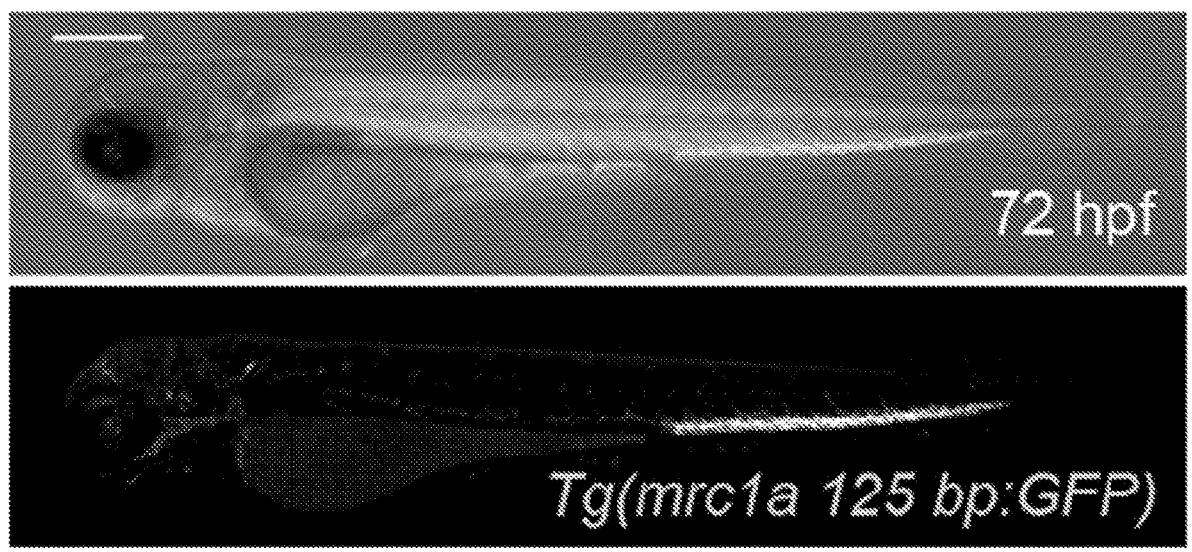
Figure 3E:
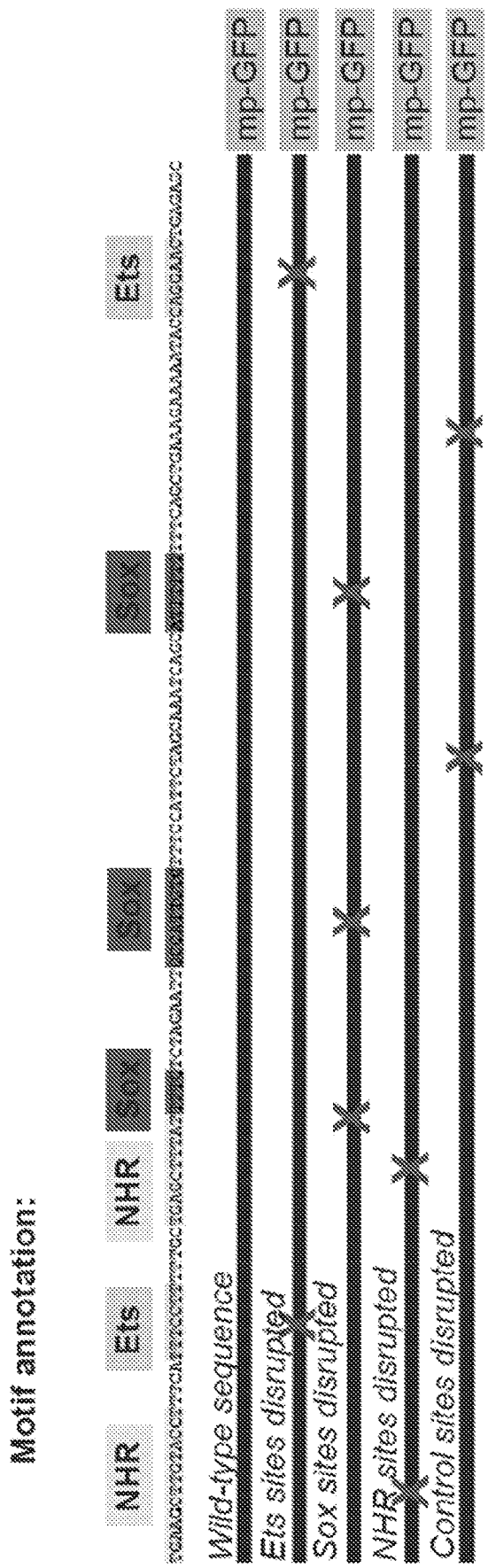
Figure 3F:
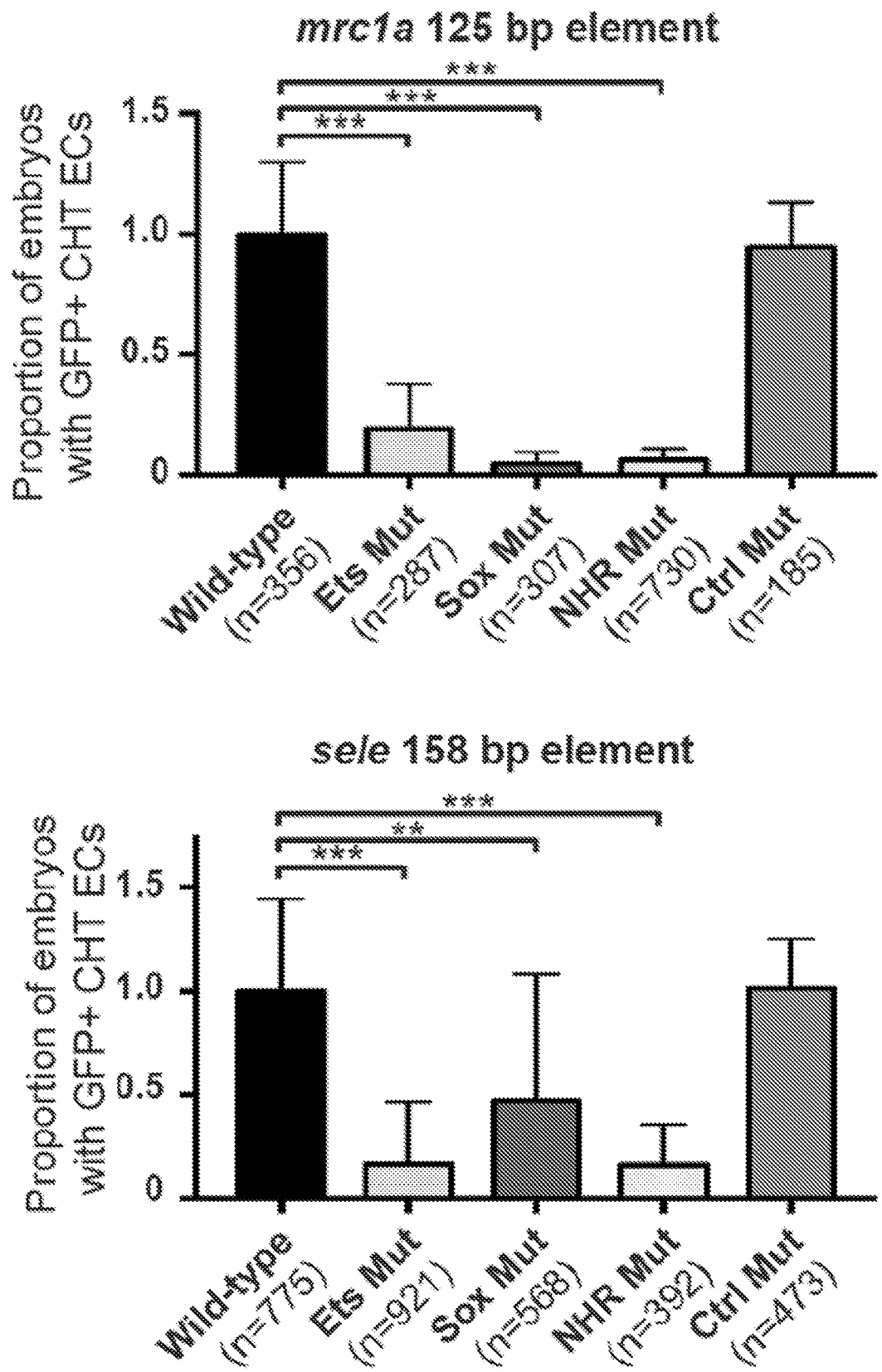

Both the 125 bp mrc1a and 158 bp sele regulatory sequences contained Ets, SoxF and NHR motifs (see e.g., FIG. 3E, FIG. 10A-FIG. 10E). To test whether these transcription factor binding sites were required for expression, variants were generated in which each class of motif was disrupted by mutation. In each case, disruption of the Ets, SoxF or NHR motifs led to a significant reduction or complete loss of GFP expression in CHT ECs (see e.g., FIG. 3F). In control constructs where mutations were targeted to intervening sequences between the Ets, SoxF and NHR motifs, GFP expression was unperturbed (see e.g., FIG. 3F). Studies of arterial-venous specification in zebrafish have shown that the NHR Nr2f2, also known as COUP-TFII, promotes venous endothelial cell fate (see e.g., Aranguren et al. Transcription factor COUP-TFII is indispensable for venous and lymphatic development in zebrafish and Xenopus laevis. Biochemical and biophysical research communications 410, 121-126, 2011). To test whether Nr2f2 could directly bind the enhancer sequences, an in vitro gel electrophoretic mobility shift assay was performed. Incubation of murine NR2F2-GST protein with labeled probe from either the 125 bp mrc1a or 158 bp sele zebrafish enhancers led to DNA:protein complexes that were super-shifted upon addition of an NR2F2 antibody and could be outcompeted by an unlabeled competitor probe (see e.g., FIG. 10A-FIG. 10E). However, unlabeled probes in which the NHR motifs were mutated were unable to outcompete the wild-type probes, demonstrating that NR2F2 binds these NHR motifs in a sequence-specific manner.

Defined Factors Induce Niche Endothelial Expression.

Figure 4A:
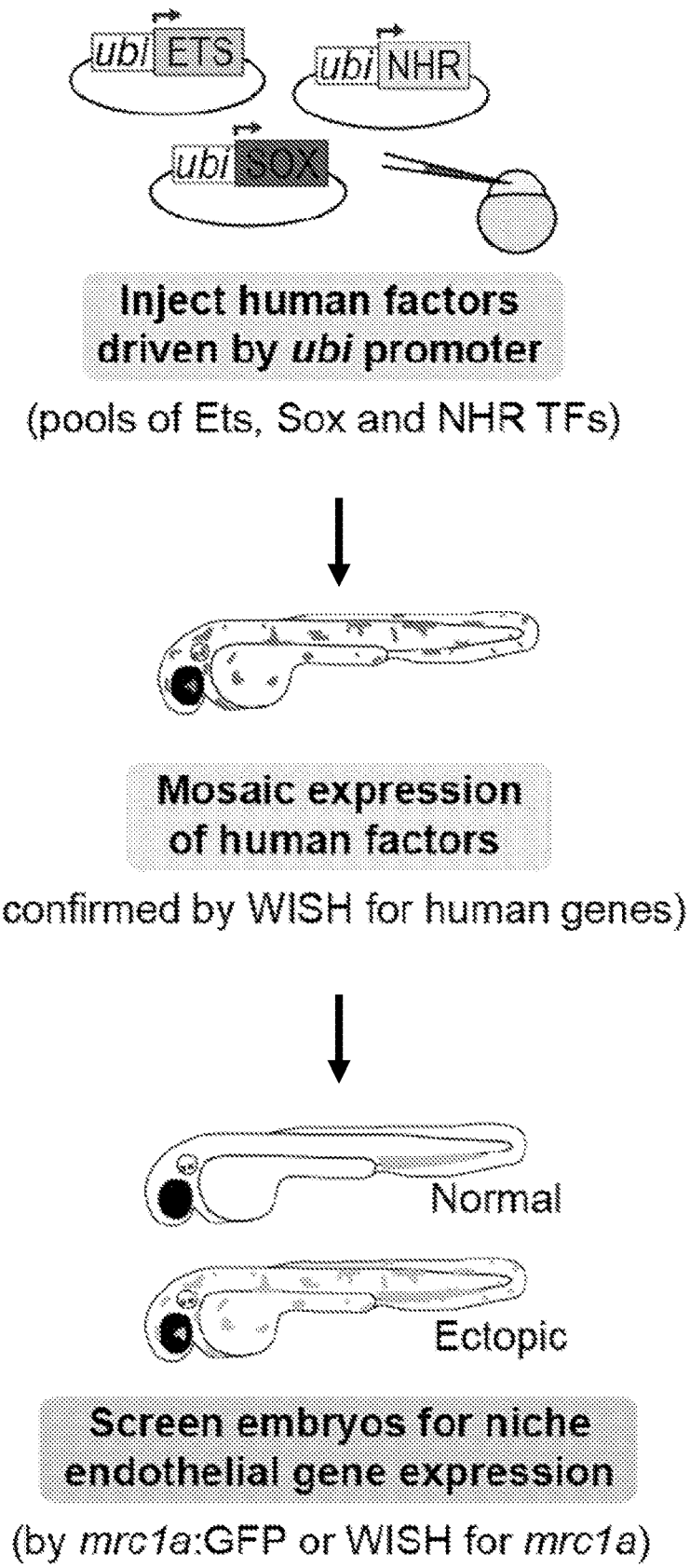
FIG. 4A-FIG. 4F is a series of images and graphs showing that the overexpression of defined factors induces ectopic vascular gene expression outside the CHT.
Figure 4B:
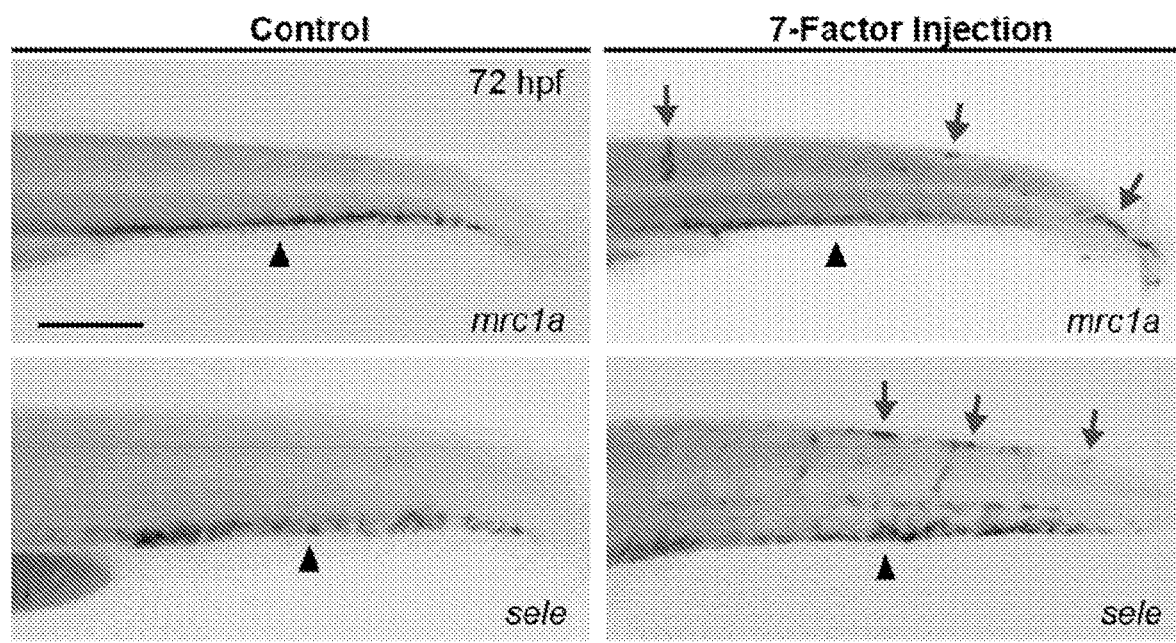
Figure 4C:
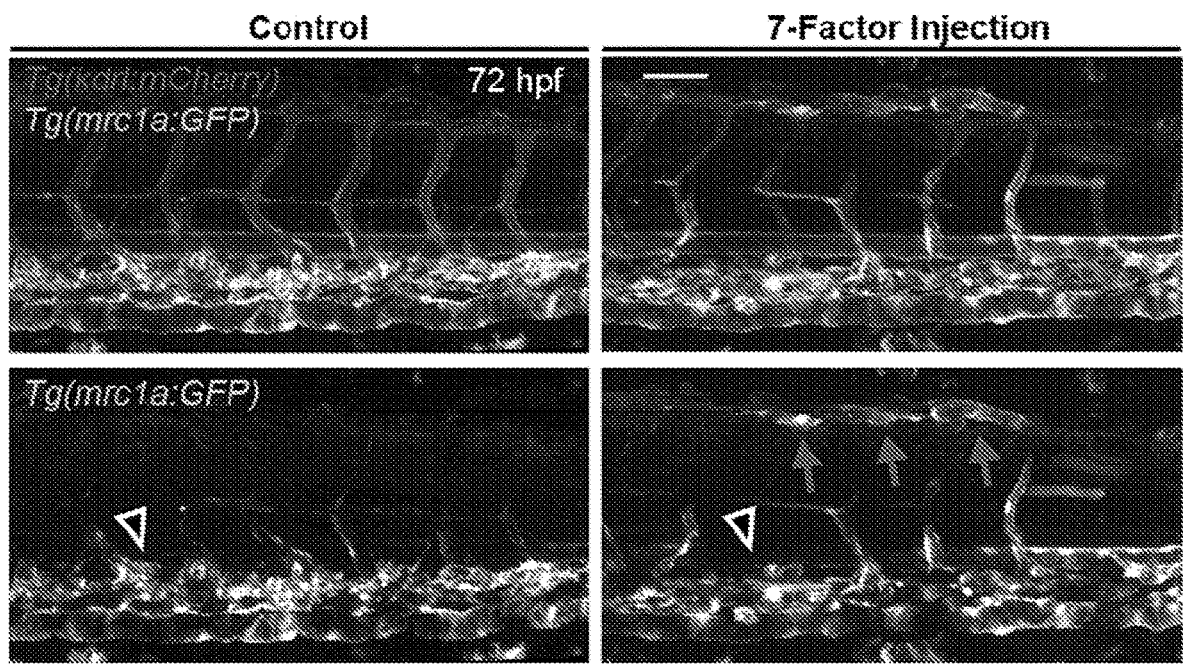

To determine which transcription factors are expressed in CHT ECs and might bind the Ets, Sox and NHR motifs in vivo, RNA-seq data from CHT ECs was examined. The most highly expressed factors were fli1a, etv2, ets1, sox18, sox7, nr2f2 and rxraa (see e.g., Table 4). To test whether these seven factors could induce niche endothelial gene expression outside the CHT, constructs were generated in which the orthologs for each transcription factor was under the control of a ubiquitous (ubi) promoter (see e.g., FIG. 4A). A pool of the seven ubi-driven factors were then injected into one cell-stage zebrafish embryos, and mrc1a and sele expression was examined by WISH at 60-72 hpf. Strikingly, 17% (12 out of 69) of these embryos had ectopic vascular patches of mrc1a expression outside of the CHT, dorsally within the trunk and tail, and over the yolk (see e.g., FIG. 4B, FIG. 11A-FIG. 11C). Control-injected embryos did not show ectopic expression (0 out of 56). Similar results were obtained with WISH for sele or when factors were injected into mrc1a:GFP/kdrl:mCherry double transgenic embryos (see e.g., FIG. 4B-FIG. 4C, FIG. 11A-FIG. 11C). Vessels ectopically expressing mrc1a were often larger than their normal counterparts in these regions and had a sinusoidal-like morphology similar to the CHT (see e.g., FIG. 4C). Using DIC microscopy, blood flow through these regions was readily visualized (data not shown). These data suggest that a small number of transcription factors are sufficient to ectopically induce the niche endothelial gene program.

Figure 4D:
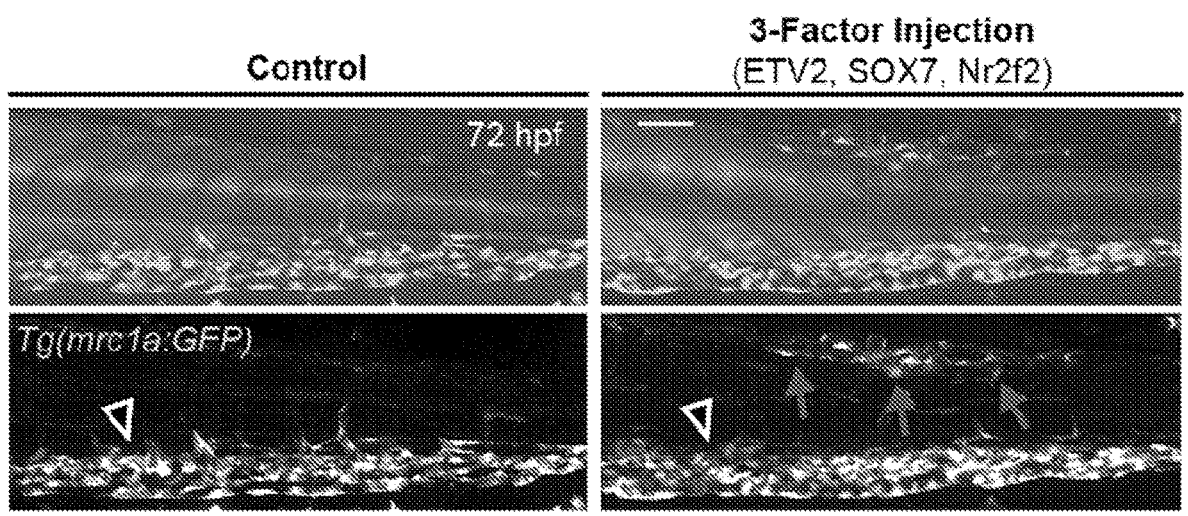
Figure 4E:
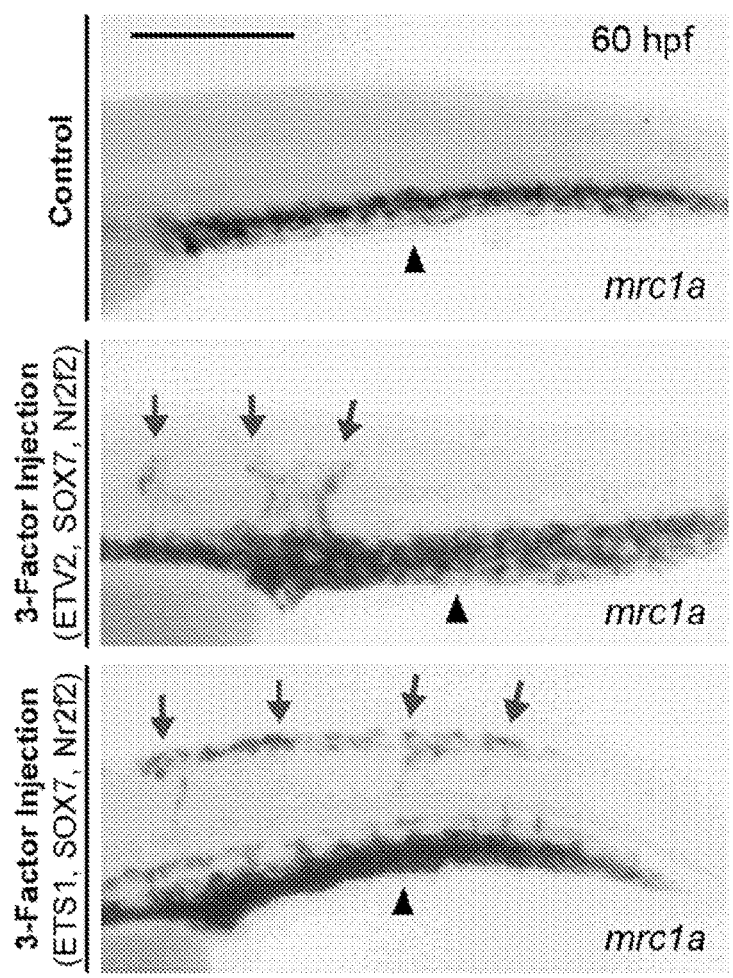
Figure 4F:
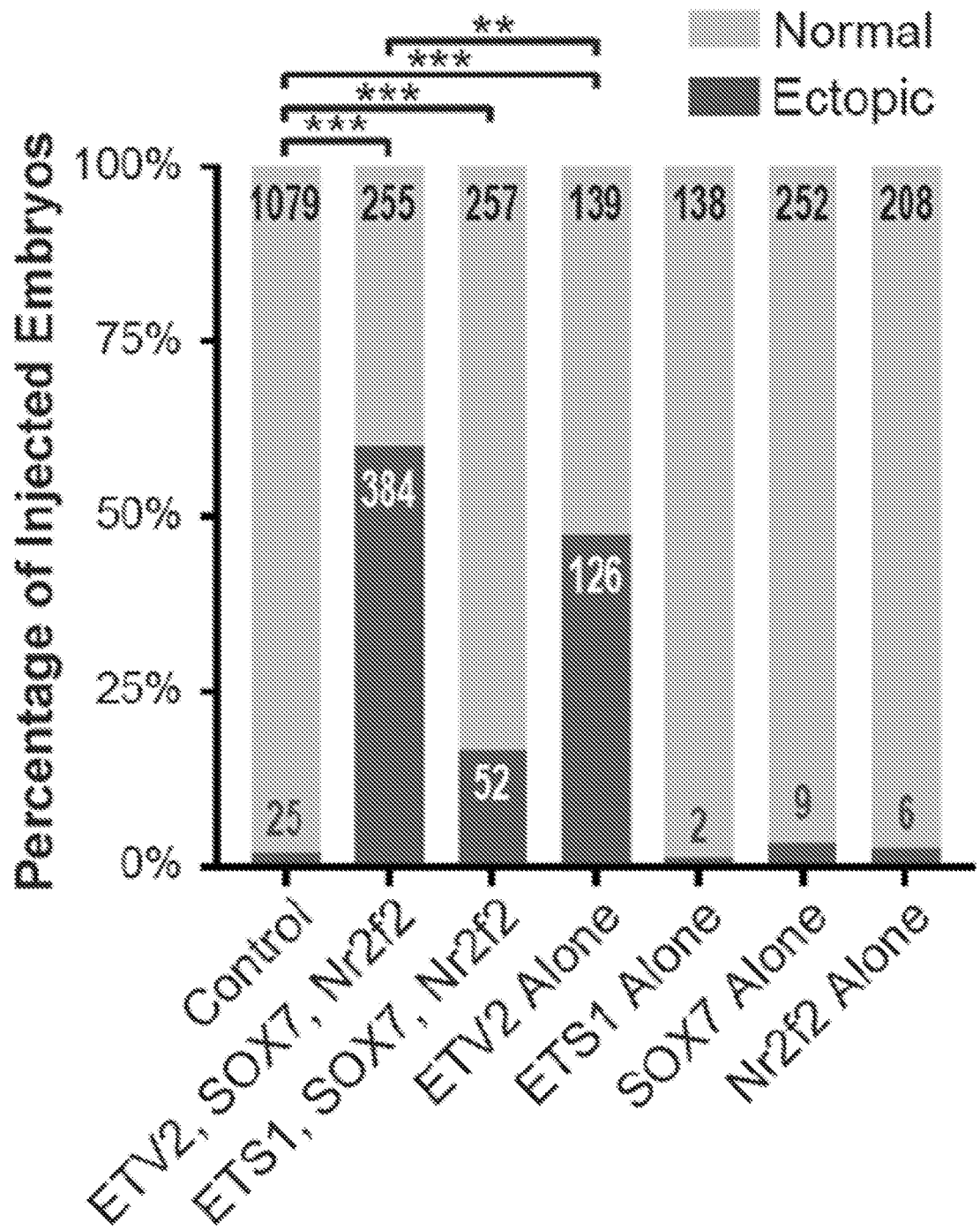

This mutational analysis of the 125 bp mrc1a and 158 bp sele enhancers indicated that a factor from each of the Ets, Sox and NHR families was required for expression, which led to the experiment of whether a combination of just three factors (one from each family) was sufficient to induce niche endothelial gene expression. ETV2 is a pioneer factor that is essential for specification of early mesodermal progenitors into vascular cell fates. Forced expression of ETV2 in nonvascular cells induces reprogramming towards an early endothelial fate that can generate many types of vasculature. Previous work in zebrafish has shown the importance of SoxF factors (sox7 and sox18) and nr2f2 during arterial-venous specification (see e.g., Swift et al. SoxF factors and Notch regulate nr2f2 gene expression during venous differentiation in zebrafish. Developmental biology 390, 116-125, 2014). A combination of three of these factors-ETV2, SOX7 and Nr2f2-could be sufficient to induce ectopic niche endothelial gene expression. Consistent with this, when these three factors were injected, significant ectopic mrc1a expression was observed (see e.g., FIG. 4D-FIG. 4F). The frequency of ectopic vessels generated with three factors was higher than the 7-factor pool, suggesting factor concentration has functional significance. Injected embryos similarly showed ectopic expression of sele, gpr182 and lgmn, indicating that the 3-factor pool induced the niche endothelial program (see e.g., FIG. 11A-FIG. 11C).

Figure 12A:
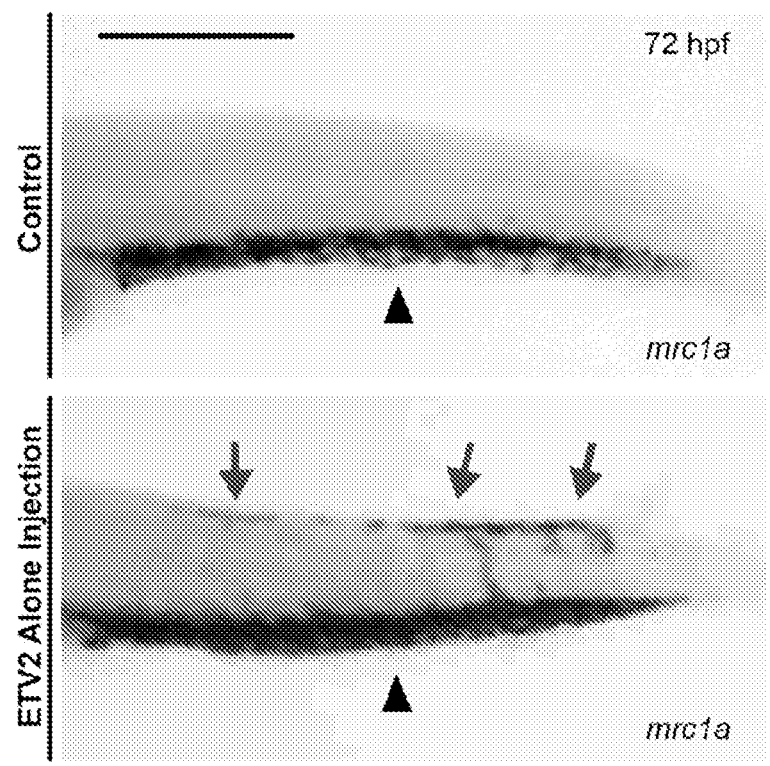
FIG. 12A-FIG. 12D is a series of images and graphs showing that CHT niche endothelial gene expression is induced ectopically by transcription factor overexpression.
Figure 12B:
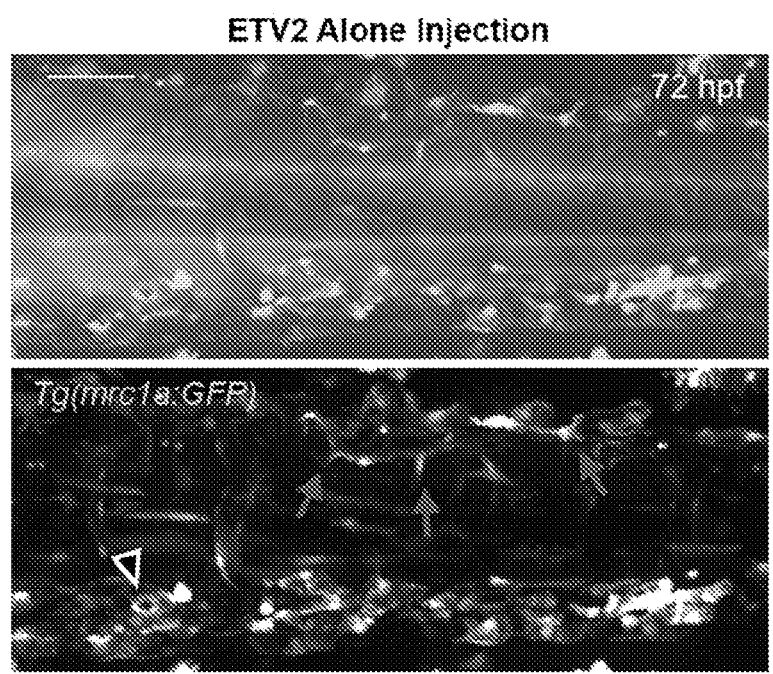
Figure 12C:
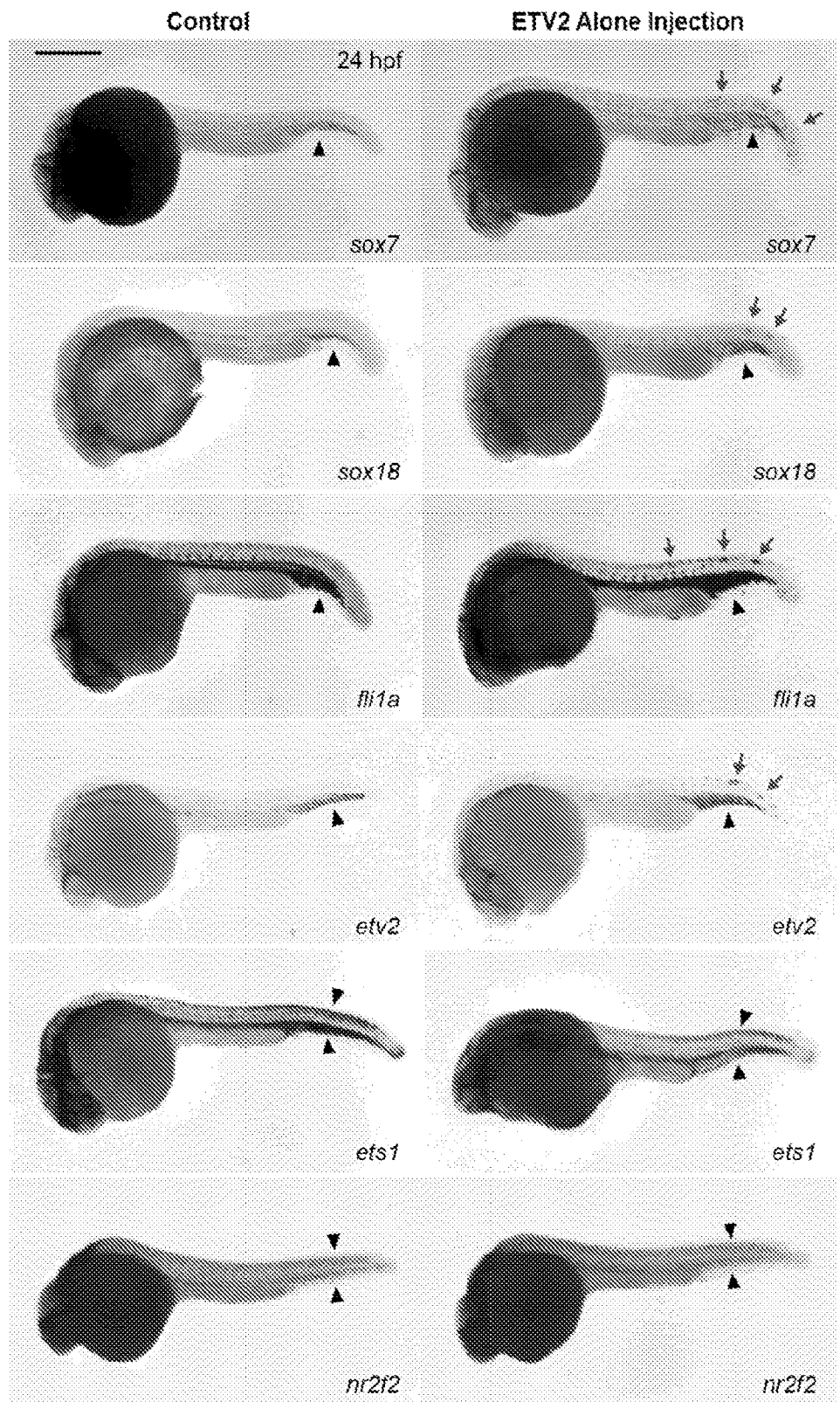
Figure 12D:
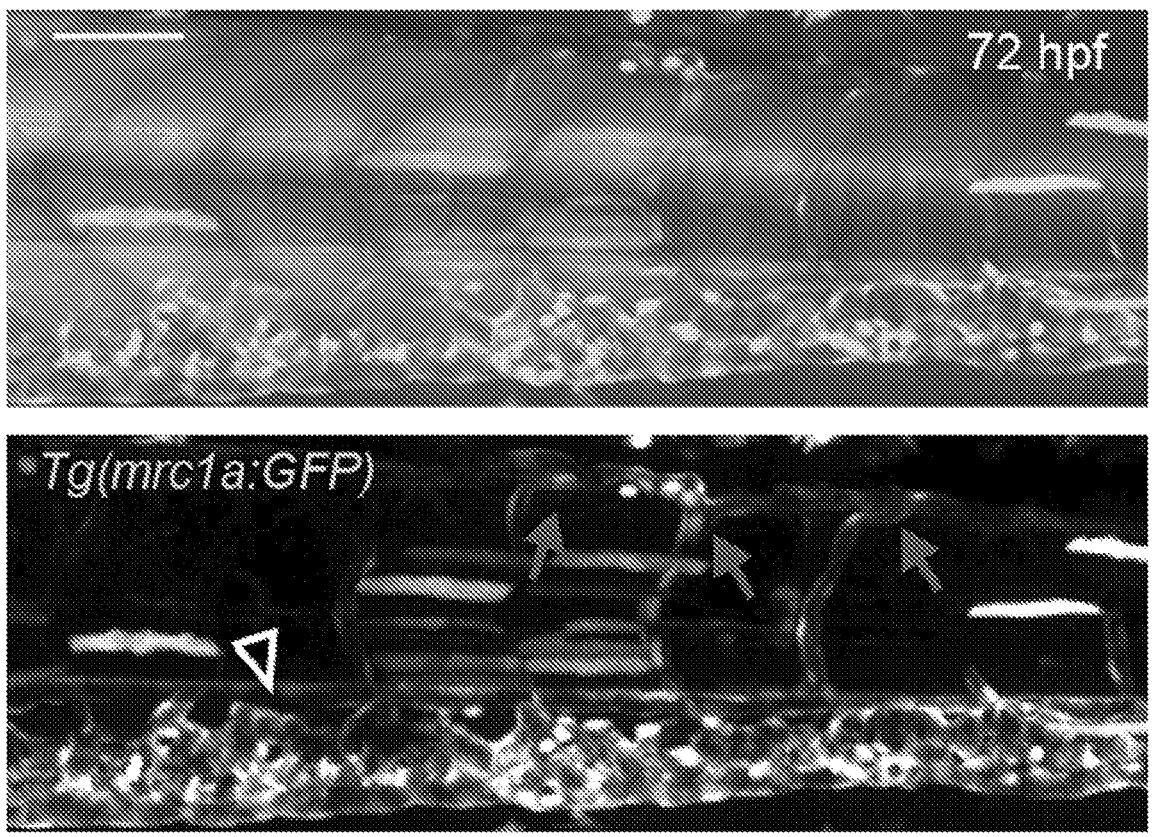

To evaluate the contribution of the individual transcription factors, each factor was injected alone, and WISH was performed for mrc1a. Embryos injected with SOX7 or Nr2f2 alone showed minimal ectopic expression (see e.g., FIG. 4F). Injection of ETV2 alone led to ectopic expression of mrc1a, although at a lower frequency than when ETV2 was injected in combination with SOX7 and Nr2f2, indicating the additional factors increase ectopic induction (see e.g., FIG. 4F, FIG. 12-FIG. 12D). Injecting ETV2 alone induced ectopic expression of the endogenous zebrafish sox7 gene, as well as sox18, fli1a and etv2, demonstrating that human ETV2 can induce several zebrafish endothelial gene programs, including artery, vein and niche endothelial genes (see e.g., FIG. 12-FIG. 12D). Because endogenous ets and nr2f2 are expressed broadly outside the CHT (e.g. in the spinal cord region), it was difficult to visualize whether they were similarly induced by ETV2 overexpression (see e.g., FIG. 12-FIG. 12D). ETS1 has the capacity to bind to the consensus ETS motif enriched in the peaks and is expressed at an appreciable level in the niche ECs. In contrast to ETV2, overexpression of ETS1 alone did not lead to widespread vessel induction or ectopic mrc1a expression (see e.g., FIG. 4F). Injection of ETS1, SOX7 and Nr2f2, however, led to significant ectopic expression of mrc1a, illustrating the combinatorial activity of these transcription factors (see e.g., FIG. 4E, FIG. 4F, FIG. 12-FIG. 12D). Notably, the zebrafish genes encoding each of the seven initial transcription factors had regions of chromatin associated with them that were uniquely accessible in the CHT EC fraction and harbored Ets, SoxF and NHR sites (see e.g., Table 5), indicating that these factors regulate one another similar to an auto-regulatory loop established during reprogramming. Thus, overexpression of the three factor combinations, including either ETV2 or ETS1 with Sox and NHR factors, mimics the endogenous expression of these factors in niche ECs at 72 hpf and drives robust specification of the niche endothelial gene program.

Ectopic Vascular Regions Recruit HSPCs.

Figure 5A:
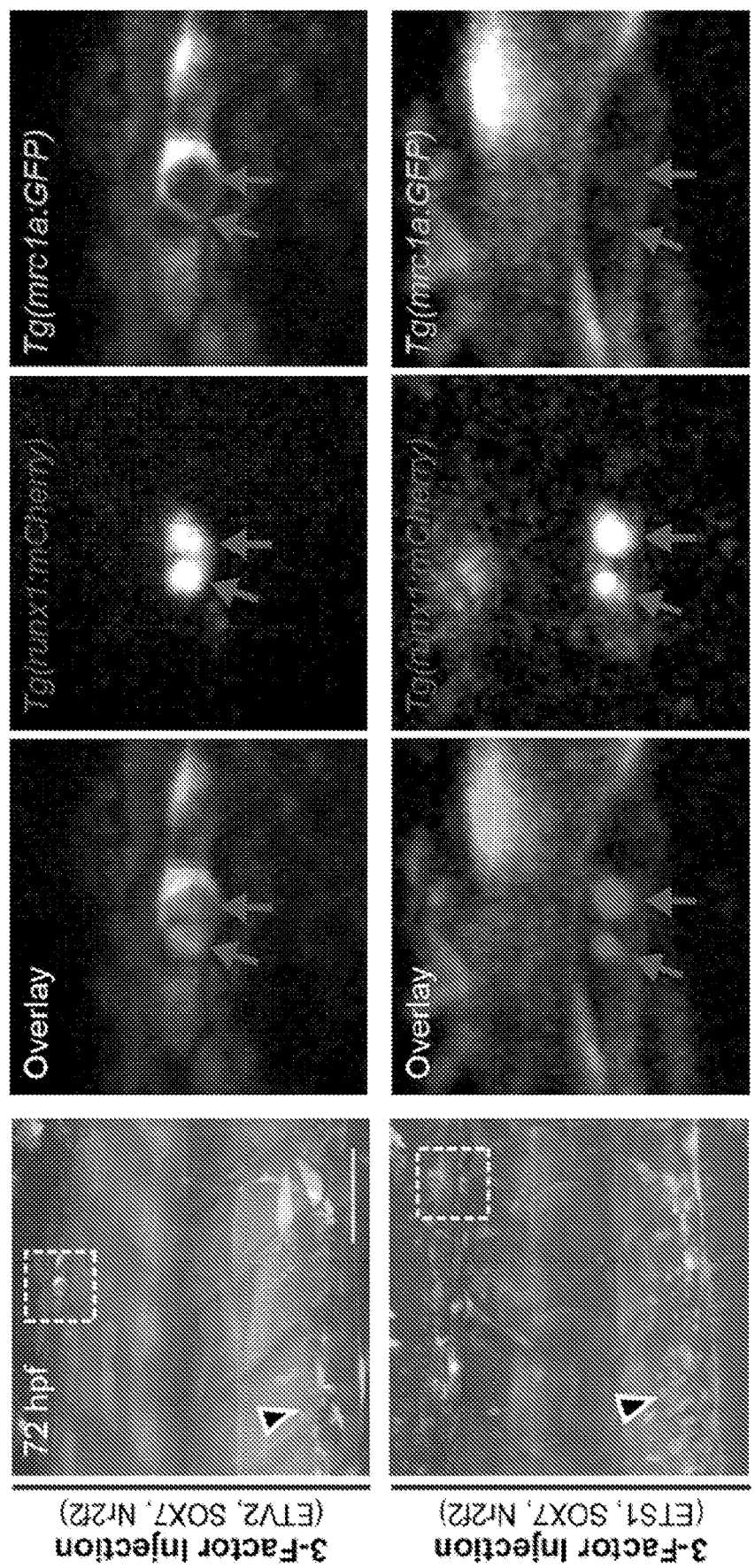
FIG. 5A-FIG. 5E is a series of images and graphs showing that HSPCs localize to regions of ectopic niche endothelial gene expression.
Figure 5B:
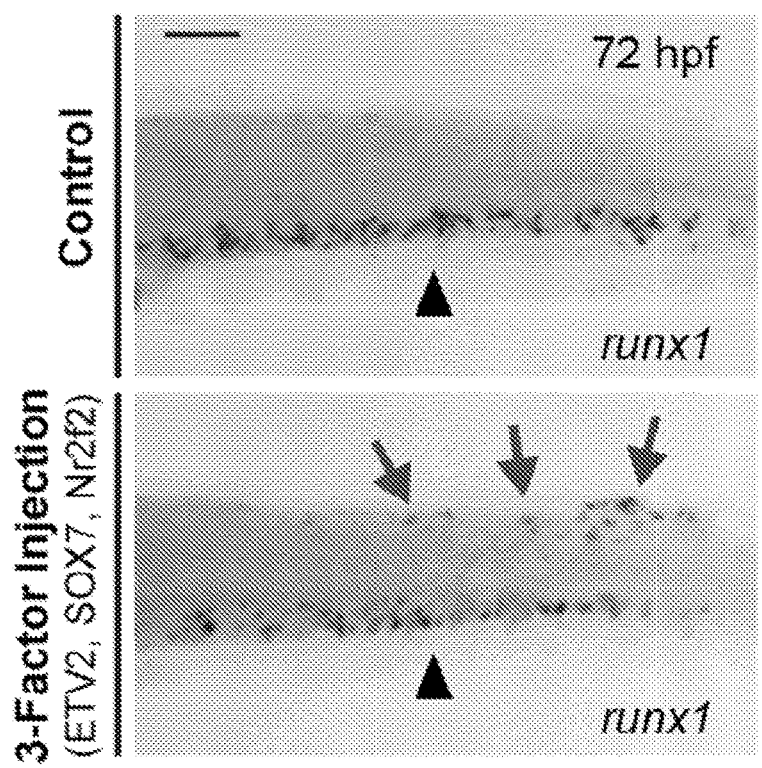

It was next asked whether the ectopic regions of CHT EC gene expression were capable of recruiting and supporting HSPCs. The ETV2, SOX7 and Nr2f2 pool was injected into mrc1a:GFP/runx1:mCherry double positive transgenic embryos, and the localization of runx1:mCherry$^+$ HSPCs was examined. Strikingly, in 12 out of 22 embryos that had ectopic vascular patches of mrc1a:GFP, HSPCs were observed localizing to these regions (see e.g., FIG. 5A). In contrast, 0 out of 27 control embryos had ectopically localized HSPCs. Similar ectopic localization of runx1$^+$ HSPCs was observed by runx1 WISH and in embryos injected with the ETS1, SOX7 and Nr2f2 combination (see e.g., FIG. 5A, FIG. 5B).

Figure 5C:
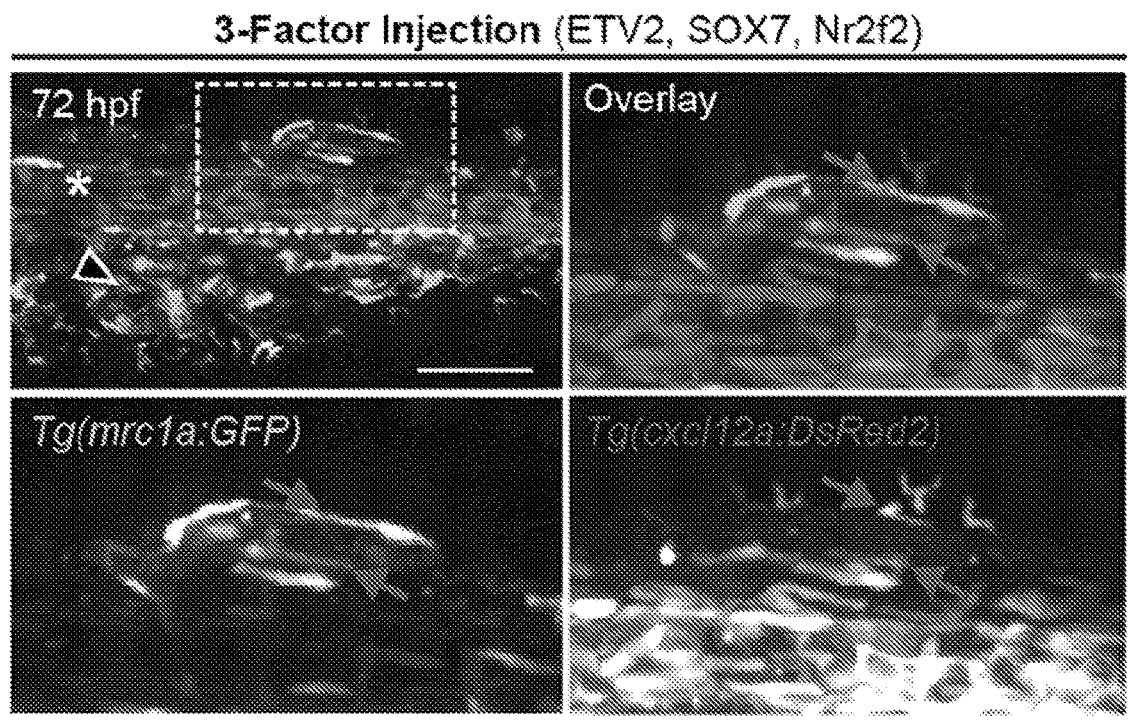

To evaluate whether these ectopic regions provide a supportive environment for HSPCs, high-resolution live cell confocal microscopy was used to more closely examine HSPC behaviors and interactions with ECs at these sites. This analysis revealed that HSPCs directly associated with the mrc1a:GFP$^+$ ECs within ectopic sites and could be found in both intraluminal and extravascular spaces. The ectopic mrc1a:GFP$^+$ ECs were often associated with cxcl12a:DsRed2' stromal cells and formed pockets around the HSPCs, similar to what is observed in the CHT (see e.g., FIG. 5A, FIG. 5C). Notably, using time-lapse microscopy, the initial recruitment, lodging and division of HSPCs was observed within these sites (see e.g., FIG. 5D). When the HSPCs divided, daughter cells migrated away from the ectopic site and entered circulation, presumably traveling to subsequent niches (see e.g., FIG. 5E). Together, these data demonstrate that reprogramming by the three factors that drive the niche endothelial gene program leads to functional ectopic niches that can recruit and sustain HSPCs.

A Conserved Endothelial Signature in the HSPC Niche.

Figure 6A:
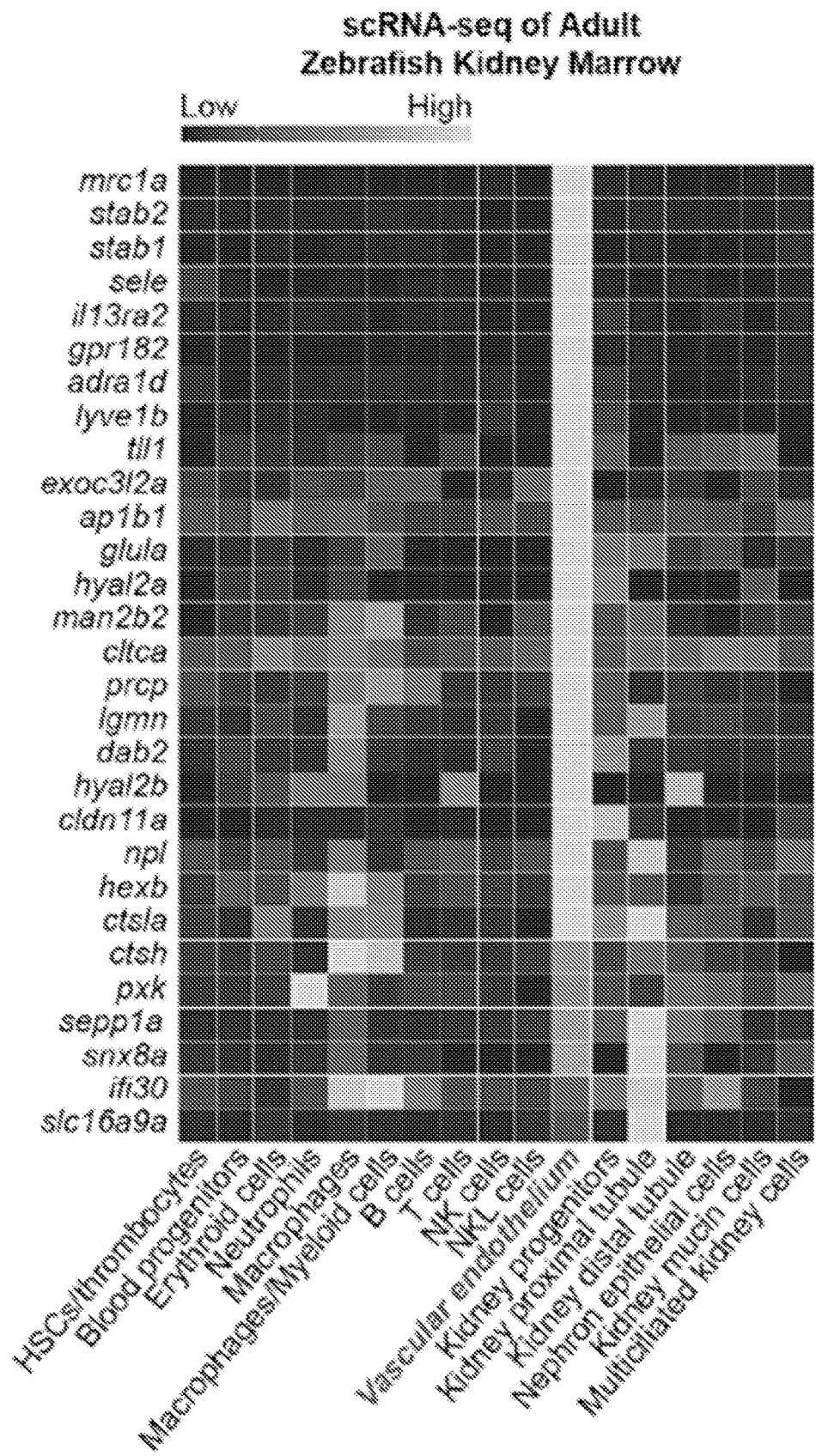
FIG. 6A-FIG. 6B is a series of images and graphs showing a conserved endothelial expression signature in the HSPC niche.
Figure 6B:
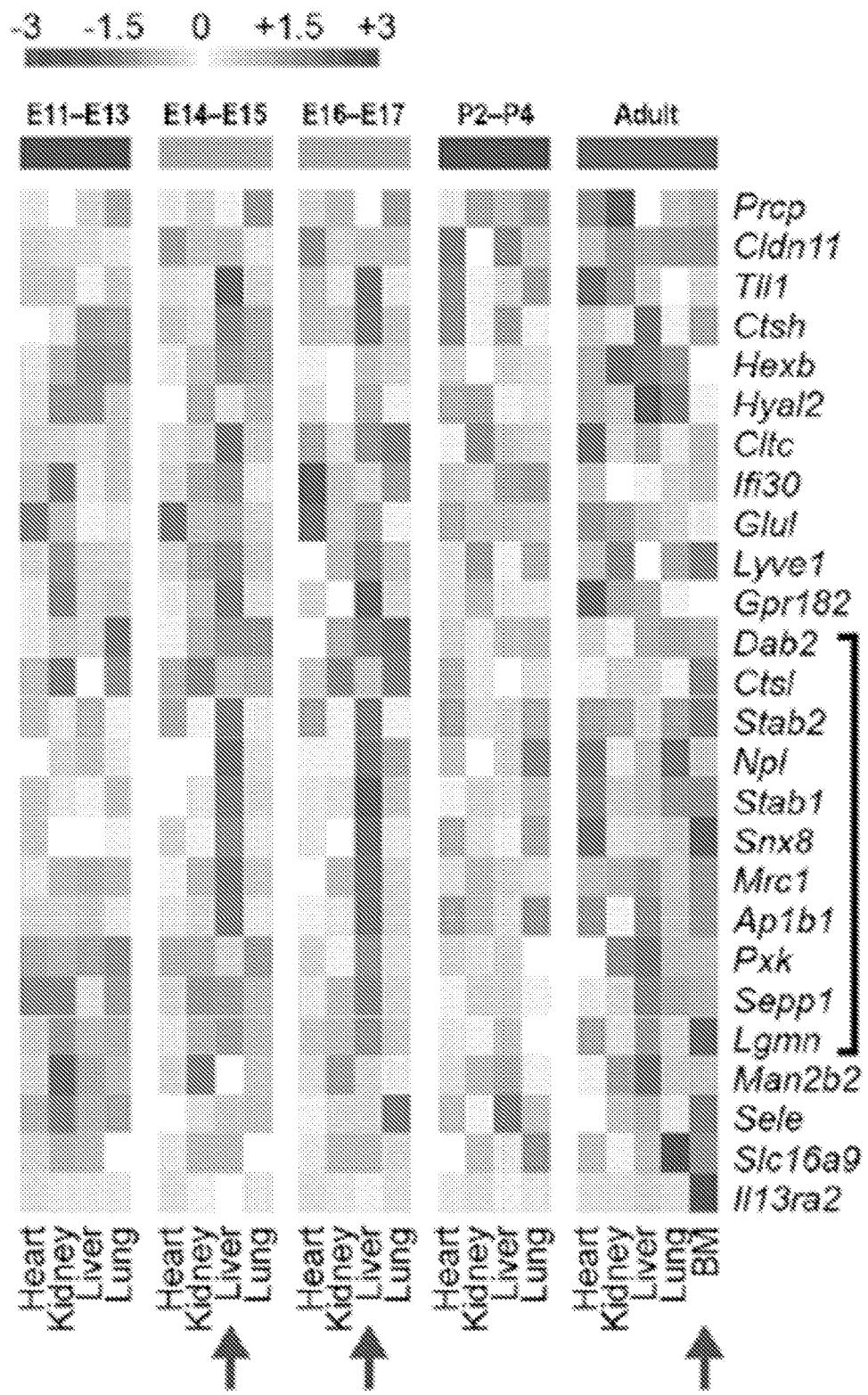
Figure 13A:
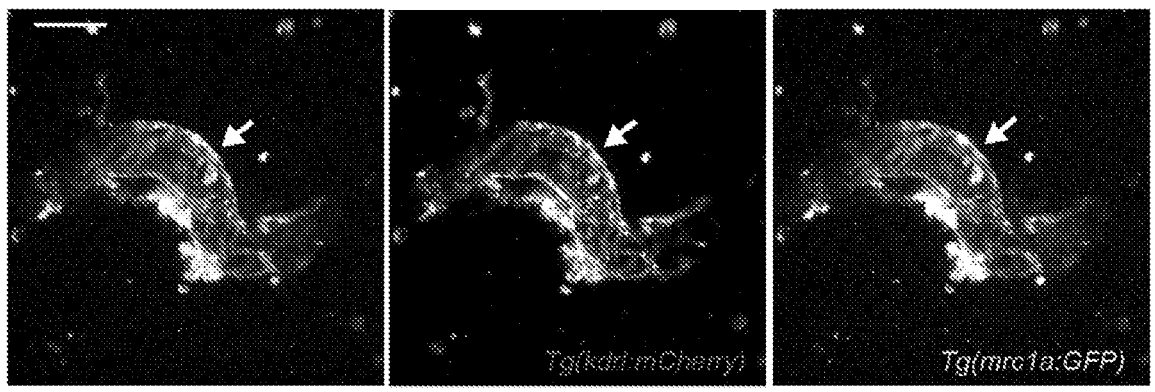
FIG. 13A-FIG. 13B is a series of images and graphs showing niche endothelial transgene expression in adult kidney ECs.
Figure 13B:
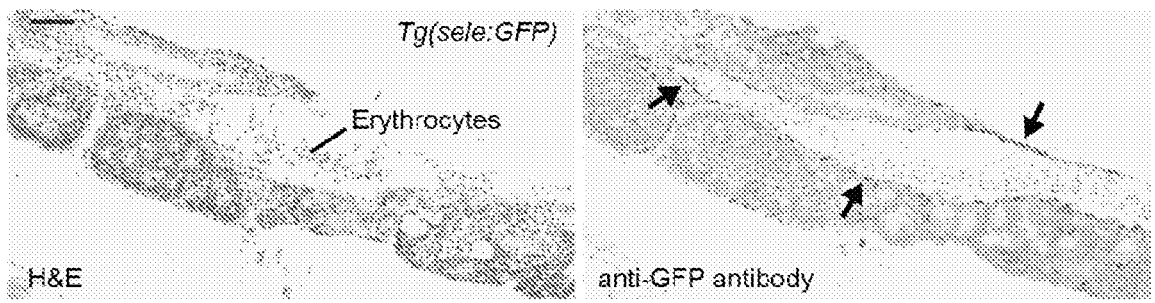
Figure 14:
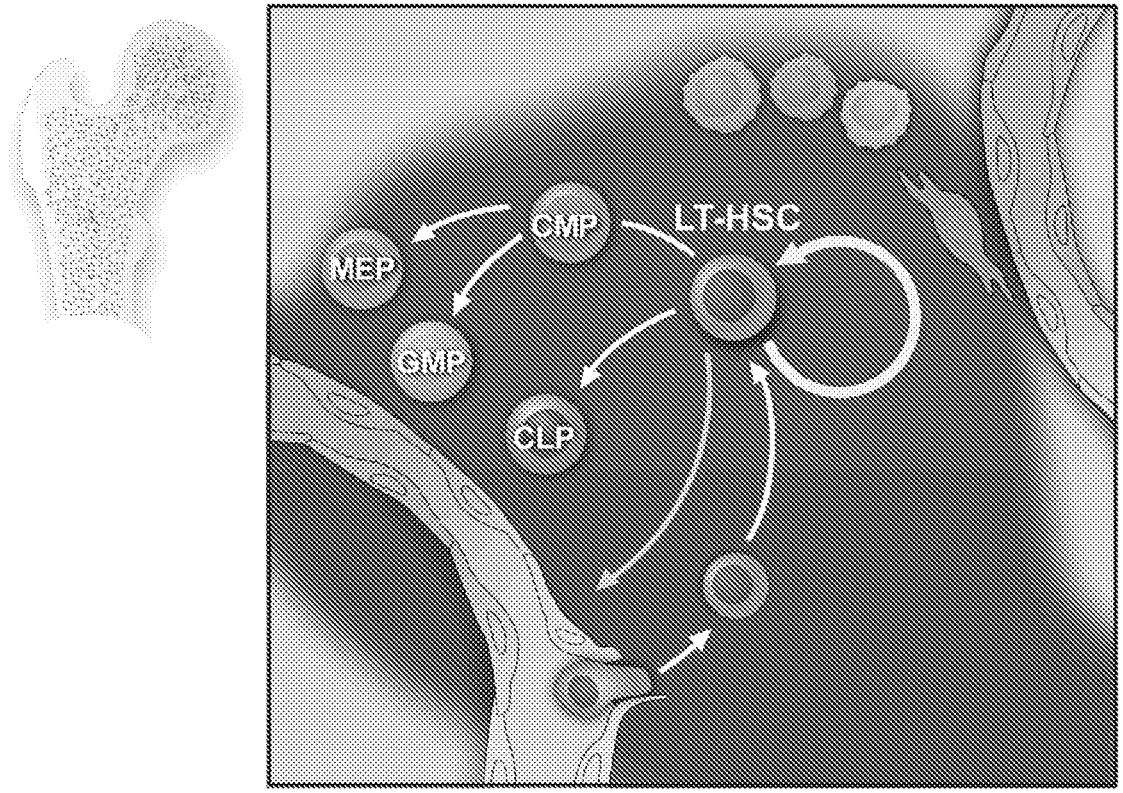
FIG. 14 is a schematic showing hematopoietic stem cell self-renewal and differentiation. LT-HSC indicates a long-term hematopoietic stem cell. CMP indicates a common myeloid progenitor. MEP indicates a megakaryocyte-erythroid progenitor. GMP indicates a granulocyte-macrophage progenitor. CLP indicates a common lymphoid progenitor.
Figure 15A:
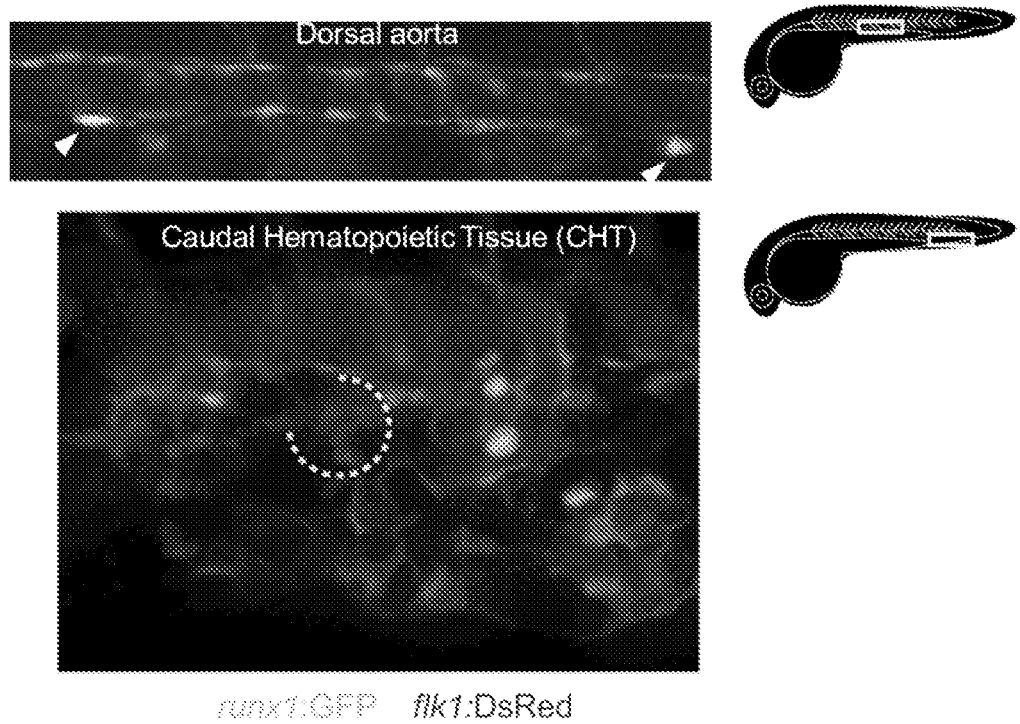
FIG. 15A-FIG. 15B is a series of images showing visualization of niche colonization by HSPCs in vivo.
Figure 15B:
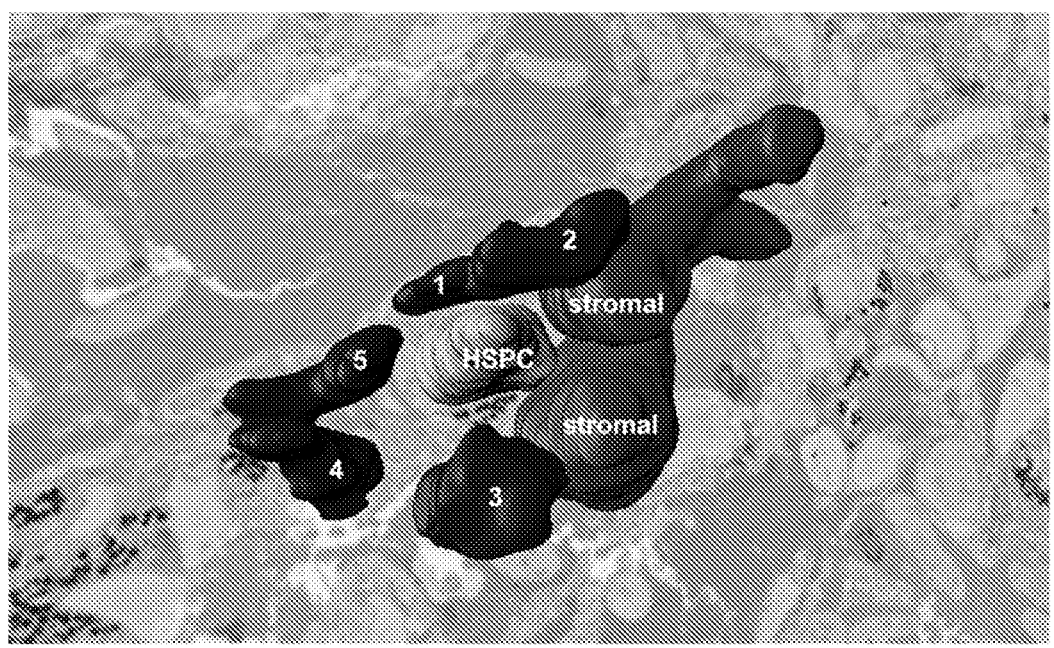
Figure 16:
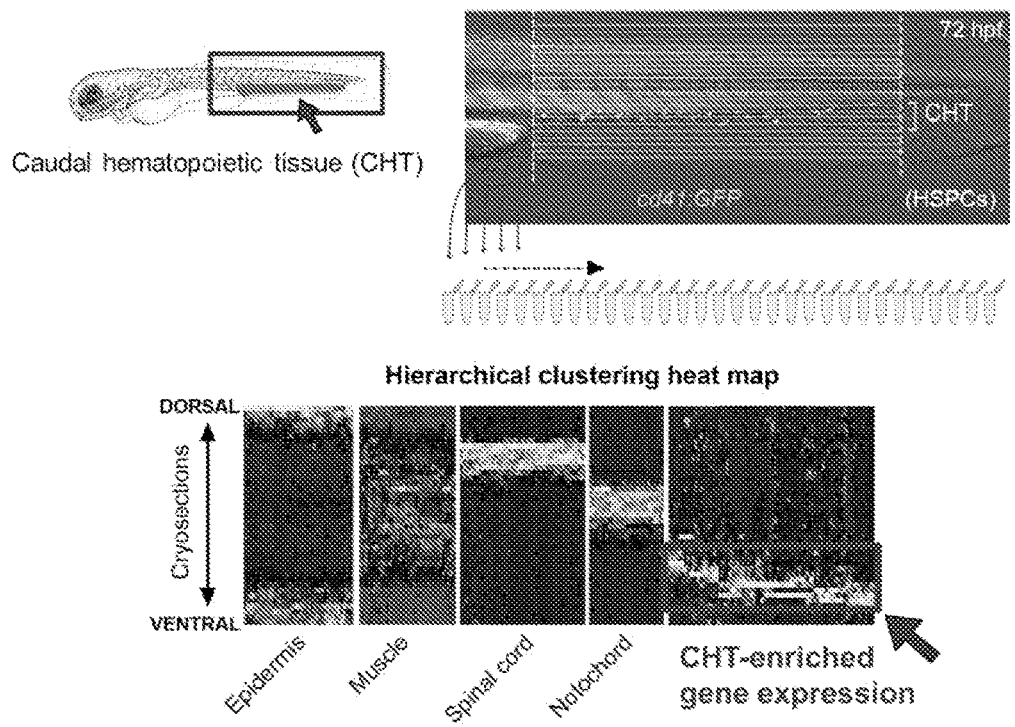
FIG. 16 is a series of images showing the use of RNA tomography (tomo-seq) to examine gene expression in the HSPC niche.
Figure 17:
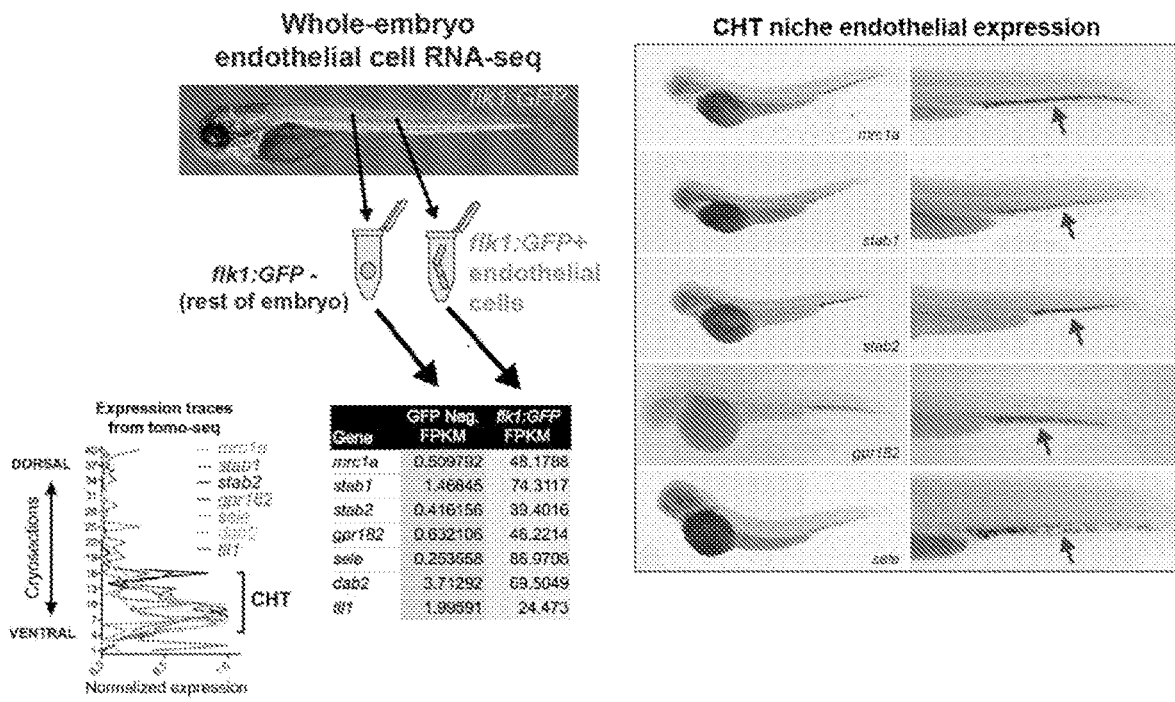
FIG. 17 is a series of images and graphs showing how Tomo-seq+endothelial RNA-seq identified ~20 genes selectively enriched in niche endothelial cells.
Figure 18:
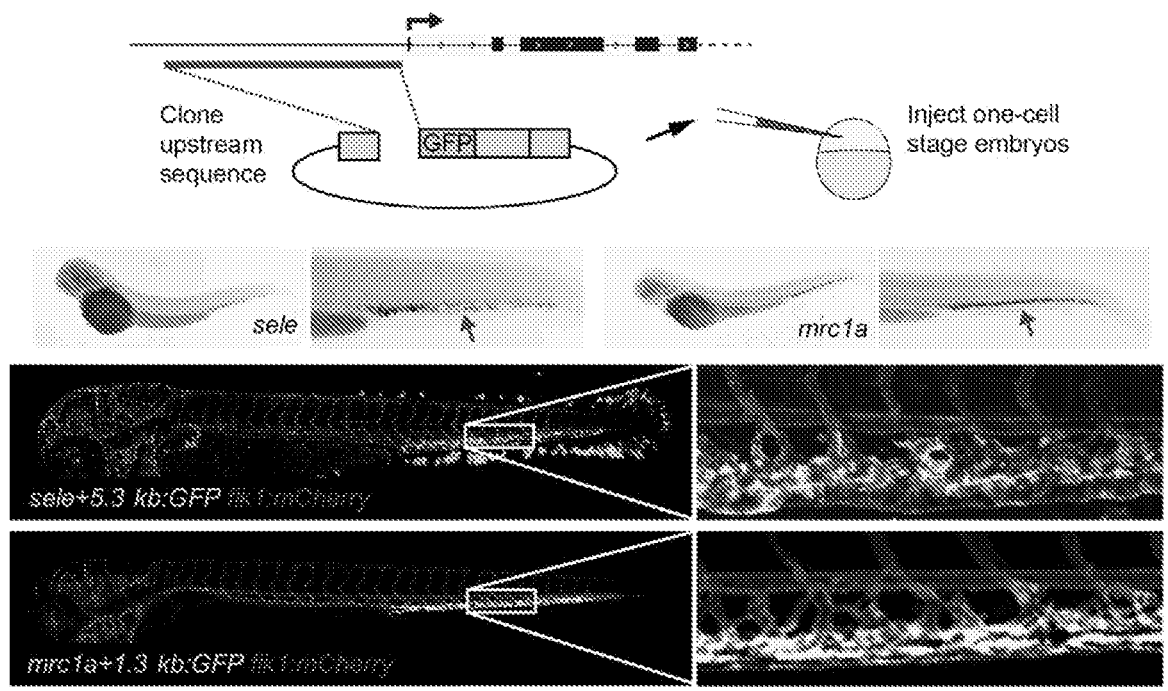
FIG. 18 is a series of images showing that sele and mrc1a promoter-GFP fusions label endothelial cells in the HSPC niche.
Figure 19:
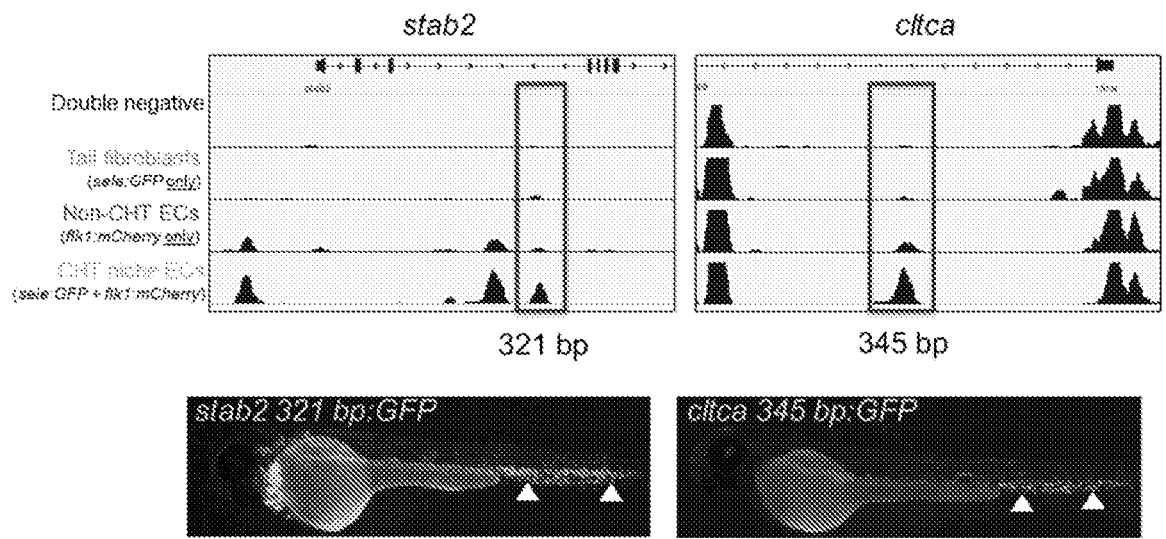
FIG. 19 is a series of images showing that specific ATAC-seq peaks near original 20 genes can drive expression in niche endothelial cells. 13 out of 19 cloned ATAC-seq peaks can drive GFP expression in CHT endothelial cells (when coupled to a minimal promoter).
Figure 20:
FIG. 20 is an image showing the TF binding motifs most enriched in the open chromatin of niche endothelial cells. Motif enrichment analysis was performed on 6,710 unique ATAC-seq peaks using HOMER.
Figure 21:
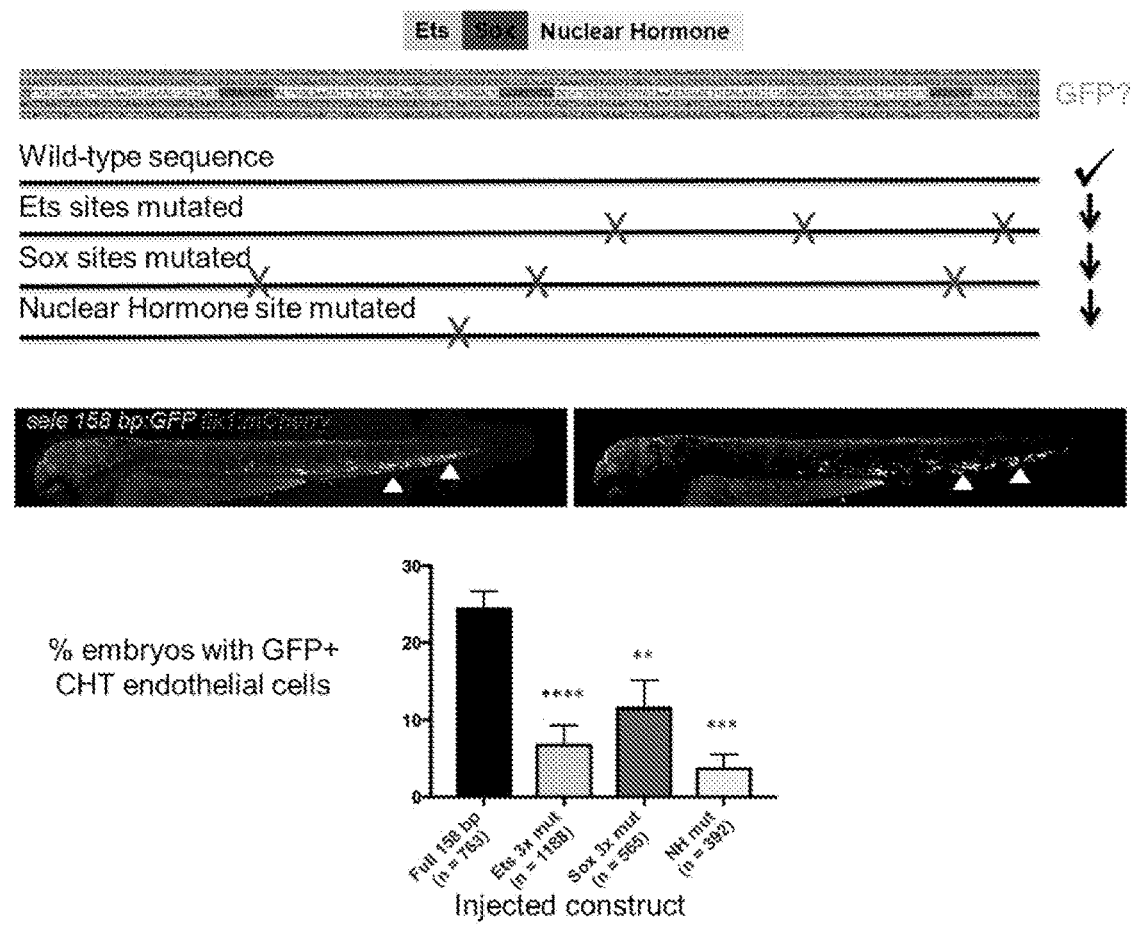
FIG. 21 is a series of images and graphs showing that Ets, Sox and NHR sites are required for niche expression of a 158 bp sele enhancer (see e.g., SEQ ID NO: 14).
Figure 22:
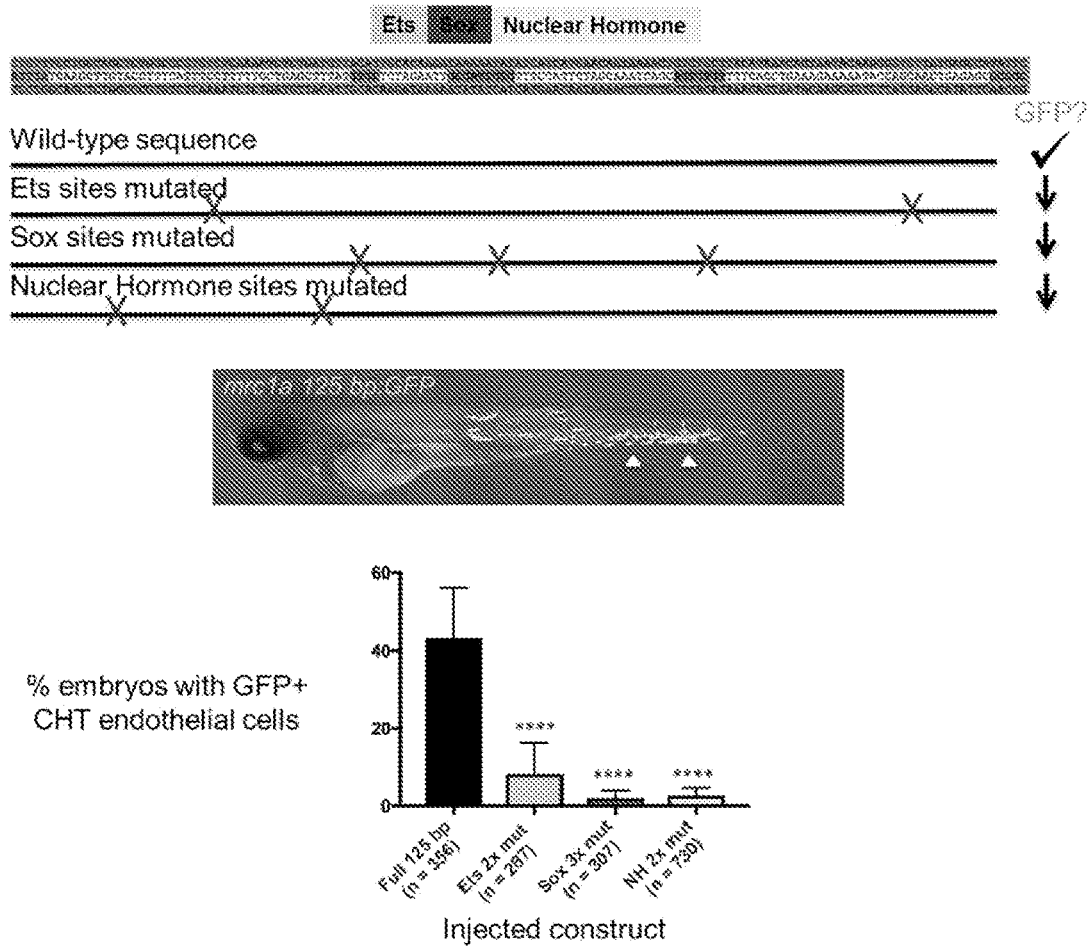
FIG. 22 is a series of images and graphs showing that Ets, Sox and NHR motifs are required for niche expression of a 125 bp mrc1a enhancer (see e.g., SEQ ID NO: 15).
Figure 23:
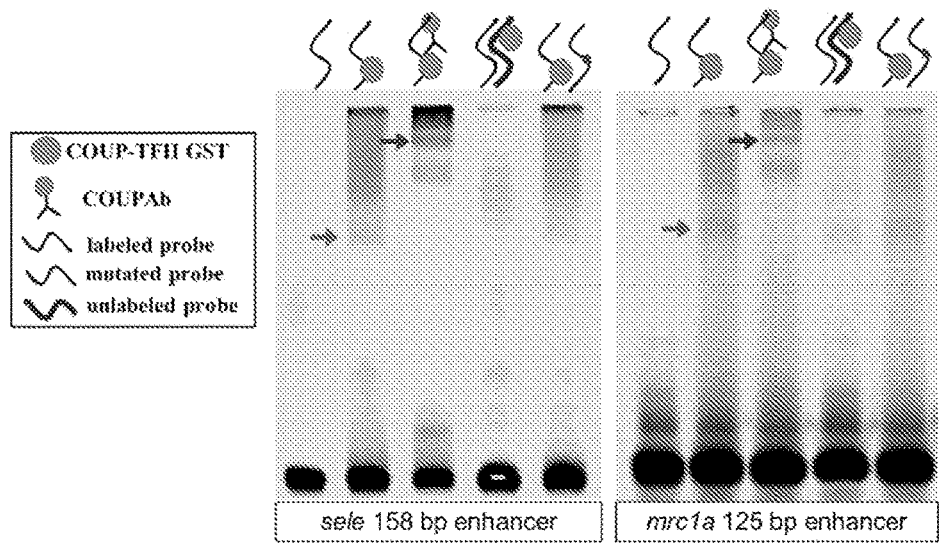
FIG. 23 is a series of images showing that mouse TFs can bind zebrafish sequences in vitro. The same mutations that disrupt enhancer:GFP expression abrogate TF binding.
Figures 24, 25:
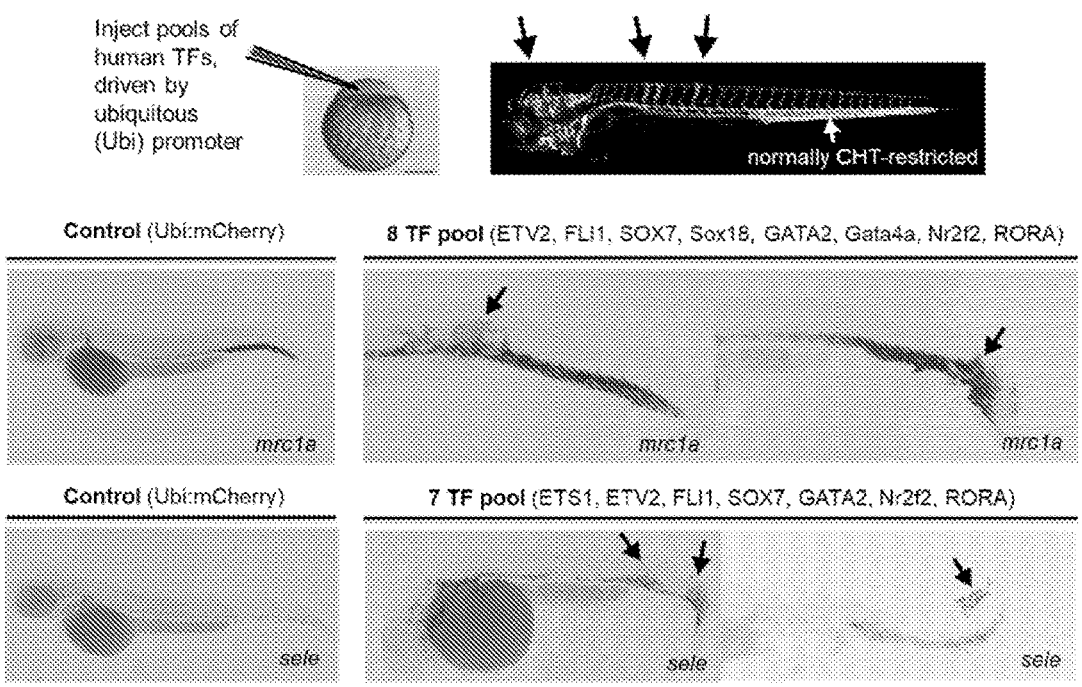
FIG. 24 is an image showing that transcription factors known to bind Ets, Sox and NH motifs are expressed in niche endothelial cells.
FIG. 25 is a series of images showing the reprogramming of niche endothelial cells.
Figure 26:
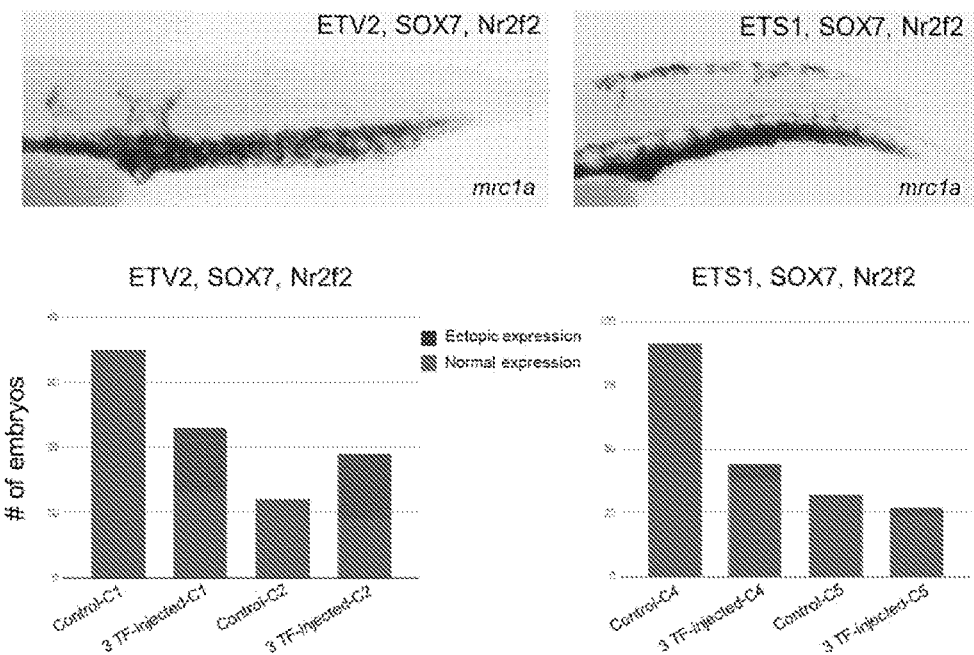
FIG. 26 is a series of images and graphs showing that 3 TF pool injections result in ectopic niche endothelial gene expression.
Figure 27A:
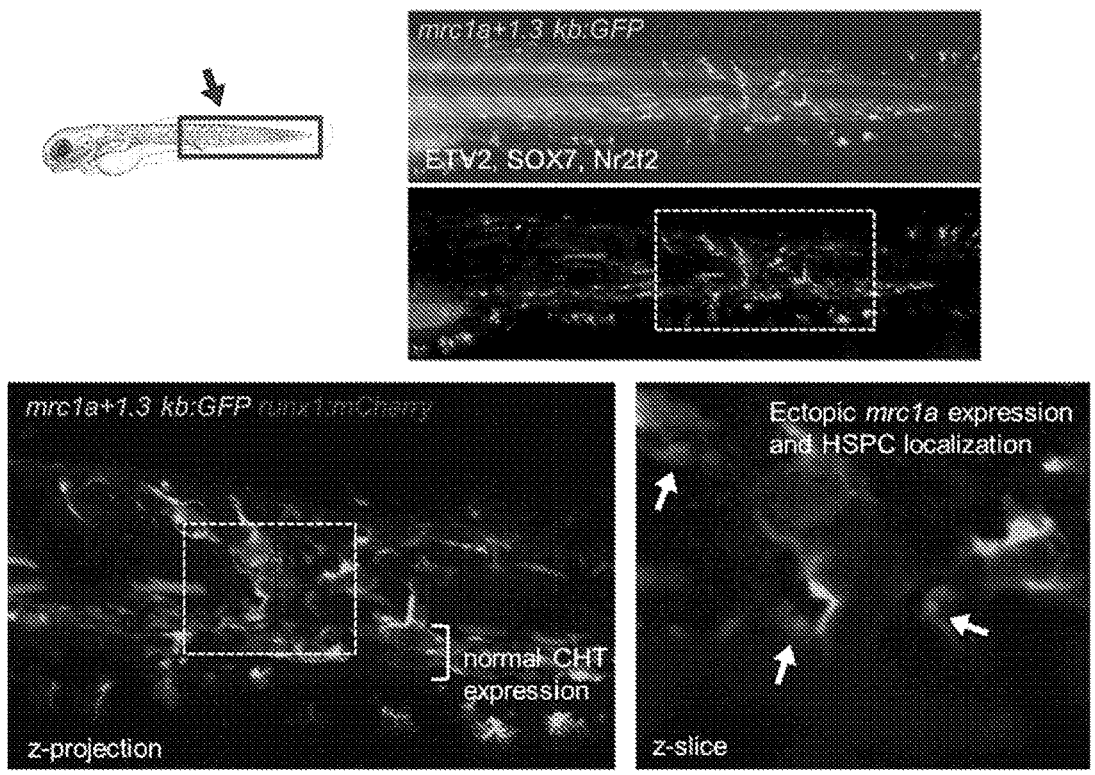
FIG. 27A-FIG. 27C is a series of images showing that ectopic vascular patches can recruit runx1+ HSPCs.
Figure 27B:
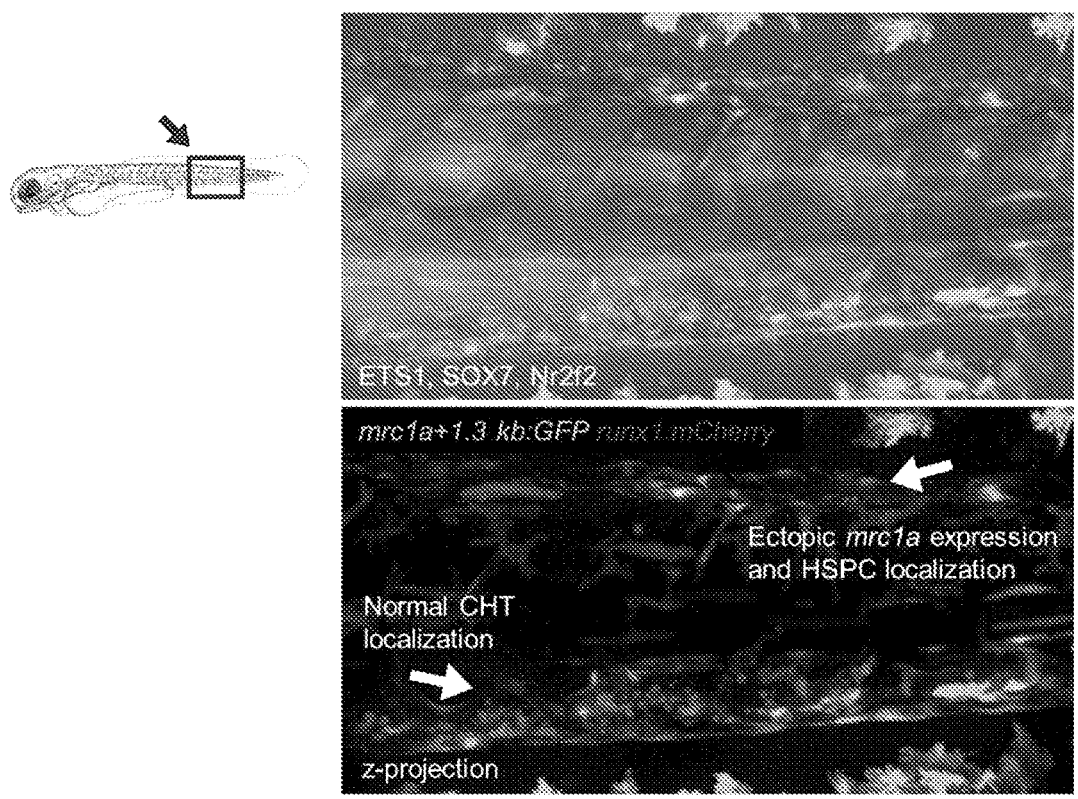
Figure 27C:
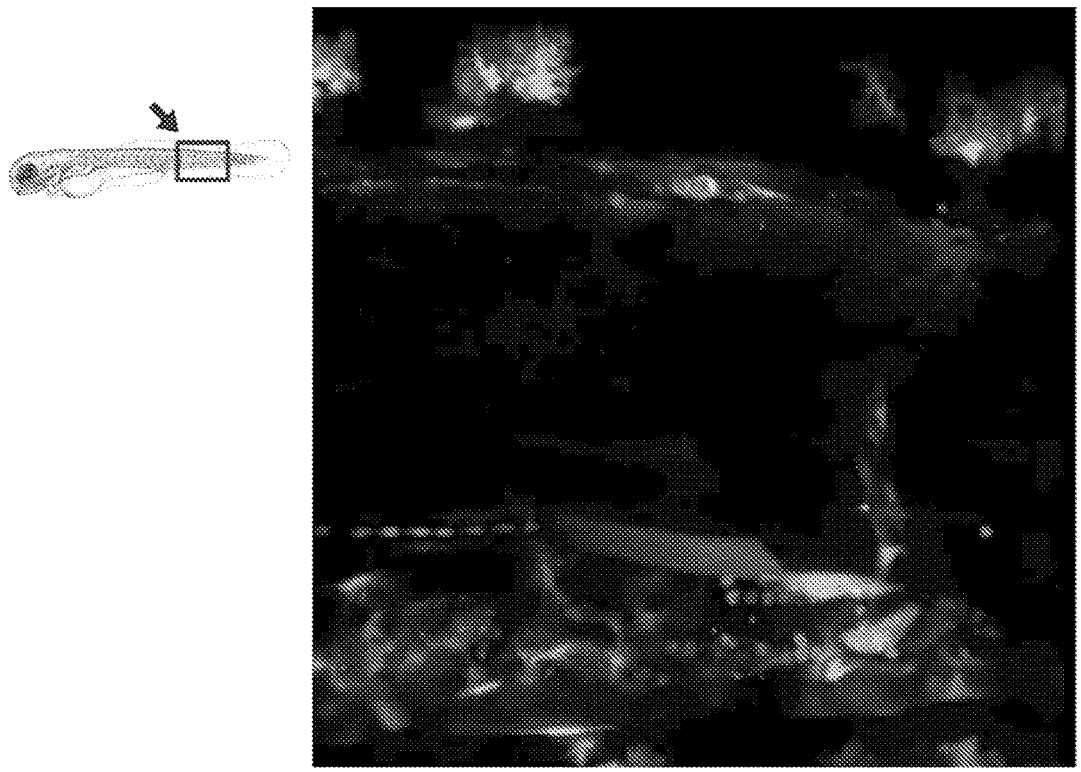
Figure 28:
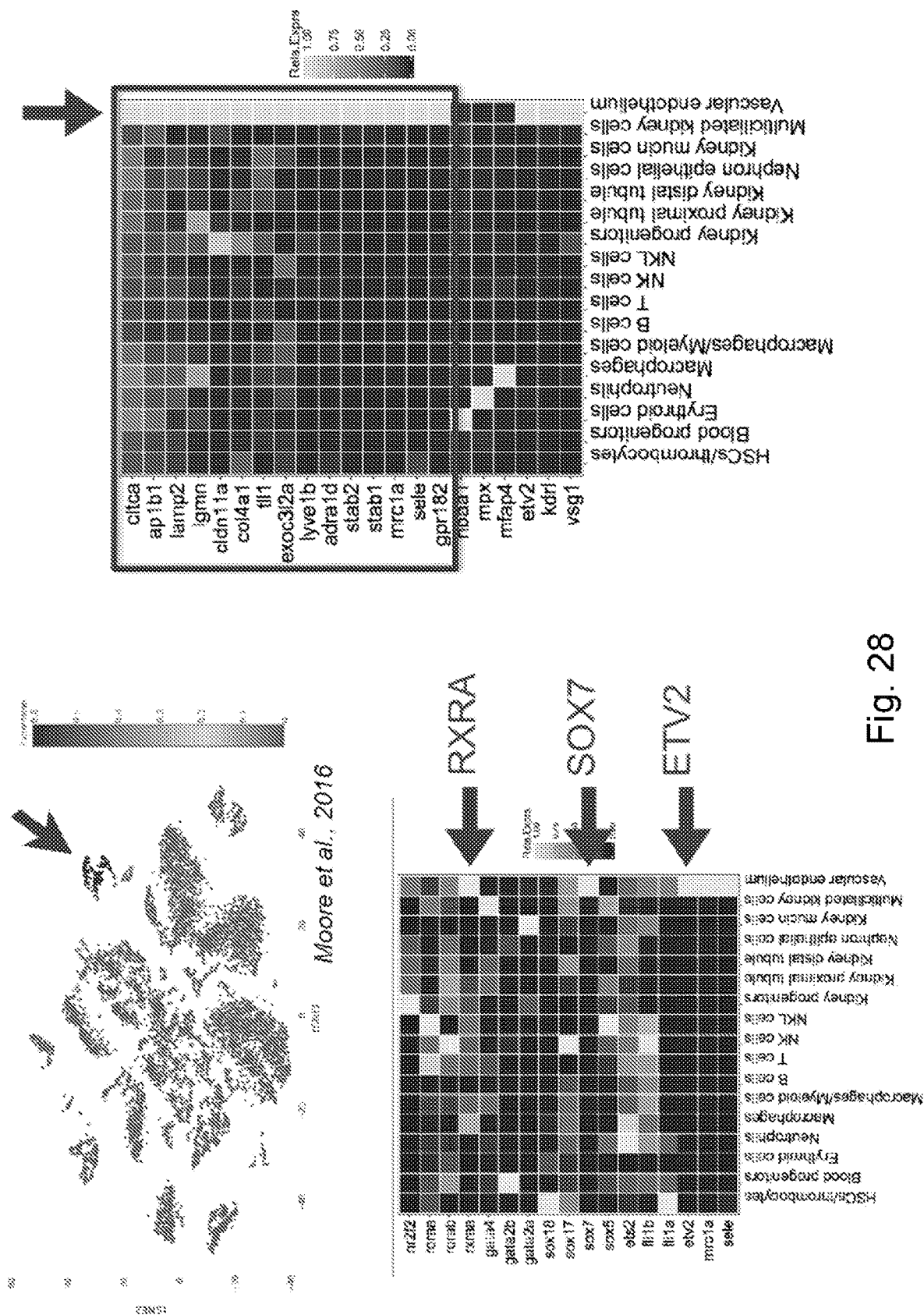
FIG. 28 is a series of images and heat maps showing that HSPC niche endothelial signature is also in adult marrow.
Figure 29:
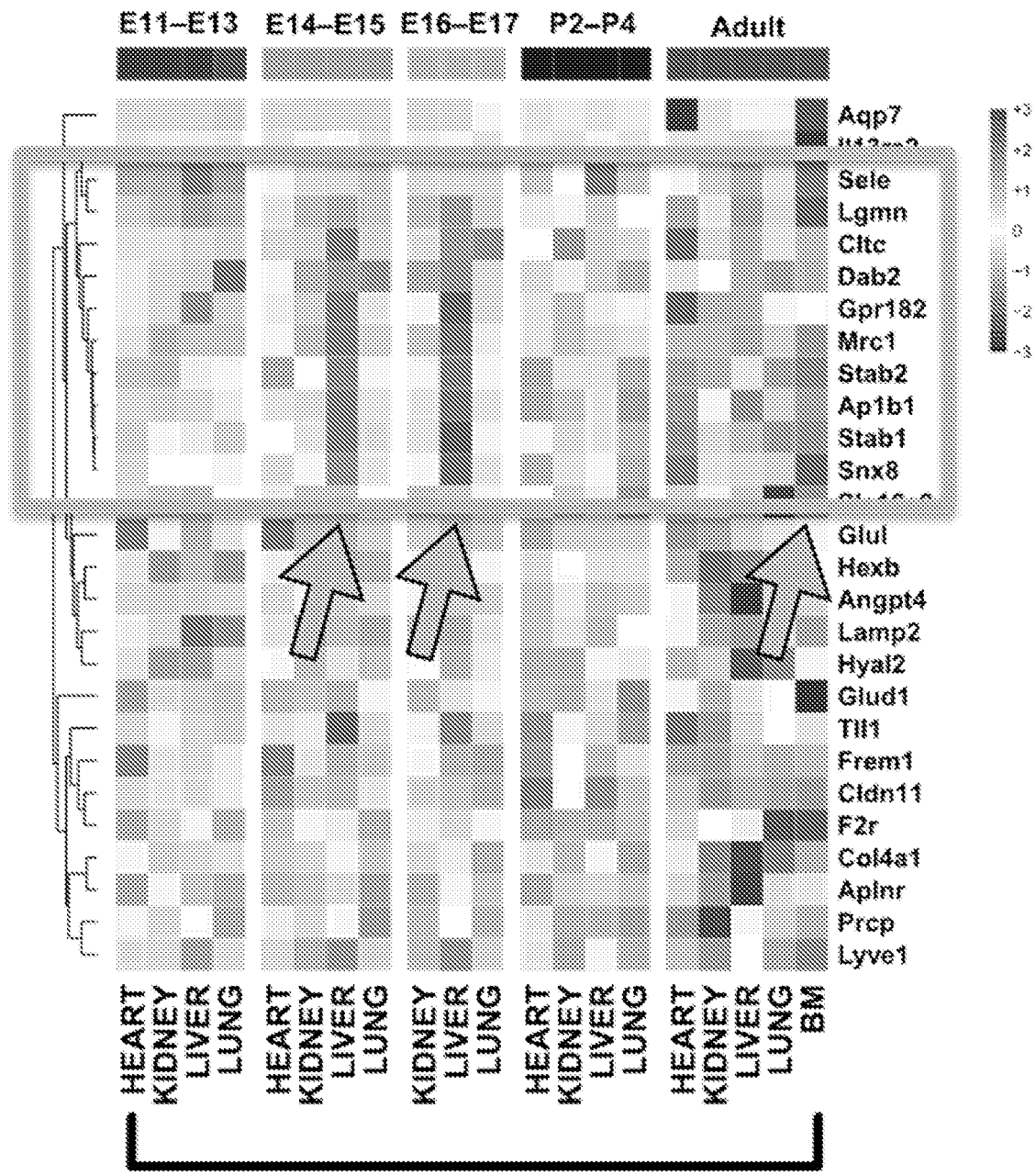
FIG. 29 is a heat map showing that a similar niche endothelial signature found in the mammalian fetal liver and bone marrow.
Figure 30:
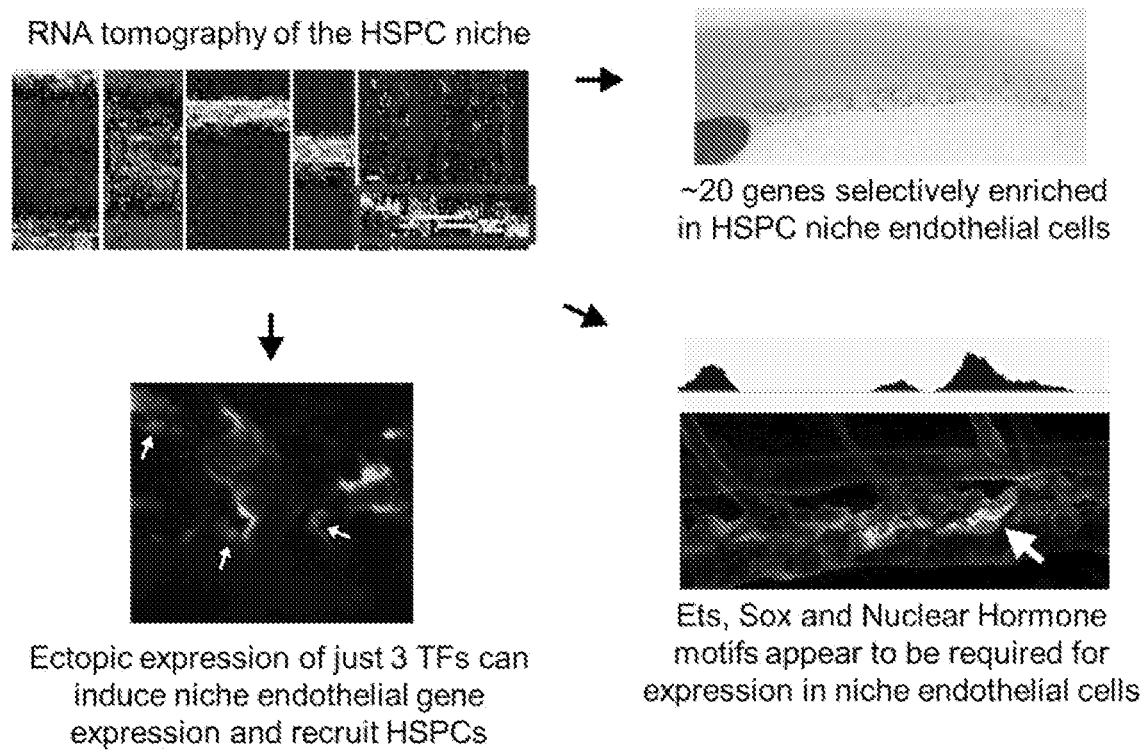
FIG. 30 is a diagram showing that RNA tomography of the HSPC niche led to the following data: ~20 genes are selectively enriched in HSPC niche endothelial cells; ectopic expression of just 3 TFs can induce niche endothelial gene expression and recruit HSPCs; and Ets, Sox and Nuclear Hormone motifs are required for expression in niche endothelial cells.

To determine whether a similar endothelial expression signature was present in the adult zebrafish niche, the mrc1a:GFP and sele:GFP transgenes were examined, and it was found that both lines had GFP expression in ECs in the kidney marrow (see e.g., FIG. 13A, FIG. 13B). In addition, a single cell RNA-seq dataset for zebrafish kidney marrow was examined (see e.g., Tang et al. Dissecting hematopoietic and renal cell heterogeneity in adult zebrafish at single-cell resolution using RNA sequencing. The Journal of experimental medicine 214, 2875-2887, 2017). This analysis found that 23 out of 29 of the CHT EC genes were strongly enriched in vascular ECs in the kidney marrow (see e.g., FIG. 6A). To determine whether this pro-haematopoietic vascular niche signature is conserved in mammals, an RNA-seq dataset was probed, which comprises gene expression for ECs from multiple organs of the mouse, including the heart, kidney, liver, lung and bone marrow, from five stages of development (E11-13, E14-15, E16-17, P2-P4 and adult). Orthologs for 21 out of 29 CHT EC genes were enriched in the ECs of a mammalian haematopoietic organ—the fetal liver and/or adult bone marrow—relative to their expression in ECs from non-haematopoietic organs at the same stage of development (see e.g., FIG. 6B). Notably, a subset of expression patterns mirrored the temporal dynamics of HSPC ontogeny, showing robust expression in fetal liver ECs at the E14-17 stages and then later displaying elevated expression in adult bone marrow ECs with a concomitant and expected reduction in liver EC expression (P2-P4 and adult; see e.g., FIG. 6B). To determine if a transcriptional program similar to the one uncovered in the zebrafish could control these genes in the mouse, the expression of transcription factors from the Ets, Sox and NHR families was examined using the same RNA-seq datasets. In both fetal liver ECs (E14-17) and adult bone marrow ECs, the most highly expressed factors were Ets1, Sox18 and Nr2f2 (see e.g., Table 5). Taken together, these data indicate that a conserved transcriptional program regulates the pro-haematopoietic niche identity of ECs in the fetal and adult HSPC niches.

DISCUSSION

These data support a model in which a transcriptional program comprised of factors from the Ets, SoxF and NHR families specifies the identity and unique capacity of vascular niche ECs to maintain and expand blood stem cells. This is a conserved feature of the haematopoietic niche at multiple stages of development and across species. The niche endothelial expression signature identified herein comprises genes with known niche functions (e.g., the adhesion receptor E-selectin and the cysteine proteinase Cathepsin L, which has been linked to Cxcl12 turnover in the bone marrow). In addition, there are numerous genes not previously associated with the HSPC niche, including several genes with scavenger functions or activities related to endocytosis and intracellular uptake, including mrc1a, stab1/2, dab2, ap1b1, pxk and snx8. These molecules could regulate ligand and receptor turnover in the niche or could function to clear potentially harmful agents, such as waste products, modified proteins, or viral, bacterial or fungal related material, from the niche microenvironment. CHT ECs share gene expression with lymphatic ECs, including genes such as lyve1b, which is consistent with their shared origin. In a recent study of the mouse bone marrow, differential gene expression was examined between SECs and AECs. The niche EC signature disclosed herein aligns with the venous SECs of the marrow. Although AECs may also support haematopoiesis, the work herein illustrates the sufficiency of SECs to instruct vascular niche formation and foster stem cell expansion. Extramedullary haematopoiesis that occurs during stress could involve the local induction of this SEC niche program. Other transcription factors have been shown to drive CHT gene expression that maintains haematopoietic cells, including tfec and klf6a, although enriched binding motifs were not observed for these factors. It is plausible that their targets are in different cells of the CHT or that these factors act downstream of our program to specify diverse populations of tissue-specific vascular niches.

Experiments with parabiotic mice have indicated that the size of the niche determines the number of HSPCs (see e.g., Chen et al. Mobilization as a preparative regimen for hematopoietic stem cell transplantation. Blood 107, 3764-3771, 2006). Functional ectopic niches, termed ossicles, have been used to assemble a bone marrow equivalent when transplanted into mice, and it is likely that SECs are present in these structures. Together, these studies and the work presented herein support a method of increasing HSPC numbers in vivo by generating ectopic vascular niches at new safe harbor locations in the body. This approach lays the foundation for novel treatments for diseases where the endogenous bone marrow niche is compromised (e.g., myelofibrosis). At a broader level, this work advances the fundamental understanding of the vascular niche that choreographs homeostasis and regeneration of blood stem cells, which can guide new therapeutic strategies to culture and expand HSPCs for transplantation.

Methods

Animal Models.

Wild-type AB, casper or casper-EKK, and transgenic lines cd41: EGFP, runx1:mCherry [runx1+23: NLS-mCherry], kdrl(flk1):GFP [kdrl:GRCFP], kdrl:mCherry [kdrl: Hsa.hras-mCherry], and cxcl12a (sdf1a):DsRed2 were used in this study. Alternative gene names are listed in parenthesis and full transgene names are listed in brackets.

Genomic Analyses.

For RNA tomography (tomo-seq), 72 hpf embryos were euthanized by tricaine overdose and the portion of the tail containing the CHT was manually dissected using a scalpel. The tissue was oriented in optimal cutting temperature (OCT) tissue freezing media in a cryomold with the ventral side facing the bottom of the mold. After snap freezing on dry ice, 40 individual 8 μm-thick cryosections were collected along the dorsal-ventral axis using a cryostat. The RNA from individual cryosections was extracted using TRIzol™ and then barcoded during a reverse transcription step prior to pooling for library preparation and sequencing (see e.g., Junker et al. Genome-wide RNA Tomography in the zebrafish embryo. Cell 159, 662-675, 2014). For single cell and bulk RNA-seq, kdrl:GFP embryos were dissociated using Liberase™ and GFP$^+$ cells were isolated by FACS. For bulk RNA-seq, total RNA was isolated using TRIzol™ and GenElute LPA™ carrier. Libraries were prepared from 50 ng of total RNA/sample as input using Ribogone™ and a SMARTer Universal Low Input RNA Kit™. For single-cell sequencing, approximately 2,000 cells were encapsulated, and libraries were prepared for sequencing. For ATAC-seq, embryos were dissociated using Liberase™ and a minimum of 12,000 cells (max 50,000) were isolated by FACS. Cells were subsequently lysed and isolated nuclei were incubated in a transposition reaction. All sequencing was done using an Illumina Hiseq 2500™. For RNA-seq, quality control was performed by Fast QC™ and Cutadapt™ to remove adaptor sequences and low quality regions. High-quality reads were aligned to UCSC build danRer7 of the zebrafish genome using Tophat™ 2.0.1158 without novel splicing form calls. Transcript abundance and differential expression were calculated with Cufflinks™ 2.2.159. FPKM values were used to normalize and quantify each transcript. For ATAC-seq, reads were aligned to UCSC build danRer7 of the zebrafish genome using Bowtie2™ (version 2.2.1) with the following parameters:—end-to-end, -N0-, -L20. The MACS2™ (version 2.1.0) peak finding algorithm was used to identify regions of ATAC-seq peaks with the following parameters: —nomodel—shift-100—extsize 200. An initial q-value threshold of enrichment of 0.05 was used for peak calling and a more stringent q-value of 14 was used to identify peaks that were distinct between different samples. Genome-wide motif enrichment analysis was performed using HOMER™ and motif annotation was done using Consite™. Gene expression analysis of the adult kidney marrow was performed data available on the world wide web at molpath.shinyapps.io/zebrafishblood/.

Whole Mount In Situ Hybridization (WISH).

In situ hybridization was performed using a standard protocol. Embryos were subsequently transferred to glycerol for scoring and imaging. In situ probes were generated by PCR amplification using a cDNA or plasmid (for transcription factors from other species) template followed by reverse transcription with digoxigenin-linked nucleotides. Primer sequences for all WISH probes used herein are provided in Table 7. WISH images for the 35 CHT-enriched genes identified by tomo-seq can be found on the world wide web at zfin.org.

Transgenesis and Enhancer-GFP Reporter Assays.

Transgenic lines were established. For the mrc1a:GFP and sele:GFP transgenes, 1.3 kb and 5.3 kb sequences, respectively, upstream of the transcriptional start site were PCR amplified off of genomic DNA and then TOPO-TA™ cloned into a p5E Gateway™ vector, which was then recombined with GFP and a polyA tail, all flanked by Tol2 sites. For the 125 bp mrc1a and 158 bp sele enhancers, the elements were PCR amplified off of genomic DNA, TOPO-TA™ cloned into a pSE Gateway™ vector and then recombined with the mouse Beta-globin minimal promoter fused to GFP with a polyA tail, all flanked by Tol2 sites. Embryos were injected at the one cell-stage with Tol2 RNA and at least two independent lines showing similar expression were established for each construct: (Tg(mrc1a(1.3 kb):GFP); Tg(sele (5.3 kb):GFP); Tg(mrc1a(125 bp):GFP); and Tg(sele(158 bp):GFP). The CHT EC and pan-EC ATAC-seq elements were similarly amplified by PCR using genomic DNA and then fused to the Beta-globin minimal promoter and GFP. Mutational variants of 125 bp mrc1a and 158 bp sele were generated by annealing overlapping oligos followed by a T4 DNA polymerase reaction to generate blunt-ended products, which were subsequently cloned into p5E Gateway™ vectors (following A-tailing with Klenow Fragment using the same work flow as for the ATAC-seq elements). Transcription factor binding motifs were disrupted by changing nucleotides in the core binding sites, purines for pyrimidines and vice versa. Injected F0 embryos were scored between 60-72 hpf. Control and experimental groups were blinded prior to scoring and all experiments were performed at least three times, with independent clutches. GFP expression in CHT ECs or pan-EC expression was scored as significant if it was observed in at least 10% of F0 injected embryos. Embryos scored as negative had either no GFP expression or had only sparse ectopic expression in muscle cells. The sequences for primers used to amplify the mrc1a and sele regulatory elements, as well as the 15 CHT EC and 6 pan-EC ATAC-seq elements, are provided in Table 7. The sequences for the overlapping oligos that were used to generate the enhancer variants are provided in Table 8. The fidelity of all constructs was confirmed by sequencing prior to injection.

Transcription Factor Overexpression Studies.

For transcription factor overexpression studies, the open reading frames for the human (FLI1, ETV2, ETS1, SOX7 and RXRA), Xenopus (Sox18) or zebrafish (Nr2f2) genes were cloned into a pME Gateway vector (Invitrogen™) and then recombined with the zebrafish ubi promoter and a polyA tail, all flanked by Tol2 sites. The fidelity of all constructs was confirmed by sequencing prior to injection. Embryos were injected with pools of ubi-driven transcription factors (1 nl at 25 ng/µl total DNA, plus Tol2 RNA) at the one cell-stage and then screened between 24-72 hpf for ectopic niche endothelial gene expression or ectopic HSPC localization. For control and single-factor injections, the empty Tol2 Gateway™ destination vector was used as filler DNA in the injection mix. Expression of the transcription factors was confirmed by WISH using species-specific in situ probes. Ectopic expression was scored as vascular staining or vascular GFP expression outside the normal domain of gene expression. Control and experimental samples were blinded prior to scoring and all experiments were performed at least three times, with independent clutches.

Microscopy and Image Analysis

Time-lapse microscopy was performed using a Yokogawa CSU-XI™ spinning disk mounted on an inverted Nikon Eclipse Ti™ microscope equipped with dual Andor iXon™ EMCCD cameras and a climate controlled (maintained at 28.5° C.) motorized x-y stage to facilitate tiling and imaging of multiple specimens simultaneously. Screening of injected enhancer-GFP constructs and imaging of WISH embryos was performed using a Nikon SMZ18™ stereomicroscope equipped with a Nikon DS-Ri2™ camera. All images were acquired using NIS-Elements™ and processed using Imaris™ or Adobe Photoshop™ software. Embryos were mounted for imaging. Briefly, specimens were mounted in 0.8% LMP agarose with tricaine (0.16 mg/ml) in glass bottom 6-well plates and covered with E3 media containing tricaine (0.16 mg/ml).

Flow Cytometry, Kidney Marrow Dissection, Dissociation and Histology.

Embryos were prepared for FACS. Briefly, embryos were chopped with a razor blade in cold PBS and then incubated in Liberase™ for 20 minutes at 37° C. before filtering the dissociated cells through a 40 µm mesh filter and transferring to 2% FBS. FACS was performed using a FACS Aria™ machine. Gates were set using transgene positive and negative control embryos, and SYTOX Blue™ was used as a live/dead stain. At least 12,000 (50,000 max) cells were collected per sample for ATAC-seq experiments and at least 10,000 (300,000 max) cells per sample were collected for RNA-seq experiments. Kidney marrow was harvested from adult zebrafish by manual dissection and then fixed in 4% PFA (for histology) or dissociated by gentle pipetting (for live cell imaging). For histology the kidney marrow was embedded in paraffin prior to sectioning; alternating sections were stained with H & E or with an antibody to GFP. Mouse EC populations were sorted as $Cd45^-Pdpn^-Cd31^+$ cells.

Electrophoretic Mobility Shift Assay.

The Nr2f2 fragment was cloned into the pGEX2TK™ vector to generate GST-tagged Nr2f2 and fidelity was verified by sequencing. The pGEX2TK-Nr2f2 protein plasmid was transformed into E. coli BL21 competent cells. Proteins were expressed and purified, and purified proteins were quantified against BSA. EMSAs were performed. Probes were generated by annealing 100 pmol of sense and anti-sense oligonucleotides, and 1-2 pmol of probe was used in each reaction. All primer and probe sequences are provided in Table 9. Gel shift reactions were conducted at 4° C. in 20% glycerol, 20 mM Tris (pH 8.0), 10 mM KCl, 1 mM DTT, 12.5 ng poly dI/C, 6.25 pmol of random, single-stranded oligonucleotides, BSA and the probe in the amount specified above. Samples involving the Nr2f2 protein were loaded on a 6% gel to resolve protein-DNA complexes. In reactions with cold competitors, 20× unlabeled probes were included in the reactions. Anti-NR2F2 antibody (R&D Biosystems™; cat #PP-H7147-00) was at the same amount of the Nr2f2 protein to obtain super-shifts.

The GEO accession number for the mammalian genomic data reported herein is GSE100910. The zebrafish genomic data reported herein was submitted to the NCBI™ Gene Expression Omnibus.

Real-time imaging can show blood circulation through region of ectopic niche endothelial gene expression. At 72 hpf show blood cells can be seen circulating through a region of vessels in the dorsal trunk that are ectopically expressing mrc1a:GFP in a 72 hpf embryo that had been injected with a pool of seven transcription factors at the one cell-stage.

Figure 5D:
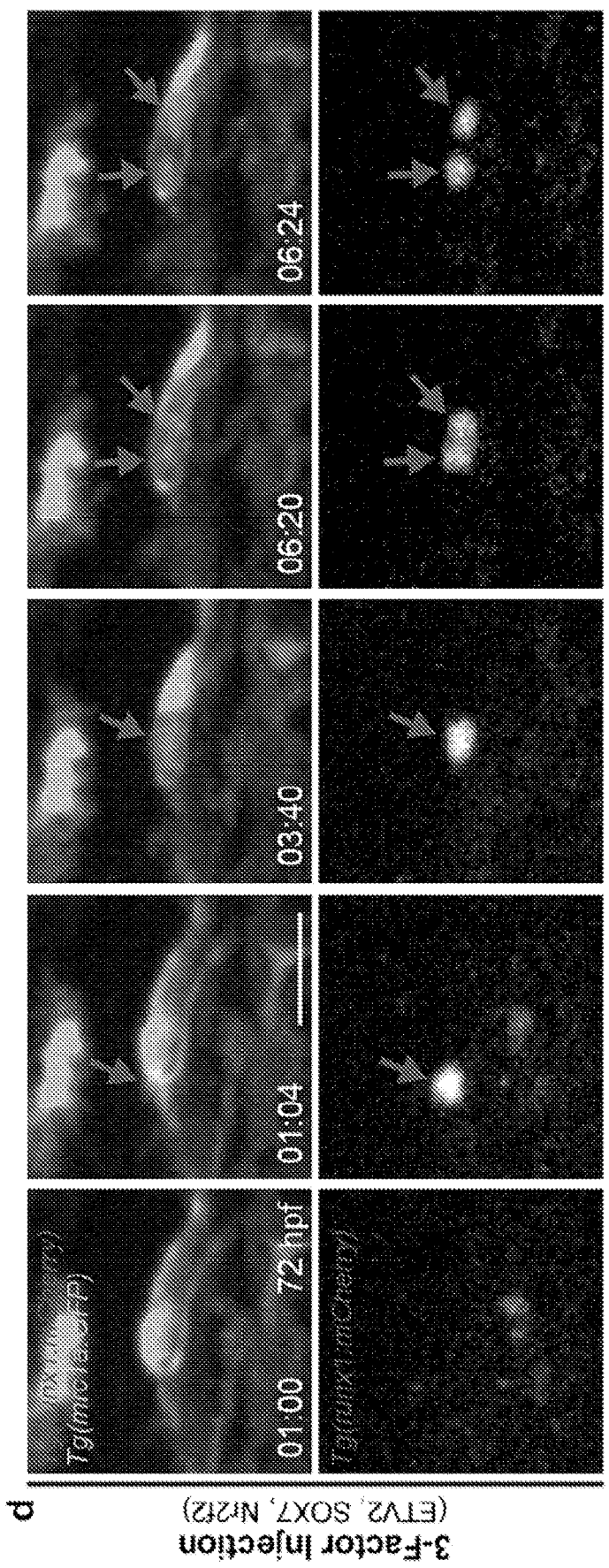
Figure 5E:
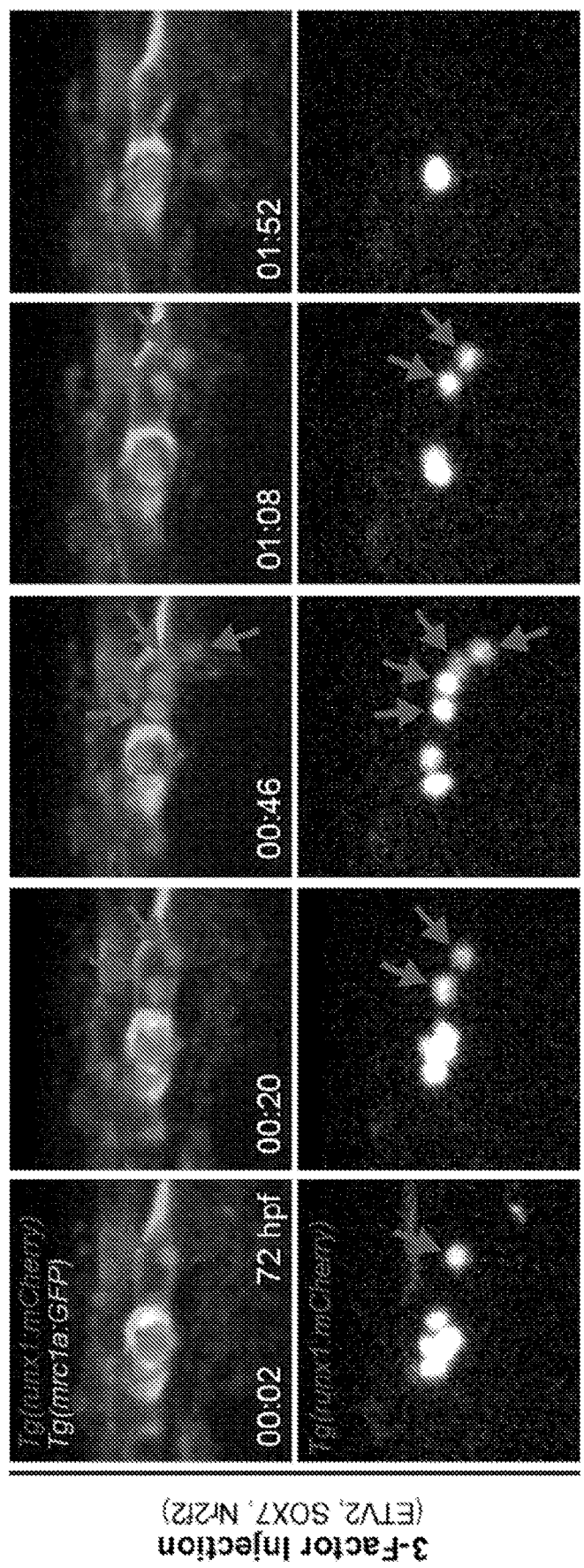

Real-time imaging can show initial recruitment of HSPC to region of ectopic niche endothelial expression. A runx1$^+$ HSPC can be seen initially lodging in a dorsal vessel that is ectopically expressing mrc1a:GFP (see e.g., FIG. 5D arrows) in a 72 hpf embryo that had been injected with a pool of ETV2, SOX7 and Nr2f2 at the one cell-stage. Black arrowhead points to HSPC localization in the CHT. The duration of the time-lapse is 6.5 hours; time intervals are 2 min. Time-series is shown in FIG. 5D.

Real-time imaging can show proliferation of HSPCs and egress from ectopic region of niche endothelial gene expression. Runx1$^+$ HSPCs can be localized to a vessel ectopically expressing mrc1a:GFP (see e.g., FIG. 5E arrows) in a 72 hpf embryo that had been injected with a pool of ETV2, SOX7 and Nr2f2 at the one cell stage. HSPCs divide several times and migrate away into circulation. Black arrowhead points to HSPC localization in the CHT. The duration of the time-lapse is 2.6 hours; time intervals are 2 min. Time-series shown in FIG. 5E.

TABLE 1

CHT EC-enriched genes.

| Gene | Full Gene Name | CHT Expression Confirmed by WISH | Associated with CHT EC ATAC-seq Element* | Function |
| --- | --- | --- | --- | --- |
| adra1d | adrenoreceptor alpha 1D | No† | Yes | G-protein coupled receptor; mitogenic response activation |
| ap1b1 | adaptor-related protein complex 1, beta 1 subunit | Yes | Yes | Coated vesicle clathrin recruitment |
| cldn11a | claudin 11a | Yes | Yes | Tight junction strand component |
| cltca | clathrin, heavy chain a (Hc) | Yes | Yes | Major coated vesicle and coated pit component |
| ctsh | cathepsin H | Yes | No | Lysosomal cysteine proteinase |
| ctsla | cathepsin La | Yes | Yes | Lysosomal cysteine proteinase |
| dab2 | Dab, mitogen-responsive phosphoprotein, homolog 2 (*Drosophila*) | n/a‡ | Yes | Mitogen-responsive phosphoprotein; clathrin-mediated endocytosis |
| exoc3l2a | exocyst complex component 3-like 2a | Yes | Yes | SNARE binding |
| glula | glutamate-ammonia ligase (glutamine synthase) a | Yes | Yes | Glutamine synthesis |
| gpr182 | G protein-coupled receptor 182 | Yes | Yes | G-protein coupled receptor; vasodilation |
| hexb | hexosaminidase B (beta polypeptide) | Yes | Yes | Degradation of N-acetyl hexosamine containing molecules |
| hyal2a | hyaluronidase 2a | n/a§ | Yes | Hyaluronan degradation |
| hyal2b | hyaluronidase 2b | Yes | Yes | Hyaluronan degradation |
| ifi30 | interferon, gamma-inducible protein 30 | Yes | Yes | Disulfide bond reduction. MHC class II-restricted antigen processing |
| il13ra2 | interleukin 13 receptor, alpha 2 | Yes | No | Interleukin 13 binding |
| igmn | legumain | Yes | Yes | Hydrolysis of asparaginyl bonds |
| lyve1b | lymphatic vessel endothelial hyaluronic receptor 1b | Yes | Yes | Hyaluronan receptor |
| man2b2 | mannosidase, alpha, class 2b, member 2 | Yes | Yes | Mannose glycosylase |
| mrc1a | mannose receptor, C type 1a | Yes | Yes | Glycoprotein endocytosis |
| npl | N-acetylneuraminate pyruvate lyase (dihydrodipicolinate synthase) | n/a‡ | Yes | N-acetylneuraminic acid cleavage |
| prcp | prolylcarboxypeptidase (angiotensinase C) | n/a‡ | Yes | C-terminal proline linked amino acid cleavage |
| pxk | PX domain containing serine/threonine kinase | No | Yes | Synaptic transmission |
| sele | selectin E | Yes | Yes | Endothelial cell adhesion to blood leukocytes |
| sepp1a | selenoprotein P | Yes | No | Selenium binding |
| slc16a9a | solute carrier family 16, member 9a | No | Yes | Symporter activity |
| snx8a | sorting nexin 8a | Yes | Yes | Phosphatidylinositol binding |
| stab1 | stabilin 1 | Yes | Yes | Scavenger receptor activity |
| stab2 | stabilin 2 | Yes | Yes | Scavenger receptor activity, hyaluronan receptor |
| tll1 | tolloid-like 1 | Yes | Yes | Procollagen C-propeptide processing |

TABLE 2

In vivo screening of predicted enhancer elements.

| Type of Element | Gene Name | Genomic Coordinates of ATAC-seq Element* | Relative to TSS (kb) | Amplicon Size (bp) | Showed Predicted GFP Expression Pattern† | Element Contains Ets, SoxF and NHR Motifs |
|---|---|---|---|---|---|---|
| CHT EC Element | ap1b1 | chr 5:26463217-26463695 | 17 | 750 | Yes | Yes |
| | cltca | chr10:29,047,274-29,047,619 | 2.8 | 404 | Yes | Yes |
| | dab2 | chr5:33,980,000-33,980.306 | −3.5 | 394 | Yes | Yes |
| | exoc3l2a | chr5:38359097-38359903 | 5.9 | 901 | Yes | Yes |
| | glula | chr2:19,458,704-19,459.047 | 4.8 | 446 | No | Yes |
| | gpr182 | chr23:36701205-36701682 | −4.9 | 481 | Yes | Yes |
| | gpr182 | chr23:36694073-36694476 | −2.8 | 398 | Yes | Yes |
| | gpr182 | chr23:36696363-36696656 | 1.6 | 577 | Yes | Yes |
| | lgmn | chr13:36,448,465-36,448,818 | 2.9 | 414 | Yes | Yes |
| | prcp | chr15:10,400,588-10,400,868 | 23 | 334 | No | No‡ |
| | sele | chr20:34,010,027-34,010,326 | −9.7 | 398 | Yes | Yes |
| | sele | chr20:34,011,251-34,011,563 | −8.5 | 360 | Yes | Yes |
| | snx8a | chr3:42,090,805-42,091,062 | 5.5 | 395 | No | Yes |
| | stab1 | chr22:10467346-10467937 | −2.8 | 874 | Yes | Yes |
| | stab2 | chr4:9790795-9791116 | 4.3 | 422 | Yes | Yes |
| Pan-EC Element | cdh5 | chr7:45457842-45458791 | 13 | 823 | Yes | Yes |
| | clec14a | chr17:10362325-10362844 | −3.1 | 455 | Yes | Yes |
| | dll4 | chr20:28219013-28219619 | −55 | 452 | Yes | No‡ |
| | fli1a | chr18:47039842-47040466 | 47 | 800 | Yes | No‡ |
| | lmo2 | chr18:36722030-36722527 | −3.6 | 367 | Yes | No‡ |
| | nrp1b | chr2:43535098-43535801 | −34 | 552 | Yes | Yes |

Table 1 shows CHT EC genes identified by tomo-seq and tissue-specific RNA-seq. Asterisks (*) indicates that gene is within 100 kb of TSS; some genes are associated with multiple elements. Cross (†) indicates that no expression was observed by WISH. Double cross (‡) indicates that WISH was not attempted but CHT expression was reported on the world web wide available at zfin.org. Double S (§) indicates that WISH was not attempted.

Table 2 shows CHT EC-specific and pan-EC ATAC-seq elements that were fused to a minimal promoter and GFP and injected into one-cell stage zebrafish embryos. Asterisks (*) indicates coordinates of MACS2 peak. Cross (†) indicates expression in CHT ECs for CHT EC elements and in vessels throughout the embryo for pan-EC elements. Double cross (‡) indicates lack of NHR motif.

TABLE 3

CHT-enriched genes identified by tomo-seq

| Gene | Full Gene Name | CHT Expression Confirmed by WISH |
|---|---|---|
| abi3bp | ABI family, member 3 (NESH) binding protein | Yes |
| ACKR3 | atypical chemokine receptor 3 | No* |
| adam8a | ADAM metallopeptidase domain 8a | Yes |
| adra1d | adrenoceptor alpha 1D | No* |
| adr53b | adrenoceptor beta 3b | No* |
| agrP | agouti related neuropeptide | No* |
| ANGPT4 | angiopoietin 4 | No* |
| ap1b1 | adaptor-related protein complex 1, beta 1 subunit | Yes |
| apinra | apelin receptor a | Yes |
| aqp7 | aguaporin 7 | Yes |
| atp1a1a.2 | ATPase Na+/K+ transporting subunit alpha 1a, tandem duplicate 2 | n/a† |
| atp1b1b | ATPase, Na+/K+ transporting, beta 1b | n/a† |
| ba1 | ba1 globin | n/a† |
| blf | bloody fingers | n/a† |
| BX005069.4 | leukocyte cell-derived chemotaxin-2-like | n/a† |
| BX323861.1 | SLAM family member 9-like isoform X2 | n/a† |
| C10H8orf4 | | n/a† |
| ca15a | carbonic anhydrase XVa | n/a† |
| CABZ01049362.1 | PREDICTED: GTPase IMAP family member 4-like [Danio rerio]. or 8-like | n/a† |
| CABZ01058863.1 | | n/a† |
| CABZ01066695.1 | PREDICTED: protein lyl-1-like isoform X1 [Danio rerio]./.lymphocytic leukemia protein | n/a† |
| ccdc88b | coiled-coil domain containing 88B | n/a† |
| ccr9a | chemokine (C-C motif) receptor 9a | Yes |
| CD209 | CD209 molecule | n/a† |
| cd28 | CD28 molecule | Yes |
| ceacam1 | carcinoembryonic antigen-related cell adhesion molecule 1 | Yes |
| ch25hl2 | cholesterol 25-hydroxylase like 2 | n/a† |
| cldn11a | claudin 11a | Yes |

TABLE 3-continued

CHT-enriched genes identified by tomo-seq

| Gene | Full Gene Name | CHT Expression Confirmed by WISH |
|---|---|---|
| cfdng | claudin g | n/a† |
| cltca | clathrin, heavy chain a (Hc) | Yes |
| cmklr1 | chemokine-like receptor 1 | n/a† |
| cndp2 | carnosine dipeptidase 2 | Yes |
| cnn1a | calponin 1, basic, smooth muscle, a | Yes |
| COL19A1 | collagen, type XIX, alpha 1 | Yes |
| col28a1 | collagen, type 28, alpha 1 | n/a† |
| coro1a | coronin, actin binding protein, 1A | n/a† |
| cpa5 | carboxypeptidase A5 | n/a† |
| CR381673.2 | Natural killer cell receptor 2B4-like isorm x1/2 or SLAM family member7/9- | n/a† |
| ctsh | cathepsin H | Yes |
| ctsla | cathepsin La | Yes |
| CU463790.1 |  | Yes |
| CU861664.1 | PREDICTED: zinc finger protein 521-like [*Danio rerio*] | n/a† |
| CU915778.1 | CU915778.1 | No* |
| cyp24a1 | cytochrome P450, family 24, subfamily A, polypeptide 1 | No* |
| cysltr1 | cysteinyl leukotriene receptor 1 | Yes |
| dab2 | Dab, mitogen-responsive phosphoprotein, homolog 2 (*Drosophila*) | n/a† |
| drl | draculin | n/a† |
| ela2 | elastase 2 | Yes |
| ENSDARG00000075833 | lymphatic vessel endothelial hyaluronic receptor 1a/b | Yes |
| entpd2a.1 | ectonucleoside triphosphate diphosphohydrolase 2a, tandem duplicate 1 | n/a† |
| exoc3l2a | exocyst complex component 3-like 2a | Yes |
| f2r | coagulation factor II (thrombin) receptor | Yes |
| foxi3b | forkhead box I3b | n/a† |
| frem1b | Fras1 related extracellular matrix 1b | Yes |
| gcm2 | glial cells missing homolog 2 (*Drosophila*) | Yes |
| glud1a | glutamate dehydrogenase 1a | Yes |
| glula | glutamate-ammonia ligase (glutamine synthase) a | Yes |
| GMIP | GEM interacting protein | n/a† |
| gpr182 | G protein-coupled receptor 182 | Yes |
| grap2b | GR82-related adaptor protein 2b | n/a† |
| gsto1 | glutathione S-transferase omega 1 | Yes |
| havcr1 | hepatitis A virus cellular receptor 1 | n/a† |
| hbaa1 | hemoglobin, alpha adult 1 | n/a† |
| hdr | hematopoietic death receptor | n/a† |
| hexb | hexosaminidase B (beta polypeptide) | Yes |
| hyal2a | hyaluronidase 2 | n/a† |
| hyal2b | hyaluronidase 2 | Yes |
| HYAL2 | hyaluronidase 2 | Yes |
| ifi30 | interferon, gamma-inducible protein 30 | Yes |
| il10ra | interleukin 10 receptor, alpha | n/a† |
| il13ra2 | interleukin 13 receptor, alpha 2 | Yes |
| il6r | interleukin 6 receptor | Yes |
| ITGAE | integrin, alpha E, tandem duplicate 1/2 | No* |
| itgb2 | integrin, beta 2 | Yes |
| kcnj1a.3 | potassium inwardly-rectifying channel, subfamily J, member 1a, tandem duplicate 3 | n/a† |
| kcnj1a.5 | potassium inwardly-rectifying channel, subfamily J, member 1a, tandem duplicate 5 |  |
| lamp2 | lysosomal-associated membrane protein 2 | Yes |
| lgals9l1 | lectin, galactoside-binding, soluble, 9 (galectin 9)-like 1 | n/a† |
| lgmn | legumain | Yes |
| lpar5a | lysophosphatidic acid receptor 5a | n/a† |
| mafbb | v-maf avian musculoaponeurotic fibrosarcoma oncogene homolog Bb | n/a† |
| man2b2 | mannosidase alpha, class 2B, member 2 | Yes |
| marco | macrophage receptor with collagenous structure | n/a† |
| MCOLN2 | mucolipin 2[WM2] | n/a† |
| mir142a | micro RNA 142a | n/a† |
| mmp13a | matrix metallopeptidase 13a | n/a† |
| MOV10L1 | putative helicase Mov10l1 [*Danio rerio*]. 95% ident. | n/a† |
| mpx | myeloid-specific peroxidase | n/a† |
| mrc1a | mannose receptor, C type 1a | Yes |
| mrc1b | mannose receptor, C type 1b | n/a† |
| myh11a | myosin, heavy chain 11a, smooth muscle | Yes |
| myha | myosin, heavy chain a | n/a† |
| myo1f | myosin IF | Yes |
| ncf1 | neutrophil cytosolic factor 1 | n/a† |
| npl | N-acetylneuraminate pyruvate lyase (dihydrodipicolinate synthase) | n/a† |

TABLE 3-continued

CHT-enriched genes identified by tomo-seq

| Gene | Full Gene Name | CHT Expression Confirmed by WISH |
|---|---|---|
| ostf1 | osteoclast stimulating factor 1 | n/a† |
| parvg | parvin, gamma | Yes |
| pdia2 | protein disulfide isomerase family A, member 2 | n/a† |
| PLCXD1 | phosphatidylinositol-specific phospholipase C, X domain containing 1 | n/a† |
| plek | pleckstrin | n/a† |
| polm | polymerase (DNA directed), mu | n/a† |
| prcp | prolylcarboxypeptidase (angiotensinase C) | n/a† |
| pxk | PX domain containing serine/threonine kinase | No* |
| rasal3 | RAS protein activator like 3 | n/a† |
| RNF223 | ring finger protein 223 | n/a† |
| s1pr4 | sphingosine-1-phosphate receptor 4 | n/a† |
| sele | selectin E | Yes |
| sepp1a | selenoprotein P | Yes |
| setx | senataxin | Yes |
| si:ch1073-429i10.1 | si:ch1073-429i10.1 | Yes |
| si:ch211-214p16.1 | si:ch211-214p16.1 | No* |
| si:ch211-214p16.2 | si:ch211-214p16.2 | Yes |
| si:ch211-250g4.3 | PREDICTED: nesprin-1 isoform X4 [Danio rerio] | n/a† |
| si:ch211-284o19.8 | si:ch211-284o19.8 | n/a† |
| si:ch211-285f17.1 | si:ch211-285f17.1 | n/a† |
| si:ch211-67e16.2 | cd28-like molecule | n/a† |
| si:ch73-248e21.7 | si:ch73-248e21.7 | n/a† |
| si:ch73-27e22.6 | si:ch73-27e22.6 | n/a† |
| si:dkey-102g19.3 | si:dkey-102g19.3 | n/a† |
| si:dkey-188i13.7 | interferon alpha inducible protein 46 | n/a† |
| si:dkey-237j10.2 | si:dkey-237j10.2 | n/a† |
| si.dkey-33i11.4 | si:dkey-33i11.4 | Yes |
| si:dkey-69c1.1 | si:dkey-69c1.1 | n/a† |
| skap2 | src kinase associated phosphoprotein 2 | n/a† |
| sla1 | src-like-adaptor 1 | n/a† |
| slc16a9a | solute carrier family 16, member 9a | No* |
| slc4a11 | solute carrier family 4, sodium borate transporter, member 11 | n/a† |
| snx8a | sorting nexin 8a | Yes |
| srgn | serglycin | Yes |
| stab1 | stabilin 1 | Yes |
| stab2 | stabilin 2 | Yes |
| syk | spleen tyrosine kinase | n/a† |
| tagapb | T-cell activation RhoGTPase activating protein b | n/a† |
| tll1 | tolloid-like 1 | Yes |
| tmem106a | transmembrane protein 106a | Yes |
| tnfsf12 | TNF superfamily member 12 | n/a† |
| tnni1b | troponin I type 1b (skeletal, slow) | Yes |
| tubb1 | tubulin, beta 1 class VI | n/a† |
| wasa | Wiskott-Aldrich syndrome (eczema-thrombocytopenia) a | n/a† |
| wasb | Wiskott-Aldrich syndrome (eczema-thrombocylopenia) b | n/a† |
| WIPF1 | WAS/WASL interacting protein family, member 1a/b | n/a† |
| zgc:158446 | complement factor b, like | n/a† |
| zgc:174945 | zgc:174945 | n/a† |
| zgc:198419 | fenitin, heavy polypeptide-like 28 | Yes |

Asterisk (*) in Table 3 indicates that no CHT expression was observed by WISH.
Dagger symbol (†) in Table 3 indicates WISH was not attempted.

TABLE 4

Transcription factor expression in CHT ECs

| Transcription Factor | Family | FPKM | Associated with CHT EC ATAC-seq Element Containing Ets, Sox and NHR Sites* | Genomic Coordinates of Representative Element |
|---|---|---|---|---|
| fli1a | Ets | 480.4 | Yes | chr18:46966409-46966698 |
| etv2 | Ets | 192.3 | Yes | chr16:44782409-44782895 |
| ets1 | Ets | 183 | Yes | chr18:46883643-46884100 |
| sox18 | SoxF | 206.4 | Yes | chr23:8886011-8886744 |
| sox7 | SoxF | 125.1 | Yes | chr20:19158376-19158663 |
| nr2f2 | NHR | 84.6 | Yes | chr18:23728906-23729747 |
| rxraa | NHR | 45.9 | Yes | chr21:16411020-16411531 |

Table 4 shows FPHM expression values in CHT ECS for highly expressed members of the Ets, Sox and NHR transcription factor families. Asterisk (*) in Table 4 indicates within 100 kb of TSS; some genes are associated with multiple elements.

TABLE 5

Transcription factor expression in mouse hematopoetic niche

| Transcription Factor | Family | Mouse E14-E15 Liver EC FPKM | Mouse E16-E17 Liver EC FPKM | Mouse Adult Bone Marrow EC FPKM |
|---|---|---|---|---|
| Ets1 | Ets | 218.4666 | 251.9493 | 153.2657 |
| Erg | Ets | 46.64156 | 78.53131 | 45.14673 |
| Elk4 | Ets | 9.369453 | 11.4226 | 22.83457 |
| Elk1 | Ets | 7.003965 | 9.08418 | 6.8779 |
| Etv1 | Ets | 2.203135 | 3.10327 | 1.488542 |
| Etv2 | Ets | 0.235977 | 0 | 0 |
| Sox18 | SoxF | 127.1509 | 262.44 | 130.1783 |
| Sox7 | SoxF | 49.94503 | 46.9365 | 19.80563 |
| Sox17 | SoxF | 33.01219 | 68.37438 | 90.24645 |
| Sox11 | SoxF | 12.01665 | 11.1584 | 0.67509 |
| Sox12 | SoxF | 11.81507 | 21.5267 | 0.556478 |
| Sox6 | SoxF | 1.741399 | 1.158524 | 0.51182 |
| Sox5 | SoxF | 0.193041 | 0.289841 | 0.437005 |
| Sox9 | SoxF | 0.119527 | 0.072563 | 0 |
| Nr2f2 | NHR | 58.97832 | 103.5558 | 63.17458 |
| Rxra | NHR | 23.98264 | 33.0942 | 22.08392 |
| Rara | NHR | 19.29841 | 27.37294 | 13.93433 |
| Nr4a2 | NHR | 10.13413 | 3.130986 | 30.30394 |
| Esrrb | NHR | 6.219864 | 7.884516 | 0.586381 |
| Rora | NHR | 1.219604 | 1.086872 | 5.922048 |

TABLE 6

Primers used for WISH probe synthesis ("Forward" primers disclosed as SEQ ID NOS 16-84 and "Reverse" primers disclosed as SEQ ID NOS 85-153, all respectively, in order of appearance)

| Category | Gene | Forward* | Reverse† |
|---|---|---|---|
| CHT EC enriched | adra1d | GCTCCATAGTATCGTCTGAACC | AAACCATTGCCATTTTGCCA |
| CHT EC enriched | ap1b1 | GGGAGTTCTTCGGGTGACTG | GCTTGCAACAAAAAGCGCAG |
| CHT EC enriched | cldn11a | TGTGTGATCTCAACTGCGCT | GGTGCAATCTAGTCTGATCGGT |
| CHT EC enriched | cltca | CCAGCAAACCCCATGGATCT | AACCGAGTACAGGACACACG |
| CHT EC enriched | ctsh | CGACTGGAGAACCAAGGGAC | TGGAGGCTAATCGAGTGTGC |
| CHT EC enriched | ctsla | CCATGCAACAGAGGAAGGGT | TACTGGGCGGGTCTCCTTTA |
| CHT EC enriched | exoc3l2a | AAGTTCCGCAGGATGGACTG | TCGCTTGTGTGATCAAGTATGAC |
| CHT EC enriched | glula | AGTTATGCCAGCTCAGTGGG | GGCCTCCCCAAGAAACCATT |
| CHT EC enriched | gpr182 | CTTCCCACAGCAGCACAAAC | GAAAGTTGTTGTTGAAGTGAACG |
| CHT EC enriched | hexb | GAATTTGCTCGCATGAGGGG | CGGCAGTGGCCAACAAATAG |
| CHT EC enriched | hyal2b | ATGGAGGTCTACCACAGGCT | AGTGCAGGTATGTGTCCGTG |
| CHT EC enriched | ifi30 | TTCGGCTTTAACCTGTGCGT | CCTGACGCGAGTAGTGTTGT |
| CHT EC enriched | il13ra2 | AGTTAGAATGGGCGCCACC | GGCAAGACCACTGGCATTTG |
| CHT EC enriched | lgmn | AACTTGAGCCACCGAGGATT | CCCTAACTCCAGCACACACT |
| CHT EC enriched | lyve1b | GCTACAGTCTGCGTAGCAT | TGGAAGCAGCTCTAAGTGACAG |
| CHT EC enriched | man2b2 | TACCCAATGGTTCGAGTGGC | GCTTAGGTGATCAATTTTGGGACA |
| CHT EC enriched | mrc1a | GTGTCCCCTCATCAATGCCA | ACGGCATTCCACAAACCAGA |
| CHT EC enriched | sele | TGCCCAGCCCTTGATAATCT | ACCCAAACTGACTTTATATGTGC |
| CHT EC enriched | sepp1a | AGGCAGCACTGGACTTTAGC | AGGTACAAATGCAAGTACAACACT |

TABLE 6-continued

Primers used for WISH probe synthesis ("Forward" primers disclosed as SEQ ID NOS 16-84 and "Reverse" primers disclosed as SEQ ID NOS 85-153, all respectively, in order of appearance)

| Category | Gene | Forward* | Reverse† |
|---|---|---|---|
| CHT EC enriched | snx8a | ACAAAGAGATCTGCATTCCAAGC | AGCCTGTCAGCTCACTTTATT |
| CHT EC enriched | stab1 | AAGGCGTACTATGTCCTCAGGC | CGCCGTTCTATAATGCACCG |
| CHT EC enriched | stab2 | TTGTGGATTACGGGGTTCGG | AAAGAGAGCTGCACCGACT |
| CHT EC enriched | tll1 | GAGCTTTACTCTGCTGGCGA | ACAAATGATGTCTGTCTCCGCT |
| CHT enriched | abi3bp | CTGTTTTCCCCCACCAGTGA | CAAAGGATTGGCAGGGACCA |
| CHT enriched | ackr3 | TGGGATTATTTGTAACTACACGGA | TTTTAAGCACATTTCTGAAGCACA |
| CHT enriched | adam8a | CCAGGAAGCGCAAAGAACAG | ACATTAGGCGGGCAAAACAAA |
| CHT enriched | adrb3b | GCAGCAAACGACTGCTACAA | CCCACTTCGCTGCTCTTTAC |
| CHT enriched | agrp | TCATCCACACCTGAGACGCA | ACACCTTAAAACCGCAGCC |
| CHT enriched | angpt4 | ATCCGACTGCTGGAATGGAC | GCTTTGAGGAGCTTAAGAGGC |
| CHT enriched | aplnra | GTGCTGGTCAACATGTACGC | CGTCACTTTTCACCCCAGA |
| CHT enriched | aqp7 | TCCACTGGGAAAAGCTGGAAT | TTTCAGATGCAGCACAGGCA |
| CHT enriched | bnip3lb | ATGGGGCTGACGGATACC | GCACAGGAAACGCACATGAT |
| CHT enriched | ccr9a | TTGTCCAGACTACCAAGGCG | TTACTTCACTGCCAGTCGG |
| CHT enriched | cd28 | ATCCAAACTGAGGCCGGAAG | AGAAAATACAGTGCATACATGTCAA |
| CHT enriched | ceacam1 | GGCCCAAGCATGGCAGAAAC | CCTACAAGCCTCATTCAGACAGT |
| CHT enriched | cndp2 | ACATGGGACATGGAGCGAAG | ACACTAGAAAACCGATCGTGTCA |
| CHT enriched | cnn1a | GACTCTCTGCGGATGTCAGG | GGTCATGCCCTTTTGGCTTG |
| CHT enriched | col19a1 | CATGTCCACCCCTGAAGCTG | GGGTTCTGTTGTGGAGTGCT |
| CHT enriched | cu463790.1 | GGCGTCTCTTTTTCTGCTGC | TGACGCTTAAACAGAGCGGT |
| CHT enriched | cu915778.1 | CCCTAGTGTCCGAGGTCTCA | TTTCCCCTGTGTGGATGAGC |
| CHT enriched | cyp24a1 | GATACCGTGCTGGGCGATTA | CCACCACTCACTCATTCAGACA |
| CHT enriched | cysltr1 | TCCCGGTGCAAAATCTGAGG | AGTCATGCACAAAATCTGCGG |
| CHT enriched | ela2 | GTTTATTGCTGGCGCCTACG | TTCTTGGGGTAGTTGCAGCC |
| CHT enriched | f2r | GCTGCCGAACAACGAAACAT | TAGGACGCGTCATTGTGCTT |
| CHT enriched | frem1b | AGTACACTCCGGACCCAAGA | CACCAGAAAGAATGTCACCGT |
| CHT enriched | gcm2 | TCCAGAGCGATTCAGCATCA | CAGTCCCTCAGTATTCCCG |
| CHT enriched | glud1a | AGTCTCCTACTTCGAGTGGCT | ACGCCTGAGATTCATCCTGC |
| CHT enriched | Il6r | AACTGTTCTTTCTCCCGGTCCC | CCTCTGGCTGAACAGGAAGG |
| CHT enriched | itgae | ACTGGTCAACCACCTCCTCT | ACACAATCAGGCAAGGTCTC |
| CHT enriched | itgb2 | TGCCTTTCAAAGTGGACCGT | ACCAGTCACACCAGCCATTC |
| CHT enriched | lamp2 | AGCCTGTTCCTGGACCATTG | AGCTACAACCATTGAGGGCT |
| CHT enriched | myh11a | GGTTCGCCAGAAGGACAAGA | AGCATCCAAAAGTACTCGGTG |
| CHT enriched | myo1f | AAGCTGTCATCAAAGCCGGA | TTCTCGACCTGTCAGCTGTT |
| CHT enriched | parvg | TGAAAGCCCTGAACGAGACC | CGTCAGCATCCAAACGCAAT |
| CHT enriched | setx | AGGAGTTTGGCTTCGACCAG | GTGACGCTGGAATATCCCGT |
| CHT enriched | skch1073-429110.1 | TCGCTCTGATGCTCAGCTTG | CACTCGGCGACAGTATTCCC |

TABLE 6-continued

Primers used for WISH probe synthesis ("Forward" primers disclosed
as SEQ ID NOS 16-84 and "Reverse" primers disclosed as SEQ ID NOS
85-153, all respectively, in order of appearance)

| Category | Gene | Forward* | Reverse† |
|---|---|---|---|
| CHT enriched | skch211-214p16.1 | TACACATTTTCTGCCCCACTGA | AATGGGGCAAGAGTCCATCT |
| CHT enriched | skch211-214p16.2 | CTCACCCTCGGTCCAGAACT | ACAGACACACTTGCCAGTCA |
| CHT enriched | skdkey-33i11.4 | ACAGCCATCAGTTCCTCTGC | AGCTTTGCATCCCCATCACT |
| CHT enriched | srgn | GGAAGCCACTCCTGATACGG | GTACAACATTTACTTGCTGTCCA |
| CHT enriched | tmem106a | GGTCACCGCACCAAATGAACC | AACAGTTCTGATTGGATTTTGCTCA |
| CHT enriched | tnni1b | TCTGCATCTCGCAAGCTGAT | CATGTGTAGTGCAGACAGAACA |
| CHT enriched | zgc: 198419 | AGAACTACGACAGCGACTGC | GGTTTTGGATAAGAGCTGTGTCA |
| Transcription Factor | ets1 | ACAGACTCTGTACGTTTGAATGCGT | GTCCAGACTTTACTCGTCCGTGTC |
| Transcription Factor | etv2 | TATGACTGCAGTGGTGAAGACC | CTTTCCCGCCGTTTTGTGAA |
| Transcription Factor | fli1a | CAGACCCGTCTCTGTGGTC | CCAGTATGGGGTTGTGGGAC |
| Transcription Factor | nr2f2 | ACCCCGAACAACAATAACA | AGAGGGCAAGCGCAGTAATA |
| Transcription Factor | sox7 | TATAGCCCTTCGTTCCCCA | ACCGAAACCGGCTAAACTGA |
| Transcription Factor | sox18 | TCCTTGGACGCTGTGGACCAAC | TCAAAGCGCTGCTTTCCTCGC |

Asterisk (*) in Table 6 indicates that the T3 sequence CATTAACCCTCATAAAGGGAA (SEQ ID NO: 10) was
added to the 5' end of each forward primer. Dagger symbol (†) in Table 6 indicates that The T7
sequence TAATACGACTCACTATAGGG (SEQ ID NO: 11) was added to the 5' end of each reverse primer.

TABLE 7

Primers used to clone promoter and enhancer elements ("Forward"
primers disclosed as SEQ ID NOS 154-178 and "Reverse" primers disclosed
as SEQ ID NOS 179-203, all respectively, in order of appearance)

| Type of Element | Gene | Genomic Coordinates of ATAC-seq Element | Amplicon Size (bp) | Forward | Reverse |
|---|---|---|---|---|---|
| 5' upstream of TSS | mrc1a (1.3 kb) | chr7: 65,468,213-65,469,565 | 1353 | CTTTTGGCCATTACTGCCG | TTCTGTCTTTTAATCAGCAATCC |
| CHT EC element | mrc1a (125 bp) | chr7: 65469086-65469210 | 125 | GCTCTCAGTTCCTGGTATT TTTCT | TGAAGCTTGTACCTTTCATTTCC |
| 5' upstream of TSS | sele (5.3 kb) | chr20: 34,001,481-34,006,781 | 5301 | TCGTTACTGCACTTGAAAG CGT | TATCAGTGATGTTCTGCAGTGGT C |
| CHT EC element | sele (158 bp) | chr20: 24004805-34004962 | 158 | CCATGAAACTGGGAAGATG AA | CAGGAAGAAATAATGGCAAAAA |
| CHT EC element | ap1b1 | chr5: 26463217-26463695 | 750 | GAAGCTCTCCAGCAGCTCA | CATTTCCACCAGCTGTCTGAT |
| CHT EC element | cltca | chr10: 29,047,274-29,047,619 | 404 | GCTGTCAGCACATTCTTTT CC | CCCTGCTGATCACACATGAC |
| CHT EC element | dab2 | chr5: 33,960,000-33,980,306 | 394 | ACTGCTCCTCACCAATCGT C | TGCACTAAATCTGTGCCAAGTC |
| CHT EC element | exoc3l2a | chr5: 38359097-38359903 | 901 | TTTATATAATCGGAAGGAA CCTTTTT | TCCTGTCAGCTGTTTTCATCC |

TABLE 7-continued

Primers used to clone promoter and enhancer elements ("Forward" primers disclosed as SEQ ID NOS 154-178 and "Reverse" primers disclosed as SEQ ID NOS 179-203, all respectively, in order of appearance)

| Type of Element | Gene | Genomic Coordinates of ATAC-seq Element | Amplicon Size (bp) | Forward | Reverse |
|---|---|---|---|---|---|
| CHT EC element | glula | chr2: 19,458,704-19,459,047 | 446 | GGCAAAATGCTTAGATGCA GA | TGCGAGGAGGACATAACAA |
| CHT EC element | gpr182 | chr23: 36701205-36701682 | 481 | TAGCCTTGTGCAATGCTTG | TGCTGAATTCAAAAGCCACTT T |
| CHT EC element | gprf82 | chr23: 36694073-36694476 | 398 | CACTTCTGGTACCAAATGA TCAAC | GAGGGTTAAACGTGGCCTTA |
| CHT EC element | gprf182 | chr23: 36696363-36696656 | 577 | GCGGCAAACTTTTTGAGTG T | GCCAGCCTCAAAGTTTGTTCT |
| CHT EC element | lgmn | chr13: 36,448,465-36,448,818 | 414 | CGCGTGATGAGGATCTGAT T | GGTGTTGAAAGGTGATGCTG |
| CHT EC element | prcp | chr15: 10,400,588-10,400,868 | 334 | AAAATTAAGAGCGGGCAGA CT | TGGAAACAACAACAGCCTGA |
| CHT EC element | sele | chr20: 34,010,027-34,010,326 | 398 | AAAGCACTTGATTGAGAAT TGC | TGTTTGGTTCAGTTACACGTTTT |
| CHT EC element | sele | chr20: 34,011,251-34,011,563 | 360 | CAGTTTCCCAAGCTTCAAG G | TGTGATTACACATTCCCACACAT |
| CHT EC element | snx8a | chr3: 42,090,805-42,091,062 | 395 | AATGGTTGCAGCATTGTGT T | GCTTTTGTTTGGTGATGTGC |
| CHT EC element | stab1 | chr22: 10467346-10467937 | 874 | GTTACCTGGCAACCACCAA C | TGGTCAGAATAAGCACGTTTCA |
| CHT EC element | stab2 | chr4: 9790795-9791116 | 422 | ACGTTAACAAGGCGATGTT TT | TCTAAACAATTTTTAAGGTAAAC CAAA |
| Pan-EC element | cdh5 | chr7: 45457842-45458791 | 823 | TGACAGGACTCATCAGCAC G | AATAGTCTCTGGTCTGCTGTTAAA |
| Pan-EC element | clec14a | chr17: 10362325-10362844 | 455 | TGGGAAAAATACCAGGAAG CGT | AAGCAGCGAGCTCTCATAATAAA |
| Pan-EC element | dll4 | chr20: 28219013-28219619 | 452 | AGATCAATGAGAGCGAGGC G | GGAGCAGATGAGGTTAAGTCCT |
| Pan-EC element | fli1a | chr18: 47039842-47040466 | 800 | CGGACAGTAATGTCTGGAT GG | CCACAACTCCATACTGGGAAA |
| Pan-EC element | lmo2 | chr18: 36722030-36722527 | 367 | TCATCATGGCCAACAGAAT G | GTGCAGGAAATGAGCACAGA |
| Pan-EC element | nrp1b | chr2: 43535098-43535801 | 552 | TGACTCAACCAATCAATCA GCCT | TAGCAAAGCTCTCAGGCCC |

TABLE 8

Sequences and primers for mutational variants of the 125 bp mrc1a and 158 bp sele enhancer elements ("Total Fragment Sequences" disclosed as SEQ ID NOS 204-208, 13 and 209-212, "Forward Primers" disclosed as SEQ ID NOS 213-222 and "Reverse Primers" disclosed as SEQ ID NOS 223-232, respectively, in order of appearance)

| Gene | Fragment Name | Total Fragment Sequence | Forward Primer | Reverse Primer |
|---|---|---|---|---|
| mrc1a | Wild-type | CCATGAAACTGGGAAGATGAAAGC ATAGTTGAATTGTTACTGGCAACA TCTTCTCTGTAATGCCCCCTGTGA CCCATATTGTCTCGCTCTTTCCTT TATAAACAGAGCTGTAGATATCCA CAGGAAATGGGGGTGTTTTTGCCA TTATTTCTTCCTGTGAAGCTTGTA CCTTTCATTTaaaTTTTG | TGAAGCTTGTACCTTTCATTTCCTTT TTGCTGAGCTTTATTTTCTCTAGAAT TGCCATTGTGTTTCCATTCTAG | GCTCTCAGTTCCTGGTATTTTTCTTTC AGCTGAAAAAAAAATGCTGATTTGCTA GAATGGAAACACAATGGCAAT |
| mrc1a | Ets mutant | CTGAGCTTTATTTTCTCTAGAATT GCCATTGTGTTTCCATTCTAGCAA ATCAGCATTTTTTTTTCAGCTGAA AGAAAAATACCAtttACTGAGAGC TGAAGCTTGTACCTTTCATTTCCT TTTTG | TGAAGCTTGTACCTTTCATTTaaaTT TTGCTGAGCTTTATTTTCTCTAGAAT TGCCATTGTGTTTCCATTCTAG | GCTCTCAGTaaaTGGTATTTTTCTTTC AGCTGAAAAAAAAATGCTGATTTGCTA GAATGGAAACACAATGGCAAT |
| mrc1a | Sox mutant | CTGACGgggcggggaTCTAGAATT GCacggtgGTTTCCATTCTAGCAA ATCAGCcgggggggTTTCAGCTGAA AGAAAAATACCAGGAACTGAGAGC attAGCagatTtaaTTTCATTTCC TTTTTGCa | TGAAGCTTGTACCTTTCATTTCCTTT TTGCTGAGCgggcggggaTCTAGAAT TGCacggtgGTTTCCATTCTAG | GCTCTCAGTTCCTGGTATTTTTCTTTC AGCTGAAAccccccgGCTGATTTGCTA GAATGGAAACcaccgtGCAAT |
| mrc1a | NHR mutant | ttaaTTTATTTTCTCTAGAATTGC CATTGTGTTTCCATTCTAGCAAAT CAGCATTTTTTTTTCAGCTGAAAG AAAAATACCAGGAACTGAGAGCTG AAGCTTGTACCTTTCATTTCCTTT TTG | attAGCagatTtaaTTTCATTTCCTT TTTGCattaaTTTATTTTCTCTAGAA TTGCCATTGTGTTTCCATTCTA | GCTCTCAGTTCCTGGTATTTTTCTTTC AGCTGAAAAAAAAAATGCTGATTTGCTA GAATGGAAACACAATGGCAAT |
| mrc1a | Control mutant | CTGAGCTTTATTTTCTCTAGAATT GCCATTGTGTTTCCATTCcGCAA ATCAGCATTTTTTTTTCAGCTGAc cGAAAAATACCAGGAACTGAGAGC CCATGAAACTGGGAAGATGAAAGC ATT | TGAAGCTTGTACCTTTCATTTCCTTT TTGCTGAGCTTTATTTTCTCTAGAAT TGCCATTGTGTTTCCATTCTAG | GCTCTCAGTTCCTGGTATTTTTCggTC AGCTGAAAAAAAAATGCTGATTTGCcg GAATGGAAACACAATGGCAAT |
| sele | Wild-type | AGTTGAATTGTAACTGGCAACATC TTCTCTGTAATGCCCCCTGTGACC CATATTGTCTCGCTCTTTCCTTTA TAAACAGAGCTGTAGATATCCACA GGAAATGGGGGTGTTTTTGCCATT ATTTCTTCCTGCCATGAAACTGGG AAGATGAAAGCATT | CCATGAAACTGGGAAGATGAAAGCAT TAGTTGAATTGTTACTGGCAACATCT TCTCTGTAATGCCCCCTGTGACCCAT ATTGTCTCGCTCT | CAGGAAGAAATAATGGCAAAAACACCC CCATTTCCTGTGGATATCTACAGCTCT GTTTATAAAGGAAAGAGCGAGACAATA TGGGTCACAG |
| sele | Ets mutant | AGTTGAATTGTTACTGGCAACATC TTCTCTGTAATGCCCCCTGTGACC CATATTGTCTCGCTCTTTaaaTTA TAAACAGAGCTGTAGATATCCACA tttAATGGGGGTGTTTTTGCCATT ATTTCTaaaTGCCATGAAACTGGG AAGATGAAAGCATT | CCATGAAACTGGGAAGATGAAAGCAT CAtttGAAATAATGGCAAAAACACCC CATTaaaTGTGGATATCTACAGCTCTG TCTCTGTAATGCCCCCTGTGACCCAT TTTATAAttTAAAGAGCGAGACAATAT ATTGTCTCGCTCT | GGGTCACAG |
| sele | Sox mutant | AGTTGAAggtggACTGGCAACATC TTCTCTGTAATGCCCCCTGTGACC CATAggtgaTCGCTCTTTCCTTTA TAAACAGAGCTGTAGATATCCACA GGAAATGGGGGTGTTTTTGCCATT ATTTCTTCCTGCCATGAAACTGGG AAGATGAAAGCATT | CCATGAAACTGGGAAGATGAAAGCAT TAGTTGAAggtggACTGGCAACATCT TCTCTGTAATGCCCCCTGTGACCCAT TAggtgaTCGCTCT | CAGGAAGtttattaGGCAAAAACACCC CCATTTCCTGTGGATATCTACAGCTCT GTTTATAAAGGAAGAGCGAtcaccTAT GGGTCACAG |
| sele | NHR mutant | AGTTGAATTGTTACTGGCAACATC TTCTCTGTAATGCCCCCTGattaa CATATTGTCTCGCTCTTTCCTTTA TAAACAGAGCTGTAGATATCCACA GGAAATGGGGGTGTTTTTGCCATT ATTTCTTCCTGCCATGAACTGGGA AtcTGAAAGCATT | CCATGAAACTGGGAAGATGAAAGCAT TAGTTGAATTGTTACTGGCAACATCT TCTCTGTAATGCCCCCTGattaaCAT ATTGTCTCGCTCT | CAGGAAGAAATAATGGCAAAAACACCC CCATTTCCTGTGGATATCTACAGCTCT GTTTATAAAGGAAAGAGCGAGACAATA TGttaatCAG |

TABLE 8-continued

Sequences and primers for mutational variants of the 125 bp mrc1a
and 158 bp sele enhancer elements ("Total Fragment Sequences"
disclosed as SEQ ID NOS 204-208, 13 and 209-212, "Forward Primers"
disclosed as SEQ ID NOS 213-222 and "Reverse Primers" disclosed as
SEQ ID NOS 223-232, respectively, in order of appearance)

| Gene | Fragment Name | Total Fragment Sequence | Forward Primer | Reverse Primer |
| --- | --- | --- | --- | --- |
| sele | Control mutant | AGTTGAATTGTTACTGGCAACATC TTCTCTGTAATGCCCCCTGTGACC CATATTGTCTCGCTCTTTCCTTTA TAAACAGAGagGTAGATATCCACA GGAAATGGGGacTTTTTGCCATT ATTTCTTCCTG | CCATGAAACTGGGAAtcTGAAAGCAT TAGTTGAATTGTTACTGGCAACATCT TCTCTGTAATGCCCCCTGTGACCCAT ATTGTCTCGCTCT | CAGGAAGAAATAATGGCAAAAAgtCCC CCATTTCCTGTGGATATCTACctCTCT GTTTATAAAGGAAAGAGCAGAGACAATT ATGGGTCACAG |

In Table 8, lowercase letters indicate base pair changes used to disrupt transcription factor binding motifs.

TABLE 9

Primers used for cloning and EMSA probe synthesis ("Forward" primers
disclosed as SEQ ID NOS 233-239 and "Reverse" primers disclosed
as SEQ ID NOS 240-246, all respectively, in order of appearance)

| Category | Primer Name | Forward | Reverse | Comment |
| --- | --- | --- | --- | --- |
| Cloning | Nr2f2 | CGGGATCCatggca atggtagtca gcacg | CCGGAATTCCGGttgaattgccat atatggc | |
| Probe synthesis | mrc1a site 1 wild-type | ttta TGAAGCTTGTACCTTTCAT TTCCTTTTTG | CAAAAAGGAAATGAAAGGTACAAG CTTCAtaaa | |
| Probe synthesis | mrc1a site 1 mutation | TTTAattAGCagatTtaaTTTCAT TTCCTTTTTG | CAAAAAGGAAATGAAAttaAatct GCTaatTAAA | 1st NHR site mutated like in vivo GFP reporter experiment |
| Probe synthesis | mrc1a site 2 wild-type | TTCATTTCCTTTTTGCTGAGCTTT ATTTTC | GAAAATAAAGCTCAGCAAAAAGGA AATGAA | |
| Probe synthesis | mrc1a site 2 mutation | TTCATTTCCTTTTTGCattaaTTT ATTTTC | GAAAATAAAttaatGCAAAAAGGA AATGAA | 2nd NHR site mutated like in vivo GFP reporter experiment |
| Probe synthesis | sele wild-type | GTAATGCCCCCTGTGACCCATATT GTCTCGCTCTTTCCTTTATA | TATAAAGGAAAGAGCGAGACAATA TGGGTCACAGGGGGCATTAC | |
| Probe synthesis | sele mutation | GTAATGCCCCCTGattaaCATATT GTCTCGCTCTTTCCTTTATA | TATAAAGGAAAGAGCGAGACAATA TGttaatCAGGGGGCATTAC | NHR site mutated like in vivo GFP reporter experiment |

Table 9 shows primers used for cloning mouse Nr2f2 into the pGEX2TK vector and DNA probes from the zebrafish mrc1a and sele enhancers.

What is claimed herein is:

1. A method to generate endothelial niche cells, comprising expressing one or more exogenous transcription factors in an endothelial cell, wherein the one or more transcription factors include at least one transcription factor from the Ets family, at least one transcription factor from the Sox family, and at least one transcription factor from the Nuclear Hormone Receptor family.

2. The method of claim 1, wherein the endothelial niche cells express one or more genes comprising: Mannose Receptor C-Type 1 (Mrc1), Stabilin 1 (Stab 1), Stabilin 2 (Stab2), or E-selectin (selectin E or Sele).

3. The method of claim 2, wherein the endothelial niche cells express Mrc1.

4. The method of claim 1, wherein the endothelial niche cells express one or more genes comprising: Sele, Exoc3l2, Snx8, Cltc, Aqp7, Aplb1, Lgmn, Prcp, Cldn11, Lyve, Adra1d, Hyal2, Tll1, Il13ra2, Glu1, Hexb, Slc16a9, or Sepp1.

5. The method of claim 1, wherein the endothelial niche cells express one or more genes comprising: Prcp, Cldn11, Tll1, Ctsh, Hexb, Hyal2, Cltc, Ifi30, Glul, Lyvel, Gpr182, Dab2, Ctsl, Stab2, Npl, Stab1, Snx8, Mrcl, Aplb1, Pxk, Sepp1, Lgmn, Man2b2, Sele, Slc16a9, or Il13ra2.

6. The method of claim 1, wherein the endothelial niche cells are mammalian.

7. The method of claim 1, wherein the endothelial cells are human.

8. The method of claim 1, wherein the transcription factor from the Ets family is human transcription factor ETV2, FLI1 or ETS1; the transcription factor from the Sox family is human transcription factor SOX18 or SOX7 and the transcription from the Nuclear Hormone Receptor family is RXRA or NR2F2.

9. The method of claim 1, wherein the transcription factor from the Ets family is ETV2, FLI1 or ETS1; the transcription factor from the Sox family is SOX18 or SOX7; and the transcription factor from the Nuclear Hormone Receptor family is RXRA or NR2F2.

10. The method of claim 1, wherein the transcription factors are expressed from at least one vector.

11. The method of claim 10, wherein the vector comprises an exogenous nucleic acid sequence(s) encoding the one or more transcription factors.

12. The method of claim 11, wherein the exogenous nucleic acid sequence(s) is incorporated into the genome of the endothelial cell.

* * * * *